(12) United States Patent
Fernandez Rodriguez et al.

(10) Patent No.: US 11,739,304 B2
(45) Date of Patent: *Aug. 29, 2023

(54) PRODUCTION OF LYTIC PHAGES

(71) Applicant: Eligo Bioscience, Paris (FR)

(72) Inventors: Jesus Fernandez Rodriguez, Paris (FR); Antoine Decrulle, Paris (FR); Aymeric Leveau, Paris (FR); Ines Canadas Blasco, Paris (FR); Aurélie Mathieu, Paris (FR); Thibault Carlier, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/742,693

(22) Filed: May 12, 2022

(65) Prior Publication Data
US 2022/0364063 A1 Nov. 17, 2022

Related U.S. Application Data

(60) Provisional application No. 63/187,532, filed on May 12, 2021, provisional application No. 63/187,531, filed on May 12, 2021.

(51) Int. Cl.
*C12N 7/00* (2006.01)
*C12N 1/20* (2006.01)
(Continued)

(52) U.S. Cl.
CPC ............ *C12N 7/00* (2013.01); *C12N 1/20* (2013.01); *C12N 15/70* (2013.01); *C12N 15/74* (2013.01);
(Continued)

(58) Field of Classification Search
None
See application file for complete search history.

(56) References Cited

U.S. PATENT DOCUMENTS 4,920,048 A 4/1990 Diderichsen
5,691,185 A 11/1997 Dickely et al.
(Continued)

FOREIGN PATENT DOCUMENTS

WO 94/17201 A1 8/1994
WO 2014/124226 A1 8/2014
(Continued)

OTHER PUBLICATIONS

Brüggemann H, Lood R. Bacteriophages infecting Propionibacterium acnes. Biomed Res Int. 2013;2013:705741. doi: 10.1155/2013/705741. Epub Apr. 11, 2013. PMID: 23691509; PMCID: PMC3652107. (Year: 2013).*

(Continued)

*Primary Examiner* — Michelle S Horning
(74) *Attorney, Agent, or Firm* — Arrigo, Lee, Guttman & Mouta-Bellum LLP

(57) ABSTRACT

The present invention concerns a production bacterial cell for producing lytic phage particles or lytic phage-derived delivery vehicles, said production bacterial cell stably comprising at least one phage structural genes and at least one phage DNA packaging genes, said phage structural gene(s) and phage DNA packaging gene(s) being derived from a lytic bacteriophage,
wherein the expression of at least one of said phage structural genes and/or at least one of said phage DNA packaging gene(s) in said production bacterial cell is controlled by an induction mechanism.

15 Claims, 8 Drawing Sheets

Specification includes a Sequence Listing.

(51) Int. Cl.
*C12N 15/74* (2006.01)
*C12N 15/70* (2006.01)

(52) U.S. Cl.
CPC ............... *C12N 2795/10322* (2013.01); *C12N 2795/10352* (2013.01); *C12N 2800/101* (2013.01); *C12N 2800/40* (2013.01)

(56) References Cited

U.S. PATENT DOCUMENTS

| | | |
|---|---|---|
| 6,291,245 B1 | 9/2001 | Kopetzki et al. |
| 6,413,768 B1 | 7/2002 | Galen |
| 6,752,994 B2 | 6/2004 | Jacobs, Jr. et al. |
| 10,113,163 B2 | 10/2018 | Liu et al. |
| 2005/0186666 A1 | 8/2005 | Schneider et al. |
| 2015/0064138 A1 | 3/2015 | Lu et al. |
| 2015/0166980 A1 | 6/2015 | Liu et al. |
| 2019/0160120 A1* | 5/2019 | Haaber ............... A61K 38/162 |
| 2022/0135986 A1 | 5/2022 | Leveau et al. |
| 2022/0135987 A1* | 5/2022 | Leveau .................... C12N 9/22 424/199.1 |

FOREIGN PATENT DOCUMENTS

| | | |
|---|---|---|
| WO | 2017/141173 A2 | 8/2017 |
| WO | 2018/164988 A1 | 9/2018 |
| WO | 2018/236548 A1 | 12/2018 |
| WO | 2019/105821 A1 | 6/2019 |
| WO | 2020/181178 A1 | 9/2020 |
| WO | 2020/181180 A1 | 9/2020 |
| WO | 2020/181193 A1 | 9/2020 |
| WO | 2020/181195 A1 | 9/2020 |
| WO | 2020/181202 A1 | 9/2020 |

OTHER PUBLICATIONS

Abudayyeh et al RNA targeting with CRISPR-Cas13a. Nature. Oct. 12, 2017; 550(7675): 280-284. doi:10.1038/nature24049.

Anne et al. Protein Secretion in Gram-Positive Bacteria: From Multiple Pathways to Biotechnology. Current Topics in Microbiology and Immunology. Nov. 25, 2016. 267-308. DOI 10.1007/82_2016_49.

Anzalone et al. Search-and-replace genome editing without double-strand breaks or donor DNA. Nature. Dec. 2019 ; 576(7785): 149-157. doi:10.1038/s41586-019-1711-4.

Brede et al. Heterologous Production of Antimicrobial Peptides in Propionibacterium freudenreichii. Applied and Environmental Microbiology, Dec. 2005, 8077-8084. doi:10.1128/AEM.71.12.8077-8084.2005.

Brüggemann H, et al. A Janus-Faced Bacterium: Host-Beneficial and -Detrimental Roles of Cutibacterium acnes. Front. Microbiol. (2021)12:673845. 1-22. doi: 10.3389/fmicb.2021.673845.

Cambray G et al. Measurement and modeling of intrinsic transcription terminator. Nucleic Acids Research, 2013, vol. 41, No. 9 5139-5148 doi:10.1093/nar/gkt163.

Dunn and Studier. Complete Nucleotide Sequence of Bacteriophage T7 DNA and the Locations of T7 Genetic Elements. J. Mol. Biol. (1983) 166, 477-535.

Chen et al. Characterization of 582 natural and synthetic terminators and quantification of their design constraints. 2013. Nature Methods, vol. 10, No. 7, 659-666.

Chen et al. Precise and programmable C:G to G:C base editing in genomic DNA.2020. 1-19. https://doi.org/10.1101/2020.07.21.213827.

Chen et al. Programmable C:G to G:C genome editing with CRISPR-Cas9-directed base excision repair proteins. Nature Communications, (2021) 12:1384. 1-7. https://doi.org/10.1038/s41467-021-21559-9.

Cheng et al. Complete genomic sequences of Propionibacterium freudenreichii phages from Swiss cheese reveal greater diversity than Cutibacterium (formerly Propionibacterium) acnes phages. BMC Microbiology (2018) 18:19, 1-13 https://doi.org/10.1186/s12866-018-1159-y.

Chung and Hinkle. Bacteriophage T7 DNA Packaging II. Analysis of the DNA Sequences Required for Packaging Using a Plasmid Transduction Assay. Journal of Molecular Biology. 1990, 216, 927-938.

Costa et al. Secretion systems in Gram-negative bacteria: structural and mechanistic insights. 2015. Nature Reviews Microbiology. vol. 13, 343-359.

Cotter et al. Bacteriocins—a viable alternative to antibiotics. 2013. Nature Reviews Microbiology. vol. 11, 95-105.

Cox et al. RNA Editing with CRISPR-Cas13. Science. Nov. 24, 2017; 358(6366): 1019-1027. doi:10.1126/science.aaq0180.

Del Solar et al. Replication and Control of Circular Bacterial Plasmids. Microbiology and Molecular Biology Reviews. 1998. vol. 62, No. 2, 434-4.

Dickely et al. Isolation of Lactococcus lactis nonsense suppressors and construction of a food-grade cloning vector. Molecular Microbiology (1992), 15 (5), 839-847.

Farzadfard and Lu. Genomically Encoded Analog Memory with Precise In vivo DNA Writing in Living Cell Population. Science. Nov. 14, 2014; 346(6211): 1256272. doi:10.1126/science.1256272.

Fiedler and Skerra. proBA complementation of an auxotrophic *E. coli* strain improves plasmid stability and expression yield during fermenter production of a recombinant antibody fragment. 2001. Gene. 274, 111-118.

Fillol-Salom et al. Phage-inducible chromosomal islands are ubiquitous within the bacterial universe. The ISME Journal (2018) 12:2114-2128.

Fonfara et al. Phylogeny of Cas9 determines functional exchangeability of dual-RNA and Cas9 among orthologous type II CRISPR-Cas systems. Nucleic Acids Research, 2014, vol. 42, No. 4 2577-2590.

Gaudelli et al. Programmable base editing of A•T to G•C in genomic DNA without DNA cleavage. Nature. 2017 Nov. 23, 2017; 551(7681): 464-471. doi:10.1038/nature24644.

Gautier et al. Bacteriophages infecting dairy propionibacteria. Lait (1995) 75, 427-434.

Gautier et al. Occurrence of Propionibacterium freudenreichii Bacteriophages in Swiss Cheese. Applied and Environmental Microbiology, Jul. 1995, vol. 61, No. 7. p. 2572-2576.

Groenen and Van de Putte. Mapping of a Site for Packaging of Bacteriophage Mu DNA. Virology. 1985, 144, 520-522.

Grunewald et al. A dual-deaminase CRISPR base editor enables concurrent adenine and cytosine editing. Nat Biotechnol. Jul. 2020 ; 38(7): 861-864. doi:10.1038/s41587-020-0535-y.

Hashimoto and Fujisawa. DNA Sequences Necessary for Packaging Bacteriophage T3 DNA. Virology 1992, 187, 7,788-795.

Henkel et al. Toxins from Bacteria. EXS. 2010 ; 100: 1-29.

Hohn. DNA sequences necessary for packaging of bacteriophage A DNA (cosmid/in vivo packaging/in vitro packaging of restriction fragments). Dec. 1983. Proc. Natl. Acad. Sci. USA vol. 80, pp. 7456-7460.

Ioannidi et al. Drag-and-drop genome insertion without DNA cleavage with CRISPR directed integrases. 2021. bioRxiv 2021.11.01.466786; doi: https://doi.org/10.1101/2021.11.01.466786.

Jinek et al. A Programmable Dual-RNA-Guided DNA Endonuclease in Adaptive Bacterial Immunity. Science. Aug. 17, 2012. vol. 337, 6096, 816-821.

Kabashima et al. The immunological anatomy of the skin. Nature Reviews Immunology. 2019. vol. 19, 19-30.

Qimron et al. Genomewide screens for *Escherichia coli* genes affecting growth of T7 bacteriophage. PNAS. 2006. 103 (50), 19039-19044.

Karberg et al. Group II introns as controllable gene targeting vectors for genetic manipulation of bacteria. Nature Biotechnology. 2001, 19, 1162-1167.

Kashaf et al. Integrating cultivation and metagenomics for a multi-kingdom view of skin microbiome diversity and functions. Nature Microbiology. 2022. 7, 169-191.

(56) References Cited

OTHER PUBLICATIONS

Komor et al. Programmable editing of a target base in genomic DNA without double-stranded DNA cleavage. Nature. 2016. 533(7603): 420-424. doi:10.1038/nature17946.
Koonin et al. Diversity, classification and evolution of CRISPR-Cas systems. 2018. Curr Opin Microbiol. Jun. 2017 ; 37: 67-78. doi:10.1016/j.mib.2017.05.008.
Krupovic et al. A classification system for virophages and satellite viruses. 2016. Arch Virology. 161:233-247.
Kues and Stahl. Replication of Plasmids in Gram-Negative Bacteria. Microbiological Reviews, Dec. 1989, 53, 4, 491-516.
Kurt et al. CRISPR C-to-G base editors for inducing targeted DNA transversions in human cells. Nat Biotechnol. Jan. 2021 ; 39(1): 41-46. doi:10.1038/s41587-020-0609-x.
Li et al. Targeted, random mutagenesis of plant genes with dual cytosine and adenine base editors. Nature Biotechnology. 2020. 38, 875-882.
Ma et al. Transposon-Associated CRISPR-Cas System: A Powerful DNA Insertion Tool. Trends in Microbiology. 2021. 29, 7, 565-586.
MacCormick et al. Construction of a food-grade host/vector system for Lactococcus lactis based on the lactose operon. FEMS Microbiology Letters 127 (1995) 105-109.
Marinelli et al. Propionibacterium acnes Bacteriophages Display Limited Genetic Diversity and Broad Killing Activity against Bacterial Skin Isolates. mBio 2012, 3(5), 1-13.
Miwa and Matsubara. Identification of sequences necessary for packaging DNA into lambda phage heads (Recombinant DNA; cosmid; MI3 dideoxynucleotide sequencing; h cohesive end; plasmid vector). Gene, 20(1982) 261-279.
Mutalik et al. Precise and reliable gene expression via standard transcription and translation initiation elements. Nature Methods. 2013, 10, 4, 354-368.
Petri and Schmieger. Isolation of fragments with pac function for phage P22 from phage LP7 DNA and comparison of packaging gene 3 sequences. Gene, 88 (1990) 47-55.
Quiles-Puchalt et al. Staphylococcal pathogenicity island DNA packaging system involving cos-site packaging and phage-encoded HNH endonucleases. PNAS. 2014. 111 (16), 6016-6021.
Rajagopala et al. The protein interaction map of bacteriophage lambda. BMC Microbiology 2011, 11:213, 1-15.
Auster et al. Optimizing DNA transduction by selection of mutations that evade bacterial defense systems. RNA Biology. 2019, 16 (4), 595-599.
Rees and Liu. Base editing: precision chemistry on the genome and transcriptome of living cells. Nat Rev Genet. Dec. 2018 ; 19(12): 770-788. doi:10.1038/S41576-018-0059-1.
Russel and Model. Genetic Analysis of the Filamentous Bacteriophage Packaging Signal and of the Proteins That Interact with It. Journal of Virology, Aug. 1989, 63 (8), 3284-3295.
Sharon et al. Functional genetic variants revealed by massively parallel precise genome editing. Cell. Oct. 4, 2018; 175(2): 544-557.e16.doi:10.1016/j.cell.2018.08.057.
Simon et al. Retrons and their applications in genome engineering. Nucleic Acids Research, 2019, vol. 47, No. 21 11007-11019 doi: 10.1093/nar/gkz86.
Sorensen et al. A Food-Grade Cloning System for Industrial Strains of Lactococcus lactis. Applied and Environmental Microbiology, Apr. 2000, 66(4), 1253-1258.
Stanton et al. Genomic Mining of Prokaryotic Repressors for Orthogonal Logic Gates. Nat Chem Biol. Feb. 2014 ; 10(2): 99-105. doi:10.1038/nchembio.1411.
Struhl et al. Functional genetic expression of eukaryotic DNA in *Escherichia coli*. Proc. Natl. Acad. Sci. May 1976. 73 (5), 1471-1475.
Tomida et al. Pan-Genome and Comparative Genome Analyses of Propionibacterium acnes Reveal Its Genomic Diversity in the Healthy and Diseased Human Skin Microbiome. mBio. 4(3), e00003-13, 1-11. doi:10.1128/mBio.00003-13.
Vo et al. CRISPR RNA-guided integrases for high-efficiency, multiplexed bacterial genome engineering. Nature Biotechnology, 2021, 39, 480-489. https://doi.org/10.1038/s41587-020-00745-y.
Wannier et al. Improved bacterial recombineering by parallelized protein discovery. PNAS, 2020, 117(24), 13689-13698.
Wannier et al. Recombineering and MAGE. Nat Rev Methods Primers. 2021, 1-51. doi:10.1038/s43586-020-00006-x.
Weigele and Raleigh. Biosynthesis and Function of Modified Bases in Bacteria and Their Viruses. Chemical Reviews. 2016, 12655-12687.
Wu et al. The DNA site utilized by bacteriophage P22 for initiation of DNA packaging. Molecular Microbiology (2002) 45(6), 1631-1646.
Yan et al. Cas13d is a compact RNA-targeting type VI CRISPR effector positively modulated by a WYL domain-containing accessory protein. Mol Cell. Apr. 19, 2018; 70(2): 327-339.e5. doi:10.1016/j.molcel.2018.02.028.
Zhao et al. New base editors change C to A in bacteria and C to G in mammalian cells. Nat Biotechnol 2021, 39, 35-40. https://doi.org/10.1038/S41587-020-0592-2.
Fernandez Rodriguez and Voigt. Post-translational control of genetic circuits using Potyvirus proteases. Nucleic Acids Research, 2016, vol. 44, No. 13, 6493-6502. doi: 10.1093/nar/gkw537.
Studier.Processing of Bacteriophages T7 RNAs by RNase III1. From Gene To Protein: Information Transfer in Normal and Abnormal Cells. 1979. Department of Biology Brookhaven National Laboratory. 261-269.
Rohde et al. Expert Opinion on Three Phage Therapy Related Topics: Bacterial Phage Resistance, Phage Training and Prophaged in Bacterial Production Strains. Viruses, 2018, 10(178), 1-15.
Brown et al. Phage engineering: how advances in molecular biology and synthetic biology are being utilized to enhance the therapeutic potential of bacteriophages. Quantitative Biology, 2017, 5(1), 42-54.
Pires et al. Current challenges and future opportunities of phage therapy. FEMS Microbiology Reviews, 2020, 44(6), 684-700.
Monteiro et al. Phage Therapy: Going Temperate? Trends in Microbiology, 2019, 27(4), 368-377.

\* cited by examiner

Production from Pf1s22904 colonies 1-8

SLST PCR
Expected size 612bp pAN594 specific PCR
Expected size 769bp

PRODUCTION OF LYTIC PHAGES

CROSS REFERENCE TO RELATED APPLICATIONS

This application claims the benefit of U.S. application 63/187,531 filed May 12, 2021, and U.S. application 63/187,532 filed May 12, 2021, which are incorporated herein by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on May 12, 2022, is named EB2021-04b_sequence_listing_ST25.txt and is 217,777 bytes in size.

FIELD OF THE INVENTION

The present invention concerns bacterial cells for producing lytic phage particles and methods using such bacterial cells.

BACKGROUND

Lytic bacteriophages (phages) are self-replicating viruses, which are capable of infecting and lysing their specific host bacteria. Because of their host specificity and nontoxicity, lytic phages are considered to be an alternative solution to combat antimicrobial-resistant pathogens.

However, lytic phages are naturally incapable of being stably maintained in the genome and/or as episomes of/in a strain, which drastically complicates their production at an industrial scale.

Moreover, most current phage or phage-derived delivery vehicle production methods imply the use, as production cell, of the bacterial species or strain which is the natural host of said phages. Such methods can turn out to be dangerous when such bacterial cells are pathogenic, for example when they produce toxins. Moreover, many bacterial species cannot be easily manipulated, for instance because of their growth conditions or because there is no efficient genetic tool for those bacteria.

There is thus a need for a method enabling the safe, easier and efficient production of a lytic phage or lytic phage-derived particle.

The present inventors considered that phages can be viewed as more or less large genetic circuits, the final output of which is the generation of more phage particles. To do this, no matter if the phage is lytic, temperate or chronic (for instance filamentous phages such as M13), the present inventors considered that the information encoded in their genomes can be roughly categorized depending on the function it performs:

Genes devoted to insertion/excision (for temperate phages).
Genes devoted to DNA replication, RNA transcription, etc. Indeed, some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.
Genes devoted to packaging of the newly synthesized phage genome into the newly synthesized phage capsids: terminases and accessory proteins, ligases, etc.
Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).
Genes related to defense from host's anti-phage mechanisms, degradation/modification of host's elements to complete the lytic cycle, super-exclusion mechanisms or genes that are advantageous for the host.

The DNA packaging and structural genes categories are deeply connected, since the packaging machinery recognizes the pre-assembled heads and the DNA to be packaged in these heads, initiates and terminates DNA packaging.

The present inventors hypothesized that by abstracting and differentiating all the modules defined above, a system could be built that contains all excision/insertion, replication and regulation elements from a non-lytic phage and encodes the packaging/structural elements for a lytic phage, since, as considered by the inventors, they could be viewed as independent genetic modules.

Treating them as independent genetic modules could also allow for the construction of a system that contains only the desired structural and/or regulatory elements of the lytic phage to be produced under the control of a master regulatory element (an inducible repressor, for example) that may not be derived from a phage. For instance, only the structural operon and the DNA packaging machinery of a lytic phage could be placed under the control of a repressor that responds to a small molecule or a physical/chemical signal (LacI, AraC, PhlF, Lambda cI, etc.), triggering the production of all the elements necessary to generate pure mature lytic phage delivery particles (phages or packaged phagemids). This "trimmed down" version of a phage genome could be stably maintained in a bacterial production strain.

SUMMARY OF THE INVENTION

The present invention arises from the unexpected finding by the inventors that it is possible, by exchanging the structural operon of an *Escherichia coli* production strain encoding a system to generate pure Lambda packaged phagemids with the structural elements of a strictly lytic phage (such as T7 phage), to drive the assembly and packaging of pure heterologous lytic phagemid particles when supplemented with a plasmid containing the correct packaging signals (LTR for T7 phage). The present inventors thus here showed that packaged phagemids can be produced structurally based on a T7 lytic phage, but regulated and maintained in a lysogenic state by the Lambda prophage machinery in an *Escherichia coli* production strain.

The inventors also showed that the structural operon of a *P. freudenreichii* prophage can be exchanged with the structural operon of a lytic phage of a *C. acnes* strain. With this approach, the inventors showed that it is possible, by exchanging the structural operon of a *P. freudenreichii* prophage with the structural operon of a lytic phage of a *C. acnes* strain, to drive the assembly and packaging of pure *C. acnes* phagemids.

The present invention thus concerns a production bacterial cell for producing lytic phage particles or lytic phage-derived delivery vehicles, said production bacterial cell stably comprising at least one phage structural genes and at least one phage DNA packaging genes, said phage structural gene(s) and phage DNA packaging gene(s) being derived from a lytic bacteriophage, wherein the expression of at least one of said phage structural genes and/or at least one of said phage DNA packaging gene(s) in said production bacterial cell is controlled by an induction mechanism.

The present invention also concerns a method for producing lytic phage particles or lytic phage-derived delivery vehicles, comprising:
  (a) providing the production bacterial cell of the invention, and
  (b) inducing, in said production bacterial cell, expression of said at least one of said phage structural gene(s) and said at least one of said phage DNA packaging gene(s), and assembly of the products expressed by said at least one phage structural gene(s) and said at least one phage DNA packaging gene(s), thereby producing lytic phage particles or lytic phage-derived delivery vehicles.

Another object of the invention concerns a hybrid helper phage system comprising:
  (i) at least one phage DNA packaging gene(s) derived from a lytic bacteriophage,
  (i') at least one phage structural gene(s) derived from said lytic bacteriophage,
  (i") optionally, at least one phage gene(s) involved in phage regulation derived from said lytic bacteriophage, and
  (ii) at least one gene, derived from a non-lytic bacteriophage, involved in phage excision/insertion, phage DNA replication, and/or phage regulation, wherein said genes (i), (i'), (i") and (ii) are comprised in a unique nucleic acid molecule or in separate nucleic acid molecules, and wherein said hybrid helper phage system does not comprise any expressed phage structural gene derived from said non-lytic bacteriophage.

DETAILED DESCRIPTION OF THE INVENTION

Production Bacterial Cell

The present invention concerns a production bacterial cell for producing lytic phage particles or lytic phage-derived delivery vehicles, said production bacterial cell stably comprising at least one phage structural gene(s) and at least one phage DNA packaging gene(s) derived from a lytic bacteriophage, wherein the expression of at least one of said phage structural gene(s) and at least one of said phage DNA packaging gene(s) in said production bacterial cell is controlled by an induction mechanism.

As used herein, the term "phage particle" refers to a functional or non-functional (for example non-reproductive and/or replicative) virion.

As used herein, the term "lytic phage particle" refers to particles derived from phages which are naturally incapable of being stably maintained in the genome and/or as episomes of/in a strain and thus have a strictly lytic (as opposed to lysogenic) lifestyle, i.e. the infection process always ends with the lysis of the target strain.

As used herein, the term "lytic phage-derived delivery vehicle" refers to any means that allows the transfer of a payload into a bacterium and which is derived from a lytic bacteriophage. In the context of the invention, the term "lytic phage-derived delivery vehicle" further encompasses lytic bacteriophage-derived particles which do not comprise any payload but are able to target bacterial cells.

The lytic phage-derived delivery vehicle can refer to a lytic bacteriophage derived scaffold and can be obtained from a natural, evolved or engineered lytic bacteriophage.

Bacterial Cell

The production bacterial cell of the invention may be of any bacterial species or strain, in particular defined below under the section "Targeted bacteria".

However, the production bacterial cell is preferably a non-pathogen bacterial cell. Still preferably, the production bacterial cell is a bacterial cell which can be easily manipulated.

By "easily manipulated" is meant herein that the bacterial cell can be cultured and/or modified using well-known techniques.

In a particular preferred embodiment, said production bacterial cell is an *E. coli* bacterial cell. Alternatively, said production bacterial cell may be a *Bacteroides* bacterial cell, more particularly a *Bacteroides thetaiotaomicron* bacterial cell, a *P. freudenreichii* bacterial cell, a *Fusobacterium* bacterial cell, or a *Streptococcus* bacterial cell. In a particular embodiment, said production bacterial cell is a *P. freudenreichii* bacterial cell.

The production bacterial cell of the invention can be obtained by any technique well-known from the skilled person, in particular by introducing into a bacterial cell, said phage structural gene(s) and phage DNA packaging gene(s) derived from a lytic bacteriophage, by any technique well-known in the art.

The production bacterial cell of the invention can typically be obtained by homologous recombination or recombineering including for example MAGE (Wannier et al. Recombineering and MAGE. *Nat Rev Methods Primers* 1, 7 (2021)), using CRISPR, TALEN, meganucleases and/or Zn-finger technologies for instance or using site specific recombination with phage integrase, PASTE (Ioannidi et al. Drag-and-drop genome insertion without DNA cleavage with CRISPR-directed integrases. Biorxiv 2021.11.01.466786 (2021) doi:10.1101/2021.11.01.466786) or Transposon-Associated CRISPR-Cas System (Ma et al. *Trends Microbiol* 29, 565-568 (2021)).

Phage DNA Packaging Genes and Phage Structural Genes

The production bacterial cell of the invention stably comprises at least one phage structural gene(s) and at least one phage DNA packaging gene(s) derived from a lytic bacteriophage.

By "stably comprise" or "stably comprising" is meant herein that the production bacterial cell retains said phage structural gene(s) and phage DNA packaging gene(s) either incorporated into its chromosome, or on an episome that is maintained in the cell typically through selection (e.g., with a nutritional, auxotrophic, or drug resistance marker). Each gene stably comprised by the production bacterial cell can independently be on a plasmid, on a helper phage, or is integrated into the production bacterial cell chromosome.

In a particular embodiment, said production bacterial cell stably comprises at least two, 3, 4, or all phage structural genes derived from said lytic bacteriophage, and at least one phage DNA packaging gene(s) derived from said lytic bacteriophage.

In a particular embodiment, said production bacterial cell stably comprises at least one phage structural gene(s)

derived from said lytic bacteriophage, and at least two or all phage DNA packaging genes derived from said lytic bacteriophage.

In a particular embodiment, said production bacterial cell stably comprises at least two, 3, 4, or all phage structural genes derived from said lytic bacteriophage, and at least two or all phage DNA packaging genes derived from said lytic bacteriophage.

In a particular embodiment, said production bacterial cell stably comprises all phage structural genes derived from said lytic bacteriophage, and all phage DNA packaging genes derived from said lytic bacteriophage.

By "phage structural genes" is meant herein genes from a bacteriophage which are involved in the building of the bacteriophage protein capsid. Phage structural genes include genes encoding phage structural elements; genes encoding phage proteins involved in the assembly of the phage structural elements; and genes encoding phage proteins packaged inside the capsid as scaffold or as pilot proteins to be injected into a targeted bacterial cell.

Phage structural elements are well-known from the skilled person and depend on the type of bacteriophage from which they are derived. Phage structural elements can be proteins but also RNAs (for example some phages like phi29 from *Bacillus subtilis* encode a structural scaffold made of RNA). Phage structural elements typically include capsid proteins, tape measure proteins, fibers, baseplate proteins, tail sheath proteins, whisker proteins, decoration proteins, etc. . . . .

Phage proteins involved in the assembly of the structural elements are well-known from the skilled person and depend on the type of bacteriophage from which they are derived, and optionally on the structural elements encoded by the other phage structural genes. Phage proteins involved in the assembly of the structural elements typically include phage chaperone proteins and phage proteases.

Phage proteins packaged inside the capsid as scaffold or as pilot proteins to be injected into a target host cell are well-known from the skilled person and depend on the type of bacteriophage from which they are derived. Examples of such phage proteins are RNA polymerase from phage N4 or minor pilot proteins.

As will be understood by the skilled person, the presence of a particular phage structural gene in the production bacterial cell of the invention will depend on the bacteriophage from which said phage structural genes are derived.

By "phage DNA packaging genes" is meant herein genes from a bacteriophage which are involved in the packaging of the bacteriophage genome into the bacteriophage capsid. Phage DNA packaging genes are well-known from the skilled person and include genes encoding phage terminases, genes encoding phage accessory proteins, genes encoding phage ligases, genes encoding phage exonucleases involved in DNA packaging and genes encoding phage endonucleases involved in DNA packaging.

In a particular embodiment, said production bacterial cell further stably comprises at least one gene involved in phage regulation derived from said lytic bacteriophage.

By "gene involved in phage regulation" is meant herein phage genes involved in the interaction of the phage with the host. Examples of genes involved in phage regulation include phage genes encoding master repressors, phage genes encoding anti-termination proteins, phage genes involved in transcription such as phage genes encoding RNA polymerases, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In a particular embodiment, said production bacterial cell stably comprises phage gene(s) involved in defense against host's anti-phage mechanisms derived from said lytic bacteriophage.

In another particular embodiment, said production bacterial cell stably comprises phage gene(s) involved in transcription such as phage genes encoding RNA polymerases, derived from said lytic bacteriophage.

In a particular embodiment, said phage structural gene(s) and phage DNA packaging gene(s) derived from said lytic bacteriophage, and optionally said gene(s) involved in phage regulation derived from said lytic bacteriophage are comprised in at least one plasmid, chromosome and/or helper phage. In a particular embodiment, said phage structural gene(s) and phage DNA packaging gene(s) derived from said lytic bacteriophage, and optionally said gene(s) involved in phage regulation derived from said lytic bacteriophage are comprised in at least two separate nucleic acid molecules, in particular at least two plasmids, chromosomes, helper phages or combinations thereof.

In a particular embodiment, said phage structural gene(s) and phage DNA packaging gene(s) derived from said lytic bacteriophage, and optionally said gene(s) involved in phage regulation derived from said lytic bacteriophage are comprised in a hybrid helper phage system as defined below.

In a particular embodiment, said phage structural gene(s) and phage DNA packaging gene(s) derived from said lytic bacteriophage, and optionally said gene(s) involved in phage regulation derived from said lytic bacteriophage are comprised in a helper phage.

Induction Mechanism

In the context of the invention, the expression of at least one of said phage structural gene(s) and/or at least one of said phage DNA packaging genes, as defined in the section "Phage DNA packaging genes, and phage structural genes" above, in said production bacterial cell is controlled by at least one induction mechanism.

In a particular embodiment, the expression of at least one of said phage structural gene(s), in particular at least two, at least three, or all said phage structural genes, in said production bacterial cell is(are) controlled by at least one induction mechanism, in particular by one induction mechanism.

In a particular embodiment, the expression of at least one of said phage DNA packaging gene(s), in particular at least two, at least three, or all said phage DNA packaging genes, in said production bacterial cell is(are) controlled by at least one induction mechanism, in particular by one induction mechanism.

In a particular embodiment, the same induction mechanism controls the expression of the at least one of said phage structural gene(s) and the at least one of said phage DNA packaging gene(s).

In an alternative embodiment, the expression of the at least one of said phage structural gene(s) and the expression of the at least one of said phage DNA packaging gene(s) are controlled by different induction mechanisms.

By "induction mechanism" is meant herein a mechanism, encoded by a gene or group of genes comprised, in particular stably comprised, in said production bacterial cell, able to induce the expression of the genes they control, in response to a given trigger.

In a particular embodiment, said induction mechanism further controls the copy number of said at least one of said phage structural gene(s) and/or said at least one of said phage DNA packaging gene(s). In other words, in a particular embodiment, said induction mechanism further controls the replication of said at least one of said phage structural gene(s) and/or of said at least one of said phage DNA packaging gene(s), in particular the replication of the nucleic acid molecule(s) carrying said at least one of said phage structural gene(s) and/or said at least one of said phage DNA packaging gene(s).

In a particular embodiment, said induction mechanism further controls the assembly of the products expressed by said at least one of said phage structural gene(s) and said at least one of said phage DNA packaging gene(s).

Examples of such induction mechanism include:
Protein repressor or activator-based induction systems responding to small molecules (for example sugars, quorum-sensing molecules, gases, synthetic molecules, peptides, amino acids, metabolites, etc), physical signals (temperature, pressure, etc.), chemical signals (osmolarity, pH, etc.), biological signals (cell density, DNA damage, etc.); these systems may be activated by a secondary protein such as an orthogonal RNA polymerase or sigma factor.
Protein degradation systems to activate or repress transcription from a promoter.
RNA-based induction systems such as aptamers responding to the signals stated above, such as RNAi, CRISPRi, toehold systems, riboswitches, etc.
One or more nucleic acids comprising at least one gene, derived from a non-lytic bacteriophage, involved in phage excision/insertion, phage DNA replication, and/or phage regulation.

In a particular embodiment, said induction mechanism comprises at least one gene, derived from a non-lytic bacteriophage, involved in phage excision/insertion, phage DNA replication, and/or phage regulation.

Therefore, in particular embodiment, said production bacterial cell further comprises at least one gene, derived from a non-lytic bacteriophage, involved in phage excision/insertion, phage DNA replication, and/or phage regulation.

Genes Involved in Phage Excision/Insertion, Phage DNA Replication, and/or Phage Regulation By "gene involved in phage excision/insertion" is meant herein genes from lysogenic phages involved in the excision of the phage, present as a prophage, from the genome or episome of a bacterial cell and/or the insertion of the phage, as a prophage, in the genome or episome of a bacterial cell.

By "gene involved in phage DNA replication" is meant herein genes from lysogenic phages, involved in the mechanism of replication of the phage DNA. Examples of genes involved in phage DNA replication include genes encoding DNA polymerase and genes involved in the segregation of the prophage sequence if it exists in a plasmid or linear plasmid form.

By "gene involved in phage regulation" is meant herein phage genes involved in the interaction of the phage with the host. Examples of genes involved in phage regulation include phage genes encoding master repressors, phage genes encoding anti-termination proteins, phage genes involved in super-exclusion mechanisms, phage genes involved in defense against host's anti-phage mechanisms, phage genes involved in degradation and/or modification of host's elements for example to complete the lytic cycle, and phage genes advantageous for the host.

In the context of the invention, said gene(s) involved in phage excision/insertion, phage DNA replication, and/or phage regulation, is(are) not DNA packaging gene(s) nor structural gene(s), as defined above.

In a preferred embodiment, the production bacterial cell of the invention comprises at least one gene, preferably all the genes, involved in phage excision/insertion derived from a second type of bacteriophage; at least one gene, preferably all the genes, involved in phage DNA replication derived from a non-lytic bacteriophage; and/or at least one gene, preferably all the genes, involved in phage regulation derived from a non-lytic bacteriophage.

In the context of the invention, said production bacterial cell does not comprise genes derived from the lytic bacteriophage which are involved in phage excision/insertion and/or phage DNA replication.

In a particular embodiment, said gene(s) involved in phage excision/insertion, phage DNA replication, and/or phage regulation derived from said non-lytic bacteriophage, are comprised in at least one plasmid, chromosome and/or helper phage. In a particular embodiment, said gene(s) involved in phage excision/insertion, phage DNA replication, and/or phage regulation derived from said non-lytic bacteriophage are comprised in at least two separate nucleic acid molecules, in particular at least two plasmids, chromosomes, helper phages or combinations thereof.

In a particular embodiment, said gene(s) involved in phage excision/insertion, phage DNA replication, and/or phage regulation derived from said non-lytic bacteriophage are comprised in a hybrid helper phage system as defined below.

In a particular embodiment, said gene(s) involved in phage excision/insertion, phage DNA replication, and/or phage regulation derived from said non-lytic bacteriophage, are comprised in a helper phage system, more particularly on the same helper phage system as said phage structural gene(s) and phage DNA packaging gene(s) derived from said lytic bacteriophage, and optionally said gene(s) involved in phage regulation derived from said lytic bacteriophage.

In a particular embodiment, said production bacterial cell is from the same bacterial species or strain as the bacterial species or strain from which said non-lytic bacteriophage comes and/or that said non-lytic bacteriophage targets.

In a more particular embodiment, said production bacterial cell is an *E. coli* bacterial cell. In another particular embodiment, said production bacterial cell is a *P. freudenreichii* bacterial cell.

Other Elements

In a particular embodiment, the production bacterial cell of the invention further comprises at least one gene involved in phage RNA transcription.

By "gene involved in phage RNA transcription" is meant genes from temperate or lytic phages, involved in the mechanism of transcription of the phage RNA. Examples of such genes include genes encoding phage RNA polymerase and phage genes encoding proteins modifying the host's RNA polymerases, typically to be able to work past terminators.

Bacteriophage and Gene Derived from a Bacteriophage

By "gene derived from a bacteriophage" is meant herein that the sequence of the gene is obtained from a bacteriophage, said sequence being optionally modified, recoded and/or optimized compared to the sequence initially present in the bacteriophage. For example, said sequence may be recoded for codon exchange or optimization or preventing recombination.

Bacteriophages are obligate intracellular parasites that multiply inside bacteria by co-opting some or all of the host biosynthetic machinery. Alternatively, some bacteriophages (lytic bacteriophages) are naturally incapable of being stably maintained in the bacterial genome and/or as episomes in bacteria and cause lysis of the bacteria. Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

By "lytic phage" is meant herein a bacteriophage which infects bacteria or archaea, and which is naturally incapable of being stably maintained in the genome and/or as episomes of/in a strain and thus has a strictly lytic (as opposed to lysogenic) lifestyle and causes lysis and destruction of the bacterial or microorganism cell after replication of the phage. As soon as the cell is destroyed, the phage progeny can find new host cells (e.g., bacteria) to infect. It is well-known from the skilled person which bacteriophages, in the bacteriophages listed below, are lytic phages.

In a particular embodiment, said non-lytic bacteriophage is a temperate bacteriophage, filamentous phage, or pseudo-lysogenic phage.

By "temperate bacteriophage" or "lysogenic bacteriophage" is meant herein a bacteriophage which infects bacteria or achaea, which can be stably maintained in the genome and/or as episomes of/in a strain, and which replicates with cells without, in their lysogenic state, producing virions. It is well-known from the skilled person which bacteriophages, in the bacteriophages listed below, are temperate phages.

By "filamentous phage" is meant herein a bacteriophage characterized by having a single-stranded DNA genome that is encased by a long protein capsid cylinder. Typically, bacteria infected by filamentous phages are not lysed during the life cycle and replication of the phage, but rather experience a reduced rate of growth as the phage particles are secreted from the membrane. It is well-known from the skilled person which bacteriophages, in the bacteriophages listed below, are filamentous phages.

By "pseudo-lysogenic phage" is meant herein a bacteriophage being at a stage of stalled development in a host cell without either multiplication of the phage genome (as in lytic development) or its replication synchronized with the cell cycle and stable maintenance in the cell line (as in lysogenization), which proceeds with no viral genome degradation, thus allowing the subsequent restart of virus development.

In a particular embodiment, the lytic bacteriophage is selected from the lytic bacteriophages of Order Caudovirales and/or the non-lytic bacteriophage is selected from the non-lytic bacteriophages of Order Caudovirales, said Order Caudovirales consisting of, based on the taxonomy of Krupovic et al. (Krupovic et al. Arch Virol. 2016 January; 161(1):233-47):

family Myoviridae (such as, without limitation, genus Cp220virus, Cp8virus, Ea214virus, Felixo1virus, Mooglevirus, Suspvirus, Hp1virus, P2virus, Kayvirus, P100virus, Silviavirus, Spo1virus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Se1virus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxz1virus, Cd119virus, Cp51virus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rsl2virus, Rslunavirus, Secunda5virus, Sep1virus, Spn3virus, Svunavirus, Tg1virus, Vhmlvirus and Wphvirus)

family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwalphavirus, Kf1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

family Siphoviridae (such as, without limitation, genus Camvirus, Likavirus, R4virus, Acadianvirus, Coopervirus, Pg1virus, Pipefishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Rogue1virus, Rtpvirus, T1virus, Tlsvirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjw1virus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, Lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdjlvirus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus)

family Ackermannviridae (such as, without limitation, genus Ag3virus, Limestonevirus, Cba120virus and Vi1virus)

In a particular embodiment, the lytic bacteriophage and/or the non-lytic bacteriophage is not part of the Order Caudovirales but from families with Unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

In a particular embodiment, the lytic bacteriophage and/or the non-lytic bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

In a particular embodiment, said lytic bacteriophage comes from a given bacterial species or strain. In another particular embodiment, said non-lytic bacteriophage comes from a same or different given bacterial species or strain.

By "bacteriophage coming from a given bacterial species or strain" is meant herein a bacteriophage specifically targeting a particular bacterial species or strain and/or a bacteriophage hosted by a particular bacterial species or strain.

A non-exhaustive listing of bacterial genera and their known host-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CTI, CT2, CT3, CT4, CT6, CT7, CT8 and 1281.

Bacteria of the genus *Aeromonas* can be infected by the following phages: AA-I, Aeh2, N, PMI, TP446, 3, 4, 11, 13, 29, 31, 32, 37, 43, 43-10T, 51, 54, 55R.1, 56, 56RR2, 57, 58, 59.1, 60, 63, Aehl, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aizl, A1-K-1, B, BCJAI, BCI, BC2, BLLI, BLI, BP142, BSLI, BSL2, BSI, BS3, BS8, BS15, BS18, BS22, BS26, BS28, BS31, BS104, BS105, BS106, BTB, B1715V1, C, CK-I, ColI, CorI, CP-53, CS-I, CSi, D, D, D, D5, entl, FP8, FP9, FSi, FS2, FS3, FS5, FS8, FS9, G, GH8, GT8, GV-I, GV-2, GT-4, g3, gI2, gI3, gI4, gI6, gI7, g21, g23, g24, g29, H2, kenl, KK-88, Kuml, Kyul, J7W-1, LP52, (syn=LP-52), L7, Mexl, MJ-I, mor2, MP-7, MPIO, MP12, MP14, MP15, Neol, N°2, N5, N6P, PBCI, PBLA, PBPI, P2, S-a, SF2, SF6, ShaI, SilI, SP02, (syn=ΦSPP1), SPβ, STI, STi, SU-II, t, TbI, Tb2, Tb5, TbIO, Tb26, Tb51, Tb53, Tb55, Tb77, Tb97, Tb99, Tb560, Tb595, Td8, Td6, Tdl5, Tgl, Tg4, Tg6, Tg7, Tg9, TgIO, Tgll, Tgl3, Tgl5, Tg21, TinI, Tin7, Tin8, TinI3, Tm3, TocI, TogI, toII, TP-1, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, YunI, α, γ, pI I, φmed-2, φT, φμ-4, φ3T, φ75, φIO5, (syn=(φIO5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), alel, ARI, AR2, AR3, AR7, AR9, Bace-11, (syn=11), Bastille, BLI, BL2, BL3, BL4, BL5, BL6, BL8, BL9, BP124, BS28, BS80, Ch, CP-51, CP-54, D-5, darI, denI, DP-7, entl, FoSi, FoS2, FS4, FS6, FS7, G, gall, gamma, GEI, GF-2, GSi, GT-I, GT-2, GT-3, GT-4, GT-5, GT-6, GT-7, GV-6, gl5, 19, 110, ISi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. I, N17, N19, PBSI, PKI, PMBI, PMB12, PMJI, S, SPOI, SP3, SP5, SP6, SP7, SP8, SP9, SPIO, SP-15, SP50, (syn=SP-50), SP82, SST, subl, SW, Tg8, Tgl2, Tgl3, Tgl4, thul, thuA, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megaterium*), 4 (*B. sphaericus*), AR13, BPP-IO, BS32, BS107, BI, B2, GA-I, GP-IO, GV-3, GV-5, g8, MP20, MP27, MP49, Nf, PPS, PP6, SF5, TgI8, TP-I, Versailles, φI5, φ29, 1-97, 837/IV, mï-*Bacillus* (1), BatIO, BSLIO, BSLI I, BS6, BSI I, BS16, BS23, BSIOI, BS102, gl8, morI, PBLI, SN45, thu2, thu3, Tml, Tm2, TP-20, TP21, TP52, type F, type G, type IV, HN-BacMus (3), BLE, (syn=θc), BS2, BS4, BS5, BS7, BIO, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, SPa, type 1 and µ.

Bacteria of the genus *Bacteroides* can be infected by the following phages: crAss-phage, ad I2, Baf-44, Baf-48B, Baf-64, Bf-I, Bf-52, B40-8, FI, βI, φAI, φBrOI, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, FOi, (syn=FOI), (syn=FQI), D, FP2, (syn=FP2), (syn=FD2), Fz, (syn=Fz75/13), (syn=Firenze 75/13), (syn=Fi), Fi, (syn=FI), Fim, (syn=FIm), (syn=Fim), FiU, (syn=FIU), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn—F44), F45, (syn=F45), F48, (syn=F48), I, Im, M, MC/75, M51, (syn=M85), P, (syn=D), S708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=FIO), 371/XXIX, (syn=371), (syn=Fn), (syn=FI I) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chpl.

Bacteria of the genus *Clostridium* can be infected by the following phages: CAKI, CA5, Ca7, CEβ, (syn=1C), CEγ, CldI, c-n71, c-203 Tox–, DEβ, (syn=ID), (syn=IDt0X+), HM3, KMI, KT, Ms, NAI, (syn=Naltox+), PA135Oe, Pfó, PL73, PL78, PL81, PI, P50, P5771, P19402, ICt0X+, 2Ct0X\2D3 (syn=2Dt0X+), 3C, (syn=3Ctox+), 4C, (syn=4Ct0X+), 56, III-I, NN-*Clostridium* (61), NBIt0X+, αI, CAI, HMT, HM2, PFI5 P-23, P-46, Q-05, Q-oe, Q-16, Q-21, Q-26, Q-40, Q-46, S111, SA02, WA01, WA03, Wm, W523, 80, C, CA2, CA3, CPTI, CPT4, cl, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, α2, 41, 112ZS23, 214/S23, 233/Ai, 234/S23, 235/S23, II-I, II-2, II-3, NN-*Clostridium* (12), CAI, FI, K, S2, 1, 5 and NN-*Clostridium* (8).

Bacteria of the genus *Corynebacterium* can be infected by the following phages: CGKI (defective), A, A2, A3, AlOI, A128, A133, A137, A139, A155, A182, B, BF, B17, B18, B51, B271, B275, B276, B277, B279, B282, C, capi, CCI, CGI, CG2, CG33, CL31, Cog, (syn=CG5), D, E, F, H, H-I, hqi, hq2, 11ZH33, li/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γI9, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phage: DF78, FI, F2, 1, 2, 4, 14, 41, 867, DI, SB24, 2BV, 182, 225, C2, C2F, E3, E62, DS96, H24, M35, P3, P9, SBIOI, S2, 2BII, 5, 182a, 705, 873, 881, 940, 1051, 1057, 21096C, NN-*Enterococcus* (1), PEI, FI, F3, F4, VD13, 1, 200, 235 and 341.

Bacteria of the genus *Erysipelothrix* can be infected by the following phage: NN-Eiysipelothrix (1).

Bacteria of the genus *Escherichia* can be infected by the following phages: BW73, B278, D6, D108, E, EI, E24, E41, FI-2, FI-4, FI-5, HI8A, Ffl8B, i, MM, Mu, (syn=mu), (syn=Mul), (syn=Mu-I), (syn=MU-I), (syn=Mul), (syn=μ), 025, Phl-5, Pk, PSP3, PI, PID, P2, P4 (defective), SI, Wφ, φK13, φR73 (defective), φI, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, FII, FI3, H, HI, H3, H8, K3, M, N, ND-2, ND-3, ND4, ND-5, ND6, ND-7, Ox-I (syn=OXI), (syn=HF), Ox-2 (syn=0x2), (syn=0X2), Ox-3, Ox-4, Ox-5, (syn=0X5), Ox-6, (syn=66F), (syn=φ66t), (syn=φ66t-)5 0111, Phl-I, RB42, RB43, RB49, RB69, S, Sal-I, Sal-2, Sal-3, Sal-4, Sal-5, Sal-6, TC23, TC45, TulI*-6, (syn=TulI*), TulP-24, TulI*46, TulP-60, T2, (syn=ganuTia), (syn=γ), (syn=PC), (syn=P.C.), (syn=T-2), (syn=T2), (syn=P4), T4, (syn=T-4), (syn=T4), T6, T35, αI, 1, IA, 3, (syn=Ac3), 3A, 3T+, (syn=3), (syn=MI), 5φ, (syn=φ5), 9266Q, CFO103, HK620, J, K, KIF, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φI, φI.2, φ20, φ95, φ263, φIO92, φI, φII, (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, ECI, EC2, E21, E29, FI, F26S, F27S, Hi, HK022, HK97, (syn=ΦHK97), HK139, HK253, HK256, K7, ND-I, no.D, PA-2, q, S2, TI, (syn=α), (syn=P28), (syn=T-1), (syn=Tx), T3C, T5, (syn=T-5), (syn=T5), UC-I, w, β4, γ2, λ (syn=lambda), (syn=Φλ), ΦD326, φγ, Φ06, ω7, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J, 933H, O157 typing phages 1 to 16, JES-2013, 121Q, 172-1, 1720a-02, ADB-2, AKFV33, av-05, bV_EcoS_AHP42, bV_EcoS_AHP24, bC_EcoS_AHS24, bV_EcoS_AKS96, CBA120.

Bacteria of the genus *Fusobacterium* are infected by the following phage: NN-*Fusobacterium* (2), fv83-554/3, fv88-531/2, 227, fv2377, fv2527 and fv8501.

Bacteria of the genus *Haemophilus* are infected by the following phage: HPI, S2 and N3.

Bacteria of the genus *Helicobacter* are infected by the following phage: HPI and ^^-*Helicobacter* (1).

Bacteria of the genus *Klebsiella* are infected by the following phage: AIO-2, KI4B, KI6B, KI9, (syn=K19), KI14, KI15, KI21, KI28, KI29, KI32, KI33, KI35, KI106B, KI171B, KI181B, KI832B, AIO-1, AO-1, AO-2, AO-3, FC3-10, K, KI1, (syn=KII), KI2, (syn=K12), KI3, (syn=K13), (syn=KI 70/11), KI4, (syn=K14), KI5, (syn=K15), KI6, (syn=K16), KI7, (syn=K17), KI8, (syn=K18), KI19, (syn=K19), KI27, (syn=K127), KI31, (syn=K131), KI35, KI171B, II, VI, IX, CI-I, KI4B, KI8, KI11, KI12, KI13, KI16, KI17 KI18, KI20, KI22, KI23, KI24, KI26, KI30, KI34, KI106B, KIi65B, KI328B, KLXI, K328, P5046, 11, 380, III, IV, VII, VIII, FC3-11, KI2B, (syn=K12B), KI25, (syn=K125), KI42B, (syn=K142), (syn=K142B), KI181B, (syn=KII 81), (syn=K1181B), KI765/!, (syn=K1765/1), KI842B, (syn=K1832B), KI937B, (syn=K1937B), LI, φ28, 7, 231, 483, 490, 632 and 864/100.

Bacteria of the genus *Lepitospira* are infected by the following phage: LEI, LE3, LE4 and ~NN-Leptospira (1).

Bacteria of the genus *Listeria* are infected by the following phage: A511, 01761, 4211, 4286, (syn=BO54), A005, A006, A020, A500, A502, A511, AI 18, A620, A640, B012, B021, B024, B025, B035, B051, B053, B054, B055, B056, BIOI, BI IO, B545, B604, B653, C707, D441, HSO47, HIOG, H8/73, H19, H21, H43, H46, H107, H108, HI IO, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phage: 13, AGI, ALi, ATCC 11759, A2, B.C3, BG2, BKI, BK5, *butyricum*, B-I, B5, B7, B30, B35, Clark, CI, C2, DNAIII, DSP1, D4, D29, GS4E, (syn=GS4E), GS7, (syn=GS-7), (syn=GS7), IPa, lacticola, Legendre, Leo, L5, (syn=ΦL-5), MC-I, MC-3, MC-4, minetti, MTPHI I, Mx4, MyF3P/59a, *phlei*, (syn=*phlei* 1), *phlei* 4, Polonus II, rabinovitschi, *smegmatis*, TM4, TM9, TMIO, TM20, Y7, YIO, φ630, IB, IF, IH, 1/1, 67, 106, 1430, BI, (syn=Bol), B24, D, D29, F-K, F-S, HP, Polonus I, Roy, RI, (syn=RI-Myb), (syn=Ri), 11, 31, 40, 50, 103a, 103b, 128, 3111-D, 3215-D and NN-*Mycobacterium* (1).

Bacteria of the genus *Neisseria* are infected by the following phage: Group I, group II and NPI.

Bacteria of the genus *Nocardia* are infected by the following phage: MNP8, NJ-L, NS-8, N5 and TtiN-*Nocardia*.

Bacteria of the genus *Proteus* are infected by the following phage: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI I, Pv2, πl , φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, π2600, φχ7, 1/1004, 5/742, 9, 12, 14, 22, 24/860, 2600/D52, Pm8 and 24/2514.

Bacteria of the genus *Providencia* are infected by the following phage: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phage: Pfl, (syn=Pf-I), Pf2, Pf3, PP7, PRRI, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PBI), pfl6, PMN17, PPI, PP8, PsaI, PsPI, PsP2, PsP3, PsP4, PsP5, PS3, PS17, PTB80, PX4, PX7, PYOI, PYO2, PYO5, PYO6, PYO9, PYOIO, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, PIK, SLPI, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, C1-2, C5, D, gh-1, FI 16, HF, H90, K5, K6, KI 04, K109, K166, K267, N4, N5, O6N-25P, PE69, Pf, PPN25, PPN35, PPN89, PPN91, PP2, PP3, PP4, PP6, PP7, PP8, PP56, PP87, PPI 14, PP206, PP207, PP306, PP651, Psp231a, Pssy401, Pssy9220, psi, PTB2, PTB20, PTB42, PXI, PX3, PXIO, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, FIO, g, gd, ge, gξ Hwl2, Jb 19, KFI, L°, OXN-32P, O6N-52P, PCH-I, PC13-1, PC35-1, PH2, PH51, PH93, PH132, PMW, PM13, PM57, PM61, PM62, PM63, PM69, PM105, PMI 13, PM681, PM682, PO4, PPI, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SDI, SLI, SL3, SL5, SM, φC5, φCI I, φCI I-1, φC13, φC15, φMO, φX, φO4, φI I, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), GIOI, M6, M6a, LI, PB2, PssyI5, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phage: b, Beccles, CT, d, Dundee, f, Fels 2, GI, GUI, GVI, GVIII, k, K, i, j, L, 01, (syn=0-1), (syn=O1), (syn=O-I), (syn=7), 02, 03, P3, P9a, PIO, Sab3, Sab5, SanIS, SanI7, SI, Taunton, Vil, (syn=Vil), 9, imSalmonella (1), N-I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22al, P22-4, P22-7, P22-11, SNT-I, SNT-2, SP6, Villi, VilV, ViV, ViVI, ViVII, Worksop, Sj5, ε34, 1,37, 1(40), (syn=φI[40]), 1,422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, GI 73, h, IRA, Jersey, MB78, P22-1, P22-3, P22-12, Sabl, Sab2, Sab2, Sab4, Sanl, San2, San3, San4, San6, San7, San8, San9, Sanl3, Sanl4, Sanl6, Sanl8, Sanl9, San20, San21, San22, San23, San24, San25, San26, SasLI, SasL2, SasL3, SasL4, SasL5, SIBL, SII, Vill, φI, 1, 2, 3a, 3al, 1010, Ym-*Salmonella* (1), N-4, SasL6 and 27.

Bacteria of the genus *Serratia* are infected by the following phage: A2P, PS20, SMB3, SMP, SMP5, SM2, V40, V56, ic, ΦCP-3, ΦCP-6, 3M, 10/Ia, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCWI, ΦCP6-1, ΦCP6-2, ΦCP6-5, 3T, 5, 8, 9F, 10/1, 2OE, 32/6, 34B, 34CT, 34P, 37, 41, 56, 56D, 56P, 6OP, 61/6, 74/6, 76/4, 101/8900, 226, 227, 228, 229F, 286, 289, 290F, 512, 764a, 2847/10, 2847/1Oa, L.359 and SMBI.

Bacteria of the genus *Shigella* are infected by the following phage: Fsa, (syn=a), FSD2d, (syn=D2d), (syn=W2d), FSD2E, (syn=W2e), fv, F6, f7.8, H-Sh, PE5, P90, SfII, Sh, SHm, SHrv, (syn=HIV), SHvi, (syn=HVI), SHVvm, (syn=HVIII), SKγ66, (syn=gamma 66), (syn=γββ), (syn=γ66b), SKm, (syn=SIIIb)5 (syn=UI), SKw, (syn=Siva), (syn=IV), SIC™, (syn=SIVA.), (syn=IVA), SKvi, (syn=KVI), (syn=Svi), (syn=VI), SKvm, (syn=Svm), (syn=VIII), SKVIIIA, (syn=SvmA), (syn=VIIIA), STvi, STK, STx1, STxn, S66, W2, (syn=D2c), (syn=D20), φI, φIVb 3-SO-R, 8368-SO-R, F7, (syn=FS7), (syn=K29), FIO, (syn=FSIO), (syn=K31), I1, (syn=alfa), (syn=FSa), (syn=KI 8), (syn=α), 12, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=IVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO—S-R), W1, (syn=D8), (syn=FSD8), W2a, (syn=D2A), (syn=FS2a), DD-2, Sf6, FSi, (syn=Fl), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, BII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI I, P2-SO-S, SG36, (syn=SO-36/G), (syn=G36), SG3204, (syn=SO-3204/G), SG3244, (syn=SO-3244/G), SHi, (syn=HI), SHvπ, (syn=HVII), SHK, (syn=HIX), SHx1, SHxπ, (syn=HXn), SKI, KI, (syn=S1), (syn=Ssl), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), STi, STffl, STrv, STVi, STvπ, S70, S206, U2-SO-S, 3210-SO-S, 3859-SO-S, 4020-SO-S, φ3, φ5, φ7, φ8, φ9, φIO, φI I, φI3, φI4, φI8, SHm, (syn=Hπi), SHχi, (syn=HXt) and SKxI, (syn=KXI), (syn=Sχi), (syn=SsXI), (syn=XI).

Bacteria of the genus *Staphylococcus* are infected by the following phage: A, EW, K, Ph5, Ph9, PhIO, Phl3, PI, P2, P3, P4, P8, P9, PIO, RG, SB-i, (syn=Sb-I), S3K, Twort, ΦSK311, φ812, 06, 40, 58, 119, 130, 131, 200, 1623, STCI, (syn=stcI), STC2, (syn=stc2), 44AHJD, 68, ACI, AC2, A6"C", A9"C", b581, CA-I, CA-2, CA-3, CA-4, CA-5, DI I, L39x35, L54a, M42, NI, N2, N3, N4, N5, N7, N8, NIO, Ni I, N12, N13, N14, N16, Ph6, Phl2, Phl4, UC-18, U4, U15, SI, S2, S3, S4, S5, X2, Z1, φB5-2, φD, ω, 11, (syn=φI I), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80α, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, AIO, A13, b594n, D, HK2, N9, N15, P52, P87, SI, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phage: EJ-I, NN-Streptococais (1), a, CI, FLOThs, H39, Cp-I, Cp-5, Cp-7, Cp-9, Cp-IO, AT298, A5, aIO/JI, aIO/J2, aIO/J5, aIO/J9, A25, BTI I, b6, CAI, c20-I, c20-2, DP-I, Dp-4, DTI, ET42, eIO, FA101, FEThs, FK, FKKIOI, FKLIO, FKP74, FKH, FLOThs, FyIOI, fI, F10, F20140/76, g, GT-234, HB3, (syn=HB-3), HB-623, HB-746, M102, O1205, φO1205, PST, PO, PI, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, SfII 1, (syn=SFiI I), (syn=φSFiII), (syn=ΦSfiI I), (syn=φSfiI I), sfiI9, (syn=SFiI9), (syn=φSFiI9), (syn=φSfiI9), Sfi21, (syn=SFi21), (syn=φSFi21), (syn=φSfi21), ST0, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φIOO, φIOI, φIO2, φ227, Φ7201, ω1, ω2, ω3, ω4, ω5, ω6, ω8, wIO, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phage: CTXΦ, fs, (syn=si), fs2, Ivpf5, Vfl2, Vf33, VPIΦ, VSK, v6, 493, CP-TI, ET25, kappa, K139, Labol,) XN-69P, OXN-86, O6N-21P, PB-I, P147, rp-1, SE3, VA-I, (syn=VcA-I), VcA-2, VPI, VP2, VP4, VP7, VP8, VP9, VPIO, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHCI-1, ΦHC1-2, ΦHC1-3, ΦHC1-4, ΦHC2-1, >HC2-2, ΦHC2-3, ΦHC2-4, ΦHC3-1, ΦHC3-2, ΦHC3-3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φI38, 1-II, 5, 13, 14, 16, 24, 32, 493, 6214, 7050, 7227, II, (syn=group II), (syn==φ2), V, VIII, ~m-*Vibrio* (13), KVP20, KVP40, nt-1, O6N-22P, P68, el, e2, e3, e4, e5, FK, G, I, K, nt-6, NI, N2, N3, N4, N5, 06N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pAI, 7, 7-8, 70A-2, 71A-6, 72A-5, 72A-8, 108A-10, 109A-6, 109A-8, I IOA-1, 110A-5, 110A-7, hv-1, OXN-52P, P13, P38, P53, P65, P108, Pill, TPI3 VP3, VP6, VP12, VP13, 70A-3, 70A-4, 70A-10, 72A-1, 108A-3, 109-B1, 110A-2, 149, (syn=φI49), IV, (syn=group IV), NN-*Vibrio* (22), VP5, VPII, VP15, VP16, αI, α2, α3a, α3b, 353B and HN-*Vibrio* (7).

Bacteria of the genus *Yersinia* are infected by the following phage: H, H-I, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/01324-76, 7/F783-76, 903, 1/M6176 and Yer2AT.

In a particular embodiment, the lytic bacteriophage is selected from the group consisting of the lytic bacteriophages listed above, and the non-lytic bacteriophage is selected from the group consisting of the non-lytic bacteriophages listed above.

In a particular embodiment, the lytic bacteriophage and/or the non-lytic bacteriophage is selected in the group consisting of *Salmonella* virus SKML39, *Shigella* virus AG3, *Dickeya* virus Limestone, *Dickeya* virus RC2014, *Escherichia* virus CBA120, *Escherichia* virus Phaxl, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus S253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus J509, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus ShfI2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, Cronobacter virus CR3, Cronobacter virus CR8, Cronobacter virus CR9, Cronobacter virus PBES02, *Pectobacterium* virus phiTE, Cronobacter virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus I3, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, *Edwardsiella* virus MSW3, *Edwardsiella* virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus gh1, *Prochlorococcus* virus PSSP7, *Synechococcus* virus P60, *Synechococcus* virus Syn5, *Streptococcus* virus Cp1, *Streptococcus* virus Cp7, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepil02, *Burkholderia* virus Bcepmigl, *Burkholderia* virus DC1, *Bordetella* virus BPP1, *Burkholderia* virus BcepC6B, *Cellulophaga* virus Cba41, *Cellulophaga* virus Cba172, *Dinoroseobacter* virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, *Edwardsiella* virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, Hamiltonella virus APSE1, *Lactococcus* virus KSY1, *Phormidium* virus WMP3, *Phormidium* virus WMP4, *Pseudomonas* virus 119X, *Roseobacter* virus SIO1, *Vibrio* virus VpV262, *Vibrio* virus VC8, *Vibrio* virus VP2, *Vibrio* virus VP5, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* virus Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wksl3, *Escherichia* virus K1G, *Escherichia* virus K1H, *Escherichia* virus K1ind1, *Escherichia* virus K1ind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Rogue1, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, *Cronobacter* virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobacterium* virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus Lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus O1205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus SI4, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sal2, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phil7, *Xanthomonas* virus Xop411, *Xanthomonas* virus Xp10, *Streptomyces* virus TP1604, *Streptomyces* virus YDN12, Alphaproteobacteria virus phiJI001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus I22, *Salmonella* virus IKe, *Acholeplasma* virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, *Spiroplasma* virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cf1c, *Spiroplasma* virus C74, *Spiroplasma* virus R8A2B, *Spiroplasma* virus SkV1CR23x, *Escherichia* virus FI, *Escherichia* virus Qbeta, *Escherichia* virus BZ13, *Escherichia* virus MS2, *Escherichia* virus alpha3, *Escherichia* virus 1D21, *Escherichia* virus ID32, *Escherichia* virus 1D62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus 1D52, *Escherichia* virus Talmos, *Escherichia* virus phiX174, *Bdellovibrio* virus MAC1, *Bdellovibrio* virus MH2K, *Chlamydia* virus Chp1, *Chlamydia* virus Chp2, *Chlamydia* virus CPAR39, *Chlamydia* virus CPG1, *Spiroplasma* virus SpV4, *Acholeplasma* virus L2, *Pseudomonas* virus PR4, *Pseudomonas* virus PRD1, *Bacillus* virus AP50, *Bacillus* virus Bam35, *Bacillus* virus GIL16, *Bacillus* virus VVip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus ECO26_P06, *Escherichia* virus ECO103_P15, *Escherichia* virus ECO103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Sp5; the first bacteriophage being different from the second bacteriophage.

In one embodiment, the first bacteriophage is selected in the group consisting of BW73, B278, D6, D108, E, EI, E24, E41, FI-2, FI-4, FI-5, HI8A, Ffl8B, i, MM, Mu, 025, PhI-5, Pk, PSP3, PI, PID, P2, P4, SI, Wφ, φK13, φI, φ2, φ7, φ92, 7 A, 8φ, 9φ, 18, 28-1, 186, 299, HH-*Escherichia* (2), AB48, CM, C4, C16, DD-VI, E4, E7, E28, FII, FI3, H, HI, H3, H8, K3, M, N, ND-2, ND-3, ND4, ND-5, ND6, ND-7, Ox-1, Ox-2, Ox-3, Ox-4, Ox-5, Ox-6, PhI-I, RB42, RB43, RB49, RB69, S, Sal-I, Sal-2, Sal-3, Sal-4, Sal-5, Sal-6, TC23, TC45, TulI*-6, TulP-24, TulI*46, TulP-60, T2, T4, T6, T35, αI, 1, IA, 3, 3A, 3T+, 5φ, 9266Q, CFO103, HK620, J, K, KIF, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φI, φI.2, φ20, φ95, φ263, φIO92, φI, φII, Ω8, 1, 3, 7, 8, 26, 27, 28-2, 29, 30, 31, 32, 38, 39, 42, 933W, NN-*Escherichia* (1), Esc-7-11, AC30, CVX-5, CI, DDUP, ECI, EC2, E21, E29, FI, F26S, F27S, Hi, HK022, HK97, HK139, HK253, HK256, K7, ND-I, PA-2, q, S2, TI,), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, KIO, ZG/3A, 5, 5A, 21EL, H19-J and 933H.

In a preferred embodiment, said lytic bacteriophage is T7 bacteriophage. In another preferred embodiment, said lytic bacteriophage is a *C. acnes* lytic bacteriophage.

In a preferred embodiment, said non-lytic bacteriophage is lambda bacteriophage. In another preferred embodiment, said non-lytic bacteriophage is a *P. freudenreichii* bacteriophage.

In a preferred embodiment, said lytic bacteriophage is T7 bacteriophage and said non-lytic bacteriophage is a lambda bacteriophage. In another preferred embodiment, said lytic bacteriophage is a *C. acnes* lytic bacteriophage and said non-lytic bacteriophage is a *P. freudenreichii* bacteriophage.

Additional Bacterial Gene

As well-known from the skilled person, some phages use products produced by their bacterial host for folding and/or assembly of their structural elements, and/or for proper packaging of their DNA.

Therefore, in a particular embodiment, said production bacterial cell further comprises at least one bacterial gene, derived from a bacterial species or strain from which the lytic bacteriophage comes, involved in folding and/or assembly of phage structural elements and/or involved in DNA packaging.

As will be understood by the skilled person, bacterial genes involved in folding and/or assembly of phage structural elements depend on the particular bacteriophage from which said phage structural elements are obtained. They typically include bacterial genes encoding chaperones.

Similarly, bacterial genes involved in phage DNA packaging depend on the particular bacteriophage from which the phage DNA packaging genes are obtained. Examples of such bacterial genes include genes encoding IHF proteins.

Payload

In a particular embodiment, said production bacterial cell further comprises a payload to be packaged into said phage particles or phage-derived delivery vehicles.

As used herein, the term "payload" refers to any nucleic acid sequence (DNA and/or RNA) or amino acid sequence, or a combination of both (such as, without limitation, peptide nucleic acid or peptide-oligonucleotide conjugate) transferred into a bacterium with a delivery vehicle. In a particular embodiment, the payload is a nucleic acid payload, more particularly a DNA and/or RNA payload, still particularly a DNA payload.

The term "payload" may also refer to a plasmid, a vector or a cargo.

The payload can be a phagemid or phasmid obtained from a natural, evolved or engineered bacteriophage genome. The payload can also be composed only in part of a phagemid or phasmid obtained from a natural, evolved or engineered bacteriophage genome.

As used herein, the term "phagemid" or "phasmid" are equivalent and refer to a recombinant DNA vector comprising at least one sequence of a bacteriophage genome and is able to permit packaging in a capsid, and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise an origin of replication and thus cannot replicate by itself once injected into a bacterium. Alternatively, the phagemid comprises a plasmid origin of replication, in particular a bacterial and/or phage origin of replication.

In a particular embodiment, said payload is to be packaged in the form of a packaged phagemid.

As used herein, the term "packaged phagemid" refers to a phagemid which is encapsidated in a bacteriophage scaffold, phage-derived delivery particle or capsid. Particularly, it refers to a bacteriophage scaffold, phage delivery particle or capsid devoid of a bacteriophage genome. The packaged phagemid may be produced with a helper phage strategy, well known from the man skilled in the art. The helper phage typically comprises all the genes coding for the structural and functional proteins that are indispensable for the phagemid according to the invention to be encapsidated.

In a particular embodiment, said payload is to be delivered into targeted bacterial cells, as defined below.

In a more particular embodiment, said payload is stably maintained in said targeted bacterial cells. In an alternative embodiment, said payload does not replicate in said targeted bacterial cells.

Sequence of Interest Under the Control of a Promoter

In a particular embodiment, the payload comprises a sequence of interest, in particular under the control of a promoter.

As known by the person skilled in the art, a promoter may be classified as strong or weak according to its affinity for RNA polymerase. The strength of a promoter may depend on whether initiation of transcription occurs at that promoter with high or low frequency. Different promoters with different strengths may be used in the present invention leading to different levels of gene/protein expression (e.g. the level of expression initiated from an mRNA originating from a weak promoter is lower than the level of expression initiated from a strong promoter).

It will be appreciated by those of ordinary skill in the art that a promoter sequence may be selected from a large number of known bacterial genes expressed by various bacterial species. Also, methods of prokaryotic promoter prediction exist, and can be based on DNA stability analysis as described in Kanhere and Bansal (BMC Bioinformatics 2005, 6:1). The choice of promoter on the payload used in the context of the present invention can thus be made based on the bacteria to target.

In some embodiments, the nucleic acid of interest may be positioned under the control of a recombinant or heterologous promoter, which refers to a promoter that is not normally associated with the nucleic acid of interest in its natural environment.

Examples of bacterial promoters for use in accordance with the present invention include, without limitation, positively regulated $E.$ $coli$ promoters such as positively regulated $\sigma$ 70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(Rhl), Pu, FecA, pRE, cadC, hns, pLas, pLux), a "s" promoter (e.g., Pdps), a 32 promoters (e.g., heat shock) and $\sigma$ 54 promoters (e.g., glnAp2); negatively regulated $E.$ $coli$ promoters such as negatively regulated $\sigma$ 70 promoters (e.g., Promoter (PRM+), modified lambda Prm promoter, TetR-TetR-4C P(Las) TetO, P(Las) CIO, P(Lac) IQ, RecA_DlexO_D-Lac01, dapAp, FecA, Pspac-hy, pel, plux-cl, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cl, pLux/cl, LacI, LacIQ, pLacIQI, pLas/cl, pLas/Lux, pLux/Las, pRecA with LexA binding site, reverse BBa_R0011, pLacl/ara-1, pLaclq, rrnB PI, cadC, hns, PfhuA, pBad/araC, nhaA, OmpF, RcnR), a S promoters (e.g., Lutz-Bujard LacO with alternative sigma factor $\sigma$ 38), $\sigma$ 32 promoters (e.g., Lutz-Bujard LacO with alternative sigma factor $\sigma$ 32), $\sigma$ 54 promoters (e.g., glnAp2); negatively regulated $B.$ $subtilis$ promoters such as repressible $B.$ $subtilis$ $\sigma$A promoters (e.g., Gram-positive IPTG-inducible, Xyl, hyper-spank), $\sigma$ promoters, and the BioFAB promoters disclosed in Mutalik V K et al (Nature Methods, 2013, 10: 354-360, see in particular the supplementary data) as well as on the BioFAB website (http://biofab.synberc.org/data). Other inducible microbial promoters and/or bacterial promoters may be used in accordance with the present invention. An inducible promoter for use in accordance with the present disclosure may be induced by (or repressed by) one or more physiological condition(s), such as changes in pH, temperature, radiation, osmotic pressure, saline gradients, cell surface binding, and the concentration of one or more extrinsic or intrinsic inducing agent(s). The extrinsic inducer or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Particularly preferred bacterial promoters for use in accordance with the present invention may be selected from constitutive promoters regulated by $\sigma$ 70 such as the promoters of the Anderson collection (http://parts.igem.org/Promoters/Catalog/Anderson): BBa_J23100, BBa_J23101, BBa_J23102, BBa_J23103, BBa_J23104, BBa_J23105, BBa_J23106, BBa_J23107, BBa_J23108, BBa_J23109, BBa_J23110, BBa_J23111, BBa_J23112, BBa_J23113, BBa_J23114, BBa_J23115, BBa_J23116, BBa_J23117, BBa_J23118, and BBa_J23119.

Other preferred bacterial promoters are the promoters disclosed in Stanton et al. (2014) Nat. Chem. Biol. 10:99-105, incorporated herein by reference, including in particular TetR, IcaR(A), AmtR, BetI, SrpR, Orf2, BM3R1, ButR, PhlF, PsrA, HlyIIR, AmeR, LmrA, QacR, ScbR, McbR, LitR, HapR, SmcR, TarA and variants thereof. In a particular embodiment, said promoter is SrpR and/or PhlF, or a variant thereof.

In some embodiments of the present invention, a promoter may or may not be used in conjunction with an "enhancer," which refers to a cis-acting regulatory sequence involved in the transcriptional activation of a nucleic acid sequence downstream of the promoter. The enhancer may be located at any functional location before or after the promoter.

In some embodiments, the payload may comprise a terminator sequence, or terminator. A "terminator," as used herein, is a nucleic acid sequence that causes transcription to stop. A terminator may be unidirectional or bidirectional. It consists of a DNA sequence involved in specific termination of an RNA transcript by an RNA polymerase. A terminator sequence prevents transcriptional activation of downstream nucleic acid sequences by upstream promoters. Thus, in certain embodiments, a terminator that ends the production of an RNA transcript is contemplated. A terminator may be necessary in vivo to achieve desirable gene/protein expression levels.

The most commonly used type of terminator is a forward terminator. When placed downstream of a nucleic acid of interest that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only. In prokaryotic systems, terminators usually fall into two categories (1) rho-independent terminators and (2) rho-dependent terminators. Rho-independent terminators are generally composed of a palindromic sequence that forms a stem loop rich in G-C base pairs followed by a string of uracil bases.

Terminators for use in accordance with the present invention include any terminator of transcription described herein or known to one of ordinary skill in the art. Examples of terminators include, without limitation, the termination sequences of genes such as, for example, the bovine growth hormone terminator, and viral termination sequences such as, for example, the TO terminator, the TE terminator, lambda TI and the T1T2 terminator found in bacterial systems. In some embodiments, the termination signal may be a sequence that cannot be transcribed or translated, such as those resulting from a sequence truncation.

Terminators for use in accordance with the present invention also include terminators disclosed in Chen Y J et al (2013, Nature Methods, 10: 659-664), and the BioFAB terminators disclosed in Cambray G et al (Nucl Acids Res, 2013, 41(9): 5139-5148).

In one embodiment, the sequence of interest is a programmable nuclease circuit to be delivered to the targeted bacteria. This programmable nuclease circuit may be able to mediate in vivo sequence-specific elimination of bacteria that contain a target gene of interest (e.g. a gene that is harmful to humans). Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Thus, the engineered autonomously distributed circuits provided herein may be used to selectively cleave DNA encoding a gene of interest such as, for example, a toxin gene, a virulence factor gene, an antibiotic resistance gene, a remodeling gene or a modulatory gene (cf. WO2014124226 and US2015/0064138).

Other sequences of interest, preferably programmable, can be added to the payload so as to be delivered to targeted bacteria. Preferably, the sequence of interest added to the payload leads to cell death of the targeted bacteria. For example, the nucleic acid sequence of interest added to the payload may encode holins, endolysins, restriction enzymes or toxins affecting the targeted bacteria.

Alternatively, the sequence of interest circuit added to the payload does not lead to death of targeted bacteria. For example, the sequence of interest may encode reporter genes leading to a luminescence or fluorescence signal. Alternatively, the sequence of interest may comprise proteins and enzymes achieving a useful function such as modifying the metabolism of the targeted bacteria, the composition of its environment or affecting the host subject. More specifically the sequence of interest can be an antigen triggering a host subject's immune response. The specific antigen can be released in the environment after induction of the lysis of the target cell or can be secreted by the target cell. (Costa et al. Nat Rev Microbiol. 2015 June; 13(6):343-59; Anné et al. Curr Top Microbiol Immunol. 2017; 404:267-308)

In a particular embodiment, the nucleic acid sequence of interest is selected from the group consisting of a Cas nuclease, a Cas9 nuclease, a guide RNA, a single guide RNA (sgRNA), a CRISPR locus, a gene expressing an enzyme such as a nuclease or a kinase, a TALEN, a ZFN, a meganuclease, a recombinase, a transposase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

In a particular embodiment, the nucleic acid sequence of interest encodes a guide RNA-assisted targeting (INTEGRATE) system, typically as disclosed in Vo et al. Nat Biotechnol. 2021 April; 39(4):480-489, said INTEGRATE system including for example a Type I-F *V. cholerae* CRISPR-transposon or a Type V-K *S. hofmanii* CRISPR-transposon. In a particular embodiment, said nucleic acid sequence of interest includes a nucleic acid encoding a crRNA, a nucleic acid encoding TniQ cascade, cas8, cas7 and cas6 proteins, a nucleic acid encoding tnsA, tnsB and tnsC proteins, and further including a donor DNA, said donor DNA encoding a protein of interest to be added into the targeted bacteria genome. In a particular embodiment, said nucleic acids encoding TniQ cascade, cas8, cas7 and cas6 proteins, and encoding tnsA, tnsB and tnsC proteins, are in the form of a single polycistronic nucleic acid. In another particular embodiment, said nucleic acid sequence of interest includes a nucleic acid encoding a guide RNA, a nucleic acid encoding cas12k protein, tnsB and tnsC proteins and TniQ cascade, and further including a donor DNA, said donor DNA encoding a protein of interest to be added into the targeted bacteria genome.

In a particular embodiment, the payload used in the context of the invention comprises a sequence of interest that encodes a bacteriocin, which can be a proteinaceous toxin produced by bacteria to kill or inhibit growth of other bacteria. Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In one embodiment, the payload used in the context of the invention further comprises a sequence of interest encoding a toxin selected in the group consisting of microcins, colicin-like bacteriocins, tailocins, Class I, Class II, Class III and Class IV bacteriocins. The circuit may also encode the transporter needed to secrete the toxin to the extracellular space.

In a particular embodiment, the corresponding immunity polypeptide (i.e. anti-toxin) may be used to protect bacterial cells (see review by Cotter et al., Nature Reviews Microbiology 11: 95, 2013) for payload production and encapsidation purpose but is absent in the pharmaceutical composition and in the targeted bacteria in which the payload used in the context of the invention is delivered.

In a particular embodiment, the payload used in the context of the invention comprises a sequence of interest that encodes a CRISPR-Cas system.

The CRISPR system contains two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR) (Jinek et al. Science. 2012 Aug. 17; 337(6096):816-21). The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR system includes two main classes depending on the nuclease mechanism of action:
Class 1 is made of multi-subunit effector complexes and includes type I, III and IV;
Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D).

The sequence of interest according to the present invention may comprise a nucleic acid sequence encoding Cas protein. A variety of CRISPR enzymes are available for use as a sequence of interest on the payload used in the context of the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA cleavage. In some other embodiments, the CRISPR enzyme catalyzes RNA cleavage. In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host subject.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, Mad4, Mad7, Cms1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the invention can be obtained from any known Cas9 protein (Fonfara et al. Nucleic Acids Res. 2014 February; 42(4):2577-90; Koonin et al. Curr Opin Microbiol. 2017 June; 37:67-78). Examples of Cas9 proteins useful in the present invention include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (CjCas9), *Francisella novicida* (FnCas9) and *Neisseria meningitides* (NmCas9).

The sequence encoding Cpf1 (Cas12a) (the entire protein or a fragment thereof) as used in the context of the invention can be obtained from any known Cpf1 (Cas12a) protein (Koonin et al. Curr Opin Microbiol. 2017 June; 37:67-78). Examples of Cpf1(Cas12a) proteins useful in the present invention include, but are not limited to, Cpf1(Cas12a) proteins of *Acidaminococcus* sp, *Lachnospiraceae bacteriu* and *Francisella novicida*.

The sequence encoding Cas13a (the entire protein or a fragment thereof) as used in the context of the invention can be obtained from any known Cas13a (C2c2) protein (Abudayyeh et al. Nature. 2017 Oct. 12; 550(7675):280-284). Examples of Cas13a (C2c2) proteins useful in the present invention include, but are not limited to, Cas13a (C2c2) proteins of *Leptotrichia wadei* (LwaCas13a).

The sequence encoding Cas13d (the entire protein or a fragment thereof) as used in the context of the invention can be obtained from any known Cas13d protein (Yan et al. Mol Cell. 2018 Apr. 19; 70(2):327-339.e5.). Examples of Cas13d proteins useful in the present invention include, but are not limited to, Cas13d proteins of *Eubacterium siraeum* and *Ruminococcus* sp.

The sequence encoding Mad4 (the entire protein or a fragment thereof) as used in the context of the invention is disclosed in international application WO2018/236548.

The sequence encoding Mad7 (the entire protein or a fragment thereof) as used in the context of the invention is disclosed in international application WO2018/236548.

The sequence encoding Cms1 (the entire protein or a fragment thereof) as used in the context of the invention is disclosed in international patent application WO2017/141173.

In a particular embodiment, the nucleic sequence of interest is a CRISPR/Cas9 system for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general and a gene causing a deleterious effect to the host subject.

In one embodiment, the CRISPR system is used to target and inactivate a virulence factor. A virulence factor can be any substance produced by a pathogen that alter host subject-pathogen interaction by increasing the degree of damage done to the host subject. Virulence factors are used by pathogens in many ways, including, for example, in cell adhesion or colonization of a niche in the host subject, to evade the host subject's immune response, to facilitate entry to and egress from host subject's cells, to obtain nutrition from the host subject, or to inhibit other physiological processes in the host subject. Virulence factors can include enzymes, endotoxins, adhesion factors, motility factors, factors involved in complement evasion, scavenging factors and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnf1, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCDI) T3SS external needle subunit). For example, such targeted virulence factor gene can be *Francisella tularensis* virulence factor gene such as, without limitation, fslA. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica* Typhi virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft. For example, such targeted virulence factor gene can be *Cutibacterium acnes* porphyrins genes, CAMP-factors (CAMP1, CAMP2, CAMP3, CAMP4), Hyaluronate lyase (HYL-IB/II, HYL-IA), Lipases (GehA, GehB), Haemolysins, Sialidases, Endoglycoceramidases, Endo-β-N-acetylglucosaminidase, Dermatan sulfate adhesin (DsA1, DsA2), Proline-Threonine Repeats (PTRs) or any virulence factors included on the acne associated genomic loci 1, 2, 3 (plasmid), 4 such as a tight adhesion locus (tad), Streptolysin S-associated genes (sag), nonribosomal peptide synthetases (NRPS) as described in Tomida et al. mBio. 2013 Apr. 30; 4(3):e00003-13.

In another embodiment, the CRISPR/Cas system is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Sul2, Sul3, sulfonamide-resistant FoIP, Tetracycline inactivation enzyme TetX, TetA, TetB, TetC, Tet30, Tet31, TetM, TetO, TetQ, Tet32, Tet36, MacAB-ToIC, MsbA, MsrA, VgaB, EmrD, EmrAB-ToIC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR/Cas system is used to target and inactivate a bacterial toxin gene. Bacterial toxins can be classified as either exotoxins or endotoxins. Exotoxins are generated and actively secreted; endotoxins remain part of the bacteria. The response to a bacterial toxin can involve severe inflammation and can lead to sepsis. Such toxin can be for example *Botulinum* neurotoxin, *Tetanus* toxin, *Staphylococus* toxins, *Diphtheria* toxin, *Anthrax* toxin, Alpha toxin, *Pertussis* toxin, *Shiga* toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

In a particular embodiment, the payload used in the context of the invention comprises a sequence of interest that encodes a base editing system.

Base editing (BE) refers to the ability to substitute a specific nucleotide base pair on a DNA or RNA molecule by another. Until recently, the only way to perform a specific substitution on DNA in vivo was using recombination of a template DNA, carrying the specific base pair change, with the locus of interest. Base editing technology relies on completely different strategies. There is no exchange of DNA, instead an enzymatic reaction converts a nucleotide to another one leading to a mismatch at the level of dsDNA that is then corrected by the cell machinery.

In some embodiments, the base editing system comprises one or more of the following enzymes and systems:

A) Cytosine base editors (CBE) and Adenosine base editors (ABE), as described in Rees, H. A. & Liu, D. R. *Nat Rev Genet* 19, 770-788 (2018).

So far there are seven types of DNA base editors described:

Cytosine Base Editor (CBE) that convert C:G into T:A (Komor, A et al. Nature 533:420-4. (2016))

Adenine Base Editor (ABE) that convert A:T into G:C (Gaudelli, N. M. et al. Nature 551(7681) 464-471 (2017))

Cytosine Guanine Base Editor (CGBE) that convert C:G into G:C (Chen, L et al. Precise and programmable C:G to G:C base editing in genomic DNA. Biorxiv (2020).; Kurt, I et al. CRISPR C-to-G base editors for inducing targeted DNA transversions in human cells. Nature Biotechnology (2020))

Cytosine Adenine Base Editor (CABE) that convert C:G into A:T (Zhao, D et al. New base editors change C to A in bacteria and C to G in mammalian cells. Nature Biotechnology (2020))

Adenine Cytosine Base Editor (ACBE) that convert A:T into C:G (WO2020181180)

Adenine Thymine Base Editor (ATBE) that convert A:T into T:A (WO2020181202)

Thymine Adenine Base Editor (TABE) that convert T:A into A:T (WO2020181193; WO2020181178; WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:

the addition of one or two uracil DNA glycosylase inhibitor domain (UGI) to prevent base excision repair mechanism to revert base edition the addition of Mu-GAM that decrease insertion-deletion rate by inhibiting Non-homologous end joining mechanism in the cell (NHEJ)

the use of nickase active Cas9 (nCas9 D10A) that, by creating nicks on the non-edited strand favors its repair and consequently the fixation of the edited base.

the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:

A cytosine deaminase (rAPOBEC) and base excision repair proteins (e.g. rXRCC1) (Chen, L et al. Precise and programmable C:G to G:C base editing in genomic DNA. Biorxiv (2020).; Chen et al. Nature Communications 12:1384 (2021))

A rat APOBEC1 variant (R33A) protein and an *E. coli*-derived uracil DNA N-glycosylase (eUNG) (Kurt, I et al. CRISPR C-to-G base editors for inducing targeted DNA transversions in human cells. Nature Biotechnology (2020))

Cytosine Adenine Base Editors (CABE) consist of a Cas9 nickase, a cytidine deaminase (e.g. AID), and a uracil-DNA glycosylase (Ung) (Zhao, D et al. New base editors change C to A in bacteria and C to G in mammalian cells. Nature Biotechnology (2020)).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald, J et al. A dual-deaminase CRISPR base editor enables concurrent adenine and cytosine editing, *Nature Biotechnology* (2020); Li, C et al. Targeted, random mutagenesis of plant genes with dual cytosine and adenine base editors, *Nature Biotechnology* (2020)).

In a particular embodiment, the base editing system comprises a Cytosine base editor (CBE) and/or an Adenosine base editor (ABE) as defined above.

B) Prime editors (PE), as described in Anzalone, A. V. et al. *Nature* 576, 149-157 (2019), consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
 a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
 a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

Cas9 Retron precISe Parallel Editing via homologY ('CRISPEY'), a retron RNA fused to the sgRNA and expressed together with Cas9 and the retron proteins including at least the reverse transcriptase (Sharon, E. et al. *Cell* 175, 544-557.e16 (2018)).

The SCRIBE strategy: a retron system expressed in combination with a recombinase promoting the recombination of single stranded DNA, also known as single stranded annealing proteins (SSAPs) (Farzadfard, F. & Lu, T. K. *Science* 346, 1256272 (2014)). Such recombinases include but are not limited to phage recombinases such as lambda red, recET, Sak, Sak4, and newly described SSAPs described in Wannier, T. M. et al. Improved bacterial recombineering by parallelized protein discovery. *Biorxiv* 2020.01.14.906594 (2020) doi:10.1101/2020.01.14.906594.

The targetron system based on group II introns described in Karberg, M. et al. *Nat Biotechnol* 19, 1162-7 (2001) which has been adapted to many bacterial species.

Other retron based gene targeting approaches are described in Simon, A. J., Ellington, A. D. & Finkelstein, I. J. *Nucleic Acids Res* 47, 11007-11019 (2019).

C) CRISPR/Cas. In various embodiments, the sequence of interest encodes fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163. In some embodiments, the fusion proteins further comprise an inhibitor of base repair, such as, a nuclease dead inosine specific nuclease (dISN), for example as disclosed in U.S. Pat. No. 10,113,163. In various embodiments, the nucleic acid of interest encodes fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify DNA encoding a DNA sequence or gene of interest such as, for example, a toxin gene, a virulence factor gene, an antibiotic resistance gene, a remodeling gene or a modulatory gene (cf. WO2014124226 and U S2015/0064138).

In one embodiment, the base editing system or base editor is used to inactivate the expression of a gene by editing one or several nucleotides involved in transcription or translation. More specifically the base editor is targeting one or several nucleotides of a promoter, a RBS, a start codon.

In one embodiment, the base editing system or base editor is used to introduce a premature stop codon.

In one embodiment, the base editing system or base editor is used to introduce one or several rare codons.

In another embodiment, the base editing system or base editor is used to modulate the expression of genes by editing one or several nucleotides involved in transcription or translation. More specifically the base editor is targeting one or several nucleotides of a promoter, a RBS, a start codon. leading to an increase or decrease of gene expression.

In another embodiment, the base editing system or base editor is used to revert a mutation that leads to the inactivation, decrease or increase in activity of a gene or pathway.

In another embodiment, the base editing system or base editor is used to revert a mutation that leads to an increase of pathogenicity.

In one embodiment, the base editing system or base editor is used to modify the regulation of a gene by editing one or several nucleotides involved in its regulation such as nucleotides of operator sequence, transcription factor binding site, riboswitch, RNAse recognition site, protease cleavage site, methylation site, post translational modification site (phosphorylation, glycosylation, acetylation, pupylation . . . ).

In some embodiments, the sequence of interest encodes a RNA base editing system. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain ($ADAR_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain ($ADAR2_{DD}$-E488Q for REPAIRv1 and $ADAR2_{DD}$-E488Q-T375G for REPAIRv2), Cox et al improved specificity and efficiency compare to previous RNA editing strategies (Cox, D. B. T. et al. *Science* 358, 1019-1027 (2017)).

Non-limiting examples of RNA based editor proteins include REPAIRv1, REPAIRv2.

In one embodiment, the RNA base editor is used to inactivate the expression of a gene by editing one or several nucleotides involved in translation. More specifically the base editor is targeting one or several nucleotides of a 5'UTR, a RBS, a start codon.

In one embodiment, the RNA base editor is used to introduce a premature stop codon.

In one embodiment, the RNA base editor is used to introduce one or several rare codons.

In another embodiment, the RNA base editor is used to modulate the expression of genes by editing one or several nucleotides involved in translation. More specifically the base editor is targeting one or several nucleotides of a 5'UTR, a RBS, a start codon leading to an increase or decrease of gene expression.

In another embodiment, the RNA base editor is used to revert a mutation that leads to the inactivation or a decrease in activity of a gene or pathway.

In another embodiment, the base editor is used to revert a mutation that leads to an increase of pathogenicity.

In a preferred embodiment, said sequence of interest only generates an effect in said targeted bacterial cells. More preferably, said sequence of interest is only expressed in said targeted bacterial cells.

Origins of Replication

In a particular embodiment, the copy number of said payload is controlled, in said production bacterial cell, by said at least one induction mechanism defined above. In an alternative embodiment, another induction mechanism controls the copy number of said payload in said production bacterial cell.

Origins of replication known in the art have been identified from species-specific plasmid DNAs (e.g. ColE1, RI, pT181, pSC101, pMB1, R6K, RK2, p15a and the like), from bacterial virus (e.g. φX174, M13, F1 and P4) and from bacterial chromosomal origins of replication (e.g. oriC).

In one embodiment, the payload used in the context of the invention comprises a bacterial origin of replication that is functional in the targeted bacteria.

Alternatively, the payload used in the context of the invention does not comprise any functional bacterial origin of replication or contains an origin of replication that is inactive in the targeted bacteria. In such embodiment, the payload used in the context of the invention cannot replicate by itself once it has been introduced into a bacterium by the phage particle or phage-derived delivery particle.

In one embodiment, the origin of replication on the payload to be packaged is inactive in the targeted bacteria, meaning that this origin of replication is not functional in the bacteria targeted by the phage particle or phage-derived delivery vehicle, thus preventing unwanted plasmid replication.

In one embodiment, the payload comprises a bacterial origin of replication that is functional in the production bacterial cell of the invention.

Bacteria-Specific Origins of Replication

Plasmid replication depends on host bacteria enzymes and on plasmid-controlled cis and trans determinants. For example, some plasmids have determinants that are recognized in almost all gram-negative bacteria and act correctly in each host bacteria during replication initiation and regulation. Other plasmids possess this ability only in some bacteria (Kues, U and Stahl, U 1989 Microbiol Rev 53:491-516).

Plasmids are replicated by three general mechanisms, namely theta type, strand displacement, and rolling circle (reviewed by Del Solar et al. 1998 Microbio and Molec Biol. Rev 62:434-464) that start at the origin of replication. These replication origins contain sites that are required for interactions of plasmid and/or host encoded proteins.

Origins of replication used on the payload used in the context of the invention may be moderate copy number, such as ColE1 ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

More preferably, the bacterial origin of replication is a *E. coli* origin of replication selected in the group consisting of ColE1, pMB1 and variants (pBR322, pET, pUC, etc), p15a, ColA, ColE2, pOSAK, pSC101, R6K, IncW(pSa etc), IncFII, pT181, P1, F IncP, IncC, IncJ, IncN, IncP1, IncP4, IncQ, IncH11, RSF1010, CloDF13, NTP16, R1, f5, pPS10.

More preferably, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

Even more preferably, the bacterial origin of replication are ColE1 and p15a.

In one embodiment, the bacterial origin of replication is functional in *Propionibacterium* and *Cutibacterium*, more specifically in *Propionibacterium freudenreichii* and *Cutibacterium acnes* and is selected from the group consisting of pLME108, pLME106, p545, pRGO1, pZGX01, pPG01, pYS1, FRJS12-3, FRJS25-1, pIMPLE-HL096PA1, A_15_1_R1. In a particular embodiment, the bacterial origin of replication is selected from the bacterial origins of replication disclosed in US applications US2022/135986 and US2022/135987.

Phage Origin of Replication

The payload used in the context of the invention may comprise a phage origin of replication which can initiate, with complementation of a complete phage genome, the replication of the payload for later encapsulation into the different capsids.

A phage origin of replication can also be engineered to act as a bacterial origin of replication without the need to package any phage particles.

A phage origin of replication comprised in the payload used in the context of the invention can be any origin of replication found in a phage.

Preferably, the phage origin of replication can be the wild-type or non-wild type sequence of the M13, f1, φX174, P4, Lambda, P2, 186, Lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 PI-like, P2-like, P22, P22-like, N15 and N15-like bacteriophages.

More preferably, the phage origin of replication is selected in the group consisting of phage origins of replication of M13, f1, φX174, P4, and Lambda.

In a particular embodiment, the phage origin of replication is the P4 origin of replication.

In a particular embodiment, the phage origin of replication is from *Propionibacterium* phages: BW-like phages such as Doucette, B22, E6, G4; BV-like phages such as Anatole, E1, B3; BX-like phages such as PFR1 and PFR2; filamentous B5 phage; BU-like phages (*Cutibacterium acnes* phages). In a particular embodiment, the phage origin of replication is selected from the phage origins of replication disclosed in US applications US2022/135986 and US2022/135987, incorporated herein by reference.

Conditional Origin of Replication

In a particular embodiment, the payload comprises a conditional origin of replication which is inactive in the targeted bacteria but is active in the production bacterial cell.

In the context of the invention, a "conditional origin of replication" refers to an origin of replication whose functionality may be controlled by the presence of a specific molecule.

In a particular embodiment, the conditional origin of replication is an origin of replication, the replication of which depends upon the presence of one or more given protein, peptid, RNA, nucleic acid, molecule or any combination thereof.

In a particular embodiment, the replication involving said origin of replication may further depend on a process, such as transcription, to activate said replication.

In the context of the invention, said conditional origin of replication is inactive in the targeted bacteria because of the absence of said given protein, peptid, RNA, nucleic acid, molecule or any combination thereof in said targeted bacteria.

In a particular embodiment, said conditional origin of replication is active in said production bacterial cell because said production bacterial cell expresses said given protein, peptid, RNA, nucleic acid, molecule or any combination thereof. In a particular embodiment, said protein, peptid, RNA nucleic acid, molecule or any combination thereof is expressed in trans in said production bacterial cell.

By "in trans" is meant herein that said protein, peptid, RNA, nucleic acid, molecule or any combination thereof is not encoded on the same nucleic acid molecule as the one comprising the origin of replication. In a particular embodiment, said protein, peptid, RNA, nucleic acid, molecule or any combination thereof is encoded on a chromosome or on a vector, in particular a plasmid. In a particular embodiment, said vector comprises an antibiotic resistance marker. In an alternative embodiment, said vector is devoid of antibiotic resistance marker.

Since said conditional origin of replication is inactive in the targeted bacteria because of the absence of said given protein, peptid, RNA, nucleic acid, molecule or any combination thereof in said targeted bacteria, said conditional origin of replication may be selected depending on the specific bacteria to be targeted.

The conditional origin of replication disclosed herein may originate from plasmids, bacteriophages or PICIs which preferably share the following characteristics: they contain in their origin of replication repeat sequences, or iterons, and they code for at least one protein interacting with said origin of replication (i.e. Rep, protein O, protein P, pri) which is specific to them.

By way of example, mention may be made of the conditional replication systems of the following plasmids and bacteriophages: RK2, R1, pSC101, F, Rts1, RSF1010, P1, P4, lambda, phi82, phi80.

In a particular embodiment, said conditional origin of replication is selected from the group consisting of the R6Kλ DNA replication origin and derivatives thereof, the IncPα oriV origin of replication and derivatives thereof, ColE1 origins of replication modified to be under an inducible promoter, and origins of replication from phage-inducible chromosomal islands (PICIs) and derivatives thereof.

In a particular embodiment, said conditional origin of replication is an origin of replication present in less than 50%, or less than 40%, less than 30%, less than 20%, less than 10% or less than 5% of the bacteria of the host subject's microbiome.

In another particular embodiment, said conditional origin of replication comprises or consists of a sequence less than 80% identical, in particular less than 70%, less than 60%, less than 50%, less than 40%, less than 30%, less than 20%, less than 10%, less than 5% or less than 1% identical to the sequences of the origins of replication of the bacteria of the host subject's microbiome, in particular of the bacteria representing more than 50%, more particularly more than 60%, more than 70%, more than 80%, more than 90% or more than 95% of the host subject's microbiome.

As used herein, the term "phage-inducible chromosomal islands" or "PICIs" refers to mobile genetic elements having a conserved gene organization, and encode a pair of divergent regulatory genes, including a PICI master repressor. Typically, in Gram-positive bacteria, left of rpr, and transcribed in the same direction, PICIs encode a small set of genes including an integrase (int) gene; right of rpr, and transcribed in the opposite direction, the PICIs encode an excision function (xis), and a replication module consisting of a primase homolog (pri) and optionally a replication initiator (rep), which are sometimes fused, followed by a replication origin (ori), next to these genes, and also transcribed in the same direction, PICIs encode genes involved in phage interference, and optionally, a terminase small subunit homolog (terS).

In a particular embodiment, said conditional origin of replication is an origin of replication derived from phage-inducible chromosomal islands (PICIs).

A particular conditional origin of replication has indeed been derived from PICIs.

It was shown that it is possible to derive novel conditionally replicative vectors, in particular based on the primase-helicase and origin of replication from PICIs. These origins may be relatively rare in target strains, and more advantageously the primase-ori pair may be unique for each PICI, significantly reducing the possibility of undesired recombination or payload spread events. They can further be modified to further limit recombination chances and remove restriction sites to bypass target bacteria defense systems.

In a particular embodiment, said conditional origin of replication is derived from the origin of replication from the PICI of the *Escherichia coli* strain CFT073, disclosed in Fillol-Salom et al. (2018) *The ISME Journal* 12:2114-2128.

In a particular embodiment, said conditional origin of replication is the primase ori from the PICI of the *Escherichia coli* strain CFT073, typically of sequence SEQ ID NO: 1.

In another particular embodiment, said conditional origin of replication is the primase ori from the PICI of the *Escherichia coli* strain CFT073, devoid of at least 1, at least 2, at least 3, at least 4, at least 5, at least 6, at least 7, at least 8, at least 9, at least 10, at least 11, at least 12, at least 13, at least 14, at least 15 or at least 16 restriction site(s) selected from the group consisting of GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD.

In a particular embodiment, said conditional origin of replication is the primase ori from the PICI of the *Escherichia coli* strain CFT073, devoid of the restriction site GAAABCC. Preferably, said conditional origin of replication is of sequence SEQ ID NO: 3.

In another particular embodiment, said conditional origin of replication is the primase ori from the PICI of the *Escherichia coli* strain CFT073 devoid of the restriction sites GAAABCC, GCCGGC, RCCGGY, GCNGC, TWCANNNNNNTGG (SEQ ID NO: 2), TGGCCA, ACCYAC, YGGCCR, AGACC, GCWGC, GGGANGC, GKAGATD, GCCGGYYD, GGCYAC, RGCCGGYYD, and VGCCGGYBD. Preferably, said conditional origin of replication is of sequence SEQ ID NO: 4.

In a particular embodiment, wherein said origin of replication is derived from phage-inducible chromosomal islands (PICIs), said conditional origin of replication is active in said production bacterial cell because said production bacterial cell expresses a rep protein, in particular a primase-helicase, in particular a primase-helicase of sequence SEQ ID NO: 5, typically encoded by a nucleic acid comprising or consisting of the sequence SEQ ID NO: 6.

It was demonstrated that these specific conditional origins of replication were particularly compatible with lambda-based packaging, leading to sufficiently high titers ($>10^{10}$/mL) required for microbiota-related applications.

Preferably, said production bacterial cell stably comprises said payload and is able to replicate said payload.

In a particular embodiment, when the conditional origin of replication of said payload is an origin of replication, the replication of which depends upon the presence of a given protein, peptid, nucleic acid, RNA, molecule or any combination thereof, said donor bacterial cell expresses said protein, peptid, nucleic acid, RNA, molecule or any combination thereof. Preferably, said protein, peptid, nucleic acid, RNA, molecule or any combination thereof is expressed in trans, as defined above.

In a particular embodiment, said production bacterial cell stably comprises a nucleic acid encoding said protein, peptid, nucleic acid, RNA, molecule or any combination thereof.

In a particular embodiment, when said origin of replication is derived from phage-inducible chromosomal islands (PICIs), said conditional origin of replication is active in said donor bacterial cell because said donor bacterial cell expresses a rep protein, in particular a primase-helicase, in particular a primase-helicase of sequence SEQ ID NO: 5.

In a particular embodiment, said production bacterial cell stably comprises a nucleic acid encoding said rep protein, in particular said primase-helicase, said nucleic acid typically comprising or consisting of the sequence SEQ ID NO: 6.

Packaging Site

In a particular embodiment, said payload is a nucleic acid payload comprising a packaging site derived from said lytic bacteriophage.

By "packaging site" is meant herein the DNA sequence on the phage genome that is required for genome packaging into the virion. Host-specific bacteriophages (and their packaging sites) include but are not limited to SPP1 (SPP1 pac site), P1 (P1 pac site), T1 (T1 pac site), T7 (T7 concatamer junction), lambda (cos site), mu (mu pac site), P22 (P22 pac site), φ8 (φ8 pac site), Sf6 (Sf6 pac site), 149 (149 pac site), and A1122 (A1122-concatamer junction). For most bacteriophages, the packaging site is termed the pac site. In some cases, the packaging site is referred to as a concatamer junction (e.g. T7 concatamer junction). In every case, the packaging site is substantially in isolation from sequences naturally occurring adjacent thereto in the bacteriophage genome.

For some bacteriophages, the packaging site may be unknown. In these cases, pac sites can be determined by taking advantage of the property that plasmids containing a functional bacteriophage pac site are packaged. For example, the DNA sequences necessary for packaging of bacteriophage λ were determined by incorporating small restriction fragments of the λ phage genomic DNA into a plasmid (Hohn 1983 PNAS USA 80:7456-7460). Following introduction into an in vivo packaging strain, the efficiency of packaging/transduction was quantitatively assessed. Using a similar strategy, the pac sites for a number of bacteriophages have been determined: λ (Miwa 1982 Gene 20:267-279); Mu (Croenen et al. 1985 Virology 144:520-522); filamentous bacteriophages including f1, fd, M13, and Ike (Russel et al. 1989 J Virol 1989 63:3284-3295); P22 (Petri et al. 1990 Gene 88:47-55; Wu et al. 2002 Molec Microbiol 45:1631-1646); T7 (Chung et al. 1990 J Mol Biol 216:927-938), and T3 (Hashimoto et al. 1992 Virology 187:788-795).

In a particular embodiment, said packaging site is as disclosed in US applications US2022/135986 and US2022/135987.

Other Components of the Payload

The payload used in the context of the invention is preferably devoid of antibiotic resistance marker.

Antibiotic resistance genes are well known in the art and include but are not limited to ampicillin resistance (Amp), chloramphenicol resistance (Cm), tetracycline resistance (Tet), kanamycin resistance (Kan), hygromycin resistance (Qiyg or hph genes), and zeomycin resistance (Zeo).

In a particular embodiment, the payload used in the context of the invention comprises an auxotrophic marker. Auxotrophic markers in bacteria have previously been described, for example, in U.S. Pat. Nos. 4,920,048, 5,691, 185, 6,291,245, 6,413,768, and 6,752,994; U.S. Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111 118, and typically include DapA and ThyA. In a particular embodiment, said auxotrophic marker is ThyA.

In a particular embodiment, said payload does not comprise any restriction site recognized by restriction enzymes which are frequently encoded by said targeted bacterial cell. In another particular embodiment, said payload comprises no more than 40, 30, 20, 10, 9, 8, 7, 6, 5, 4, 3, 2 or 1 restriction site(s) recognized by restriction enzymes which are frequently encoded by said targeted bacterial cell or a population or a group of targeted bacterial cell(s).

As used herein, the terms "restriction site" and "restriction enzyme site" are equivalent and refer to locations on a nucleic acid containing specific sequences of nucleotides, which are recognized by restriction enzymes. In particular, the nucleic acid comprises specific sequences which are bound and cleaved by restriction enzymes. Restriction sites are generally palindromic sequences of 4-8 base pairs in length. More precisely, the restriction site refers to a particular sequence and a modification state, so as to be bound and cleaved by restriction enzymes. In particular, it refers to a particular unmodified sequence, so as to be bound and cleaved by restriction enzymes. Especially the sequence is not methylated, hydroxymethylated and glucosyl-hydroxymethylated. In this context, the restriction enzyme is of type I, II or III. Alternatively, it may refer to a particular modified sequence, so as to be bound and cleaved by restriction enzymes, for instance a methylated, hydroxymethylated and glucosyl-hydroxymethylated DNA. In this context, the restriction enzyme is of type IV.

As used herein, "recognized by" with respect to a restriction site and a restriction enzyme means that the restriction site is cleaved by the restriction enzyme.

In a restriction site sequence N means that the nucleotide can be A, C, G or T; B means that the nucleotide can be C, G or T; Y means that the nucleotide can be C or T; W means that the nucleotide can be A or T; R means that the nucleotide can be A or G; and D means A, G or T.

As used herein, the terms "restriction enzyme" and "restriction endonuclease" are equivalent and refer to an enzyme that cuts nucleic acids at or near restriction sites. Restriction enzymes are commonly classified into four types (types I to type IV). The REBASE database allow to list the restriction sites that a given bacterium can recognize according to the restriction enzymes that it expresses.

By "frequent" or "frequently" in a group of bacteria of interest is meant that at least 10, 20, 30, 40, 50, 60, 70, 75, 80, 85, 90, 95 or 99% of the bacteria of the group encode the restriction enzyme.

The payload according to the invention preferably comprises no more than 100 restriction sites. In a preferred embodiment, the payload according to the invention comprises no more than 10 restriction sites. In a most preferred embodiment, the payload according to the invention does not comprise any restriction site.

Targeted Bacteria

The bacteria targeted by the phage particles or phage-derived delivery particles of the invention can be any bacteria present in a mammal organism, a plant or in the environment. It can be any commensal, symbiotic or pathogenic bacteria of the microbiota or microbiome.

A microbiome may comprise a variety of endogenous bacterial species, any of which may be targeted in accordance with the present disclosure. In some embodiments, the genus and/or species of targeted endogenous bacterial cells may depend on the first type of bacteriophage as defined in the section "Bacteriophage and gene derived from a bacteriophage" above. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., *Francisella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucella* spp., *Campylobacter* spp., *Chlamydophila* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., *Lactobacillus* spp., *Faecalibacterium* spp., *Ruminococcus* spp. and a mixture thereof.

Thus, phage particles, phage delivery particles and/or phages may target (e.g., specifically target) a bacterial cell from any one or more of the foregoing genus of bacteria in particular to specifically deliver the payload according to the invention.

Preferably, the targeted bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. and *Gardnerella* spp.

In some embodiments, the targeted bacteria are anaerobic bacterial cells (e.g., cells that do not require oxygen for growth). Anaerobic bacterial cells include facultative anaerobic cells such as but not limited to *Escherichia coli*, *Shewanella oneidensi*, *Gardnerella vaginalis* and *Listeria*. Anaerobic bacterial cells also include obligate anaerobic cells such as, for example, *Bacteroides*, *Clostridium*, *Cutibacterium*, *Propionibacterium*, *Fusobacterium* and *Porphyromonas* species. In humans, anaerobic bacteria are most commonly found in the gastrointestinal tract. In some particular embodiments, the targeted bacteria are thus bacteria most commonly found in the gastrointestinal tract. Bacteriophages used for preparing the hybrid helper phage, and then the phage particles, phage delivery vehicles and/or phages, may target (e.g., to specifically target) anaerobic bacterial cells according to their specific spectra known by the person skilled in the art to specifically deliver the plasmid.

In some embodiments, the targeted bacterial cells are, without limitation, *Bacteroides thetaiotaomicron*, *Bacteroides fragilis*, *Bacteroides distasonis*, *Bacteroides vulgatus*, *Clostridium leptum*, *Clostridium coccoides*, *Staphylococcus aureus*, *Bacillus subtilis*, *Clostridium butyricum*, *Brevibacterium lactofermentum*, *Streptococcus agalactiae*, *Lactococcus lactis*, *Leuconostoc lactis*, *Actinobacillus actinobycet-* emcomitans, cyanobacteria, *Escherichia coli*, *Helicobacter pylori*, *Selnomonas ruminatium*, *Shigella sonnei*, *Zymomonas mobilis*, *Mycoplasma mycoides*, *Treponema denticola*, *Bacillus thuringiensis*, *Staphylococcus lugdunensis*, *Leuconostoc oenos*, *Corynebacterium xerosis*, *Lactobacillus plantarum*, *Lactobacillus rhamnosus*, *Lactobacillus casei*, *Lactobacillus acidophilus*, *Enterococcus faecalis*, *Bacillus coagulans*, *Bacillus cereus*, *Bacillus popillae*, *Synechocystis* strain PCC6803, *Bacillus liquefaciens*, *Pyrococcus abyssi*, *Selenomonas nominantium*, *Lactobacillus hilgardii*, *Streptococcus ferus*, *Lactobacillus pentosus*, *Bacteroides fragilis*, *Staphylococcus epidermidis*, *Streptomyces phaechromogenes*, *Streptomyces ghanaensis*, *Klebsiella pneumoniae*, *Enterobacter cloacae*, *Enterobacter aerogenes*, *Serratia marcescens*, *Morganella morganii*, *Citrobacter freundii*, *Propionibacterium freudenreichii*, *Pseudomonas aeruginosa*, *Parvimonas micra*, *Prevotella intermedia*, *Fusobacterium nucleatum*, *Prevotella nigrescens*, *Actinomyces israelii*, *Porphyromonas endodontalis*, *Porphyromonas gingivalis Micrococcus luteus*, *Bacillus megaterium*, *Aeromonas hydrophila*, *Aeromonas caviae*, *Bacillus anthracis*, *Bartonella henselae*, *Bartonella Quintana*, *Bordetella pertussis*, *Borrelia burgdorferi*, *Borrelia garinii*, *Borrelia afzelii*, *Borrelia recurrentis*, *Brucella abortus*, *Brucella canis*, *Brucella melitensis*, *Brucella suis*, *Campylobacter jejuni*, *Campylobacter coli*, *Campylobacter fetus*, *Chlamydia pneumoniae*, *Chlamydia trachomatis*, *Chlamydophila psittaci*, *Clostridium botulinum*, *Clostridium difficile*, *Clostridium perfringens*, *Clostridium tetani*, *Corynebacterium diphtheria*, *Cutibacterium acnes* (formerly *Propionibacterium acnes*), *Ehrlichia canis*, *Ehrlichia chaffeensis*, *Enterococcus faecium*, *Francisella tularensis*, *Haemophilus influenza*, *Legionella pneumophila*, *Leptospira interrogans*, *Leptospira santarosai*, *Leptospira weilii*, *Leptospira noguchii*, *Listeria monocytogenes*, *Mycobacterium leprae*, *Mycobacterium tuberculosis*, *Mycobacterium ulcerans*, *Mycoplasma pneumonia*, *Neisseria gonorrhoeae*, *Neisseria meningitides*, *Nocardia asteroids*, *Rickettsia rickettsia*, *Salmonella enteritidis*, *Salmonella typhi*, *Salmonella paratyphi*, *Salmonella typhimurium*, *Shigella flexneri*, *Shigella dysenteriae*, *Staphylococcus saprophyticus*, *Streptococcus pneumoniae*, *Streptococcus pyogenes*, *Gardnerella vaginalis*, *Streptococcus viridans*, *Treponema pallidum*, *Ureaplasma urealyticum*, *Vibrio cholera*, *Vibrio parahaemolyticus*, *Yersinia pestis*, *Yersinia enterocolitica*, *Yersinia pseudotuberculosis*, *Actinobacter baumanii*, *Pseudomonas aeruginosa*, and a mixture thereof, preferably the bacteria of interest are selected from the group consisting of *Escherichia coli*, *Enterococcus faecium*, *Staphylococcus aureus*, *Klebsiella pneumoniae*, *Acinetobacter baumanii*, *Pseudomonas aeruginosa*, *Enterobacter cloacae*, and *Enterobacter aerogenes*, and a mixture thereof.

In some embodiments, the targeted bacterial cells are, without limitation, *Anaerotruncus*, *Acetanaerobacterium*, *Acetitomaculum*, *Acetivibrio*, *Anaerococcus*, *Anaerofilum*, *Anaerosinus*, *Anaerostipes*, *Anaerovorax*, *Butyrivibrio*, *Clostridium*, *Capracoccus*, *Dehalobacter*, *Dialister*, *Dorea*, *Enterococcus*, *Ethanoligenens*, *Faecalibacterium*, *Fusobacterium*, *Gracilibacter*, *Guggenheimella*, *Hespellia*, *Lachnobacterium*, *Lachnospira*, *Lactobacillus*, *Leuconostoc*, *Megamonas*, *Moryella*, *Mitsuokella*, *Oribacterium*, *Oxobacter*, *Papillibacter*, *Proprionispira*, *Pseudobutyrivibrio*, *Pseudoramibacter*, *Roseburia*, *Ruminococcus*, *Sarcina*, *Seinonella*, *Shuttleworthia*, *Sporobacter*, *Sporobacterium*, *Streptococcus*, *Subdoligranulum*, *Syntrophococcus*, *Thermobacillus*, *Turibacter*, *Weisella*, *Clostridium*, *Bacteroides*, *Ruminococcus*, *Faecalibacterium*, *Treponema*, *Phascolarctobacterium*, *Megasphaera*, *Faecalibacterium*, *Bifidobacterium*, *Lactobacillus*, *Sutterella*, and/or *Prevotella*.

In other embodiments, the targeted bacteria cells are, without limitation, *Achromobacter xylosoxidans*, *Acidaminococcus fermentans*, *Acidaminococcus intestini*, *Acidaminococcus* sp., *Acinetobacter baumannii*, *Acinetobacter junii*, *Acinetobacter lwoffii*, *Actinobacillus capsulatus*, *Actinomyces naeslundii*, *Actinomyces neuii*, *Actinomyces odontolyticus*, *Actinomyces radingae*, *Adlercreutzia equolifaciens*, *Aeromicrobium massiliense*, *Aggregatibacter actinomycetemcomitans*, *Akkermansia muciniphila*, *Aliagarivorans marinus*, *Alistipes finegoldii*, *Alistipes indistinctus*, *Alistipes inops*, *Alistipes onderdonkii*, *Alistipes putredinis*, *Alistipes senegalensis*, *Alistipes shahii*, *Alistipes timonensis*, *Alloscardovia omnicolens*, *Anaerobacter polyendosporus*, *Anaerobaculum hydrogeniformans*, *Anaerococcus hydrogenalis*, *Anaerococcus prevotii*, *Anaerococcus senegalensis*, *Anaerofustis stercorihominis*, *Anaerostipes caccae*, *Anaerostipes hadrus*, *Anaerotruncus colihominis*, *Aneurinibacillus aneurinilyticus*, *Bacillus licheniformis*, *Bacillus massilioanorexius*, *Bacillus massiliosenegalensis*, *Bacillus simplex*, *Bacillus smithii*, *Bacillus subtilis*, *Bacillus thuringiensis*, *Bacillus timonensis*, *Bacteroides xylanisolvens*, *Bacteroides acidifaciens*, *Bacteroides caccae*, *Bacteroides capillosus*, *Bacteroides cellulosilyticus*, *Bacteroides clarus*, *Bacteroides coprocola*, *Bacteroides coprophilus*, *Bacteroides dorei*, *Bacteroides eggerthii*, *Bacteroides faecis*, *Bacteroides finegoldii*, *Bacteroides fluxus*, *Bacteroides fragilis*, *Bacteroides gallinarum*, *Bacteroides intestinalis*, *Bacteroides nordii*, *Bacteroides oleiciplenus*, *Bacteroides ovatus*, *Bacteroides pectinophilus*, *Bacteroides plebeius*, *Bacteroides salanitronis*, *Bacteroides salyersiae*, *Bacteroides* sp., *Bacteroides stercoris*, *Bacteroides thetaiotaomicron*, *Bacteroides uniformis*, *Bacteroides vulgatus*, *Bacteroides xylanisolvens*, *Bacteroides pectinophilus* ATCC, *Barnesiella intestinihominis*, *Bavariicoccus seileri*, *Bifidobacterium adolescentis*, *Bifidobacterium angulatum*, *Bifidobacterium animalis*, *Bifidobacterium bifidum*, *Bifidobacterium breve*, *Bifidobacterium catenulatum*, *Bifidobacterium dentium*, *Bifidobacterium gallicum*, *Bifidobacterium longum*, *Bifidobacterium pseudocatenulatum*, *Bifidobacterium stercoris*, *Bilophila wadsworthia*, *Blautia faecis*, *Blautia hansenii*, *Blautia hydrogenotrophica*, *Blautia luti*, *Blautia obeum*, *Blautia producta*, *Blautia wexlerae*, *Brachymonas chironomi*, *Brevibacterium senegalense*, *Bryantella formatexigens*, butyrate-producing bacterium, *Butyricicoccus pullicaecorum*, *Butyricimonas virosa*, *Butyrivibrio crossotus*, *Butyrivibrio fibrisolvens*, *Caldicoprobacter faecalis*, *Campylobacter concisus*, *Campylobacter jejuni*, *Campylobacter upsaliensis*, *Catenibacterium mitsuokai*, *Cedecea davisae*, *Cellulomonas massiliensis*, *Cetobacterium somerae*, *Citrobacter braakii*, *Citrobacter freundii*, *Citrobacter pasteurii*, *Citrobacter* sp., *Citrobacter youngae*, *Cloacibacillus evryensis*, *Clostridiales bacterium*, *Clostridioides difficile*, *Clostridium asparagiforme*, *Clostridium bartlettii*, *Clostridium boliviensis*, *Clostridium bolteae*, *Clostridium hathewayi*, *Clostridium hiranonis*, *Clostridium hylemonae*, *Clostridium leptum*, *Clostridium methylpentosum*, *Clostridium nexile*, *Clostridium orbiscindens*, *Clostridium ramosum*, *Clostridium scindens*, *Clostridium sp*, *Clostridium* sp., *Clostridium spiroforme*, *Clostridium sporogenes*, *Clostridium symbiosum*, *Collinsella aerofaciens*, *Collinsella intestinalis*, *Collinsella stercoris*, *Collinsella tanakaei*, *Coprobacillus cateniformis*, *Coprobacter fastidiosus*, *Coprococcus catus*, *Coprococcus comes*, *Coprococcus eutactus*, *Corynebacterium ammoniagenes*, *Corynebacterium amycolatum*, *Corynebacterium pseudodiphthe-

*riticum, Cutibacterium acnes, Dermabacter hominis, Desulfitobacterium hafniense, Desulfovibrio fairfieldensis, Desulfovibrio piger, Dialister succinatiphilus, Dielma fastidiosa, Dorea formicigenerans, Dorea longicatena, Dysgonomonas capnocytophagoides, Dysgonomonas gadei, Dysgonomonas mossii, Edwardsiella tarda, Eggerthella lenta, Eisenbergiella tayi, Enorma massiliensis, Enterobacter aerogenes, Enterobacter asburiae, Enterobacter cancerogenus, Enterobacter cloacae, Enterobacter massiliensis, Enterococcus casseliflavus, Enterococcus durans, Enterococcus faecalis, Enterococcus faecium, Enterococcus flavescens, Enterococcus gallinarum, Enterococcus sp., Enterovibrio nigricans, Erysipelatoclostridium ramosum, Escherichia coli, Escherichia sp., Eubacterium biforme, Eubacterium dolichum, Eubacterium hallii, Eubacterium limosum, Eubacterium ramulus, Eubacterium rectale, Eubacterium siraeum, Eubacterium ventriosum, Exiguobacterium marinum, Exiguobacterium undae, Faecalibacterium cf, Faecalibacterium prausnitzii, Faecalitalea cylindroides, Ferrimonas balearica, Finegoldia magna, Flavobacterium daejeonense, Flavonifractor plautii, Fusicatenibacter saccharivorans, Fusobacterium gonidiaformans, Fusobacterium mortiferum, Fusobacterium necrophorum, Fusobacterium nucleatum, Fusobacterium periodonticum, Fusobacterium sp., Fusobacterium ulcerans, Fusobacterium varium, Gallibacterium anatis, Gemmiger formicilis, Gordonibacter pamelaeae, Hafnia alvei, Helicobacter bilis, Helicobacter bills, Helicobacter canadensis, Helicobacter canis, Helicobacter cinaedi, Helicobacter macacae, Helicobacter pametensis, Helicobacter pullorum, Helicobacter pylori, Helicobacter rodentium, Helicobacter winghamensis, Herbaspirillum massiliense, Holdemanella biformis, Holdemania fdiformis, Holdemania filiformis, Holdemania massiliensis, Holdemania filiformis, Hungatella hathewayi, Intestinibacter bartlettii, Intestinimonas butyriciproducens, Klebsiella oxytoca, Klebsiella pneumoniae, Kurthia massiliensis, Lachnospira pectinoschiza, Lactobacillus acidophilus, Lactobacillus amylolyticus, Lactobacillus animalis, Lactobacillus antri, Lactobacillus brevis, Lactobacillus buchneri, Lactobacillus casei, Lactobacillus curvatus, Lactobacillus delbrueckii, Lactobacillus fermentum, Lactobacillus gasseri, Lactobacillus helveticus, Lactobacillus hilgardii, Lactobacillus iners, Lactobacillus intestinalis, Lactobacillus johnsonii, Lactobacillus murinus, Lactobacillus paracasei, Lactobacillus plantarum, Lactobacillus reuteri, Lactobacillus rhamnosus, Lactobacillus ruminis, Lactobacillus sakei, Lactobacillus salivarius, Lactobacillus ultunensis, Lactobacillus vaginalis, Lactobacillus plantarum subsp., Leuconostoc mesenteroides, Leuconostoc pseudomesenteroides, Listeria grayi, Listeria innocua, Mannheimia granulomatis, Marvinbryantia formatexigens, Megamonas funiformis, Megamonas hypermegale, Methanobrevibacter smithii, Methanobrevibacter smithii FI, Micrococcus luteus, Microvirgula aerodenitrificans, Mitsuokella jalaludinii, Mitsuokella multacida, Mollicutes bacterium, Murimonas intestini, Neisseria macacae, Nitriliruptor alkaliphilus, Oceanobacillus massiliensis, Odoribacter laneus, Odoribacter splanchnicus, Ornithobacterium rhinotracheale, Oxalobacter formigenes, Paenibacillus barengoltzii, Paenibacillus chitinolyticus, Paenibacillus lautus, Paenibacillus motobuensis, Paenibacillus senegalensis, Paenisporosarcina quisquiliarum, Parabacteroides distasonis, Parabacteroides goldsteinii, Parabacteroides gordonii, Parabacteroides johnsonii, Parabacteroides merdae, Paraprevotella xylaniphila, Parasutterella excrementihominis, Parvimonas micra, Pediococcus acidilactici, Peptoclostridium difficile, Peptoniphilus harei, Peptoniphilus obesi, Peptoniphilus senegalensis, Peptoniphilus timonensis, Phascolarctobacterium succinatutens, Porphyromonas asaccharolytica, Porphyromonas uenonis, Prevotella baroniae, Prevotella bivia, Prevotella copri, Prevotella dentalis, Prevotella micans, Prevotella multisaccharivorax, Prevotella oralis, Prevotella salivae, Prevotella stercorea, Prevotella veroralis, Propionibacterium acnes, Propionibacterium avidum, Propionibacterium freudenreichii, Propionimicrobium lymphophilum, Proteus mirabilis, Proteus penneri ATCC, Providencia alcalifaciens, Providencia rettgeri, Providencia rustigianii, Providencia stuartii, Pseudoflavonifractor capillosus, Pseudomonas aeruginosa, Pseudomonas luteola, Ralstonia pickettii, Rheinheimera perlucida, Rheinheimera texasensis, Riemerella columbina, Romboutsia lituseburensis, Roseburia faecis, Roseburia intestinalis, Roseburia inulinivorans, Ruminococcus bicirculans, Ruminococcus bromii, Ruminococcus callidus, Ruminococcus champanellensis, Ruminococcus faecis, Ruminococcus gnavus, Ruminococcus lactaris, Ruminococcus obeum, Ruminococcus sp, Ruminococcus sp., Ruminococcus torques, Sarcina ventriculi, Sellimonas intestinalis, Senegalimassilia anaerobia, Shigella sonnei, Slackia piriformis, Staphylococcus epidermidis, Staphylococcus lentus, Staphylococcus nepalensis, Staphylococcus pseudintermedius, Staphylococcus xylosus, Stenotrophomonas maltophilia, Streptococcus agalactiae, Streptococcus anginosus, Streptococcus australis, Streptococcus caballi, Streptococcus castoreus, Streptococcus didelphis, Streptococcus equinus, Streptococcus gordonii, Streptococcus henryi, Streptococcus hyovaginalis, Streptococcus infantarius, Streptococcus infantis, Streptococcus lutetiensis, Streptococcus merionis, Streptococcus mitis, Streptococcus mutans, Streptococcus oralis, Streptococcus ovis, Streptococcus parasanguinis, Streptococcus plurextorum, Streptococcus porci, Streptococcus pyogenes, Streptococcus salivarius, Streptococcus sobrinus, Streptococcus thermophilus, Streptococcus thoraltensis, Streptomyces albus, Subdoligranulum variabile, Succinatimonas hippei, Sutterella parvirubra, Sutterella wadsworthensis, Terrisporobacter glycolicus, Terrisporobacter mayombei, Thalassobacillus devorans, Timonella senegalensis, Turicibacter sanguinis, unknown sp, unknown sp., Varibaculum cambriense, Veillonella atypica, Veillonella dispar, Veillonella parvula, Vibrio cincinnatiensis, Virgibacillus salexigens* and/or *Weissella paramesenteroides.*

In other embodiments, the targeted bacteria cells are those commonly found on the skin microbiota and are without limitation *Acetobacter farinalis, Acetobacter malorum, Acetobacter orleanensis, Acetobacter sicerae, Achromobacter anxifer, Achromobacter denitrificans, Achromobacter marplatensis, Achromobacter spanius, Achromobacter xylosoxidans* subsp. *xylosoxidans, Acidovorax konjaci, Acidovorax radicis, Acinetobacter johnsonii, Actinomadura citrea, Actinomadura coerulea, Actinomadura fibrosa, Actinomadura fulvescens, Actinomadura jiaoheensis, Actinomadura luteofluorescens, Actinomadura mexicana, Actinomadura nitritigenes, Actinomadura verrucosospora, Actinomadura yumaensis, Actinomyces odontolyticus, Actinomycetospora atypica, Actinomycetospora corticicola, Actinomycetospora rhizophila, Actinomycetospora rishiriensis, Aeromonas australiensis, Aeromonas bestiarum, Aeromonas bivalvium, Aeromonas encheleia, Aeromonas eucrenophila, Aeromonas hydrophila* subsp. *hydrophila, Aeromonas piscicola, Aeromonas popoffii, Aeromonas rivuli, Aeromonas salmonicida* subsp. *pectinolytica, Aeromonas salmonicida* subsp. *smithia, Amaricoccus kaplicensis, Amaricoccus veronensis, Aminobacter aganoensis, Ami-* nobacter ciceronei, Aminobacter lissarensis, Aminobacter niigataensis, Ancylobacter polymorphus, Anoxybacillus flavithermus subsp. yunnanensis, Aquamicrobium aerolatum, Archangium gephyra, Archangium gephyra, Archangium minus, Archangium violaceum, Arthrobacter viscosus, Bacillus anthracis, Bacillus australimaris, Bacillus drentensis, Bacillus mycoides, Bacillus pseudomycoides, Bacillus pumilus, Bacillus safensis, Bacillus vallismortis, Bosea thiooxidans, Bradyrhizobium huanghuaihaiense, Bradyrhizobium japonicum, Brevundimonas aurantiaca, Brevundimonas intermedia, Burkholderia aspalathi, Burkholderia choica, Burkholderia cordobensis, Burkholderia diffusa, Burkholderia insulsa, Burkholderia rhynchosiae, Burkholderia terrestris, Burkholderia udeis, Buttiauxella gaviniae, Caenimonas terrae, Capnocytophaga gingivalis, Chitinophaga dinghuensis, Chryseobacterium gleum, Chryseobacterium greenlandense, Chryseobacterium jejuense, Chryseobacterium piscium, Chryseobacterium sediminis, Chryseobacterium tructae, Chryseobacterium ureilyticum, Chryseobacterium vietnamense, Corynebacterium accolens, Corynebacterium afermentans subsp. lipophilum, Corynebacterium minutissimum, Corynebacterium sundsvallense, Cupriavidus metallidurans, Cupriavidus nantongensis, Cupriavidus necator, Cupriavidus pampae, Cupriavidus yeoncheonensis, Curtobacterium flaccumfaciens, Devosia epidermidihirudinis, Devosia riboflavina, Devosia riboflavina, Diaphorobacter oryzae, Dietzia psychralcaliphila, Ensifer adhaerens, Ensifer americanus, Enterococcus malodoratus, Enterococcus pseudoavium, Enterococcus viikkiensis, Enterococcus xiangfangensis, Erwinia rhapontici, Falsirhodobacter halotolerans, Flavobacterium araucananum, Flavobacterium frigidimaris, Gluconobacter frateurii, Gluconobacter thailandicus, Gordonia alkanivorans, Halomonas aquamarina, Halomonas axialensis, Halomonas meridiana, Halomonas olivaria, Halomonas songnenensis, Halomonas variabilis, Herbaspirillum chlorophenolicum, Herbaspirillum frisingense, Herbaspirillum hiltneri, Herbaspirillum huttiense subsp. putei, Herbaspirillum lusitanum, Herminiimonas fonticola, Hydrogenophaga intermedia, Hydrogenophaga pseudoflava, Klebsiella oxytoca, Kosakonia sacchari, Lactobacillus delbrueckii subsp. bulgaricus, Lactobacillus modestisalitolerans, Lactobacillus plantarum subsp. argentoratensis, Lactobacillus xiangfangensis, Lechevalieria roselyniae, Lentzea albida, Lentzea californiensis, Leuconostoc carnosum, Leuconostoc citreum, Leuconostoc gelidum subsp. gasicomitatum, Leuconostoc mesenteroides subsp. suionicum, Luteimonas aestuarii, Lysobacter antibioticus, Lysobacter koreensis, Lysobacter oryzae, Magnetospirillum moscoviense, Marinomonas alcarazii, Marinomonas primoryensis, Massilia aurea, Massilia jejuensis, Massilia kyonggiensis, Massilia timonae, Mesorhizobium acaciae, Mesorhizobium qingshengii, Mesorhizobium shonense, Methylobacterium haplocladii, Methylobacterium platani, Methylobacterium pseudosasicola, Methylobacterium zatmanii, Microbacterium oxydan, Micromonospora chaiyaphumensis, Micromonospora chalcea, Micromonospora citrea, Micromonospora coxensis, Micromonospora echinofusca, Micromonospora halophytica, Micromonospora kangleipakensis, Micromonospora maritima, Micromonospora nigra, Micromonospora purpureochromogene, Micromonospora rhizosphaerae, Micromonospora saelicesensis, Microvirga subterranea, Microvirga zambiensis, Mycobacterium alvei, Mycobacterium avium subsp. silvaticum, Mycobacterium colombiense, Mycobacterium conceptionense, Mycobacterium conceptionense, Mycobacterium farcinogenes, Mycobacterium fortuitum subsp. fortuitum, Mycobacterium goodii, Mycobacterium insubricum, Mycobacterium Ilatzerense, Mycobacterium neoaurum, Mycobacterium neworleansense, Mycobacterium obuense, Mycobacterium peregrinum, Mycobacterium saopaulense, Mycobacterium septicum, Mycobacterium setense, Mycobacterium smegmatis, Neisseria subflava, Nocardia lijiangensis, Nocardia thailandica, Novosphingobium barchaimii, Novosphingobium lindaniclasticum, Novosphingobium lindaniclasticum, Novosphingobium mathurense, Ochrobactrum pseudogrignonense, Oxalicibacterium solurbis, Paraburkholderia glathei, Paraburkholderia humi, Paraburkholderia phenazinium, Paraburkholderia phytofirmans, Paraburkholderia sordidicola, Paraburkholderia terricola, Paraburkholderia xenovorans, Paracoccus laeviglucosivorans, Patulibacter ginsengiterrae, Polymorphospora rubra, Porphyrobacter colymbi, Prevotella jejuni, Prevotella melaninogenica, Propionibacterium acnes subsp. elongatum, Proteus vulgaris, Providencia rustigianii, Pseudoalteromonas agarivorans, Pseudoalteromonas atlantica, Pseudoalteromonas paragorgicola, Pseudomonas asplenii, Pseudomonas asuensis, Pseudomonas benzenivorans, Pseudomonas cannabina, Pseudomonas cissicola, Pseudomonas congelans, Pseudomonas costantinii, Pseudomonas ficuserectae, Pseudomonas frederiksbergensis, Pseudomonas graminis, Pseudomonas jessenii, Pseudomonas koreensis, Pseudomonas koreensis, Pseudomonas kunmingensis, Pseudomonas marginalis, Pseudomonas mucidolens, Pseudomonas panacis, Pseudomonas plecoglossicida, Pseudomonas poae, Pseudomonas pseudoalcaligenes, Pseudomonas putida, Pseudomonas reinekei, Pseudomonas rhizosphaerae, Pseudomonas seleniipraecipitans, Pseudomonas umsongensis, Pseudomonas zhaodongensis, Pseudonocardia alaniniphila, Pseudonocardia ammonioxydans, Pseudonocardia autotrophica, Pseudonocardia kongjuensis, Pseudonocardia yunnanensis, Pseudorhodoferax soli, Pseudoxanthomonas daejeonensis, Pseudoxanthomonas indica, Pseudoxanthomonas kaohsiungensis, Psychrobacter aquaticus, Psychrobacter arcticus, Psychrobacter celer, Psychrobacter marincola, Psychrobacter nivimaris, Psychrobacter okhotskensis, Psychrobacter okhotskensis, Psychrobacter piscatorii, Psychrobacter pulmonis, Ramlibacter ginsenosidimutans, Rheinheimera japonica, Rheinheimera muenzenbergensis, Rheinheimera soli, Rheinheimera tangshanensis, Rheinheimera texasensis, Rheinheimera tilapiae, Rhizobium alamii, Rhizobium azibense, Rhizobium binae, Rhizobium daejeonense, Rhizobium endophyticum, Rhizobium etli, Rhizobium fabae, Rhizobium freirei, Rhizobium gallicum, Rhizobium loessense, Rhizobium sophoriradicis, Rhizobium taibaishanense, Rhizobium vallis, Rhizobium vignae, Rhizobium vignae, Rhizobium yanglingense, Rhodococcus baikonurensis, Rhodococcus enclensis, Rhodoferax saidenbachensis, Rickettsia canadensis, Rickettsia heilongjiangensis, Rickettsia honei, Rickettsia raoultii, Roseateles aquatilis, Roseateles aquatilis, Salmonella enterica subsp. salamae, Serratia ficaria, Serratia myotis, Serratia vespertilionis, Shewanella aestuarii, Shewanella decolorationis, Sphingobium amiense, Sphingobium baderi, Sphingobium barthaii, Sphingobium chlorophenolicum, Sphingobium cupriresistens, Sphingobium czechense, Sphingobium fuliginis, Sphingobium indicum, Sphingobium indicum, Sphingobium japonicum, Sphingobium lactosutens, Sphingomonas dokdonensis, Sphingomonas pseudosanguinis, Sphingopyxis chilensis, Sphingopyxis fribergensis, Sphingopyxis granuli, Sphingopyxis indica, Sphingopyxis witflariensis, Staphylococcus agnetis, Staphylococcus aureus subsp. aureus, Staphylococcus epidermidis, Staphylococcus hominis subsp. novobiosepticus, Staphylo-

*coccus nepalensis, Staphylococcus saprophyticus* subsp. *bovis, Staphylococcus sciuri* subsp. *carnaticus, Streptomyces caeruleatus, Streptomyces canarius, Streptomyces capoamus, Streptomyces ciscaucasicus, Streptomyces griseorubiginosus, Streptomyces olivaceoviridis, Streptomyces panaciradicis, Streptomyces phaeopurpureus, Streptomyces pseudovenezuelae, Streptomyces resistomycificus, Tianweitania sediminis, Tsukamurella paurometabola, Variovorax guangxiensis, Vogesella alkaliphila, Xanthomonas arboricola, Xanthomonas axonopodis, Xanthomonas cassavae, Xanthomonas cucurbitae, Xanthomonas cynarae, Xanthomonas euvesicatoria, Xanthomonas fragariae, Xanthomonas gardneri, Xanthomonas perforans, Xanthomonas pisi, Xanthomonas populi, Xanthomonas vasicola, Xenophilus aerolatus, Yersinia nurmii, Abiotrophia defectiva, Acidocella aminolytica, Acinetobacter guangdongensis, Acinetobacter parvus, Acinetobacter radioresistens, Acinetobacter soli, Acinetobacter variabilis, Actinomyces cardiffensis, Actinomyces dentalis, Actinomyces europaeus, Actinomyces gerencseriae, Actinomyces graevenitzii, Actinomyces haliotis, Actinomyces johnsonii, Actinomyces massiliensis, Actinomyces meyeri, Actinomyces meyeri, Actinomyces naeslundii, Actinomyces neuii* subsp. *anitratus, Actinomyces odontolyticus, Actinomyces oris, Actinomyces turicensis, Actinomycetospora corticicola, Actinotignum schaalii, Aerococcus christensenii, Aerococcus urinae, Aeromicrobium flavum, Aeromicrobium massiliense, Aeromicrobium tamlense, Aeromonas sharmana, Aggregatibacter aphrophilus, Aggregatibacter segnis, Agrococcus baldri, Albibacter methylovorans, Alcaligenes faecalis* subsp. *faecalis, Algoriphagus ratkowskyi, Alkalibacterium olivapovliticus, Alkalibacterium pelagium, Alkalibacterium pelagium, Alloprevotella rava, Alsobacter metallidurans, Amaricoccus kaplicensis, Amaricoccus veronensis, Anaerococcus hydrogenalis, Anaerococcus lactolyticus, Anaerococcus murdochii, Anaerococcus octavius, Anaerococcus prevotii, Anaerococcus vaginalis, Aquabacterium citratiphilum, Aquabacterium olei, Aquabacterium olei, Aquabacterium parvum, Aquincola tertiaricarbonis, Arcobacter venerupis, Arsenicicoccus bolidensis, Arthrobacter russicus, Asticcacaulis excentricus, Atopobium deltae, Atopobium parvulum, Atopobium rimae, Atopobium vaginae, Aureimonas altamirensis, Aureimonas rubiginis, Azospira oryzae, Azospirillum oryzae, Bacillus circulans, Bacillus drentensis, Bacillus fastidiosus, Bacillus lehensis, Bacillus oceanisediminis, Bacillus rhizosphaerae, Bacteriovorax stolpii, Bacteroides coagulans, Bacteroides dorei, Bacteroides fragilis, Bacteroides ovatus, Bacteroides stercoris, Bacteroides uniformis, Bacteroides vulgatus, Bdellovibrio bacteriovorus, Bdellovibrio exovorus, Belnapia moabensis, Belnapia soli, Blautia hansenii, Blautia obeum, Blautia wexlerae, Bosea lathyri, Brachybacterium fresconis, Brachybacterium muris, Brevibacterium ammoniilyticum, Brevibacterium casei, Brevibacterium epidermidis, Brevibacterium iodinum, Brevibacterium luteolum, Brevibacterium paucivorans, Brevibacterium pityocampae, Brevibacterium sanguinis, Brevundimonas albigilva, Brevundimonas diminuta, Brevundimonas vancanneytii, Caenimonas terrae, Calidifontibacter indicus, Campylobacter concisus, Campylobacter gracilis, Campylobacter hominis, Campylobacter rectus, Campylobacter showae, Campylobacter ureolyticus, Capnocytophaga gingivalis, Capnocytophaga leadbetteri, Capnocytophaga ochracea, Capnocytophaga sputigena, Cardiobacterium hominis, Cardiobacterium valvarum, Carnobacterium divergens, Catonella morbi, Caulobacter henricii, Cavicella subterranea, Cellulomonas xylanilytica, Cellvibrio vulgaris, Chitinimonas taiwanensis, Chryseobacterium arachidis, Chryseobacterium daecheongense, Chryseobacterium formosense, Chryseobacterium formosense, Chryseobacterium greenlandense, Chryseobacterium indologenes, Chryseobacterium piscium, Chryseobacterium rigui, Chryseobacterium solani, Chryseobacterium taklimakanense, Chryseobacterium ureilyticum, Chryseobacterium ureilyticum, Chryseobacterium zeae, Chryseomicrobium aureum, Cloacibacterium haliotis, Cloacibacterium normanense, Cloacibacterium normanense, Collinsella aerofaciens, Comamonas denitrificans, Comamonas terrigena, Corynebacterium accolens, Corynebacterium afermentans* subsp. *lipophilum, Corynebacterium ammoniagenes, Corynebacterium amycolatum, Corynebacterium aurimucosum, Corynebacterium aurimucosum, Corynebacterium coyleae, Corynebacterium durum, Corynebacterium freiburgense, Corynebacterium glaucum, Corynebacterium glyciniphilum, Corynebacterium imitans, Corynebacterium jeikeium, Corynebacterium jeikeium, Corynebacterium kroppenstedtii, Corynebacterium lipophiloflavum, Corynebacterium massiliense, Corynebacterium mastitidis, Corynebacterium matruchotii, Corynebacterium minutissimum, Corynebacterium mucifaciens, Corynebacterium mustelae, Corynebacterium mycetoides, Corynebacterium pyruviciproducens, Corynebacterium simulans, Corynebacterium singulare, Corynebacterium sputi, Corynebacterium suicordis, Corynebacterium tuberculostearicum, Corynebacterium tuberculostearicum, Corynebacterium ureicelerivorans, Corynebacterium variabile, Couchioplanes caeruleus* subsp. *caeruleus, Cupriavidus metallidurans, Curtobacterium herbarum, Dechloromonas agitata, Deinococcus actinosclerus, Deinococcus antarcticus, Deinococcus caeni, Deinococcus ficus, Deinococcus geothermalis, Deinococcus radiodurans, Deinococcus wulumuqiensis, Deinococcus xinjiangensis, Dermabacter hominis, Dermabacter vaginalis, Dermacoccus nishinomiyaensis, Desemzia incerta, Desertibacter roseus, Dialister invisus, Dialister micraerophilus, Dialister propionicifaciens, Dietzia aurantiaca, Dietzia cercidiphylli, Dietzia timorensis, Dietzia timorensis, Dokdonella koreensis, Dokdonella koreensis, Dolosigranulum pigrum, Eikenella corrodens, Elizabethkingia miricola, Elstera litoralis, Empedobacter brevis, Enhydrobacter aerosaccus, Enterobacter xiangfangensis, Enterococcus aquimarinus, Enterococcus faecalis, Enterococcus olivae, Erwinia rhapontici, Eubacterium eligens, Eubacterium infirmum, Eubacterium rectale, Eubacterium saphenum, Eubacterium sulci, Exiguobacterium mexicanum, Facklamia tabacinasalis, Falsirhodobacter halotolerans, Finegoldia magna, Flavobacterium cutihirudinis, Flavobacterium lindanitolerans, Flavobacterium resistens, Friedmanniella capsulata, Fusobacterium nucleatum* subsp. *polymorphum, Gemella haemolysans, Gemella morbillorum, Gemella palaticanis, Gemella sanguinis, Gemmobacter aquaticus, Gemmobacter caeni, Gordonia jinhuaensis, Gordonia kroppenstedtii, Gordonia polyisoprenivorans, Gordonia polyisoprenivorans, Granulicatella adiacens, Granulicatella elegans, Haemophilus parainfluenzae, Haemophilus sputorum, Halomonas suffidaeris, Herpetosiphon aurantiacus, Hydrocarboniphaga effusa, Idiomarina marls, Janibacter anophelis, Janibacter hoylei, Janibacter indicus, Janibacter limosus, Janibacter melonis, Jeotgalicoccus halophilus, Jonquetella anthropi, Kaistia geumhonensis, Kingella denitrificans, Kingella oralis, Klebsiella oxytoca, Knoellia aerolata, Knoellia locipacati, Kocuria atrinae, Kocuria carniphila, Kocuria kristinae, Kocuria palustris, Kocuria turfanensis, Lachnoanaerobaculum saburreum, Lachnoanaerobaculum saburreum, Lactobacillus crispatus, Lactobacillus iners,*

*Lactococcus lactis* subsp. *lactis*, *Lactococcus lactis* subsp. *lactis*, *Lactococcus piscium*, *Lapillicoccus jejuensis*, *Lautropia mirabilis*, *Legionella beliardensis*, *Leptotrichia buccalis*, *Leptotrichia goodfellowii*, *Leptotrichia hofstadii*, *Leptotrichia hongkongensis*, *Leptotrichia shahii*, *Leptotrichia trevisanii*, *Leptotrichia wadei*, *Luteimonas terricola*, *Lysinibacillus fusiformis*, *Lysobacter spongiicola*, *Lysobacter xinjiangensis*, *Macrococcus caseolyticus*, *Marmoricola pocheonensis*, *Marmoricola scoriae*, *Massilia alkalitolerans*, *Massilia alkalitolerans*, *Massilia aurea*, *Massilia plicata*, *Massilia timonae*, *Megamonas rupellensis*, *Meiothermus silvanus*, *Methylobacterium dankookense*, *Methylobacterium goesingense*, *Methylobacterium goesingense*, *Methylobacterium isbiliense*, *Methylobacterium jeotgali*, *Methylobacterium oxalidis*, *Methylobacterium platani*, *Methylobacterium pseudosasicola*, *Methyloversatilis universalis*, *Microbacterium foliorum*, *Microbacterium hydrothermale*, *Microbacterium hydrothermale*, *Microbacterium lacticum*, *Microbacterium lacticum*, *Microbacterium laevaniformans*, *Microbacterium paludicola*, *Microbacterium petrolearium*, *Microbacterium phyllosphaerae*, *Microbacterium resistens*, *Micrococcus antarcticus*, *Micrococcus cohnii*, *Micrococcus flavus*, *Micrococcus lylae*, *Micrococcus terreus*, *Microlunatus aurantiacus*, *Micropruina glycogenica*, *Microvirga aerilata*, *Microvirga aerilata*, *Microvirga subterranea*, *Microvirga vignae*, *Microvirga zambiensis*, *Microvirgula aerodenitrificans*, *Mogibacterium timidum*, *Moraxella atlantae*, *Moraxella catarrhalis*, *Morganella morganii* subsp. *morganii*, *Morganella psychrotolerans*, *Murdochiella asaccharolytica*, *Mycobacterium asiaticum*, *Mycobacterium chubuense*, *Mycobacterium crocinum*, *Mycobacterium gadium*, *Mycobacterium holsaticum*, *Mycobacterium iranicum*, *Mycobacterium longobardum*, *Mycobacterium neoaurum*, *Mycobacterium neoaurum*, *Mycobacterium obuense*, *Negativicoccus succinicivorans*, *Neisseria bacilliformis*, *Neisseria oralis*, *Neisseria sicca*, *Neisseria subflava*, *Nesterenkonia lacusekhoensis*, *Nesterenkonia rhizosphaerae*, *Nevskia persephonica*, *Nevskia ramosa*, *Niabella yanshanensis*, *Niveibacterium umoris*, *Nocardia niwae*, *Nocardia thailandica*, *Nocardioides agariphilus*, *Nocardioides dilutus*, *Nocardioides ganghwensis*, *Nocardioides hwasunensis*, *Nocardioides nanhaiensis*, *Nocardioides sediminis*, *Nosocomiicoccus ampullae*, *Noviherbaspirillum malthae*, *Novosphingobium lindaniclasticum*, *Novosphingobium rosa*, *Ochrobactrum rhizosphaerae*, *Olsenella uli*, *Ornithinimicrobium murale*, *Ornithinimicrobium tianjinense*, *Oryzobacter terrae*, *Ottowia beijingensis*, *Paenalcaligenes suwonensis*, *Paenibacillus agaridevorans*, *Paenibacillus phoenicis*, *Paenibacillus xylanexedens*, *Paludibacterium yongneupense*, *Pantoea cypripedii*, *Parabacteroides distasonis*, *Paraburkholderia andropogonis*, *Paracoccus alcaliphilus*, *Paracoccus angustae*, *Paracoccus kocurii*, *Paracoccus laeviglucosivorans*, *Paracoccus sediminis*, *Paracoccus sphaerophysae*, *Paracoccus yeei*, *Parvimonas micra*, *Parviterribacter multiflagellatus*, *Patulibacter ginsengiterrae*, *Pedobacter aquatilis*, *Pedobacter ginsengisoli*, *Pedobacter xixiisoli*, *Peptococcus niger*, *Peptoniphilus coxii*, *Peptoniphilus gorbachii*, *Peptoniphilus harei*, *Peptoniphilus koenoeneniae*, *Peptoniphilus lacrimalis*, *Peptostreptococcus anaerobius*, *Peptostreptococcus stomatis*, *Phascolarctobacterium faecium*, *Phenylobacterium haematophilum*, *Phenylobacterium kunshanense*, *Pluralibacter gergoviae*, *Polymorphobacter multimanifer*, *Porphyromonas bennonis*, *Porphyromonas endodontalis*, *Porphyromonas gingivalis*, *Porphyromonas gingivicanis*, *Porphyromonas pasteri*, *Porphyromonas pogonae*, *Porphyromonas somerae*, *Povalibacter uvarum*, *Prevotella aurantiaca*, *Prevotella baroniae*, *Prevotella bivia*, *Prevotella buccae*, *Prevotella buccalis*, *Prevotella copri*, *Prevotella corporis*, *Prevotella denticola*, *Prevotella enoeca*, *Prevotella histicola*, *Prevotella intermedia*, *Prevotella jejuni*, *Prevotella jejuni*, *Prevotella maculosa*, *Prevotella melaninogenica*, *Prevotella melaninogenica*, *Prevotella micans*, *Prevotella multiformis*, *Prevotella nanceiensis*, *Prevotella nigrescens*, *Prevotella oris*, *Prevotella oulorum*, *Prevotella pallens*, *Prevotella pleuritidis*, *Prevotella saccharolytica*, *Prevotella salivae*, *Prevotella shahii*, *Prevotella timonensis*, *Prevotella veroralis*, *Propionibacterium acidifaciens*, *Propionibacterium acnes* subsp. *acnes*, *Propionibacterium acnes* subsp. *acnes*, *Propionibacterium acnes* subsp. *elongatum*, *Propionibacterium granulosum*, *Propionimicrobium lymphophilum*, *Propionispira arcuata*, *Pseudokineococcus lusitanus*, *Pseudomonas aeruginosa*, *Pseudomonas chengduensis*, *Pseudonocardia benzenivorans*, *Pseudorhodoplanes sinuspersici*, *Psychrobacter sanguinis*, *Ramlibacter ginsenosidimutans*, *Rheinheimera aquimaris*, *Rhizobium alvei*, *Rhizobium daejeonense*, *Rhizobium larrymoorei*, *Rhizobium rhizoryzae*, *Rhizobium soli*, *Rhizobium taibaishanense*, *Rhizobium vignae*, *Rhodanobacter glycinis*, *Rhodobacter veldkampii*, *Rhodococcus enclensis*, *Rhodococcus fascians*, *Rhodococcus fascians*, *Rhodovarius lipocyclicus*, *Rivicola pingtungensis*, *Roseburia inulinivorans*, *Rosenbergiella nectarea*, *Roseomonas aerilata*, *Roseomonas aquatica*, *Roseomonas mucosa*, *Roseomonas rosea*, *Roseomonas vinacea*, *Rothia aeria*, *Rothia amarae*, *Rothia dentocariosa*, *Rothia endophytica*, *Rothia mucilaginosa*, *Rothia nasimurium*, *Rubellimicrobium mesophilum*, *Rubellimicrobium roseum*, *Rubrobacter bracarensis*, *Rudaea cellulosilytica*, *Ruminococcus gnavus*, *Runella zeae*, *Saccharopolyspora rectivirgula*, *Salinicoccus qingdaonensis*, *Scardovia wiggsiae*, *Sediminibacterium ginsengisoli*, *Selenomonas artemidis*, *Selenomonas infelix*, *Selenomonas noxia*, *Selenomonas sputigena*, *Shewanella aestuarii*, *Shuttleworthia satelles*, *Simonsiella muelleri*, *Skermanella aerolata*, *Skermanella stibiiresistens*, *Slackia exigua*, *Smaragdicoccus niigatensis*, *Sneathia sanguinegens*, *Solirubrobacter soli*, *Sphingobacterium caeni*, *Sphingobacterium daejeonense*, *Sphingobacterium hotanense*, *Sphingobacterium kyonggiense*, *Sphingobacterium multivorum*, *Sphingobacterium nematocida*, *Sphingobacterium spiritivorum*, *Sphingobium amiense*, *Sphingobium indicum*, *Sphingobium lactosutens*, *Sphingobium subterraneum*, *Sphingomonas abaci*, *Sphingomonas aestuarii*, *Sphingomonas canadensis*, *Sphingomonas daechungensis*, *Sphingomonas dokdonensis*, *Sphingomonas echinoides*, *Sphingomonas fonticola*, *Sphingomonas fonticola*, *Sphingomonas formosensis*, *Sphingomonas gei*, *Sphingomonas hankookensis*, *Sphingomonas hankookensis*, *Sphingomonas koreensis*, *Sphingomonas kyeonggiensis*, *Sphingomonas laterariae*, *Sphingomonas mucosissima*, *Sphingomonas oligophenolica*, *Sphingomonas pseudosanguinis*, *Sphingomonas sediminicola*, *Sphingomonas yantingensis*, *Sphingomonas yunnanensis*, *Sphingopyxis indica*, *Spirosoma rigui*, *Sporacetigenium mesophilum*, *Sporocytophaga myxococcoides*, *Staphylococcus auricularis*, *Staphylococcus epidermidis*, *Staphylococcus epidermidis*, *Staphylococcus hominis* subsp. *novobiosepticus*, *Staphylococcus lugdunensis*, *Staphylococcus pettenkoferi*, *Stenotrophomonas koreensis*, *Stenotrophomonas rhizophila*, *Stenotrophomonas rhizophila*, *Streptococcus agalactiae*, *Streptococcus canis*, *Streptococcus cristatus*, *Streptococcus gordonii*, *Streptococcus infantis*, *Streptococcus intermedius*, *Streptococcus mutans*, *Streptococcus oligofermentans*, *Streptococcus oralis*, *Streptococcus sanguinis*, *Streptomyces iconiensis*, *Streptomyces yanglin-* ensis, *Tabrizicola aquatica, Tahibacter caeni, Tannerella forsythia, Tepidicella xavieri, Tepidimonas fonticaldi, Terracoccus luteus, Tessaracoccus flavescens, Thermus thermophilus, Tianweitania sediminis, Tianweitania sediminis, Treponema amylovorum, Treponema denticola, Treponema lecithinolyticum, Treponema medium, Turicella otitidis, Turicibacter sanguinis, Undibacterium oligocarboniphilum, Undibacterium squillarum, Vagococcus salmoninarum, Varibaculum cambriense, Vibrio metschnikovii, Xanthobacter tagetidis, Xenophilus aerolatus, Xenophilus arseniciresistens, Yimella lutea, Zimmermannella alba, Zimmermannella bifida* and/or *Zoogloea caeni*.

In other embodiments, the targeted bacteria cells are those commonly found in the vaginal microbiota and are, without limitation, *Acinetobacter antiviralis, Acinetobacter baumannii, Acinetobacter calcoaceticus, Acinetobacter johnsonii, Actinobaculum massiliense, Actinobaculum schaalii, Actinomyces europaeus, Actinomyces graevenitzii, Actinomyces israelii, Actinomyces meyeri, Actinomyces naeslundii, Actinomyces neuii, Actinomyces odontolyticus, Actinomyces turicensis, Actinomyces urogenitalis, Actinomyces viscosus, Aerococcus christensenii, Aerococcus urinae, Aerococcus viridans, Aeromonas encheleia, Aeromonas salmonicida, Afipia massiliensis, Agrobacterium tumefaciens, Algoriphagus aquatilis, Aliivibrio wodanis, Alistipes finegoldii, Alloiococcus otitis, Alloprevotella tannerae, Alloscardovia omnicolens, Altererythrobacter epoxidivorans, Ammoniphilus oxalaticus, Amnibacterium kyonggiense, Anaerococcus hydrogenalis, Anaerococcus lactolyticus, Anaerococcus murdochii, Anaerococcus obesiensis, Anaerococcus prevotii, Anaerococcus tetradius, Anaerococcus vaginalis, Anaeroglobus geminatus, Anoxybacillus pushchinoensis, Aquabacterium parvum, Arcanobacterium phocae, Arthrobacter aurescens, Asticcacaulis excentricus, Atopobium minutum, Atopobium parvulum, Atopobium rimae, Atopobium vaginae, Avibacterium gallinarum, Bacillus acidicola, Bacillus atrophaeus, Bacillus cereus, Bacillus cibi, Bacillus coahuilensis, Bacillus gaemokensis, Bacillus methanolicus, Bacillus oleronius, Bacillus pumilus, Bacillus shackletonii, Bacillus sporothermodurans, Bacillus subtilis, Bacillus wakoensis, Bacillus weihenstephanensis, Bacteroides barnesiae, Bacteroides coagulans, Bacteroides dorei, Bacteroides faecis, Bacteroides forsythus, Bacteroides fragilis, Bacteroides nordii, Bacteroides ovatus, Bacteroides salyersiae, Bacteroides stercoris, Bacteroides uniformis, Bacteroides vulgatus, Bacteroides xylanisolvens, Bacteroides zoogleoformans, Barnesiella viscericola, Bhargavaea cecembensis, Bifidobacterium adolescentis, Bifidobacterium bifidum, Bifidobacterium breve, Bifidobacterium dentium, Bifidobacterium logum* subsp. *infantis, Bifidobacterium longum, Bifidobacterium pseudocatenulatum, Bifidobacterium scardovii, Bilophila wadsworthia, Blautia hydrogenotrophica, Blautia obeum, Blautia producta, Brachybacterium faecium, Bradyrhizobium japonicum, Brevibacterium mcbrellneri, Brevibacterium otitidis, Brevibacterium paucivorans, Bulleidia extructa, Burkholderia fungorum, Burkholderia phenoliruptix, Caldicellulosiruptor saccharolyticus, Caldimonas taiwanensis, Campylobacter gracilis, Campylobacter hominis, Campylobacter sputorum, Campylobacter ureolyticus, Capnocytophaga ochracea, Cardiobacterium hominis, Catonella morbi, Chlamydia trachomatis, Chlamydophila abortus, Chondromyces robustus, Chryseobacterium aquaticum, Citrobacter youngae, Cloacibacterium normanense, Clostridium cavendishii, Clostridium colicanis, Clostridium jejuense, Clostridium perfringens, Clostridium ramosum, Clostridium sordellii, Clostridium viride, Comamonas terrigena, Corynebacterium accolens, Corynebacterium appendicis, Corynebacterium coyleae, Corynebacterium glucuronolyticum, Corynebacterium glutamicum, Corynebacterium jeikeium, Corynebacterium kroppenstedtii, Corynebacterium lipophiloflavum, Corynebacterium minutissimum, Corynebacterium mucifaciens, Corynebacterium nuruki, Corynebacterium pseudogenitalium, Corynebacterium pyruviciproducens, Corynebacterium singulare, Corynebacterium striatum, Corynebacterium tuberculostearicum, Corynebacterium xerosis, Cryobacterium psychrophilum, Curtobacterium flaccumfaciens, Cutibacterium acnes, Cutibacterium avidum, Cytophaga xylanolytica, Deinococcus radiophilus, Delftia tsuruhatensis, Desulfovibrio desulfuricans, Dialister invisus, Dialister micraerophilus, Dialister pneumosintes, Dialister propionicifaciens, Dickeya chrysanthemi, Dorea longicatena, Eggerthella lenta, Eggerthia catenaformis, Eikenella corrodens, Enhydrobacter aerosaccus, Enterobacter asburiae, Enterobacter cloacae, Enterococcus avium, Enterococcus durans, Enterococcus faecalis, Enterococcus faecium, Enterococcus hirae, Erwinia persicina, Erwinia rhapontici, Erwinia toletana, Escherichia coli, Escherichia fergusonii, Eubacterium brachy, Eubacterium eligens, Eubacterium nodatum, Eubacterium rectale, Eubacterium saphenum, Eubacterium siraeum, Eubacterium sulci, Eubacterium yurii, Exiguobacterium acetylicum, Facklamia ignava, Faecalibacterium prausnitzii, Filifactor alocis, Finegoldia magna, Fusobacterium gonidiaformans, Fusobacterium nucleatum, Fusobacterium periodonticum, Gardnerella vaginalis, Gemella asaccharolytica, Gemella bergeri, Gemella haemolysans, Gemella sanguinis, Geobacillus stearothermophilus, Geobacillus thermocatenulatus, Geobacillus thermoglucosidasius, Geobacter grbiciae, Granulicatella elegans, Haemophilus ducreyi, Haemophilus haemolyticus, Haemophilus parahaemolyticus, Haemophilus parainfluenzae, Hafnia alvei, Halomonas meridiana, Halomonas phoceae, Halomonas venusta, Herbaspirillum seropedicae, Janthinobacterium lividum, Jonquetella anthropi, Klebsiella granulomatis, Klebsiella oxytoca, Klebsiella pneumoniae, Lactobacillus acidophilus, Lactobacillus amylovorus, Lactobacillus brevis, Lactobacillus coleohominis, Lactobacillus crispatus, Lactobacillus curvatus, Lactobacillus delbrueckii, Lactobacillus fermentum, Lactobacillus gasseri, Lactobacillus helveticus, Lactobacillus iners, Lactobacillus jensenii, Lactobacillus johnsonii, Lactobacillus kalixensis, Lactobacillus kefiranofaciens, Lactobacillus kimchicus, Lactobacillus kitasatonis, Lactobacillus mucosae, Lactobacillus panis, Lactobacillus paracasei, Lactobacillus plantarum, Lactobacillus pontis, Lactobacillus reuteri, Lactobacillus rhamnosus, Lactobacillus salivarius, Lactobacillus ultunensis, Lactobacillus vaginalis, Lactococcus lactis, Leptotrichia buccalis, Leuconostoc carnosum, Leuconostoc citreum, Leuconostoc garlicum, Leuconostoc lactis, Leuconostoc mesenteroides, Lysinimonas kribbensis, Mageeibacillus indolicus, Maribacter orientalis, Marinomonas protea, Marinospirillum insulare, Massilia timonae, Megasphaera elsdenii, Megasphaera micronuciformis, Mesorhizobium amorphae, Methylobacterium radiotolerans, Methylotenera versatilis, Microbacterium halophilum, Micrococcus luteus, Microterricola viridarii, Mobiluncus curtisii, Mobiluncus mulieris, Mogibacterium timidum, Moorella glycerini, Moraxella osloensis, Morganella morganii, Moryella indoligenes, Murdochiella asaccharolytica, Mycoplasma alvi, Mycoplasma genitalium, Mycoplasma hominis, Mycoplasma muris, Mycoplasma salivarium, Negativicoccus succinicivorans, Neisseria flava, Neisseria gonorrhoeae, Neisseria mucosa, Neisseria subflava, Nevskia ramosa, Nevskia soli, Nitriliruptor alkaliphilus, Odor-* ibacter splanchnicus, Oligella urethralis, Olsenella uli, Paenibacillus amylolyticus, Paenibacillus humicus, Paenibacillus pabuli, Paenibacillus pasadenensis, Paenibacillus pini, Paenibacillus validus, Pantoea agglomerans, Parabacteroides merdae, Paraburkholderia caryophylli, Paracoccus yeei, Parastreptomyces abscessus, Parvimonas micra, Pectobacterium betavasculorum, Pectobacterium carotovorum, Pediococcus acidilactici, Pediococcus ethanolidurans, Pedobacter alluvionis, Pedobacter wanjuense, Pelomonas aquatica, Peptococcus niger, Peptoniphilus asaccharolyticus, Peptoniphilus gorbachii, Peptoniphilus harei, Peptoniphilus indolicus, Peptoniphilus lacrimalis, Peptoniphilus massiliensis, Peptostreptococcus anaerobius, Peptostreptococcus massiliae, Peptostreptococcus stomatis, Photobacterium angustum, Photobacterium frigidiphilum, Photobacterium phosphoreum, Porphyromonas asaccharolytica, Porphyromonas bennonis, Porphyromonas catoniae, Porphyromonas endodontalis, Porphyromonas gingivalis, Porphyromonas somerae, Porphyromonas uenonis, Prevotella amnii, Prevotella baroniae, Prevotella bergensis, Prevotella bivia, Prevotella buccae, Prevotella buccalis, Prevotella colorans, Prevotella copri, Prevotella corporis, Prevotella dentalis, Prevotella denticola, Prevotella disiens, Prevotella intermedia, Prevotella loescheii, Prevotella marshii, Prevotella melaninogenica, Prevotella micans, Prevotella nigrescens, Prevotella oris, Prevotella pleuritidis, Prevotella ruminicola, Prevotella shahii, Prevotella stercorea, Prevotella timonensis, Prevotella veroralis, Propionimicrobium lymphophilum, Proteus mirabilis, Pseudomonas abietaniphila, Pseudomonas aeruginosa, Pseudomonas amygdali, Pseudomonas azotoformans, Pseudomonas chlororaphis, Pseudomonas cuatrocienegasensis, Pseudomonas fluorescens, Pseudomonas fulva, Pseudomonas lutea, Pseudomonas mucidolens, Pseudomonas oleovorans, Pseudomonas orientalis, Pseudomonas pseudoalcaligenes, Pseudomonas psychrophila, Pseudomonas putida, Pseudomonas synxantha, Pseudomonas syringae, Pseudomonas tolaasii, Pseudopropionibacterium propionicum, Rahnella aquatilis, Ralstonia pickettii, Ralstonia solanacearum, Raoultella planticola, Rhizobacter dauci, Rhizobium etli, Rhodococcus fascians, Rhodopseudomonas palustris, Roseburia intestinalis, Roseburia inulinivorans, Rothia mucilaginosa, Ruminococcus bromii, Ruminococcus gnavus, Ruminococcus torques, Sanguibacter keddieii, Sediminibacterium salmoneum, Selenomonas bovis, Serratia fonticola, Serratia liquefaciens, Serratia marcescens, Shewanella algae, Shewanella amazonensis, Shigella boydii, Shigella sonnei, Slackia exigua, Sneathia amnii, Sneathia sanguinegens, Solobacterium moorei, Sorangium cellulosum, Sphingobium amiense, Sphingobium japonicum, Sphingobium yanoikuyae, Sphingomonas wittichii, Sporosarcina aquimarina, Staphylococcus aureus, Staphylococcus auricularis, Staphylococcus capitis, Staphylococcus epidermidis, Staphylococcus haemolyticus, Staphylococcus hominis, Staphylococcus lugdunensis, Staphylococcus saprophyticus, Staphylococcus schleiferi, Staphylococcus simiae, Staphylococcus simulans, Staphylococcus warneri, Stenotrophomonas maltophilia, Stenoxybacter acetivorans, Streptococcus agalactiae, Streptococcus anginosus, Streptococcus australis, Streptococcus equinus, Streptococcus gallolyticus, Streptococcus infantis, Streptococcus intermedius, Streptococcus lutetiensis, Streptococcus marimammalium, Streptococcus mitis, Streptococcus mutans, Streptococcus oralis, Streptococcus parasanguinis, Streptococcus phocae, Streptococcus pseudopneumoniae, Streptococcus salivarius, Streptococcus sanguinis, Streptococcus thermophilus, Sutterella wadsworthensis, Tannerella forsythia, Terrahaemophilus aromaticivorans, Treponema denticola, Treponema maltophilum, Treponema parvum, Treponema vincentii, Trueperella bernardiae, Turicella otitidis, Ureaplasma parvum, Ureaplasma urealyticum, Varibaculum cambriense, Variovorax paradoxus, Veillonella atypica, Veillonella dispar, Veillonella montpellierensis, Veillonella parvula, Virgibacillus proomii, Viridibacillus arenosi, Viridibacillus arvi, Weissella cibaria, Weissella soli, Xanthomonas campestris, Xanthomonas vesicatoria, Zobellia laminariae and/or Zoogloea ramigera.

In one embodiment, the targeted bacteria are *Escherichia coli*.

In one embodiment, the targeted bacteria are *Cutibacterium acnes* more specifically the acne related *Cutibacterium acnes* from the phylogroup IA1 or RT4, RT5, RT8, RT9, RT10 or Clonal Complex(CC) CC1, CC3, CC4, more specifically the ST1, ST3, ST4.

Thus, the first type of bacteriophage disclosed herein, and therefore the phage particles or phage-derived delivery particles of the invention, may target (e.g., specifically target) a bacterial cell from any one or more of the foregoing genus and/or species of bacteria in particular to specifically deliver the payload.

In one embodiment, the targeted bacteria are pathogenic bacteria. The targeted bacteria can be virulent bacteria.

The targeted bacteria can be antibacterial resistance bacteria, preferably selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. Preferably, the targeted bacteria can be selected from the group consisting of extended-spectrum beta-lactamase-producing (ESBL) *Escherichia coli* strains.

Alternatively, the targeted bacterium can be a bacterium of the microbiome of a given species, preferably a bacterium of the human microbiota.

In a particular embodiment, said targeted bacterial cells are from a species or strain different from the production bacterial cell.

Hybrid Helper Phage System and Hybrid Helper Phage

The present invention also concerns a hybrid helper phage system comprising:
- (i) at least one phage DNA packaging gene(s), as defined in the section "Production bacterial cell" above, derived from a lytic bacteriophage, as defined in the section "Bacteriophage and gene derived from a bacteriophage" above,
- (i') at least one phage structural gene(s), as defined in the section "Production bacterial cell" above, derived from said lytic bacteriophage,
- (i") optionally, at least one phage gene(s) involved in phage regulation, as defined in the section "Production bacterial cell" above, derived from said lytic bacteriophage, and
- (ii) at least one gene, derived from a non-lytic bacteriophage, as defined in the section "Bacteriophage and gene derived from a bacteriophage" above, involved in phage excision/insertion, phage DNA replication, and/or phage regulation, as defined in the section "Production bacterial cell" above, wherein said genes (i), (i'), (i") and (ii) are comprised in a unique nucleic acid molecule or in separate nucleic acid molecules, and wherein said hybrid helper phage system does not comprise any expressed phage structural gene derived from said non-lytic bacteriophage.

In the context of the invention, the term "hybrid helper phage system" is meant a group of at least one nucleic acid molecule, preferably of at least two separate nucleic acid molecules, comprising the genes (i), (i'), optionally (i"), and (ii) defined above, which enables the production of lytic phage particles and/or lytic phage-derived delivery vehicles by the production bacterial cell comprising said system, wherein when the system comprises at least two separate nucleic acid molecules, said genes (i), (i'), optionally (i"), and (ii) are distributed on said at least two separate nucleic acid molecules.

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Weigele et al. Chem Rev. 2016 Oct. 26; 116(20):12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present invention.

In a particular embodiment, said genes (i), (i'), optionally (i"), and (ii) are comprised in a bacterial chromosome, in particular in a production bacterial cell chromosome. In a more particular embodiment, said genes (i), (i'), optionally (i"), and (ii) are comprised in a bacterial chromosome in a same region. In an alternative embodiment, said genes (i), (i'), optionally (i"), and (ii) are comprised in a bacterial chromosome in distinct regions.

In an alternative embodiment, said genes (i), (i'), optionally (i"), and (ii) are comprised in separate plasmids. In another particular embodiment, said genes (i), (i'), optionally (i"), and (ii) are all comprised in a same plasmid.

In another particular embodiment, said genes (i), (i'), optionally (i"), and (ii) are each independently comprised in a bacterial chromosome or in a plasmid.

In a more particular embodiment, said genes (i), (i'), optionally (i"), and (ii) are comprised in a hybrid helper phage.

Therefore, in a particular embodiment, said hybrid helper phage system consists of a hybrid helper phage comprising:
(i) at least one phage DNA packaging gene(s), as defined in the section "Production bacterial cell" above, at least one phage structural gene(s), as defined in the section "Production bacterial cell" above, and optionally at least one phage gene(s) involved in phage regulation, as defined in the section "Production bacterial cell" above, derived from a lytic bacteriophage, as defined in the section "Bacteriophage and gene derived from a bacteriophage" above, and
(ii) at least one gene, derived from a non-lytic bacteriophage, as defined in the section "Bacteriophage and gene derived from a bacteriophage" above, involved in phage excision/insertion, phage DNA replication, and/or phage regulation, as defined in the section "Production bacterial cell" above, wherein said hybrid helper phage does not comprise any phage structural gene derived from said non-lytic bacteriophage.

By "helper phage" is meant herein an engineered phage providing all the necessary gene products for particle formation when using phagemid vectors. Helper phages typically have a defective origin of replication or packaging signal, and hence, are inefficient in self-packaging.

By "hybrid helper phage" is meant herein an engineered helper phage which is constituted of elements derived from at least a lytic bacteriophage and a non-lytic bacteriophage.

In a particular embodiment, the hybrid helper phage of the invention is integrated in the genome of the production bacterial cell as a prophage.

Production Method

The present invention further concerns a method for producing lytic phage particles or lytic phage-derived delivery vehicles, comprising:
(a) providing the production bacterial cell of the invention, and
(b) inducing, in said production bacterial cell, expression of said at least one of said phage structural gene(s) and at least one of said phage DNA packaging gene(s), and assembly of the products expressed by said at least one phage structural gene(s) and said at least one phage DNA packaging gene(s), thereby producing lytic phage particles or lytic phage-derived delivery vehicles.

The inducing step (b) can be carried out by any technique well-known from the skilled person. In particular, as will be understood by the skilled person, said inducing step will depend on the particular induction mechanism controlling the expression of said at least one of said phage structural genes and phage DNA packaging genes, in said production bacterial cell.

More particularly, it will be understood by the skilled person that, when said induction mechanism comprises at least one gene, derived from a non-lytic bacteriophage, involved in phage excision/insertion, phage DNA replication, and/or phage regulation, said inducing step will depend on the bacteriophage from which said sequences are derived. Typically, said inducing step can be a thermal induction (for phages that are naturally triggered by this signal or engineered repressors such as lambda cI), small molecule inducers (depending on the phage), any signal triggering SOS response (for instance addition of mitomycin), etc.

Unless defined otherwise, all technical and scientific terms used herein have the same meaning as commonly understood by one of ordinary skills in the art to which this invention belongs.

It must be noted that as used herein, the singular forms "a", "an" and "the" include plural referents unless the context clearly dictates otherwise. Thus, for example, reference to "a cell" includes a plurality of such cells (e.g., a population of such cells). Similarly, reference to "a nucleic acid" includes one or more of such nucleic acids.

Although the invention has been described in conjunction with specific embodiments thereof, many alternatives, modifications and variations will be apparent to those skilled in the art. Accordingly, it is intended to embrace all such alternatives, modifications and variations to fall within the spirit and broad scope of the appended claims.

All publications, patents and patent applications mentioned in this specification are herein incorporated in their entirety by reference into the specification, to the same extent as if such individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The following examples are given for the purpose of illustrating various embodiments of the invention and are not meant to limit the present invention in any fashion.

SEQUENCES

| SEQ ID NO: | Description | Type |
|---|---|---|
| 1 | primase ori from the PICI of the *Escherichia coli* strain CFT073 | DNA |
| 2 | Restriction site | DNA |
| 3 | Primase ori deltaGAAABCC | DNA |
| 4 | Primase ori devoid of restriction sites | DNA |
| 5 | PICI primase-helicase | Protein |
| 6 | PICI primase-helicase | DNA |
| 7 | Lambda prophage structural operon | DNA |
| 8 | Complete edited structural "operon" | DNA |
| 9 | Payload pJ23115-GFP T7 cos 2.0 | DNA |
| 10 | p1884 plasmid | DNA |
| 11 | p1885 plasmid | DNA |
| 12 | T7 RNA polymerase version AAV | DNA |
| 13 | T7 RNA polymerase version AAV | Protein |
| 14 | T7 RNA polymerase version LVA | DNA |
| 15 | T7 RNA polymerase version LVA | Protein |
| 16 | AD1334 primer | DNA |
| 17 | AD1335 primer | DNA |
| 18 | AD1336 primer | DNA |
| 19 | AD1337 primer | DNA |
| 20 | AD1322 primer | DNA |
| 21 | AD1323 primer | DNA |
| 22 | BW4 genome | DNA |
| 23 | PAC7 genome | DNA |
| 24 | pANS514 plasmid | DNA |
| 25 | PAC7 cos of pAN594 | DNA |
| 26 | operon of gp15-gp19+gp45 | DNA |
| 27 | pAN241 vector | DNA |

EXAMPLES

Figure 1:
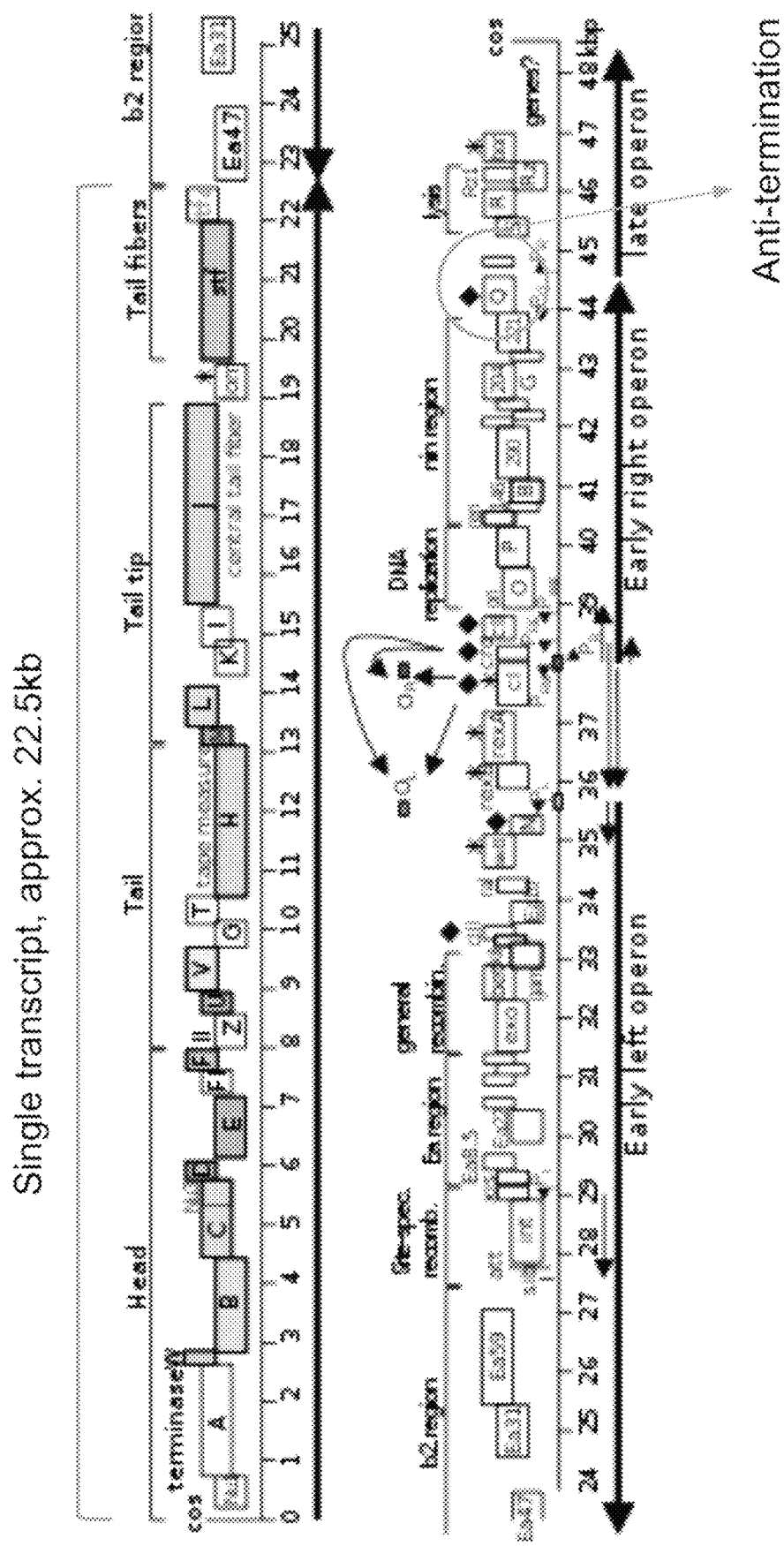
FIG. 1: Lambda genome organization (packaged variant). The structural operon is marked with a red line as well as the antitermination protein Q that allows transcription of the late structural operon. Figure adapted from Rajagopala et al. BMC Microbiol 11, 213 (2011).

Example 1: Exchange of the Structural Operon of Lambda for Elements of a Lytic Phage The inventors considered that phages can be viewed as more or less large genetic circuits whose final output is the generation of more phage particles. To do this, no matter if the phage is lytic, temperate or chronic (for instance filamentous phages such as M13), the information encoded in their genomes can be roughly categorized depending on the function it performs:

Genes devoted to insertion/excision (for temperate phages).

Genes devoted to DNA replication, RNA transcription, etc. . . . . Some lytic phages encode their own RNA or DNA polymerases, for instance. Some genes modify the host's RNA polymerases to be able to work past terminators, and some other genes are involved in the segregation of the prophage sequence if it exists in a plasmid or linear plasmid form.

Genes related to defense from host's anti-phage mechanisms, degradation/modification of host's elements to complete the lytic cycle, super-exclusion mechanisms or genes that are advantageous for the host.

Genes devoted to DNA packaging: terminases and accessory proteins, ligases, etc.

Structural genes devoted to building a protein capsid for the DNA: apart from strictly structural genes, such as capsid genes, tape measure, fibers, baseplate etc, many other genes are needed to assemble the components (chaperones, proteases) as well as proteins that can be packaged inside the capsid, be it as scaffold or as pilot proteins injected into the cell (for instance, the RNA polymerase of phage N4 or some minor pilot proteins in other phages).

The last two categories (DNA packaging and structural genes) are deeply connected, since the packaging machinery recognizes the pre-assembled heads and the DNA to be packaged, initiates and terminates DNA packaging.

The inventors hypothesized that by abstracting and differentiating all the modules defined above, in principle a system could be built that contains all excision/insertion, replication and regulation elements from one phage, in particular a non-lytic phage, and encodes the packaging/structural elements from another phage, in particular from a lytic phage, since, in principle, they could be viewed as independent genetic modules.

In the present example, it is referred to "structural elements" for proteins needed for DNA packaging and structural proteins needed to assemble a mature virion.

Such a "hybrid structural phage" could be very advantageous for different approaches, because:

a species which is more amenable for laboratory work/large scale production/safer could be used to produce such particles where the structural genes come from another species;

pure phagemid producing strains could be constructed using the regulatory elements of a well-characterized phage (for instance, Lambda) driving the production of capsids of a different phage, etc., and and finally, structural hybrid prophages (i.e. carried in the genome) driving the production of lytic phage capsids could be constructed.

This is the approach that was developed herein. Using a production strain encoding a system to generate pure Lambda phagemids, its structural operon has been exchanged (from the small terminase to the STF gene, about 23 kb) with the structural elements of a strictly lytic *E. coli* phage, T7. A schematic diagram shows the lambda genome organization (FIG. 1).

In this system, the thermolabile version of the prophage Lambda contains all regulatory elements needed to excise the prophage, replicate the circularized excised genome and drive the expression of the long, late operon, including the presence of the antitermination protein Q. This should drive the assembly and packaging of pure phagemid particles completely based on other phages when supplemented with a plasmid containing the correct packaging signals (LTR for T7)

Construction of the Hybrid

The Lambda prophage structural operon (SEQ ID NO: 7) was exchanged with the structural "operon" of the lytic phage T7, from gp6.5 to gp19.5 (not strictly an operon since the T7 RNA polymerase drives the transcription of different mRNAs within this region), using the lambda red recombineering system, starting from a production strain containing a Lambda prophage without the cos site (s1965). Several changes were further made:

Removal of putative holin and lysis genes in T7 (gp17.5 and gp18.5)

Recoding of the 3' part of the gp19 DNA maturation protein and the intergenic region between this gp19 and the next one, gp19.5 (explained below)

All T7 RNA polymerase promoters were left intact but no T7 RNA polymerase was added to the system.

The complete edited structural "operon" spans about 20 kb (SEQ ID NO: 8). The final production was named CY-L7 and was built without any specific remarks.

Production and Titrations

A payload was built that should be packaged by T7 as described in Auster et al. *RNA Biol.* 2019 April; 16(4):595-599, called pJ23115-GFP T7 cos 2.0 (p1883, SEQ ID NO: 9). This payload contains the 5' LTR necessary to be efficiently packaged by T7. The putative packaging region of this plasmid contains the 3' part of gp19 and the intergenic region between gp19 and gp19.5. It is for this reason that the 3' part of gp19 was recoded before inserting it into the genome of the production strain, so recombination is prevented.

Next, the CY-L7 strain was transformed with the p1883 payload and productions carried out as described below.

Overnight cultures were diluted 1:6 in a final volume of LB+5 mM $CaCl_2$ supplemented with chloramphenicol and grown for 30 min at 30° C. with shaking. After that, a 45-minute-long heat shock at 42° C. was performed. Finally the cultures were grown at 37° C. for 3 hours with shaking. After this period, cells were recovered by centrifugation and lysed using 3 mL of B-PER protein extraction reagent, 600 mg of detergent removal bio-beads were added and an incubation at room temperature with mild shaking performed for 1 hour. After that, the lysates were centrifuged for 10 min at 10,000 g and the supernatants filtered through a 0.2 micron pore-size membrane.

The lysates were titrated in *E. coli* MG1655 and KEIO-waaG (a derivative with a deletion of the waaG gene, which has been shown to be necessary for T7 binding, (Qimron et al. Proc Natl Acad Sci USA. (2006) 103(50):19039-19044)). If phagemids are produced, colonies should only be detected in the MG1655 strain, since the KEIO-waaG does not contain the receptor for T7.

Figure 2:
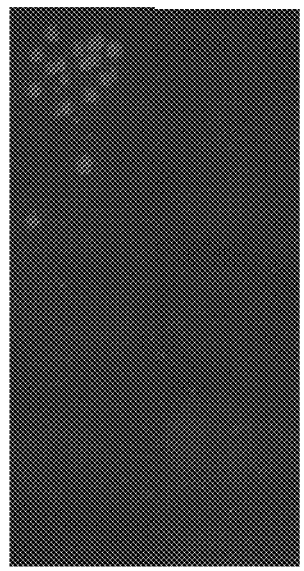
FIG. 2: Titration of T7 phagemids produced in a Lambda-T7 hybrid prophage system. Production strain CY-L7 contains the payload p1883. Left panel, titration on MG1655; right panel, titration on KEIO-waaG.

As can be seen in FIG. 2, a small number of colonies could be detected only in the MG1655 columns. This result is the first proof that a strictly lytic phage can be "tamed" and its structural and packaging genes controlled by a lysogenic one (lambda) to yield pure phagemid particles based on T7.

The titers obtained were very low, although pure T7-based phagemids were produced. The inventors sought to improve the titers by applying different rational approaches. For instance, it is known that for T7 plasmid or genome packaging, transcription by the T7 RNA polymerase from a promoter within the 5' LTR is needed (Chung et al. J Mol Biol. 1990 Dec. 20; 216(4):927-38). Additionally, the T7 genome is transcribed by its cognate RNA polymerase and many different T7 promoters are found, even within the region encoding the different structural elements (Dunn et al. J Mol Biol. 1983 Jun. 5; 166(4):477-535). This produces different mRNAs that are then processed by the *E. coli* RNAse III (Studier et al. "Processing of bacteriophage T7 RNAs by RNase III" Ed: Thomas R. Russell, Keith Brew, Harvey Faber, Julius Schultz, From Gene to Protein: Information Transfer in Normal and Abnormal Cells, Academic Press, 1979, p. 261-269). For these two reasons, the production strain was complemented with the T7 RNA polymerase in trans, in an inducible plasmid under the control of the PhlF repressor.

Initially, the transformation of the T7 RNA polymerase plasmid in the CY-L7 strain containing the p1883 payload gave no colonies, presumably due to toxicity coming from leakiness of the inducible pphlF promoter (data not shown). For this reason, two alternative plasmids encoding the T7 RNA polymerase with two different degradation tags of different strengths were built (p1884, SEQ ID NO: 10; and p1885, SEQ ID NO: 11). The sequences of the T7 RNA polymerase encoded in these two plasmids are disclosed (SEQ ID NO: 12 and SEQ ID NO: 13 for version AAV; SEQ ID NO: 14 and SEQ ID NO: 15 for version LVA). It has been demonstrated that by adding a degradation tag to a protein, the potential effects of leaky expression from a repressible promoter are improved (Fernandez-Rodriguez et al. Nucleic Acids Res. (2016) 44(13):6493-6502).

Productions were carried out from strain CY-L7 harboring the payload p1883 and supplemented with the T7 RNA polymerase variants encoded in plasmids p1884 or p1885, with the same protocol specified above. The lysates were then titrated on MG1655 or on KEIO-waaG.

Figure 3:
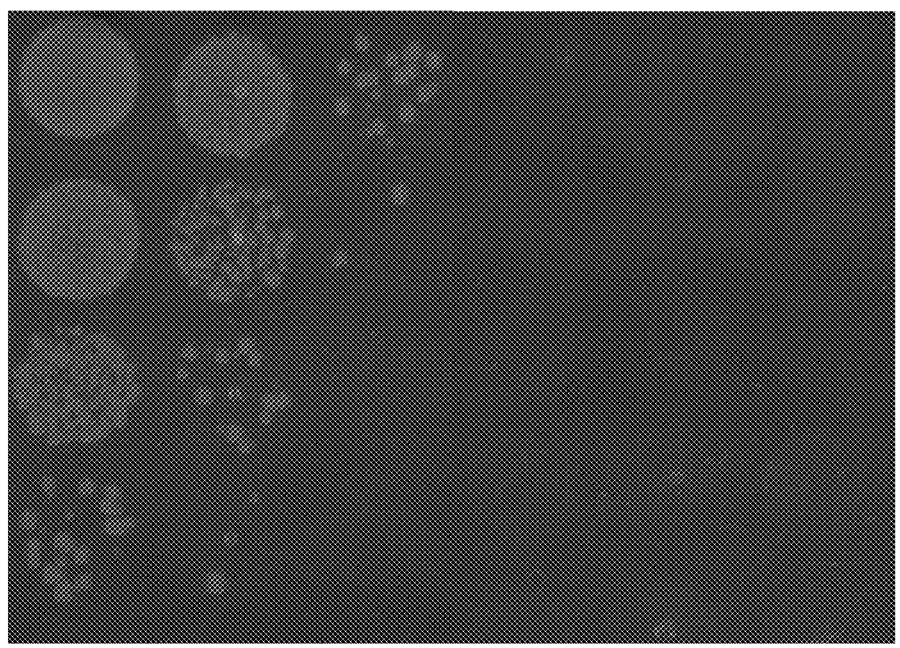
FIG. 3: Titration of T7 phagemids produced in a Lambda-T7 hybrid prophage system. Left panel, titration on MG1655. Right panel, titration on KEIO-waaG. From left to right: left) payload p1883+p1885 (T7 RNA polymerase with fast degradation); middle) payload p1883+p1884 (T7 RNA polymerase with medium strength degradation); right) payload p1883 only.

As can be seen on FIG. 3, the introduction of the T7 RNA polymerase increases the titers obtained by a factor of 100× (for the medium degradation tag) or by 1000× (for the fast degradation tag) as compared to productions harboring the p1883 payload only. The titers obtained in this system are about $2 \times 10^6$ TU/mL.

These experiments show that, for certain types of phages, a regulatory protein not belonging strictly to the structural categories defined above may be needed, in this case the T7 RNA polymerase, either to improve or promote the packaging reaction or to control the amount or processing of the mRNAs encoding the structural components.

Example 2: Production of *Cutibacterium acnes* Phage-Derived Particles

*Cutibacterium acnes* is one of the most prevalent and abundant species of the skin (Kashaf et al. Nat Microbiol 7, 169-179 (2022)) where it colonizes the pilosebaceous unit (PSU). Unlike on the stratum corneum, bacteria present in the PSU are surrounded by living cells notably keratinocytes, sebocytes and different immune cells (Kabashima et al. Nat Rev Immunol 19, 19-30 (2019)). Close contact between *C. acnes* and these cells might lead to either beneficial or detrimental interactions. (Bruggemann et al. *Front Microbiol* 12, 673845 (2021)). Being able to genetically modify *C. acnes* was notoriously challenging before the applicant's' new tools as disclosed in US applications US2022/135986 and US2022/135987. In these patent applications, the inventors described, for the first time, the production of *C. acnes* phage-derived particles using *C. acnes* as a production strain.

In the present example, the inventors used *P. freudenreichii* strain to produce *C. acnes* phage-derived particles by swapping the structural genes from a *P. freudenreichii* prophage for the structural genes of a *C. acnes* phage.

Results

Isolation of BW4 Phage

*P. freudenreichii* and associated bacteriophages are known to be present in some dairy products (Gautier et al. (1995) *Lait* 75:427-434; Gautier et al. (1995) *Appl. Environ. Microbiol.* 61:2572-2576; Cheng et al. (2018) *BMC Microbiology* 18:19). The inventors therefore screened for the presence of both *Propionibacterium* phages or *P. freudenreichii* lysogens in cheese samples.

Different types of cheese samples were grinded, resuspended in Reinforced Clostridial Medium (RCM) and incubated at 30° C. in anaerobic conditions for 2 days. After incubation, a dilution of the culture was performed in lithium glycerol broth, a media selective for Propionibacteria (WO1994017201), and incubated for 6 days at 30° C. A final dilution in RCM+mitomycin C was incubated for 1 day at 30° C. in order to induce potential prophages. The induced cultures were filtered (0.2 μm) and spotted on different indicator strains. One of the samples led to turbid plaque formation on top agar of the *P. freudenreichii* strain Pf0s2841. Three individual plaques were isolated by two successive picking and streaking on Pf0s2841 and amplification was performed on top agar of Pf0s2841. For the three different plaques, amplification led to phage suspension $\sim 10^{10}$ PFU/mL.

Two clusters of temperate dsDNA *P. freudenreichii* phages (BW and BV) have been previously identified (Cheng et al. (2018) *BMC Microbiology* 18:19). Using PCRs, designed on BW genome from Doucette phage (KX620751), two different fragments were extracted:

ORF3 with AD1334 (SEQ ID NO: 16)/AD1335 (SEQ ID NO: 17)

ORF5 with AD1336 (SEQ ID NO: 18)/AD1337 (SEQ ID NO: 19).

Figure 4:
FIG. 4: Identification of *P. freudenreichii* phages with PCR. PCR on ORF3 and ORF5 was performed on all phage suspensions. BW4 from plaques 1-3 give a band at the expected size for both orf3 and orf5. Ladder is GeneRuler 1 kb plus.
Figure 4:
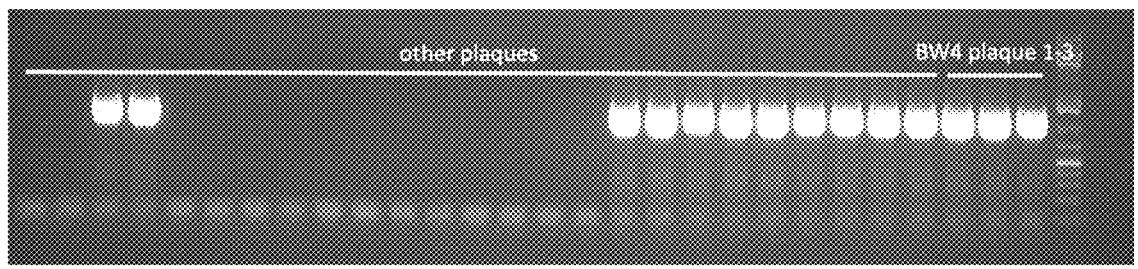

The inventors could classify the isolated phages as BW-like (FIG. 4). Sequencing of ORF5 revealed that all phages were most probably identical and therefore were coming from the same BW-like phage that was named BW4.

Isolation of Pf0s2841 Lysogen Carrying the BW4 Phage

The inventors then isolated *P. freudenreichii* lysogen carrying the BW4 phage as a prophage. For that, BW4 phage suspension was spotted on strain Pf0s2841 and incubated for 3 days. Turbid plaques were picked, resuspended and streaked. After 5 days, single colonies were obtained, several colonies were streaked and incubated a second and third time and presence of the phage genes was checked, at each streaking, by PCR, after DNAse treatment, across the cohesive ends (AD1322 (SEQ ID NO: 20)/AD1323 (SEQ ID NO: 21)) to ensure presence of the phage but absence of phage particles.

Figure 5:
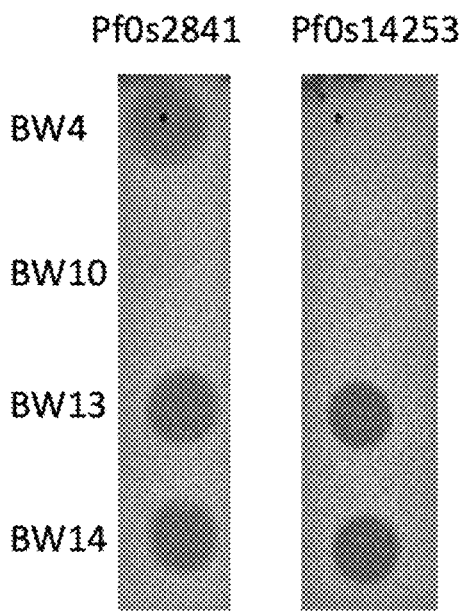
FIG. 5: Immunity to superinfection of lysogen Pf0s14253. Left panel: Top agar of Pf0s2841 with spots of 4 different BW-like phage suspensions. Right panel: Top agar of Pf0s14253 with spots of 4 different BW-like phage suspensions.

After the third streak, colonies were grown as a top agar and a spot of non diluted BW-like phages suspensions were spotted on the putative lysogenic strain (Pf0s14253) and on the ancestor strain (Pf0s2841). After incubation, clearance was observed for both strains for BW13 and BW14 spots whereas clearance was only observed for Pf0s2841 in the case of BW4 spot (FIG. 5). This indicates that the strain Pf0s14253 is immune to BW4 phage superinfection and carries the BW4 prophage. The absence of immunity for BW14 and BW13 indicates that these phages have likely a different immunity repressor.

BW4 Prophage Induction

Figure 6:
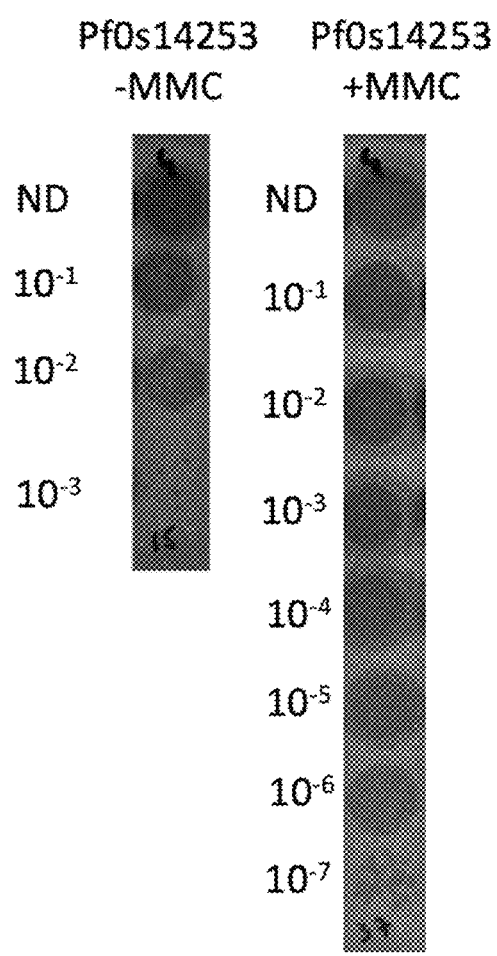
FIG. 6: High induction of BW4 phage after mitomycin C treatment. Left panel: Top agar of Pf0s2841 with spots of culture supernatant from Pf0s14253 without mitomycin C (MMC) induction (ND: non diluted to dilution $10^{-3}$). Right panel: Top agar of Pf0s2841 with spots of culture supernatant from Pf0s14253 with 0.5 µg/ml of mitomycin C induction (ND: non diluted to dilution $10^{-7}$)

In order to use the BW4 lysogen strain as a production strain for phage-derived particles the inventors first had to test the ability to produce high concentration of the BW4 phage upon induction of the lytic cycle. To do so, Pf0s14253 was grown in absence or presence of mitomycin C (MMC), an antibiotic known to induce prophages, and the culture supernatant was titered for the presence of BW4 phage particles on the indicator strain Pf0s2841. A high amount of BW4 phage particles was observed in the condition supplemented with mitomycin C (FIG. 6) with $7.4 \times 10^7$ PFU/μL against $3.0 \times 10^3$ PFU/μL for the condition without mitomycin C. This indicates a high dynamic range between lytic and lysogenic cycle for BW4 prophage under such conditions and confirmed the potential of BW4 for the production of phage-derived particles.

Sequencing and Annotation of BW4 Phage

To engineer the BW4 prophage towards production of *C. acnes* phage-derived particles, the BW4 phage was sequenced. DNA isolation (Promega Wizard DNA Clean-Up System) followed by Illumina sequencing was performed on BW4 phage suspension. Raw reads were assembled into a single contig using Spades and termini were corrected by sanger sequencing (SEQ ID NO: 22). Annotation was performed using Phaster and manually curated based on homologies with other BW-like phages (Cheng et al. (2018) *BMC Microbiology* 18:19).

As described in Cheng et al. (2018) *BMC Microbiology* 18:19, BW-like phages have typical genomic architecture of other temperate phages with a large putative structural operon (also called lytic operon) organized in different functional modules with, in order of transcription: packaging, head, tail, and lysis module. Surprisingly, the first gene of the putative operon (gp1) appears to be related to DNA replication based on HHpred as it contains a domain similar to bifunctional primase and polymerase proteins. Other parts of the BW4 phage genome contain the genes necessary for prophage integration/excision, DNA replication, DNA recombination, regulation of the lytic/lysogenic cycle and other accessory proteins. This modular architecture confirms the possibility to swap the genes necessary for the production of BW4 phage capsid and the packaging of the phage genome by their equivalent from a *C. acnes* phage genome.

Isolation of *C. acnes* PAC7 Phage

*C. acnes* phages were isolated from skin of healthy volunteers. Briefly a patch (Biore) was applied to the nose allowing to extract comedones that were resuspended in RCM, plated on MRS and incubated at 37° C. in anaerobic conditions. For some of the plates, plaques could be observed in the dense lawn of *C. acnes*. DPBS (Dulbecco's Phosphate Buffered Saline) was poured on the plate to resuspend potential phages and filtered to remove bacteria. This phage suspension was streaked on plate and a top agar of strain Ca0s2345 was added. Plates were incubated for 2 days and plaques were reisolated by three successive picking, streaking and top agar plating. Finally a plaque was amplified on top agar with Ca0s2345 strain and the resulting phage suspension was PEG precipitated. High titer ($>10^6$ PFU/μL) phage suspension was obtained when titered on Ca0s2345.

Sequencing and Annotation of PAC7 Phage

Figure 7:
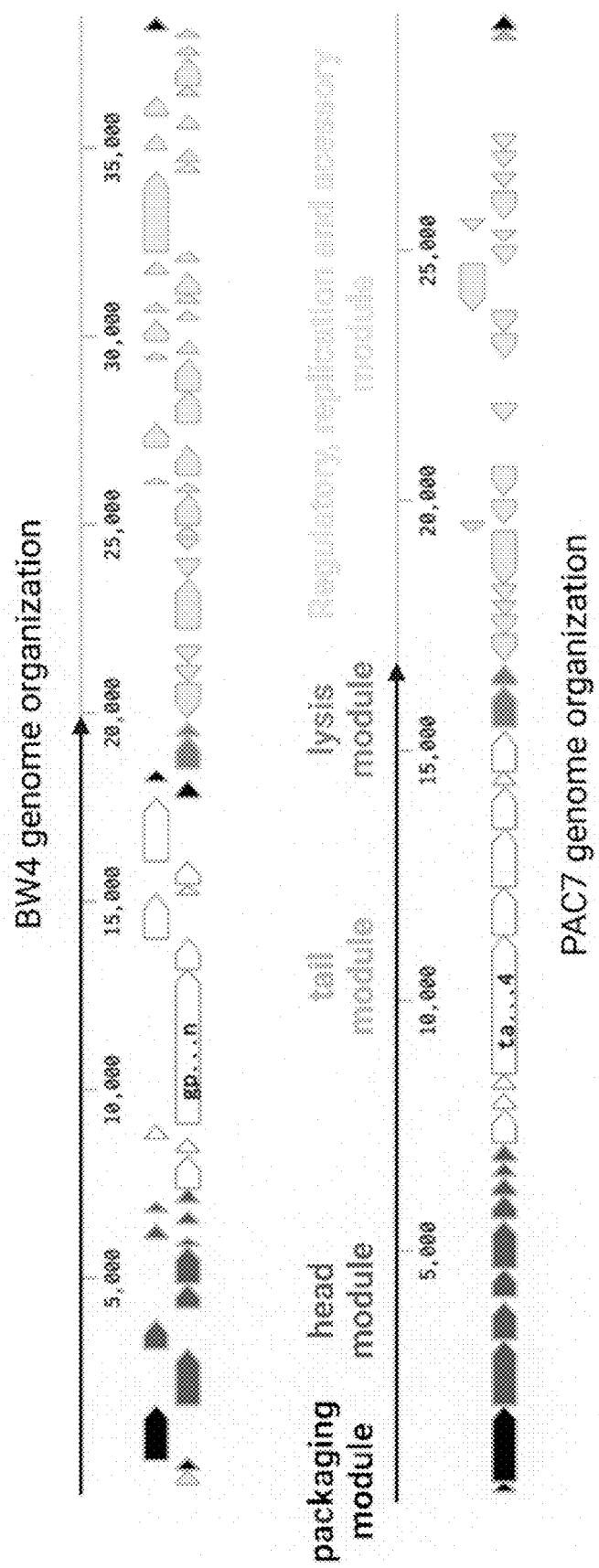
FIG. 7: Genome organization of BW4 and PAC7 bacteriophages. BW4 and PAC7 genome organization is similar with both putative structural operons (represented by the arrows) containing the packaging, head, tail and lysis modules.

DNA isolation (Promega Wizard DNA Clean-Up System) followed by Illumina sequencing was performed on PAC7 phage suspension. Raw reads were assembled into a single contig using Spades and termini were corrected by sanger sequencing (SEQ ID NO: 23). Annotation was performed using Phaster and manually curated based on homologies with other *C. acnes* phages (Marinelli et al. (2012) *mBio* 3:e00279-12). Similar to the *P. freudenreichii* BW4 phage, a structural operon comprising modules for packaging, head and tail assembly and cell lysis was identified (FIG. 7). An HNH endonuclease was identified as the last gene of the phage (gp45). Such endonuclease has already been shown to be essential for efficient packaging (Quiles-Puchalt et al. (2014) *Proc Nat. Acad. Sci.* 111:6016-6021).

Construction of Lysogen Strain with a Chimeric BW4-PAC7 Prophage

Figure 8:
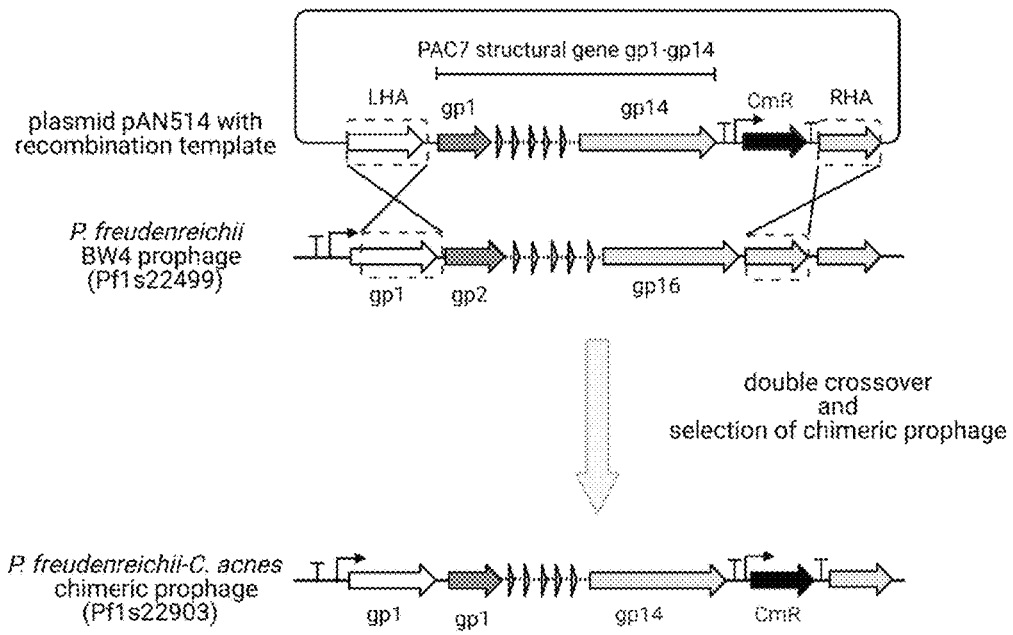
FIG. 8: Construction of chimeric BW4-PAC7 prophage. Transformation of the pAN514 suicide plasmid into strain Pf1s22499 containing the BW4 prophage. Selection on chloramphenicol was used to select for double crossover at the Left Homology Arm (LHA) and Right Homology Arm (RHA). The prophage obtained is a chimer containing a structural operon with first BW4 gp1 followed by gp1-gp14 of PAC7 and after the chloramphenicol selection cassette (CmR) the leftover of BW4 structural genes (gp15-gp25).

The genes in the structural operon of BW4 prophage, from the small terminase gp2 to the tape-measure protein gp16 included, were replaced by the structural PAC7 genes from gp1 to gp14 (FIG. 8). This was performed by homologous recombination using plasmid pAN514 (SEQ ID NO: 24), a *P. freudenreichii* suicide vector that was cloned in *E. coli* DH10B. After transformation of the vector, a double crossing over event was selected in *P. freudenreichii* (Pf1s22499) by selection on chloramphenicol. The chimeric BW4-PAC7 structural operon integrity was globally confirmed by PCR and sanger sequencing of the entire chimeric structural operon.

Figure 9:
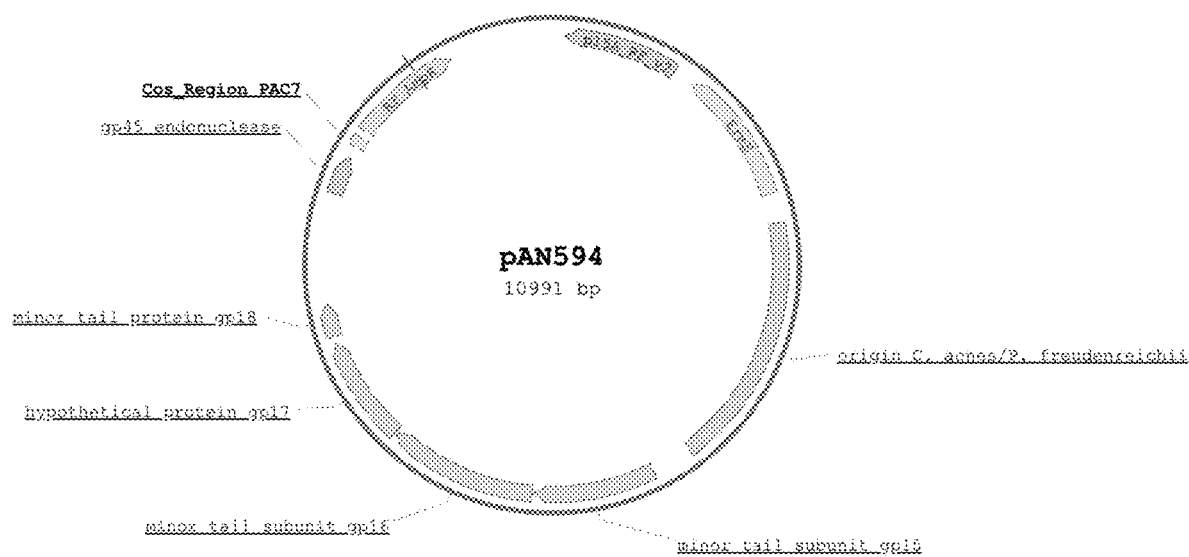
FIG. 9: Plasmid map of cosmid pAN594.

Production and Titration of PAC7 Derived Particles from a Lysogen Strain Carrying a Chimeric BW4-PAC7 Propage In order to produce *C. acnes* phage-derived particles from a *P. freudenreichii* BW4-PAC7 chimeric lysogen, the pAN594 cosmid (FIG. 9) containing the packaging signal of the PAC7 phage (SEQ ID NO: 25), an operon expressing five genes of the PAC7 tail module (gp15-gp19) and the gp45 endonuclease (SEQ ID NO: 26) and an origin of replication functional in *P. freudenreichii* and *C. acnes* (as disclosed in US applications US2022/135986 and US2022/135987) were transformed into Pf1s22903. Transformants were streaked and grown in presence of both chloramphenicol (1 µg/ml) to select for the presence of the prophage and erythromycin (2.5 µg/ml) to select for the presence of pAN594. At $OD_{600nm}$~0.4, culture was supplemented with 0.5 µg/ml of mitomycin C and grown overnight at 30° C. in anaerobic conditions. After incubation, cells were collected by centrifugation, lysed by bead beating (2×20 min at 30 Hz with 0.1 mm glass beads), supernatant was filtered and the presence of phage derived particles was titered on *C. acnes* Ca0s2258.

Figure 10:
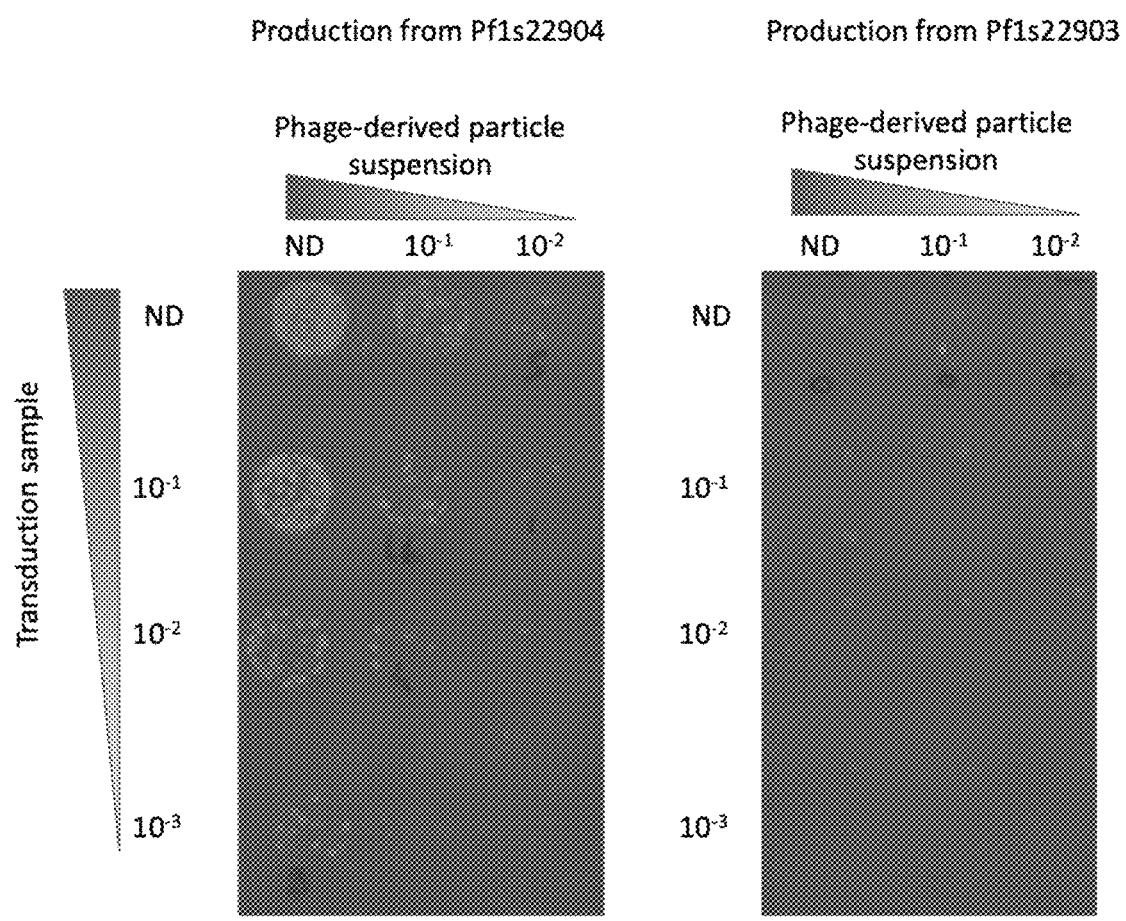
FIG. 10: Titration of PAC7 phage-derived particles. Left Panel: Titration from Pf1s22904 plated on erythromycin. Right Panel: Titration from control suspension of strain Pf1s22903 that does not carry any cosmid plated on erythromycin.
Figure 11:
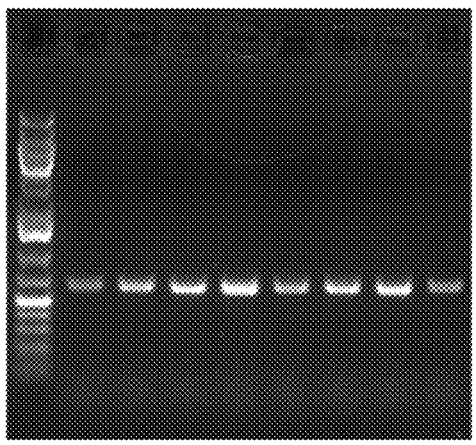
FIG. 11: Confirmation for 8 colonies streaked from phage-derived particles titration of Pf1s22904 production by PCR. Top Panel: SLTS PCR (Scholz 2014) on 8 colonies streaked from the phage derived titration assay. Expected size is 612 bp. Bottom Panel: pAN594 specific PCR on 8 colonies. Expected size is 769 bp. Ladder is generuler 1 kb plus.
Figure 11:
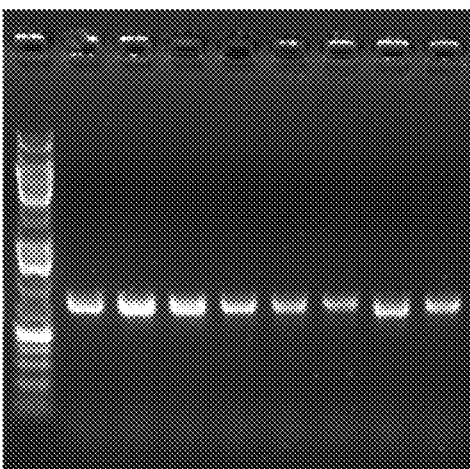

Up to ~$10^2$ potential transductants per µL were obtained (FIG. 10). 8 colonies were streaked on Brain Heart Infusion (BHI) erythromycin (5 µg/mL) and confirmed to be *C. acnes* and transductants carrying pAN594 using PCR (FIG. 11).

The inventors thus demonstrated for the first time that *C. acnes* phage-derived particles able to deliver DNA into *Cutibacterium acnes* can be produced by swapping structural genes of a *P. freudenreichii* prophage for the structural genes of a *Cutibacterium acnes* phage.

Material and Methods

Strain Used and Generated

TABLE 1

Strains used and generated

| Eligo ID | Description |
|---|---|
| Pf0s2841 | Indicator strain for *P. freudenreichii* BW4 phage (CIRM-BIA 509, TL110 belonging to INRAE) |
| Pf0s14253 | Strain Pf0s2841 with a BW4 prophage |
| Pf1s22499 | Strain Pf0s14253 with the packaging signal of BW4 deleted |
| Pf1s22903 | Strain Pf1s22499 with the BW4 genes gp2-gp16 replaced by PAC7 gp1-gp14 |
| Pf1s22904 | Strain Pf1s22903 with pAN594 |
| Ca0s2345 | Indicator strain for *C. acnes* PAC7 phage |
| Ca0s2258 | *Cutibacterium acnes* ATCC 11828 |

Culture Conditions

All incubations of *P. freudenreichii* strains were performed at 30° C. in anaerobic conditions (Thermo Scientific™ Sachet Oxoid™ AnaeroGen).

All incubations of *C. acnes* strains were performed at 37° C. in anaerobic chamber.

Construction of Strain Pf1s22499

Deletion of the packaging signal from BW4 prophage was performed by homologous recombination and CRISPR-Cas selection of the recombinant using the pAN241 *P. freudenreichii* vector that was cloned in *E. coli* and then transformed into Pf0s14253 strain. The pAN241 vector contains a template for homologous recombination (SEQ ID NO: 27) and a FnCpf1 transcriptional cassette with a crRNA targeting the cos of the BW4 prophage.

Transformation Protocol for *P. freudenreichii*

Transformation of *P. freudenreichii* was adapted from Brede, D. A. et al. *Appl Environ Microb* 71, 8077-8084 (2005), replacing SLB (sodium lactate broth) media for BHI.

Phage-Derived Particles Titration

Strain Ca0s2258 was streaked on BHI agar plate. Once dense growth on plate was obtained, a liquid culture was set up in BHI. After overnight incubation, the turbid culture was concentrated 10× in BHI. 90 µl of cells were mixed with pure, diluted 1/10 and diluted 1/100 solutions of 10 µL of phage-derived particles produced from either Pf1s22904 or Pf1s22903 as negative control. Samples were incubated 2 hours at room temperature and then 1/10 serial dilutions were performed in BHI, samples were incubated 2 h at 37° C. in anaerobic conditions before spotting 4 µL on BHI+5 µg/mL erythromycin. Plates were incubated for 7 days at 37° C. in anaerobic conditions.

The invention claimed is:

1. Production bacterial cell for producing lytic phage particles or lytic phage-derived delivery vehicles, said production bacterial cell stably comprising the phage structural genes and phage DNA packaging genes of a lytic bacteriophage,
   wherein the expression of said phage structural genes and said phage DNA packaging genes in said production bacterial cell is controlled by an induction mechanism comprising phage excision/insertion genes, phage DNA replication genes, and phage regulation genes of a second, non-lytic bacteriophage, wherein said phage excision/insertion genes, phage DNA replication genes and phage regulation genes are neither phage DNA packaging genes nor phage structural genes,
   wherein said production bacterial cell does not comprise phage excision/insertion genes and/or phage replication genes of the lytic bacteriophage,
   wherein said production bacterial cell is a *P. freudenreichii* bacterial cell,
   wherein the lytic bacteriophage is a *C. acnes* phage and wherein the second, non-lytic bacteriophage is a *P. freudenreichii* phage.

2. The production bacterial cell according to claim 1, wherein said bacterial cell further comprises a payload to be packaged into said phage particles or phage-derived delivery vehicles.

3. The production bacterial cell according to claim 2, wherein said payload is a nucleic acid payload comprising a packaging site derived from said lytic bacteriophage.

4. The production bacterial cell according to claim 2, wherein said payload is to be delivered into targeted bacterial cells.

5. The production bacterial cell according to claim 4, wherein said payload is stably maintained in said targeted bacterial cells.

6. The production bacterial cell according to claim 4, wherein said payload does not replicate in said targeted bacterial cells.

7. The production bacterial cell according to claim 4, wherein said payload comprises a sequence of interest.

8. The production bacterial cell according to claim 7, wherein said sequence of interest only generates an effect in said targeted bacterial cells.

9. The production bacterial cell according to claim 8, wherein said targeted bacterial cells are from a species or strain different from the production bacterial cell.

10. The production bacterial cell according to claim 1, wherein said induction mechanism further controls the copy number of said phage structural genes and said phage DNA packaging genes.

11. The production bacterial cell according to claim 2, wherein said induction mechanism further controls the copy number of said payload in said production bacterial cell.

12. The production bacterial cell according to claim 2, wherein another induction mechanism controls the copy number of said payload in said production bacterial cell.

13. The production bacterial cell of claim 1, wherein said phage structural genes and phage DNA packaging genes of said lytic bacteriophage are comprised in at least one plasmid, chromosome and/or helper phage.

14. The production bacterial cell according to claim 1, wherein said production bacterial cell is from the same bacterial strain as the bacterial strain from which said non-lytic bacteriophage comes and/or that said non-lytic bacteriophage targets.

15. The production bacterial cell according to claim 1, comprising the entire structural operon of the lytic bacteriophage.

* * * * *

SEQUENCE LISTING

<160> NUMBER OF SEQ ID NOS: 27

<210> SEQ ID NO 1
<211> LENGTH: 282
<212> TYPE: DNA
<213> ORGANISM: Artificial Sequence
<220> FEATURE:
<223> OTHER INFORMATION: primase ori from the PICI of the Escherichia coli strain CFT073

<400> SEQUENCE: 1

-continued

```
tttgttgcaa tggctgtcta ccctgtctac ctgagtaaag aaaaatacat ttaattcagt    60
acattaactt gggtagacag cctttttta ctgtctacct actatctacc ctctctacct    120
gattttacct gaatcagaca gggaggtaga tacggggtag atagtggata aaagcactct   180
accccactga aagccgcgcc attactggca tggtggccag taaggtagat aaggtagaca   240
aggggaggca caactcaaaa cttttaaac gagggggtaa aa                       282
```

<210> SEQ ID NO 2
<211> LENGTH: 13
<212> TYPE: DNA
<213> ORGANISM: Artificial Sequence
<220> FEATURE:
<223> OTHER INFORMATION: restriction site
<220> FEATURE:
<221> NAME/KEY: misc_feature
<222> LOCATION: (5)..(10)
<223> OTHER INFORMATION: n is a, c, g, or t

<400> SEQUENCE: 2

```
twcannnnnn tgg                                                       13
```

<210> SEQ ID NO 3
<211> LENGTH: 282
<212> TYPE: DNA
<213> ORGANISM: Artificial Sequence
<220> FEATURE:
<223> OTHER INFORMATION: Primase ori deltaGAAABCC

<400> SEQUENCE: 3

```
tttgttgcaa tggctgtcta ccctgtctac ctgagtaaag aaaaatacat ttaattcagt    60
acattaactt gggtagacag cctttttta ctgtctacct actatctacc ctctctacct    120
gattttacct gaatcagaca gggaggtaga tacggggtag atagtggata aaagcactct   180
accccactga aagcagcgcc attactggca tggtggccag taaggtagat aaggtagaca   240
aggggaggca caactcaaaa cttttaaac gagggggtaa aa                       282
```

<210> SEQ ID NO 4
<211> LENGTH: 282
<212> TYPE: DNA
<213> ORGANISM: Artificial Sequence
<220> FEATURE:
<223> OTHER INFORMATION: Primase ori devoid of restriction sites

<400> SEQUENCE: 4

```
tttgttgcaa tggctgtcta ccctgtctac ctgagtaaag aaaaatacat ttaattcagt    60
atattaactt gggtagacag cctttttta ctgtctacct tctgtctacc ctctctacct    120
gattttacct gaatcagaca gggaggtaga cacggggtag acagtggata aaagcactct   180
accccactga aagcagtgcc attactggca tggttgccag taaggttgat aaggtagaca   240
aggggaggga caactcaaaa cttttaaac gagggggtaa aa                       282
```

<210> SEQ ID NO 5
<211> LENGTH: 584
<212> TYPE: PRT
<213> ORGANISM: Artificial Sequence
<220> FEATURE:
<223> OTHER INFORMATION: PICI primase-helicase

<400> SEQUENCE: 5

```
Met Lys Leu Ala Pro Asn Val Lys Gln Gln Ser Arg Gly Ile Lys His
1               5                   10                  15
```

-continued

```
Lys Glu Thr Glu Val Ile Ile Phe Ala Gly Ser Asp Ala Trp Ser His
             20                  25                  30

Ala Lys Gln Trp Gln Glu His Asp Ala Arg Met Ala Gly Asp Asn Glu
         35                  40                  45

Pro Pro Val Trp Leu Gly Glu Gln Gln Leu Ser Glu Leu Asp Lys Leu
 50                  55                  60

Gln Ile Val Pro Glu Gly Arg Lys Ser Val Arg Ile Phe Arg Ala Gly
 65                  70                  75                  80

Tyr Leu Ala Pro Val Met Ile Lys Ala Ile Gly Gln Lys Leu Ala Ala
                 85                  90                  95

Ala Gly Val Gln Asp Ala Asn Phe Tyr Pro Asp Gly Met His Gly Gln
             100                 105                 110

Lys Val Glu Asn Trp Arg Glu Tyr Leu Ala Arg Glu Arg Gln Asn Leu
         115                 120                 125

Ser Asp Gly Leu Val Ile Glu Leu Pro Val Lys Gln Lys Ala Gln Leu
130                 135                 140

Ser Gln Met Ala Asp Ser Glu Arg Ala Gln Leu Leu Ala Asp Arg Phe
145                 150                 155                 160

Asp Gly Val Cys Val His Pro Glu Ser Glu Ile Val His Val Trp Cys
                165                 170                 175

Gly Gly Val Trp Cys Pro Val Ser Thr Met Glu Leu Ser Arg Glu Met
            180                 185                 190

Val Ala Ile Tyr Ser Glu His Arg Ala Thr Phe Ser Lys Arg Val Ile
        195                 200                 205

Asn Asn Ala Val Glu Ala Leu Lys Val Ile Ala Glu Pro Met Gly Glu
210                 215                 220

Pro Ser Gly Asp Leu Leu Pro Phe Ala Asn Gly Ala Leu Asp Leu Lys
225                 230                 235                 240

Thr Gly Glu Phe Ser Pro His Thr Pro Glu Asn Trp Ile Thr Thr His
                245                 250                 255

Asn Gly Ile Glu Tyr Thr Pro Pro Ala Pro Gly Glu Asn Ile Arg Asp
            260                 265                 270

Asn Ala Pro Asn Phe His Lys Trp Leu Glu His Ala Ala Gly Lys Asp
        275                 280                 285

Pro Arg Lys Met Met Arg Ile Cys Ala Ala Leu Tyr Met Ile Met Ala
290                 295                 300

Asn Arg Tyr Asp Trp Gln Met Phe Ile Glu Ala Thr Gly Asp Gly Gly
305                 310                 315                 320

Ser Gly Lys Ser Thr Phe Thr His Ile Ala Ser Leu Leu Ala Gly Lys
                325                 330                 335

Gln Asn Thr Val Ser Ala Glu Met Thr Ser Leu Asp Asp Ala Gly Gly
            340                 345                 350

Arg Ala Gln Val Val Gly Ser Arg Leu Ile Val Leu Ala Asp Gln Pro
        355                 360                 365

Lys Tyr Thr Gly Glu Gly Thr Gly Ile Lys Lys Ile Thr Gly Gly Asp
370                 375                 380

Pro Val Glu Ile Asn Pro Lys Tyr Glu Lys Arg Phe Thr Ala Val Ile
385                 390                 395                 400

Arg Ala Val Val Leu Ala Thr Asn Asn Asn Pro Met Ile Phe Thr Glu
                405                 410                 415

Arg Ala Gly Gly Val Ala Arg Arg Val Ile Phe Arg Phe Asp Asn
            420                 425                 430
```

```
Ile Val Ser Glu Ala Glu Lys Asp Arg Glu Leu Pro Glu Lys Ile Ala
        435                 440                 445

Ala Glu Ile Pro Val Ile Ile Arg Arg Leu Leu Ala Asn Phe Ala Asp
450                 455                 460

Pro Glu Lys Ala Arg Ala Leu Leu Ile Glu Gln Arg Asp Gly Asp Glu
465                 470                 475                 480

Ala Leu Ala Ile Lys Gln Gln Thr Asp Pro Val Ile Glu Phe Cys Gln
                485                 490                 495

Phe Leu Asn Phe Leu Glu Glu Ala Arg Gly Leu Met Met Gly Gly Gly
            500                 505                 510

Gly Asp Ser Val Lys Tyr Thr Thr Arg Asn Ser Leu Tyr Arg Val Tyr
        515                 520                 525

Leu Ala Phe Met Ala Tyr Ala Gly Arg Ser Lys Pro Leu Asn Val Asn
    530                 535                 540

Asp Phe Gly Lys Ala Met Lys Pro Ala Ala Lys Val Tyr Gly His Glu
545                 550                 555                 560

Tyr Ile Thr Arg Lys Val Lys Gly Val Thr Gln Thr Asn Ala Ile Thr
                565                 570                 575

Thr Asp Asp Cys Asp Ala Phe Leu
            580
```

<210> SEQ ID NO 6
<211> LENGTH: 1752
<212> TYPE: DNA
<213> ORGANISM: Artificial Sequence
<220> FEATURE:
<223> OTHER INFORMATION: PICI primase-helicase

<400> SEQUENCE: 6

```
atgaaactgg caccgaacgt aaaacagcag tcacgcggca taaaacacaa agaaacagaa      60
gtcattattt ttgcgggtag tgatgcctgg tcacacgcaa acaatggcag gaacatgac     120
gcgcgtatgg ccggagataa tgagcctcct gtgtggcttg gggagcagca gttatccgaa     180
ctggataagc tgcaaattgt gccggaaggc agaaaatccg tgcgcatatt cagggccgga     240
tatcttgcgc agtaatgat aaaggcgatt ggtcagaagc tggcggcggc aggcgtacag     300
gatgcaaatt tttacccctga tggtatgcac ggtcagaagg tggagaactg cgcgaatat     360
ctggcccgtg agcgccagaa tctttctgat ggtctggtca ttgagcttcc ggtaaagcaa     420
aaggcgcaac tttcgcagat ggcggacagt gagcgcgcgc agctgcttgc cgatcgcttt     480
gatgccgttt gcgtacatcc tgaaagtgaa atcgttcacg tatggtgcgg cggggtatgg     540
tgtccggtca gcacaatgga gctgagccgc gaaatggtgg cgatctattc agagcacagg     600
gccactttca gcaagcgcgt aatcaataac gccgtggaag cgttaaaagt tattgccgaa     660
ccaatgggcg agccgtccgg cgatttgctg ccgttcgcca atggtgcgct tgacctgaaa     720
acggggggaat tttcccccgca cacgccgagg aactggatca ccacgcacaa cggcattgag     780
tacacgccac cagcacccgg ggagaacatc cgcgataacg cgccaaactt tcataaatgg     840
cttgagcacg cagccggaaa agacccgcgc aagatgatgc gtatatgtgc cgcgctgtac     900
atgattatgg cgaaccggta cgactggcag atgtttattg aggccaccgg agacggcggg     960
agcggtaaaa gtacattcac acacatagcc agccttctgg cagggaaaca aaacacggta    1020
agcgctgaaa tgcatcgct tgatgatgct ggtgggcgtg cgcaggttgt cgggagtcgt    1080
cttatcgtcc tggcagacca gccgaaatat acaggcgaag gaacgggcat caagaaaatc    1140
acgggcggcg accccgtgga aattaacccg aaatatgaaa agcgttttac ggcggtaatc    1200
```

| | |
|---|---|
| agggcggtgg tgctggcaac caataacaat ccgatgatat tcaccgaacg ggccggaggt | 1260 |
| gtggcacgtc gtcgggtgat attccggttc gataacatcg taagcgaggc agaaaaagac | 1320 |
| agggagctac cggaaaagat cgcggctgaa atccctgtca ttatccgccg cttgctggcg | 1380 |
| aactttgccg accctgaaaa ggcacgggct ttactcattg aacagcgtga cggtgatgaa | 1440 |
| gcactggcaa taaagcaaca gacggatccg gttattgagt tttgccagtt cctgaatttt | 1500 |
| ctggaggaag cacgcggcct gatgatgggc ggcggtggcg attcagtgaa gtacacgacc | 1560 |
| agaaacagcc tttaccgcgt ctatctggcg tttatggcgt acgcaggcag gagcaaaccg | 1620 |
| ctaaacgtaa atgactttgg caaggctatg aagccagccg cgaaagttta cggacatgaa | 1680 |
| tatattacgc ggaaagttaa aggagtaacg cagactaacg caataacaac agacgattgc | 1740 |
| gacgcgtttt ta | 1752 |

<210> SEQ ID NO 7
<211> LENGTH: 22368
<212> TYPE: DNA
<213> ORGANISM: Artificial Sequence
<220> FEATURE:
<223> OTHER INFORMATION: Lambda prophage structural operon

<400> SEQUENCE: 7

| | |
|---|---|
| atggaagtca acaaaaagca gctggctgac attttcggtg cgagtatccg taccattcag | 60 |
| aactggcagg aacagggaat gcccgttctg cgaggcggtg gcaagggtaa tgaggtgctt | 120 |
| tatgactctg ccgccgtcat aaaatggtat gccgaaaggg atgctgaaat tgagaacgaa | 180 |
| aagctgcgcc gggaggttga agaactgcgg caggccagcg aggcagatct ccagccagga | 240 |
| actattgagt acgaacgcca tcgacttacg cgtgcgcagg ccgacgcaca ggaactgaag | 300 |
| aatgccagag actccgctga agtggtggaa accgcattct gtactttcgt gctgtcgcgg | 360 |
| atcgcaggtg aaattgccag tattctcgac gggctccccc tgtcggtgca gcggcgtttt | 420 |
| ccggaactgg aaaaccgaca tgttgatttc ctgaaacggg atatcatcaa agccatgaac | 480 |
| aaagcagccg cgctggatga actgataccg gggttgctga gtgaatatat cgaacagtca | 540 |
| ggttaacagg ctgcggcatt tgtccgcgc cgggcttcgc tcactgttca ggccggagcc | 600 |
| acagaccgcc gttgaatggg cggatgctaa ttactatctc ccgaaagaat ccgcatacca | 660 |
| ggaagggcgc tgggaaacac tgcccttca gcgggccatc atgaatgcga tgggcagcga | 720 |
| ctacatccgt gaggtgaatg tggtgaagtc tgcccgtgtc ggttattcca aaatgctgct | 780 |
| gggtgtttat gcctacttta tagagcataa gcagcgcaac accctatctc ggttgccgac | 840 |
| ggatggtgat gccgagaact ttatgaaaac ccacgttgag ccgactattc gtgatattcc | 900 |
| gtcgctgctg cgctggccc gtggtatgg caaaaagcac cgggataaca cgctcaccat | 960 |
| gaagcgtttc actaatgggc gtggcttctg gtgcctgggc ggtaaagcgg caaaaaacta | 1020 |
| ccgtgaaaag tcggtggatg tggcgggtta tgatgaactt gctgcttttg atgatgatat | 1080 |
| tgaacaggaa ggctctccga cgttcctggg tgacaagcgt attgaaggct cggtctggcc | 1140 |
| aaagtccatc cgtggctcca cgccaaaagt gagaggcacc tgtcagattg agcgtgcagc | 1200 |
| cagtgaatcc ccgcatttta tgcgttttca tgttgcctgc ccgcattgcg gggaggagca | 1260 |
| gtatcttaaa tttggcgaca agagacgcc gtttggcctc aaatggacgc cggatgaccc | 1320 |
| ctccagcgtg tttatctct gcagcataa tgcctgcgtc atccgccagc aggagctgga | 1380 |
| ctttactgat gcccgttata tctgcgaaaa gaccgggatc tggacccgtg atggcattct | 1440 |

```
ctggttttcg tcatccggtg aagagattga gccacctgac agtgtgacct ttcacatctg    1500
gacagcgtac agcccgttca ccacctgggt gcagattgtc aaagactgga tgaaaacgaa    1560
aggggatacg ggaaaacgta aaaccttcgt aaacaccacg ctcggtgaga cgtgggaggc    1620
gaaaattggc gaacgtccgg atgctgaagt gatggcagag cggaaagagc attattcagc    1680
gcccgttcct gaccgtgtgg cttacctgac cgccggtatc gactcccagc tggaccgcta    1740
cgaaatgcgc gtatgggat gggggccggg tgaggaaagc tggctgattg accggcagat    1800
tattatgggc cgccacgacg atgaacagac gctgctgcgt gtggatgagg ccatcaataa    1860
aacctatacc cgccggaatg gtgcagaaat gtcgatatcc cgtatctgct gggatactgg    1920
cgggattgac ccgaccattg tgtatgaacg ctcgaaaaaa catgggctgt tccgggtgat    1980
ccccattaaa ggggcatccg tctacggaaa gccggtggcc agcatgccac gtaagcgaaa    2040
caaaaacggg gtttacctta ccgaaatcgg tacggatacc gcgaaagagc agatttataa    2100
ccgcttcaca ctgacgccgg aaggggatga accgcttccc ggtgccgttc acttcccgaa    2160
taacccggat atttttgatc tgaccgaagc gcagcagctg actgctgaag agcaggtcga    2220
aaaatgggtg gatggcagga aaaaaatact gtgggacagc aaaaagcgac gcaatgaggc    2280
actcgactgc ttcgttatg cgctggcggc gctgcgcatc agtatttccc gctggcagct    2340
ggatctcagt gcgctgctgg cgagcctgca ggaagaggat ggtgcagcaa ccaacaagaa    2400
aacactggca gattacgccc gtgccttatc cggagaggat gaatgacgcg acaggaagaa    2460
cttgccgctg cccgtgcggc actgcatgac ctgatgacag gtaaacgggt ggcaacagta    2520
cagaaagacg gacgaagggt ggagtttacg gccacttccg tgtctgacct gaaaaaatat    2580
attgcagagc tggaagtgca gaccggcatg acacagcgac gcaggggacc tgcaggattt    2640
tatgtatgaa aacgcccacc attcccaccc ttctggggcc ggacggcatg acatcgctgc    2700
gcgaatatgc cggttatcac ggcggtggca gcggatttgg agggcagttg cggtcgtgga    2760
acccaccgag tgaaagtgtg gatgcagccc tgttgcccaa ctttacccgt ggcaatgccc    2820
gcgcagacga tctggtacgc aataacggct atgccgccaa cgccatccag ctgcatcagg    2880
atcatatcgt cggtctttt ttccggctca gtcatcgccc aagctggcgc tatctgggca    2940
tcggggagga agaagcccgt gccttttccc gcgaggttga gcggcatgg aaagagtttg    3000 ccgaggatga ctgctgctgc attgacgttg agcgaaaacg cacgtttacc atgatgattc    3060
gggaaggtgt ggccatgcac gcctttaacg tgaactgtt cgttcaggcc acctgggata    3120
ccagttcgtc gcggcttttc cggacacagt tccggatggt cagcccgaag cgcatcagca    3180
acccgaacaa taccggcgac agccggaact gccgtgccgg tgtgcagatt aatgacagcg    3240
gtgcggcgct gggatattac gtcagcgagg acgggtatcc tggctggatg ccgcagaaat    3300
ggacatggat accccgtgag ttacccggcg gcgcgcctc gttcattcac gttttttgaac    3360 ccgtggagga cgggcagact cgcggtgcaa atgtgtttta cagcgtgatg gagcagatga    3420
agatgctcga cacgctgcag aacacgcagc tgcagagcgc cattgtgaag gcgatgtatg    3480
ccgccaccat tgagagtgag ctggatacgc agtcagcgat ggattttatt ctgggcgcga    3540
acagtcagga gcagcgggaa aggctgaccg gctggattgg tgaaattgcc gcgtattacg    3600
ccgcagcgcc ggtccggctg ggaggcgcaa aagtaccgca cctgatgccg ggtgactcac    3660
tgaacctgca gacggctcag gatacggata acggctactc cgtgtttgag cagtcactgc    3720
tgcggtatat cgctgccggg ctgggtgtct cgtatgagca gctttcccgg aattacgccc    3780
agatgagcta ctccacggca cgggccagtg cgaacgagtc gtgggcgtac tttatggggc    3840
```

```
ggcgaaaatt cgtcgcatcc cgtcaggcga gccagatgtt tctgtgctgg ctggaagagg   3900
ccatcgttcg ccgcgtggtg acgttacctt caaaagcgcg cttcagtttt caggaagccc   3960
gcagtgcctg ggggaactgc gactggatag gctccggtcg tatggccatc gatggtctga   4020
aagaagttca ggaagcggtg atgctgatag aagccggact gagtacctac gagaaagagt   4080
gcgcaaaacg cggtgacgac tatcaggaaa tttttgccca gcaggtccgt gaaacgatgg   4140
agcgccgtgc agccggtctt aaaccgcccg cctgggcggc tgcagcattt gaatccgggc   4200
tgcgacaatc aacagaggag gagaagagtg acagcagagc tgcgtaatct cccgcatatt   4260
gccagcatgg cctttaatga gccgctgatg cttgaacccg cctatgcgcg gttttctttt   4320
tgtgcgcttg caggccagct tgggatcagc agcctgacgg atgcggtgtc cggcgacagc   4380
ctgactgccc aggaggcact cgcgacgctg gcattatccg gtgatgatga cggaccacga   4440
caggcccgca gttatcaggt catgaacggc atcgccgtgc tgccggtgtc cggcacgctg   4500
gtcagccgga cgcgggcgct gcagccgtac tcggggatga ccggttacaa cggcattatc   4560
gcccgtctgc aacaggctgc cagcgatccg atggtggacg gcattctgct cgatatggac   4620
acgcccggcg ggatggtggc gggggcattt gactgcgctg acatcatcgc ccgtgtgcgt   4680
gacataaaac cggtatgggc gcttgccaac gacatgaact gcagtgcagg tcagttgctt   4740
gccagtgccg cctcccggcg tctggtcacg cagaccgccc ggacaggctc catcggcgtc   4800
atgatggctc acagtaatta cggtgctgcg ctggagaaac agggtgtgga aatcacgctg   4860
atttacagcg gcagccataa ggtggatggc aaccccctaca gccatcttcc ggatgacgtc   4920
cgggagacac tgcagtcccg gatggacgca acccgccaga tgtttgcgca gaaggtgtcg   4980
gcatataccg gcctgtccgt gcaggttgtg ctggataccg aggctgcagt gtacagcggt   5040
caggaggcca ttgatgccgg actggctgat gaacttgtta acagcaccga tgcgatcacc   5100
gtcatgcgtg atgcactgga tgcacgtaaa tcccgtctct caggagggcg aatgaccaaa   5160
gagactcaat caacaactgt ttcagccact gcttcgcagg ctgacgttac tgacgtggtg   5220
ccagcgacgg agggcgagaa cgccagcgcg gcgcagccgg acgtgaacgc gcagatcacc   5280
gcagcggttg cggcagaaaa cagccgcatt atggggatcc tcaactgtga ggaggctcac   5340
ggacgcgaag aacaggcacg cgtgctggca gaaaccccccg gtatgaccgt gaaaacggcc   5400
cgccgcattc tggccgcagc accacagagt gcacaggcgc gcagtgacac tgcgctggat   5460
cgtctgatgc aggggcacc ggcaccgctg gctgcaggta acccggcatc tgatgccgtt   5520
aacgatttgc tgaacacacc agtgtaaggg atgtttatga cgagcaaaga aacctttacc   5580
cattaccagc cgcagggcaa cagtgacccg gctcataccg caaccgcgcc cggcggattg   5640
agtgcgaaag cgcctgcaat gacccccgctg atgctggaca cctccagccg taagctggtt   5700
gcgtgggatg gcaccaccga cggtgctgcc gttggcattc ttgcggttgc tgctgaccag   5760
accagcacca cgctgacgtt ctacaagtcc ggcacgttcc gttatgagga tgtgctctgg   5820
ccggaggctg ccagcgacga gacgaaaaaa cggaccgcgt ttgccggaac ggcaatcagc   5880
atcgtttaac tttaccccttc atcactaaag gccgcctgtg cggctttttt tacgggattt   5940
ttttatgtcg atgtacacaa ccgcccaact gctggcggca aatgagcaga aatttaagtt   6000
tgatccgctg tttctgcgtc tcttttttccg tgagagctat cccttcacca cggagaaagt   6060
ctatctctca caaattccgg gactggtaaa catggcgctg tacgtttcgc cgattgtttc   6120
cggtgaggtt atccgttccc gtggcggctc cacctctgaa tttacgccgg gatatgtcaa   6180
```

```
gccgaagcat gaagtgaatc cgcagatgac cctgcgtcgc ctgccggatg aagatccgca    6240
gaatctggcg gacccggctt accgccgccg tcgcatcatc atgcagaaca tgcgtgacga    6300
agagctggcc attgctcagg tcgaagagat gcaggcagtt tctgccgtgc ttaagggcaa    6360
atacaccatg accggtgaag ccttcgatcc ggttgaggtg gatatgggcc gcagtgagga    6420
gaataacatc acgcagtccg gcggcacgga gtggagcaag cgtgacaagt ccacgtatga    6480
cccgaccgac gatatcgaag cctacgcgct gaacgccagc ggtgtggtga atatcatcgt    6540
gttcgatccg aaaggctggg cgctgttccg ttccttcaaa gccgtcaagg agaagctgga    6600
tacccgtcgt ggctctaatt ccgagctgga cagcggtg aaagacctgg gcaaagcggt    6660
gtcctataag gggatgtatg gcgatgtggc catcgtcgtg tattccggac agtacgtgga    6720
aaacggcgtc aaaagaact tcctgccgga caacacgatg gtgctgggga acactcaggc    6780
acgcggtctg cgcacctatg gctgcattca ggatgcggac gcacagcgcg aaggcattaa    6840
cgcctctgcc cgttacccga aaaactgggt gaccaccggc gatccggcgc gtgagttcac    6900
catgattcag tcagcaccgc tgatgctgct ggctgaccct gatgagttcg tgtccgtaca    6960
actggcgtaa tcatggccct tcggggccat tgtttctctg tggaggagtc catgacgaaa    7020
gatgaactga ttgcccgtct ccgctcgctg ggtgaacaac tgaaccgtga tgtcagcctg    7080
acggggacga agaagaact ggcgctccgt gtggcagagc tgaaagagga gcttgatgac    7140
acggatgaaa ctgccggtca ggacacccct ctcagccggg aaaatgtgct gaccggacat    7200
gaaaatgagg tgggatcagc gcagccggat accgtgattc tggatacgtc tgaactggtc    7260
acggtcgtgg cactggtgaa gctgcatact gatgcacttc acgccacgcg ggatgaacct    7320
gtggcatttg tgctgccggg aacggcgttt cgtgtctctg ccggtgtggc agccgaaatg    7380
acagagcgcg gcctggccag aatgcaataa cgggaggcgc tgtggctgat ttcgataacc    7440
tgttcgatgc tgccattgcc cgcgccgatg aaacgatacg cgggtacatg gaacgtcag    7500 ccaccattac atccggtgag cagtcaggtg cggtgatacg tggtgttttt gatgaccctg    7560
aaaatatcag ctatgccgga cagggcgtgc gcgttgaagg ctccagcccg tccctgtttg    7620
tccggactga tgaggtgcgg cagctgcggc gtggagacac gctgaccatc ggtgaggaaa    7680
atttctgggt agatcgggtt tcgccggatg atggcggaag ttgtcatctc tggcttggac    7740
ggggcgtacc gcctgccgtt aaccgtcgcc gctgaaaggg ggatgtatgg ccataaaagg    7800
tcttgagcag gccgttgaaa acctcagccg tatcagcaaa acggcggtgc tggtgccgc    7860 cgcaatggcc attaaccgcg ttgcttcatc cgcgatatcg cagtcggcgt cacaggttgc    7920
ccgtgagaca aaggtacgcc ggaaactggt aaaggaaagg gccaggctga aaagggccac    7980
ggtcaaaaat ccgcaggcca gaatcaaagt taaccggggg gatttgcccg taatcaagct    8040
gggtaatgcg cgggttgtcc tttcgcgccg caggcgtcgt aaaaaggggc agcgttcatc    8100
cctgaaaggt ggcggcagcg tgcttgtggt gggtaaccgt cgtattcccg gcgcgtttat    8160
tcagcaactg aaaaatggcc ggtggcatgt catgcagcgt gtggctggga aaaccgtta    8220 ccccattgat gtggtgaaaa tcccgatggc ggtgccgctg accacggcgt ttaaacaaaa    8280
tattgagcgg atacgcgtg aacgtcttcc gaaagagctg ggctatgcgc tgcagcatca    8340
actgaggatg gtaataaagc gatgaaacat actgaactcc gtgcagccgt actggatgca    8400
ctggagaagc atgacaccgg ggcgactttt tttgatggtc gccccgctgt ttttgatgag    8460
gcggattttc cggcagttgc cgtttatctc accggcgctg aatacacggg cgaagagctg    8520
gacagcgata cctggcaggc ggagctgcat atcgaagttt tcctgcctgc tcaggtgccg    8580
```

```
gattcagagc tggatgcgtg gatggagtcc cggatttatc cggtgatgag cgatatcccg   8640
gcactgtcag atttgatcac cagtatggtg gccagcggct atgactaccg gcgcgacgat   8700
gatgcgggct tgtggagttc agccgatctg acttatgtca ttacctatga aatgtgagga   8760
cgctatgcct gtaccaaatc ctacaatgcc ggtgaaaggt gccgggacca ccctgtgggg   8820
ttataagggg agcggtgacc cttacgcgaa tccgctttca gacgttgact ggtcgcgtct   8880
ggcaaaagtt aaagacctga cgcccggcga actgaccgct gagtcctatg acgacagcta   8940
tctcgatgat gaagatgcag actggactgc gaccgggcag gggcagaaat ctgccggaga   9000
taccagcttc acgctggcgt ggatgcccgg agagcagggg cagcaggcgc tgctggcgtg   9060
gtttaatgaa ggcgataccc gtgcctataa aatccgcttc ccgaacggca cggtcgatgt   9120
gttccgtggc tgggtcagca gtatcggtaa ggcggtgacg cgcaaggaag tgatcacccg   9180
cacggtgaaa gtcaccaatg tgggacgtcc gtcgatggca gaagatcgca gcacggtaac   9240
agcggcaacc ggcatgaccg tgacgcctgc cagcacctcg gtggtgaaag ggcagagcac   9300
cacgctgacc gtggccttcc agccggaggg cgtaaccgac aagagctttc gtgcggtgtc   9360
tgcggataaa acaaaagcca ccgtgtcggt cagtggtatg accatcaccg tgaacggcgt   9420
tgctgcaggc aaggtcaaca ttccggttgt atccggtaat ggtgagtttg ctgcggttgc   9480
agaaattacc gtcaccgcca gttaatccgg agagtcagcg atgttcctga aaaccgaatc   9540
atttgaacat aacggtgtga ccgtcacgct ttctgaactg tcagccctgc agcgcattga   9600
gcatctcgcc ctgatgaaac ggcaggcaga acaggcggag tcagacagca accggaagtt   9660
tactgtggaa gacgccatca gaaccggcgc gtttctggtg gcgatgtccc tgtggcataa   9720
ccatccgcag aagacgcaga tgccgtccat gaatgaagcc gttaaacaga ttgagcagga   9780
agtgcttacc acctggccca cggaggcaat ttctcatgct gaaaacgtgg tgtaccggct   9840
gtctggtatg tatgagtttg tggtgaataa tgcccctgaa cagacagagg acgccgggcc   9900
cgcagagcct gtttctgcgg gaaagtgttc gacggtgagc tgagttttgc cctgaaactg   9960
gcgcgtgaga tggggcgacc cgactggcgt gccatgcttg ccgggatgtc atccacggag  10020
tatgccgact ggcaccgctt ttacagtacc cattatttc atgatgttct gctggatatg  10080
cacttttccg ggctgacgta caccgtgctc agcctgtttt tcagcgatcc ggatatgcat  10140
ccgctggatt tcagtctgct gaaccggcgc gaggctgacg aagagcctga agatgatgtg  10200
ctgatgcaga aagcggcagg gcttgccgga ggtgtccgct ttggcccgga cgggaatgaa  10260
gttatccccg cttccccgga tgtggcggac atgacggagg atgacgtaat gctgatgaca  10320
gtatcagaag ggatcgcagg aggagtccgg tatggctgaa ccggtaggcg atctggtcgt  10380
tgatttgagt ctggatgcgg ccagatttga cgagcagatg ccagagtca ggcgtcattt  10440 ttctggtacg gaaagtgatg cgaaaaaaac agcggcagtc gttgaacagt cgctgagccg  10500
acaggcgctg gctgcacaga aagcggggat tccgtcgggg cagtataaag ccgccatgcg  10560
tatgctgcct gcacagttca ccgacgtggc cacgcagctt gcaggcgggc aaagtccgtg  10620
gctgatcctg ctgcaacagg gggcaggt gaaggactcc ttcggcggga tgatccccat  10680 gttcagggggg cttgccggtg cgatcaccct gccgatggtg gggccacct cgctggcggt  10740 ggcgaccggt gcgctggcgt atgcctggta tcagggcaac tcaaccctgt ccgatttcaa  10800
caaaacgctg gtcctttccg gcaatcaggg gggactgacg gcagatcgta tgctggtcct  10860
gtccagagcc gggcaggcgg cagggctgac gtttaaccag accagcgagt cactcagcgc  10920
```

```
actggttaag gcggggtaa gcggtgaggc tcagattgcg tccatcagcc agagtgtggc    10980
gcgtttctcc tctgcatccg gcgtggaggt ggacaaggtc gctgaagcct tcgggaagct    11040
gaccacagac ccgacgtcgg ggctgacggc gatggctcgc cagttccata acgtgtcggc    11100
ggagcagatt gcgtatgttg ctcagttgca gcgttccggc gatgaagccg ggcattgca     11160 ggcggcgaac gaggccgcaa cgaaagggtt tgatgaccag acccgccgcc tgaaagagaa    11220
catgggcacg ctggagacct gggcagacag gactgcgcgg gcattcaaat ccatgtggga    11280
tgcggtgctg gatattggtc gtcctgatac cgcgcaggag atgctgatta aggcagaggc    11340
tgcgtataag aaagcagacg acatctggaa tctgcgcaag gatgattatt ttgttaacga    11400
tgaagcgcgg gcgcgttact gggatgatcg tgaaaaggcc cgtcttgcgc ttgaagccgc    11460
ccgaaagaag gctgagcagc agactcaaca ggacaaaaat gcgcagcagc agagcgatac    11520
cgaagcgtca cggctgaaat ataccgaaga ggcgcagaag gcttacgaac ggctgcagac    11580
gccgctggag aaatataccg cccgtcagga agaactgaac aaggcactga agacgggaa     11640 aatcctgcag gcggattaca acacgctgat ggcggcgggc aaaaaggatt atgaagcgac    11700
gctgaaaaag ccgaaacagt ccagcgtgaa ggtgtctgcg ggcgatcgtc aggaagacag    11760
tgctcatgct gccctgctga cgcttcaggc agaactccgg acgctggaga agcatgccgg    11820
agcaaatgag aaaatcagcc agcagcgccg ggatttgtgg aaggcggaga gtcagttcgc    11880
ggtactggag gaggcggcgc aacgtcgcca gctgtctgca caggagaaat ccctgctggc    11940
gcataaagat gagacgctgg agtacaaacg ccagctggct gcacttggcg acaaggttac    12000
gtatcaggag cgcctgaacg cgctggcgca gcaggcggta aaattcgcac agcagcaacg    12060
ggcaaaacgg gccgccattg atgcgaaaag ccggggggctg actgaccggc aggcagaacg    12120
ggaagccacg gaacagcgcc tgaaggaaca gtatggcgat aatccgctgg cgctgaataa    12180
cgtcatgtca gagcagaaaa agacctgggc ggctgaagac cagcttcgcg ggaactggat    12240
ggcaggcctg aagtccggct ggagtgagtg ggaagagagc gccacggaca gtatgtcgca    12300
ggtaaaaagt gcagccacgc agacctttga tggtattgca cagaatatgg cggcgatgct    12360
gaccggcagt gagcagaact ggcgcagctt cacccgttcc gtgctgtcca tgatgacaga    12420
aattctgctt aagcaggcaa tggtggggat tgtcgggagt atcggcagcg ccattggcgg    12480
ggctgttggt ggcggcgcat ccgcgtcagg cggtacagcc attcaggccg ctgcggcgaa    12540
attccatttt gcaaccggag gatttacggg aaccggcggc aaatatgagc cagcggggat    12600
tgttcaccgt ggtgagtttg tcttcacgaa ggaggcaacc agccggattg gcgtggggaa    12660
tctttaccgg ctgatgcgcg gctatgccac cggcggttat gtcggtacac cgggcagcat    12720
ggcagacagc cggtcgcagg cgtccgggac gtttgagcag aataaccatg tggtgattaa    12780
caacgacggc acgaacgggc agataggtcc ggctgctctg aaggcggtgt atgacatggc    12840
ccgcaagggt gcccgtgatg aaattcgaca acagatgcgt gatggtggcc tgttctccgg    12900
aggtggacga tgaagacctt ccgctggaaa gtgaaacccg gtatgatgt ggcttcggtc     12960 ccttctgtaa gaaaggtgcg ctttggtgat ggctattctc agcgagcgcc tgccgggctg    13020
aatgccaacc tgaaaacgta cagcgtgacg ctttctgtcc cccgtgagga ggccacggta    13080
ctggagtcgt ttctggaaga gcacggggc tggaaatcct ttctgtggac gccgccttat      13140
gagtggcggc agataaaggt gacctgcgca aaatggtcgt cgcgggtcag tatgctgcgt    13200
gttgagttca gcgcagagtt tgaacaggtg gtgaactgat gcaggatatc cggcaggaaa    13260
cactgaatga atgcacccgt gcggagcagt cggccagcgt ggtgctctgg gaaatcgacc    13320
```

```
tgacagaggt cggtggagaa cgttattttt tctgtaatga gcagaacgaa aaaggtgagc    13380
cggtcacctg gcaggggcga cagtatcagc cgtatcccat tcaggggagc ggttttgaac    13440
tgaatggcaa aggcaccagt acgcgcccca cgctgacggt ttctaacctg tacggtatgg    13500
tcaccgggat ggcggaagat atgcagagtc tggtcggcgg aacggtggtc cggcgtaagg    13560
tttacgcccg ttttctggat gcggtgaact tcgtcaacgg aaacagttac gccgatccgg    13620
agcaggaggt gatcagccgc tggcgcattg agcagtgcag cgaactgagc gcggtgagtg    13680
cctcctttgt actgtccacg ccgacggaaa cggatggcgc tgttttttccg ggacgtatca    13740 tgctggccaa cacctgcacc tggacctatc gcggtgacga gtgcggttat agcggtccgg    13800
ctgtcgcgga tgaatatgac cagccaacgt ccgatatcac gaaggataaa tgcagcaaat    13860
gcctgagcgg ttgtaagttc cgcaataacg tcggcaactt tggcggcttc ctttccatta    13920
acaaactttc gcagtaaatc ccatgacaca gacagaatca gcgattctgg cgcacgcccg    13980
gcgatgtgcg ccagcggagt cgtgcggctt cgtggtaagc acgccggagg gggaaagata    14040
tttcccctgc gtgaatatct ccggtgagcc ggaggcgtat ttccgtatgt cgccggaaga    14100
ctggctgcag gcagaaatgc agggtgagat tgtggcgctg gtccacagcc accccgtgg    14160 tctgccctgg ctgagtgagg ccgaccggcg gctgcaggtg cagagtgatt tgccgtggtg    14220
gctggtctgc cggggacga ttcataagtt ccgctgtgtg ccgcatctca ccgggcggcg    14280
ctttgagcac ggtgtgacgg actgttacac actgttccgg gatgcttatc atctggcggg    14340
gattgagatg ccggactttc atcgtgagga tgactggtgg cgtaacggcc agaatctcta    14400
tctggataat ctggaggcga cggggctgta tcaggtgccg ttgtcagcgg cacagccggg    14460
cgatgtgctg ctgtgctgtt ttggttcatc agtgccgaat cacgccgcaa tttactgcgg    14520
cgacggcgag ctgctgcacc atattcctga caactgagc aaacgagaga ggtacaccga    14580
caaatggcag cgacgcacac actccctctg gcgtcaccgg gcatggcgcg catctgcctt    14640
tacggggatt tacaacgatt tggtcgccgc atcgaccttc gtgtgaaaac gggggctgaa    14700
gccatccggg cactgccac acagctcccg gcgtttcgtc agaaactgag cgacggctgg    14760
tatcaggtac ggattgccgg gcgggacgtc agcacgtccg ggttaacggc gcagttacat    14820
gagactctgc ctgatggcgc tgtaattcat attgttccca gagtcgccgg ggccaagtca    14880
ggtggcgtat tccagattgt cctgggggct gccgccattg ccggatcatt ctttaccgcc    14940
ggagccaccc ttgcagcatg gggggcagcc attggggccg gtggtatgac cggcatcctg    15000
ttttctctcg gtgccagtat ggtgctcggt ggtgtggcgc agatgctggc accgaaagcc    15060
agaactcccc gtatacagac aacggataac ggtaagcaga acacctattt ctcctcactg    15120
gataacatgt tgcccagggg caatgttctg cctgttctgt acgggaaat gcgcgtgggg    15180 tcacgcgtgg tttctcagga gatcagcacg gcagacgaag gggacggtgg tcaggttgtg    15240
gtgattggtc gctgatgcaa aatgttttat gtgaaaccgc ctgcgggcgg ttttgtcatt    15300
tatggagcgt gaggaatggg taaaggaagc agtaaggggc ataccccgcg cgaagcgaag    15360
gacaacctga agtccacgca gttgctgagt gtgatcgatg ccatcagcga agggccgatt    15420
gaaggtccgg tggatggctt aaaaagcgtg ctgctgaaca gtacgccggt gctgacact    15480 gagggaata ccaacatatc cggtgtcacg gtggtgttcc gggctggtga gcaggagcag    15540 actccgccg agggatttga atcctccggc tccgagacgg tgctgggtac ggaagtgaaa    15600
tatgacacgc cgatcacccg caccattacg tctgcaaaca tcgaccgtct gcgctttacc    15660
```

```
ttcggtgtac aggcactggt ggaaaccacc tcaaagggtg acaggaatcc gtcggaagtc   15720
cgcctgctgg ttcagataca acgtaacggt ggctgggtga cggaaaaaga catcaccatt   15780
aagggcaaaa ccacctcgca gtatctggcc tcggtggtga tgggtaacct gccgccgcgc   15840
ccgtttaata tccggatgcg caggatgacg ccggacagca ccacagacca gctgcagaac   15900
aaaacgctct ggtcgtcata cactgaaatc atcgatgtga acagtgcta cccgaacacg    15960 gcactggtcg gcgtgcaggt ggactcgag cagttcggca gccagcaggt gagccgtaat    16020
tatcatctgc gcgggcgtat tctgcaggtg ccgtcgaact ataacccgca gacgcggcaa   16080
tacagcggta tctgggacgg aacgtttaaa ccggcataca gcaacaacat ggcctggtgt   16140
ctgtgggata tgctgaccca tccgcgctac ggcatgggga aacgtcttgg tgcggcggat   16200
gtggataaat gggcgctgta tgtcatcggc cagtactgcg accagtcagt gccggacggc   16260
tttggcggca cggagccgcg catcacctgt aatgcgtacc tgaccacaca gcgtaaggcg   16320
tgggatgtgc tcagcgattt ctgctcggcg atgcgctgta tgccggtatg aacgggcag    16380 acgctgacgt tcgtgcagga ccgaccgtcg gataagacgt ggacctataa ccgcagtaat   16440
gtggtgatgc cggatgatgg cgcgccgttc cgctacagct tcagcgccct gaaggaccgc   16500
cataatgccg ttgaggtgaa ctggattgac ccgaacaacg gctgggagac ggcgacagag   16560
cttgttgaag atacgcaggc cattgcccgt tacggtcgta atgttacgaa gatggatgcc   16620
tttggctgta ccagccgggg gcaggcacac cgcgccgggc tgtggctgat taaaacagaa   16680
ctgctggaaa cgcagaccgt ggatttcagc gtcggcgcag aagggcttcg ccatgtaccg   16740
ggcgatgtta ttgaaatctg cgatgatgac tatgccggta tcagcaccgg tggtcgtgtg   16800
ctggcggtga acagccagac ccggacgctg acgctcgacc gtgaaatcac gctgccatcc   16860
tccggtaccg cgctgataag cctggttgac ggaagtggca atccggtcag cgtggaggtt   16920
cagtccgtca ccgacggcgt gaaggtaaaa gtgagccgtg ttcctgacgg tgttgctgaa   16980
tacagcgtat gggagctgaa gctgccgacg ctgcgccagc gactgttccg ctgcgtgagt   17040
atccgtgaga cgacgacgg cacgtatgcc atcaccgccg tgcagcatgt gccggaaaaa    17100
gaggccatcg tggataacgg ggcgcacttt gacggcgaac agagtggcac ggtgaatggt   17160
gtcacgccgc cagcggtgca gcacctgacc gcagaagtca ctgcagacag cggggaatat   17220
caggtgctgg cgcgatggga cacaccgaag gtggtgaagg gcgtgagttt cctgctccgt   17280
ctgaccgtaa cagcggacga cggcagtgag cggctggtca gcacggcccg gacgacggaa   17340
accacatacc gcttcacgca actggcgctg ggaactaca ggctgacagt ccgggcggta    17400
aatgcgtggg ggcagcaggg cgatccggcg tcggtatcgt tccggattgc cgcaccggca   17460
gcaccgtcga ggattgagct gacgccgggc tattttcaga taaccgccac gccgcatctt   17520
gccgtttatg acccgacggt acagtttgag ttctggttct cggaaaagca gattgcggat   17580
atcagacagg ttgaaaccag cacgcgttat cttggtacgg cgctgtactg gatagccgcc   17640
agtatcaata tcaaaccggg ccatgattat tactttttata tccgcagtgt gaacaccgtt   17700
ggcaaatcgg cattcgtgga ggccgtcggt cgggcgagcg atgatgcgga aggttacctg   17760 gatttttca aaggcaagat aaccgaatcc catctcggca aggagctgct ggaaaaagtc    17820
gagctgacgg aggataacgc cagcagactg gaggagtttt cgaaagagtg gaaggatgcc   17880
agtgataagt ggaatgccat gtgggctgtc aaaattgagc agaccaaaga cggcaaacat   17940
tatgtcgcgt gtattggcct cagcatggag gacacggagg aaggcaaact gagccagttt   18000
ctggttgccg ccaatcgtat cgcatttatt gacccggcaa acgggaatga aacgccgatg   18060
```

```
tttgtggcgc agggcaacca gatattcatg aacgacgtgt tcctgaagcg cctgacggcc     18120
cccaccatta ccagcggcgg caatcctccg gccttttccc tgacaccgga cggaaagctg     18180
accgctaaaa atgcggatat cagtggcagt gtgaatgcga actccgggac gctcagtaat     18240
gtgacgatag ctgaaaactg tacgataaac ggtacgctga gggcggaaaa aatcgtcggg     18300
gacattgtaa aggcggcgag cgcggctttt ccgcgccagc gtgaaagcag tgtggactgg     18360
ccgtcaggta cccgtactgt caccgtgacc gatgaccatc cttttgatcg ccagatagtg     18420
gtgcttccgc tgacgtttcg cggaagtaag cgtactgtca gcggcaggac aacgtattcg     18480
atgtgttatc tgaaagtact gatgaacggt gcggtgattt atgatggcgc ggcgaacgag     18540
gcggtacagg tgttctcccg tattgttgac atgccagcgg tcggggaaa cgtgatcctg      18600 acgttcacgc ttacgtccac acggcattcg gcagatattc cgccgtatac gtttgccagc     18660
gatgtgcagg ttatggtgat taagaaacag gcgctgggca tcagcgtggt ctgagtgtgt     18720
tacagaggtt cgtccgggaa cgggcgtttt attataaaac agtgagaggt gaacgatgcg     18780
taatgtgtgt attgccgttg ctgtctttgc cgcacttgcg gtgacagtca ctccggcccg     18840
tgcggaaggt ggacatggta cgtttacggt gggctatttt caagtgaaac cgggtacatt     18900
gccgtcgttg tcgggcgggg ataccggtgt gagtcatctg aaagggatta acgtgaagta     18960
ccgttatgag ctgacggaca gtgtgggggt gatggcttcc ctggggttcg ccgcgtcgaa     19020
aaagagcagc acagtgatga ccggggagga tacgtttcac tatgagagcc tgcgtggacg     19080
ttatgtgagc gtgatggccg gaccggtttt acaaatcagt aagcaggtca gtgcgtacgc     19140
catggccgga gtggctcaca gtcggtggtc cggcagtaca atggattacc gtaagacgga     19200
aatcactccc gggtatatga aagagacgac cactgccagg gacgaaagtg caatgcggca     19260
tacctcagtg gcgtggagtg caggtataca gattaatccg gcagcgtccg tcgttgttga     19320
tattgcttat gaaggctccg gcagtggcga ctggcgtact gacggattca tcgttgggg t    19380 cggttataaa ttctgattag ccaggtaaca cagtgttatg acagcccgcc ggaaccggtg     19440
ggcttttttg tggggtgaat atggcagtaa agatttcagg agtcctgaaa gacggcacag     19500
gaaaaccggt acagaactgc accattcagc tgaaagccag acgtaacagc accacggtgg     19560
tggtgaacac ggtgggctca gagaatccgg atgaagccgg gcgttacagc atggatgtgg     19620
agtacggtca gtacagtgtc atcctgcagg ttgacggttt tccaccatcg cacgccggga     19680
ccatcaccgt gtatgaagat tcacaaccgg ggacgctgaa tgattttctc tgtgccatga     19740
cggaggatga tgcccggccg gaggtgctgc gtcgtcttga actgatggtg gaagaggtgg     19800
cgcgtaacgc gtccgtggtg gcacagagta cggcagacgc gaagaaatca gccggcgatg     19860
ccagtgcatc agctgctcag gtcgcggccc ttgtgactga tgcaactgac tcagcacgcg     19920
ccgccagcac gtccgccgga caggctgcat cgtcagctca ggaagcgtcc tccggcgcag     19980
aagcggcatc agcaaaggcc actgaagcgg aaaaaagtgc cgcagccgca gagtcctcaa     20040
aaaacgcggc ggccaccagt gccggtgcgg cgaaaacgtc agaaacgaat gctgcagcgt     20100
cacaacaatc agccgccacg tctgcctcca ccgcggccac gaaagcgtca gaggccgcca     20160
cttcagcacg agatgcggtg gcctcaaaag aggcagcaaa atcatcagaa acgaacgcat     20220
catcaagtgc cggtcgtgca gcttcctcgg caacggcggc agaaaattct gccagggcgg     20280
caaaaacgtc cgagacgaat gccaggtcat ctgaaacagc agcggaacgg agcgcctctg     20340
ccgcggcaga cgcaaaaaca gcggcggcgg ggagtgcgtc aacggcatcc acgaaggcga     20400
```
cagaggctgc gggaagtgcg gtatcagcat cgcagagcaa agtgcggca gaagcggcgg    20460
caatacgtgc aaaaaattcg gcaaaacgtg cagaagatat agcttcagct gtcgcgcttg    20520
aggatgcgga cacaacgaga aaggggatag tgcagctcag cagtgcaacc aacagcacgt    20580
ctgaaacgct tgctgcaacg ccaaaggcgg ttaaggtggt aatggatgaa cgaacagaa     20640
aagcccactg gacagtccgg cactgaccgg aacgccaaca gcaccaaccg cgctcagggg    20700
aacaaacaat acccgattg cgaacaccgc ttttgtactg gccgcgattg cagatgttat     20760
cgacgcgtca cctgacgcac tgaatacgct gaatgaactg gccgcagcgc tcgggaatga    20820
tccagatttt gctaccacca tgactaacgc gcttgcgggt aaacaaccga gaatgcgac    20880
actgacggcg ctggcagggc tttccacggc gaaaaataaa ttaccgtatt ttgcggaaaa    20940
tgatgccgcc agcctgactg aactgactca ggttggcagg gatattctgg caaaaaattc    21000
cgttgcagat gttcttgaat accttggggc cggtgagaat tcggcctttc cggcaggtgc    21060
gccgatcccg tggccatcag atatcgttcc gtctggctac gtcctgatgc aggggcaggc    21120
gtttgacaaa tcagcctacc caaaacttgc tgtcgcgtat ccatcgggtg tgcttcctga    21180
tatgcgaggc tggacaatca gggaaaacc cgccagcggt cgtgctgtat tgtctcagga    21240
acaggatgga attaagtcgc acacccacag tgccagtgca tccggtacgg atttggggac    21300
gaaaaccaca tcgtcgtttg attacggac gaaaacaaca ggcagtttcg attacggcac    21360
caaatcgacg aataacacgg gggctcatgc tcacagtctg agcggttcaa caggggccgc    21420
gggtgctcat gcccacacaa gtggtttaag gatgaacagt tctggctgga gtcagtatgg    21480
aacagcaacc attacaggaa gtttatccac agttaaagga accagcacac agggtattgc    21540
ttatttatcg aaaacggaca gtcagggcag ccacagtcac tcattgtccg gtacagccgt    21600
gagtgccggt gcacatgcgc atacagttgg tattggtgcg caccagcatc cggttgttat    21660
cggtgctcat gccattctt tcagtattgg ttcacacgga cacaccatca ccgttaacgc     21720
tgcgggtaac gcgaaaaca ccgtcaaaaa cattgcattt aactatattg tgaggcttgc     21780
ataatggcat tcagaatgag tgaacaacca cggaccataa aaatttataa tctgctggcc    21840
ggaactaatg aatttattgg tgaaggtgac gcatatattc cgcctcatac cggtctgcct    21900
gcaaacagta ccgatattgc accgccagat attccggctg gctttgtggc tgttttcaac    21960
agtgatgagg catcgtggca tctcgttgaa gaccatcggg gtaaaaccgt ctatgacgtg    22020
gcttccggcg acgcgttatt tatttctgaa ctcggtccgt taccggaaaa ttttacctgg    22080
ttatcgccgg gaggggaata tcagaagtgg aacggcacag cctgggtgaa ggatacggaa    22140
gcagaaaaac tgttccggat ccgggaggcg gaagaaacaa aaaaagcct gatgcaggta    22200
gccagtgagc atattgcgcc gcttcaggat gctgcagatc tggaaattgc aacgaaggaa    22260
gaaacctcgt tgctggaagc ctggaagaag tatcgggtgt tgctgaaccg tgttgataca    22320
tcaactgcac ctgatattga gtggcctgct gtccctgtta tggagtaa                22368

<210> SEQ ID NO 8
<211> LENGTH: 20330
<212> TYPE: DNA
<213> ORGANISM: Bacteriophage lambda

<400> SEQUENCE: 8
tcaaggtccc taaattaata cgactcacta tagggagata ggggccttta cgattattac       60
tttaagattt aactctaaga ggaatcttta ttatgttaac acctattaac caattactta      120
agaaccctaa cgatattcca gatgtacctc gtgcaaccgc tgagtatcta caggttcgat      180

```
tcaactatgc gtacctcgaa gcgtctggtc atataggact tatgcgtgct aatggttgta      240
gtgaggccca catcttgggt ttcattcagg gcctacagta tgcctctaac gtcattgacg      300
agattgagtt acgcaaggaa caactaagag atgatgggga ggattgacac tatgtgtttc      360
tcaccgaaaa ttaaaactcc gaagatggat accaatcaga ttcgagccgt tgagccagcg      420
cctctgaccc aagaagtgtc aagcgtggag ttcggtgggt cttctgatga cggataccc      480 gagggcaccg aagtgtctgg acgcaaaggc ctcaaggtcg aacgtgatga ttccgtagcg      540
aagtctaaag ccagcggcaa tggctccgct cgtatgaaat cttccatccg taagtccgca      600
tttggaggta agaagtgatg tctgagttca catgtgtgga ggctaagagt cgcttccgtg      660
caatccggtg gactgtggaa caccttgggt tgcctaaagg attcgaagga cactttgtgg      720
gctacagcct ctacgtagac gaagtgatgg acatgtctgg ttgccgtgaa gagtacattc      780
tggactctac cggaaaacat gtagcgtact tcgcgtggtg cgtaagctgt gacattcacc      840
acaaaggaga cattctggat gtaacgtccg ttgtcattaa tcctgaggca gactctaagg      900
gcttacagcg attcctagcg aaacgcttta agtaccttgc ggaactccac gattgcgatt      960
gggtgtctcg ttgtaagcat gaaggcgaga caatgcgtgt atactttaag gaggtataag     1020
ttatgggtaa gaaagttaag aaggccgtga agaaagtcac caagtccgtt aagaaagtcg     1080
ttaaggaagg ggctcgtccg gttaaacagg ttgctgcgg tctagctggt ctggctggtg      1140
gtactggtga agcacagatg gtggaagtac cacaagctgc cgcacagatt gttgacgtac     1200
ctgagaaaga ggtttccact gaggacgaag cacagacaga aagcggacgc aagaaagctc     1260
gtgctggcgg taagaaatcc ttgagtgtag cccgtagctc cggtggcggt atcaacattt     1320
aatcaggagg ttatcgtgga agactgcatt gaatggaccg gaggtgtcaa ctctaagggt     1380
tatggtcgta agtgggttaa tggtaaactt gtgactccac ataggcacat ctatgaggag     1440
acatatggtc cagttccaac aggaattgtg gtgatgcata tctgcgataa ccctaggtgc     1500
tataacataa agcaccttac gcttggaact ccaaaggata attccgagga catggttacc     1560
aaaggtagac aggctaaagg agaggaacta agcaagaaac ttacagagtc agacgttctc     1620
gctatacgct cttcaacctt aagccaccgc tccttaggag aactgtatgg agtcagtcaa     1680
tcaaccataa cgcgaatact acagcgtaag acatggagac acatttaatg gctgagaaac     1740
gaacaggact tgcggaggat ggcgcaaagt ctgtctatga gcgtttaaag aacgaccgtg     1800
ctccctatga gacacgcgct cagaattgcg ctcaatatac catcccatca ttgttcccta     1860
aggactccga taacgcctct acagattatc aaactccgtg gcaagccgtg ggcgctcgtg     1920
gtctgaacaa tctagcctct aagctcatgc tggctctatt ccctatgcag acttggatgc     1980
gacttactat atctgaatat gaagcaaagc agttactgag cgaccccgat ggactcgcta     2040
aggtcgatga gggcctctcg atggtagagc gtatcatcat gaactacatt gagtctaaca     2100
gttaccgcgt gactctcttt gaggctctca acagttagt cgtagctggt aacgtcctgc     2160
tgtacctacc ggaaccggaa gggtcaaact ataatcccat gaagctgtac cgattgtctt     2220
cttatgtggt ccaacgagac gcattcggca acgttctgca aatggtgact cgtgaccaga     2280
tagcttttgg tgctctccct gaggacatcc gtaaggctgt agaaggtcaa ggtggtgaga     2340
agaaagctga tgagacaatc gacgtgtaca ctcacatcta tctggatgag gactcaggtg     2400
aataccttcg atacgaagag gtcgagggta tggaagtcca aggctccgat gggacttatc     2460
ctaaagaggc ttgcccatac atcccgattc ggatggtcag actagatggt gaatcctacg     2520
```

```
gtcgttcgta cattgaggaa tacttaggtg acttacggtc ccttgaaaat ctccaagagg   2580
ctatcgtcaa gatgtccatg attagctcta aggttatcgg cttagtgaat cctgctggta   2640
tcacccagcc acgccgactg accaaagctc agactggtga cttcgttact ggtcgtccag   2700
aagacatctc gttcctccaa ctggagaagc aagcagactt tactgtagct aaagccgtaa   2760
gtgacgctat cgaggctcgc ctttcgtttg cctttatgtt gaactctgcg gttcagcgta   2820
caggtgaacg tgtgaccgcc gaagagattc ggtatgtagc ttctgaactt gaagatactt   2880
taggtggtgt ctactctatc ctttctcaag aattacaatt gcctctggta cgagtgctct   2940
tgaagcaact acaagccacg caacagattc ctgagttacc taaggaagcc gtagagccaa   3000
ccattagtac aggtctggaa gcaattggtc gaggacaaga ccttgataag ctggagcggt   3060
gtgtcactgc gtgggctgca ctggcaccta tgcgggacga ccctgatatt aaccttgcga   3120
tgattaagtt acgtattgcc aacgctatcg gtattgacac ttctggtatt ctactcaccg   3180
aagaacagaa gcaacagaag atgcccaac agtctatgca aatgggtatg gataatggtg   3240
ctgctgcgct ggctcaaggt atggctgcac aagctacagc ttcacctgag gctatggctg   3300
ctgccgctga ttccgtaggt ttacagccgg gaatttaata cgactcacta tagggagacc   3360
tcatctttga aatgagcgat gacaagaggt tggagtcctc ggtcttcctg tagttcaact   3420
ttaaggagac aataataatg gctgaatcta atgcagacgt atatgcatct tttggcgtga   3480
actccgctgt gatgtctggt ggttccgttg aggaacatga gcagaacatg ctggctcttg   3540
atgttgctgc ccgtgatggc gatgatgcaa tcgagttagc gtcagacgaa gtggaaacag   3600
aacgtgacct gtatgacaac tctgacccgt tcggtcaaga ggatgacgaa ggccgcattc   3660
aggttcgtat cggtgatggc tctgagccga ccgatgtgga cactggagaa gaaggcgttg   3720
agggcaccga aggttccgaa gagtttaccc cactgggcga gactccagaa gaactggtag   3780
ctgcctctga gcaacttggt gagcacgaag agggcttcca agagatgatt aacattgctg   3840
ctgagcgtgg catgagtgtc gagaccattg aggctatcca gcgtgagtac gaggagaacg   3900
aagagttgtc cgccgagtcc tacgctaagc tggctgaaat tggctacacg aaggctttca   3960
ttgactcgta tatccgtggt caagaagctc tggtggagca gtacgtaaac agtgtcattg   4020
agtacgctgg tggtcgtgaa cgttttgatg cactgtataa ccaccttgag acgcacaacc   4080
ctgaggctgc acagtcgctg gataatgcgt tgaccaatcg tgacttagcg accgttaagg   4140
ctatcatcaa cttggctggt gagtctcgcg ctaaggcgtt cggtcgtaag ccaactcgta   4200
gtgtgactaa tcgtgctatt ccggctaaac tcaggctac caagcgtgaa ggctttgcgg   4260
accgtagcga gatgattaaa gctatgagtg accctcggta tcgcacagat gccaactatc   4320
gtcgtcaagt cgaacagaaa gtaatcgatt cgaacttctg atagacttcg aaattaatac   4380
gactcactat agggagacca caacggtttc cctctagaaa taattttgtt taactttaag   4440
aaggagatat acatatggct agcatgactg gtggacagca aatgggtact aaccaaggta   4500
aaggtgtagt tgctgctgga gataaactgg cgttgttctt gaaggtattt ggcggtgaag   4560
tcctgactgc gttcgctcgt acctccgtga ccacttctcg ccacatggta cgttccatct   4620
ccagcggtaa atccgctcag ttccctgttc tgggtcgcac tcaggcagcg tatctggctc   4680
cgggcgagaa cctcgacgat aaacgtaagg acatcaaaca caccgagaag gtaatcacca   4740
ttgacggtct cctgacggct gacgttctga tttatgatat tgaggacgcg atgaaccact   4800
acgacgttcg ctctgagtat acctctcagt gggtgaatc tctggcgatg gctgcggatg   4860
gtgcggttct ggctgagatt gccggtctgt gtaacgtgga aagcaaatat aatgagaaca   4920
```

```
tcgagggctt aggtactgct accgtaattg agaccactca gaacaaggcc gcacttaccg    4980
accaagttgc gctgggtaag gagattattg cggctctgac taaggctcgt gcggctctga    5040
ccaagaacta tgttccggct gctgaccgtg tgttctactg tgacccagat agctactctg    5100
cgattctggc agcactgatg ccgaacgcag caaactacgc tgctctgatt gaccctgaga    5160
agggttctat ccgcaacgtt atgggctttg aggttgtaga agttccgcac ctcaccgctg    5220
gtggtgctgg taccgctcgt gagggcacta ctggtcagaa gcacgtcttc cctgccaata    5280
aaggtgaggg taatgtcaag gttgctaagg acaacgttat cggcctgttc atgcaccgct    5340
ctgcggtagg tactgttaag ctgcgtgact tggctctgga gcgcgctcgc cgtgctaact    5400
tccaagcgga ccagattatc gctaagtacg caatgggcca cggtggtctt cgcccagaag    5460
ctgctggtgc agtggttttc aaagtggagt aatgctgggg gtggcctcaa cggtcgctgc    5520
tagtcccgaa gaggcgagtg ttacttcaac agaagaaacc ttaacgccag cacaggaggc    5580
cgcacgcacc cgcgctgcta acaaagcccg aaaggaagct gagttggctg ctgccaccgc    5640
tgagcaataa ctagcataac cccttggggc ctctaaacgg tcttgaggg gttttttgct    5700 gaaaggagga actatatgcg ctcatacgat atgaacgttg agactgccgc tgagttatca    5760
gctgtgaacg acattctggc gtctatcggt gaacctccgg tatcaacgct ggaaggtgac    5820
gctaacgcag atgcagcgaa cgctcggcgt attctcaaca agattaaccg acagattcaa    5880
tctcgtggat ggacgttcaa cattgaggaa ggcataacgc tactacctga tgtttactcc    5940
aacctgattg tatacagtga cgactattta tccctaatgt ctacttccgg tcaatccatc    6000
tacgttaacc gaggtggcta tgtgtatgac cgaacgagtc aatcagaccg ctttgactct    6060
ggtattactg tgaacattat tcgtctccgc gactacgatg agatgcctga gtgcttccgt    6120
tactggattg tcaccaaggc ttcccgtcag ttcaacaacc gattctttgg ggcaccggaa    6180
gtagagggtg tactccaaga agaggaagat gaggctagac gtctctgcat ggagtatgag    6240
atggactacg gtgggtacaa tatgctggat ggagatgcgt tcacttctgg tctactgact    6300
cgctaacatt aataaataag gaggctctaa tggcactcat tagccaatca atcaagaact    6360
tgaagggtgg tatcagccaa cagcctgaca tccttcgtta tccagaccaa gggtcacgcc    6420
aagttaacgg ttggtcttcg gagaccgagg gcctccaaaa gcgtccacct cttgttttct    6480
taaatacact tggagacaac ggtgcgttag gtcaagctcc gtacatccac ctgattaacc    6540
gagatgagca cgaacagtat tacgctgtgt tcactggtag cggaatccga gtgttcgacc    6600
tttctggtaa cgagaagcaa gttaggtatc ctaacggttc caactacatc aagaccgcta    6660
atccacgtaa cgacctgcga atggttactg tagcagacta tacgttcatc gttaaccgta    6720
acgttgttgc acagaagaac acaaagtctg tcaacttacc gaattacaac cctaatcaag    6780
acggattgat taacgttcgt ggtggtcagt atggtaggga actaattgta cacattaacg    6840
gtaaagacgt tgcgaagtat aagataccag atggtagtca acctgaacac gtaaacaata    6900
cggatgccca atggttagct gaagagttag ccaagcagat gcgcactaac ttgtctgatt    6960
ggactgtaaa tgtagggcaa gggttcatcc atgtgaccgc acctagtggt caacagattg    7020
actccttcac gactaaagat ggctacgcag accagttgat taaccctgtg acccactacg    7080
ctcagtcgtt ctctaagctg ccacctaatg ctcctaacgg ctacatggtg aaaatcgtag    7140
gggacgcctc taagtctgcc gaccagtatt acgttcggta tgacgctgag cggaaagttt    7200
ggactgagac tttaggttgg aacactgagg accaagttct atgggaaacc atgccacacg    7260
```

```
ctcttgtgcg agccgctgac ggtaatttcg acttcaagtg gcttgagtgg tctcctaagt    7320
cttgtggtga cgttgacacc aaccettggc cttcttttgt tggttcaagt attaacgatg    7380
tgttcttctt ccgtaaccgc ttaggattcc ttagtgggga gaacatcata ttgagtcgta    7440
cagccaaata cttcaacttc taccctgcgt ccattgcgaa ccttagtgat gacgaccta    7500
tagacgtagc tgtgagtacc aaccgaatag caatccttaa gtacgccgtt ccgttctcag    7560
aagagttact catctggtcc gatgaagcac aattcgtcct gactgcctcg ggtactctca    7620
catctaagtc ggttgagttg aacctaacga cccagtttga cgtacaggac cgagcgagac    7680
cttttgggat tgggcgtaat gtctactttg ctagtccgag gtccagcttc acgtccatcc    7740
acaggtacta cgctgtgcag gatgtcagtt ccgttaagaa tgctgaggac attacatcac    7800
acgttcctaa ctacatccct aatggtgtgt tcagtatttg cggaagtggt acggaaaact    7860
tctgttcggt actatctcac ggggaccta gtaaaatctt catgtacaaa ttcctgtacc    7920
tgaacgaaga gttaaggcaa cagtcgtggt ctcattggga ctttgggaa aacgtacagg    7980
ttctagcttg tcagagtatc agctcagata tgtatgtgat tcttcgcaat gagttcaata    8040
cgttcctagc tagaatctct ttcactaaga acgccattga cttacaggga gaaccctatc    8100
gtgcctttat ggacatgaag attcgataca cgattcctag tggaacatac aacgatgaca    8160
cattcactac ctctattcat attccaacaa tttatggtgc aaacttcggg aggggcaaaa    8220
tcactgtatt ggagcctgat ggtaagataa ccgtgtttga gcaacctacg gctgggtgga    8280
atagcgaccc ttggctgaga ctcagcggta acttggaggg acgcatggtg tacattgggt    8340
tcaacattaa cttcgtatat gagttctcta agttcctcat caagcagact gccgacgacg    8400
ggtctacctc cacggaagac attgggcgct acagttacg ccgagcgtgg gttaactacg    8460
agaactctgg tacgtttgac atttatgttg agaaccaatc gtctaactgg aagtacacaa    8520
tggctggtgc ccgattaggc tctaacactc tgagggctgg gagactgaac ttagggaccg    8580
gacaatatcg attccctgtg gttggtaacg ccaagttcaa cactgtatac atcttgtcag    8640
atgagactac ccctctgaac atcattgggt gtggctggga aggtaactac ttacggagaa    8700
gttccggtat ttaattaaat attctcctg tggtggctcg aaattaatac gactcactat    8760
agggagaaca atacgactac gggagggttt tcttatgatg actataagac ctactaaaag    8820
tacagacttt gaggtattca ctccggctca ccatgacatt cttgaagcta aggctgctgg    8880
tattgagccg agtttccctg atgcttccga gtgtgtcacg ttgagcctct atgggttccc    8940
tctagctatc ggtggtaact gcggggacca gtgctggttc gttacgagcg accaagtgtg    9000
gcgacttagt ggaaaggcta agcgaaagtt ccgtaagtta atcatggagt atcgcgataa    9060
gatgcttgag aagtatgata ctctttggaa ttacgtatgg gtaggcaata cgtcccacat    9120
tcgtttcctc aagactatcg gtgcggtatt ccatgaagag tacacacgag atggtcaatt    9180
tcagttattt acaatcacga aaggaggata accatatgtg ttgggcagcc gcaataccta    9240
tcgctatatc tggcgctcag gctatcagtg gtcagaacgc tcaggccaaa atgattgccg    9300
ctcagaccgc tgctggtcgt cgtcaagcta tggaaatcat gaggcagacg aacatccaga    9360
atgctgacct atcgttgcaa gctcgaagta aacttgagga agcgtccgcc gagttgacct    9420
cacagaacat gcagaaggtc caagctattg ggtctatccg agcggctatc ggagagagta    9480
tgcttgaagg ttcctcaatg gaccgcatta gcgagtcac agaaggacag ttcattcggg    9540
aagccaatat ggtaactgag aactatcgcc gtgactacca agcaatcttc gcacagcaac    9600
ttggtggtac tcaaagtgct gcaagtcaga ttgacgaaat ctataagagc gaacagaaac    9660
```

```
agaagagtaa gctacagatg gttctggacc cactggctat catgggtct tccgctgcga    9720
gtgcttacgc atccggtgcg ttcgactcta agtccacaac taaggcacct attgttgccg    9780
ctaaaggaac caagacgggg aggtaatgag ctatgagtaa aattgaatct gcccttcaag    9840
cggcacaacc gggactctct cggttacgtg gtggtgctgg aggtatgggc tatcgtgcag    9900
caaccactca ggccgaacag ccaaggtcaa gcctattgga caccattggt cggttcgcta    9960
aggctggtgc cgatatgtat accgctaagg aacaacgagc acgagaccta gctgatgaac   10020
gctctaacga gattatccgt aagctgaccc ctgagcaacg tcgagaagct ctcaacaacg   10080
ggacccttct gtatcaggat gacccatacg ctatggaagc actccgagtc aagactggtc   10140
gtaacgctgc gtatcttgtg gacgatgacg ttatgcagaa gataaaagag ggtgtcttcc   10200
gtactcgcga agagatggaa gagtatcgcc atagtcgcct tcaagagggc gctaaggtat   10260
acgctgagca gttcggcatc gaccctgagg acgttgatta tcagcgtggt ttcaacgggg   10320
acattaccga gcgtaacatc tcgctgtatg gtgcgcatga taacttcttg agccagcaag   10380
ctcagaaggg cgctatcatg aacagccgag tggaactcaa cggtgtcctt caagaccctg   10440
atatgctgcg tcgtccagac tctgctgact tctttgagaa gtatatcgac aacggtctgg   10500
ttactggcgc aatcccatct gatgctcaag ccacacagct tataagccaa gcgttcagtg   10560
acgcttctag ccgtgctggt ggtgctgact tcctgatgcg agtcggtgac aagaaggtaa   10620
cacttaacgg agccactacg acttaccgag agttgattgg tgaggaacag tggaacgctc   10680
tcatggtcac agcacaacgt tctcagtttg agactgacgc gaagctgaac gagcagtatc   10740
gcttgaagat taactctgcg ctgaaccaag aggacccaag gacagcttgg gagatgcttc   10800
aaggtatcaa ggctgaacta gataaggtcc aacctgatga gcagatgaca ccacaacgtg   10860
agtggctaat ctccgcacag gaacaagttc agaatcagat gaacgcatgg acgaaagctc   10920
aggccaaggc tctggacgat tccatgaagt caatgaacaa acttgacgta atcgacaagc   10980
aattccagaa gcgaatcaac ggtgagtggg tctcaacgga ttttaaggat atgccagtca   11040
acgagaacac tggtgagttc aagcatagcg atatggttaa ctacgccaat aagaagctcg   11100
ctgagattga cagtatggac attccagacg gtgccaagga tgctatgaag ttgaagtacc   11160
ttcaagcgga ctctaaggac ggagcattcc gtacagccat cggaaccatg gtcactgacg   11220
ctggtcaaga gtggtctgcc gctgtgatta acggtaagtt accagaacga accccagcta   11280
tggatgctct gcgcagaatc cgcaatgctg accctcagtt gattgctgcg ctatacccag   11340
accaagctga gctattcctg acgatggaca tgatggacaa gcagggtatt gacccctcagg   11400
ttattcttga tgccgaccga ctgactgtta agcggtccaa agagcaacgc tttgaggatg   11460
ataaagcatt cgagtctgca ctgaatgcat ctaaggctcc tgagattgcc cgtatgccag   11520
cgtcactgcg cgaatctgca cgtaagattt atgactccgt taagtatcgc tcggggaacg   11580
aaagcatggc tatggagcag atgaccaagt tccttaagga atctacctac acgttccactg   11640
gtgatgatgt tgacggtgat accgttggtg tgattcctaa gaatatgatg caggttaact   11700
ctgacccgaa atcatgggag caaggtcggg atattctgga ggaagcacgt aagggaatca   11760
ttgcgagcaa cccttggata accaataagc aactgaccat gtattctcaa ggtgactcca   11820
tttaccttat ggacaccaca ggtcaagtca gagtccgata cgacaaagag ttactctcga   11880
aggtctggag tgagaaccag aagaaactcg aagagaaagc tcgtgagaag gctctggctg   11940
atgtgaacaa gcgagcacct atagttgccg ctacgaaggc ccgtgaagct gctgctaaac   12000
```

```
gagtccgaga gaaacgtaaa cagactccta agttcatcta cggacgtaag gagtaactaa    12060
aggctacata aggaggccct aaatggataa gtacgataag aacgtaccaa gtgattatga    12120
tggtctgttc caaaaggctg ctgatgccaa cggggtctct tatgaccttt tacgtaaagt    12180
cgcttggaca gaatcacgat ttgtgcctac agcaaaatct aagactggac cattaggcat    12240
gatgcaattt accaaggcaa ccgctaaggc cctcggtctg cgagttaccg atggtccaga    12300
cgacgaccga ctgaaccctg agttagctat taatgctgcc gctaagcaac ttgcaggtct    12360
ggtagggaag tttgatggcg atgaactcaa agctgcccct gcgtacaacc aaggcgaggg    12420
acgcttgggt aatccacaac ttgaggcgta ctctaaggga gacttcgcat caatctctga    12480
ggagggacgt aactacatgc gtaaccttct ggatgttgct aagtcaccta ggctggaca    12540 gttggaaact tttggtggca taaccccaaa gggtaaaggc attccggctg aggtaggatt    12600
ggctggaatt ggtcacaagc agaaagtaac acaggaactt cctgagtcca caagttttga    12660
cgttaagggt atcgaacagg aggctacggc gaaaccattc gccaaggact tttgggagac    12720
ccacggagaa acacttgacg agtacaacag tcgttcaacc ttcttcggat tcaaaaatgc    12780
tgccgaagct gaactctcca actcagtcgc tgggatggct ttccgtgctg gtcgtctcga    12840
taatggtttt gatgtgttta aagacaccat tacgccgact cgctggaact ctcacatctg    12900
gactccagag gagttagaga agattcgaac agaggttaag aaccctgcgt acatcaacgt    12960
tgtaactggt ggttcccctg agaacctcga tgacctcatt aaattggcta acgagaactt    13020
tgagaatgac tcccgcgctg ccgaggctgg cctaggtgcc aaactgagtg ctggtattat    13080
tggtgctggt gtggacccgc ttagctatgt tcctatggtc ggtgtcactg gtaagggctt    13140
taagttaatc aataaggctc ttgtagttgg tgccgaaagt gctgctctga acgttgcatc    13200
cgaaggtctc cgtacctccg tagctggtgg tgacgcagac tatgcgggtg ctgccttagg    13260
tggctttgtg tttggcgcag gcatgtctgc aatcagtgac gctgtagctg ctggactgaa    13320
acgcagtaaa ccagaagctg agttcgacaa tgagttcatc ggtcctatga tgcgattgga    13380
agcccgtgag acagcacgaa acgccaactc tgcggacctc tctcggatga acactgagaa    13440
catgaagttt gaaggtgaac ataatggtgt cccttatgag gacttaccaa cagagagagg    13500
tgccgtggtg ttacatgatg gctccgttct aagtgcaagc aacccaatca accctaagac    13560
tctaaaagag ttctccgagg ttgaccctga gaaggctgcg cgaggaatca aactggctgg    13620
gttcaccgag attggcttga agaccttggg gtctgacgat gctgacatcc gtagagtggc    13680
tatcgacctc gttcgctctc ctactggtat gcagtctggt gcctcaggta agttcggtgc    13740
aacagcttct gacatccatg agagacttca tggtactgac cagcgtactt ataatgactt    13800
gtacaaagca atgtctgacg ctatgaaaga ccctgagttc tctactggcg gcgctaagat    13860
gtcccgtgaa gaaactcgat acactatcta ccgtagagcg gcactagcta ttgagcgtcc    13920
agaactacag aaggcactca ctccgtctga gagaatcgtt atggacatca ttaagcgtca    13980
ctttgacacc aagcgtgaac ttatggaaaa cccagcaata ttcggtaaca caaaggctgt    14040
gagtatcttc cctgagagtc gccacaaagg tacttacgtt cctcacgtat atgaccgtca    14100
tgccaaggcg ctgatgattc aacgctacg tgccgaaggt ttgcaggaag ggattgcccg    14160
ctcatggatg aacagctacg tctccagacc tgaggtcaag gccagagtcg atgagatgct    14220
taaggaatta cacggggtga aggaagtaac accagagatg gtagagaagt acgctatgga    14280
taaggcttat ggtatctccc actcagacca gttcaccaac agttccataa tagaagagaa    14340
cattgagggc ttagtaggta tcgagaataa ctcattcctt gaggcacgta acttgtttga    14400
```

```
ttcggaccta tccatcacta tgccagacgg acagcaattc tcagtgaatg acctaaggga   14460
cttcgatatg ttccgcatca tgccagcgta tgaccgccgt gtcaatggtg acatcgccat   14520 catgggtct actggtaaaa ccactaagga acttaaggat gagattttgg ctctcaaagc    14580
gaaagctgag ggagacggta agaagactgg cgaggtacat gctttaatgg ataccgttaa   14640
gattcttact ggtcgtgcta gacgcaatca ggacactgtg tgggaaacct cactgcgtgc   14700
catcaatgac ctaggttct tcgctaagaa cgcctacatg ggtgctcaga acattacgga    14760
gattgctggg atgattgtca ctggtaacgt tcgtgctcta gggcatggta tcccaattct   14820
gcgtgataca ctctacaagt ctaaaccagt ttcagctaag gaactcaagg aactccatgc   14880
gtctctgttc gggaaggagg tggaccagtt gattcggcct aaacgtgctg acattgtgca   14940
gcgcctaagg gaagcaactg ataccggacc tgccgtggcg aacatcgtag ggaccttgaa   15000
gtattcaaca caggaactgg ctgctcgctc tccgtggact aagctactga acggaaccac   15060
taactacctt ctggatgctg cgcgtcaagg tatgcttggg gatgttatta gtgccaccct   15120
aacaggtaag actacccgct gggagaaaga aggcttcctt cgtggtgcct ccgtaactcc   15180
tgagcagatg gctggcatca agtctctcat caaggaacat atggtacgcg gtgaggacgg   15240
gaagtttacc gttaaggaca agcaagcgtt ctctatggac ccacgggcta tggacttatg   15300
gagactggct gacaaggtag ctgatgaggc aatgctgcgt ccacataagg tgtccttaca   15360
ggattcccat gcgttcggag cactaggtaa gatggttatg cagtttaagt ctttcactat   15420
caagtccctt aactctaagt tcctgcgaac cttctatgat ggatacaaga caaccgagc   15480 gattgacgct gcgctgagca tcatcacctc tatgggtctc gctggtggtt tctatgctat   15540
ggctgcacac gtcaaagcat acgctctgcc taaggagaaa cgtaaggagt acttggagcg   15600
tgcactggac ccaaccatga ttgcccacgc tgcgttatct cgtagttctc aattgggtgc   15660
tcctttggct atggttgacc tagttggtgg tgttttaggg ttcgagtcct ccaagatggc   15720
tcgctctacg attctaccta aggacaccgt gaaggaacgt gacccaaaca aaccgtacac   15780
ctctagagag gtaatgggcg ctatgggttc aaaccttctg gaacagatgc cttcggctgg   15840 cttttgtggct aacgtagggg ctaccttaat gaatgctgct ggcgtggtca actcacctaa   15900
taaagcaacc gagcaggact tcatgactgg tcttatgaac tccacaaaag agttagtacc   15960
gaacgaccca ttgactcaac agcttgtgtt gaagatttat gaggcgaacg tgttaacttt   16020
gagggagcgt aggaaataat acgactcact atagggagag cgaaataat cttctccctg   16080 tagtctctta gatttacttt aaggaggtca aatggctaac gtaattaaaa ccgttttgac   16140
ttaccagtta gatggctcca atcgtgattt taatatcccg tttgagtatc tagcccgtaa   16200
gttcgtagtg gtaactctta ttggtgtaga ccgaaaggtc cttacgatta atacagacta   16260
tcgctttgct acacgtacta ctatctctct gacaaaggct tggggtccag ccgatggcta   16320
cacgaccatc gagttacgtc gagtaacctc cactaccgac cgattggttg actttacgga   16380
tggttcaatc ctccgcgcgt atgaccttaa cgtcgctcag attcaaacga tgcacgtagc   16440
ggaagaggcc cgtgacctca ctacggatac tatcggtgtc aataacgatg gtcacttgga   16500
tgctcgtggt cgtcgaattg tgaacctagc gaacgccgtg gatgaccgcg atgctgttcc   16560
gtttggtcaa ctaaagacca tgaaccagaa ctcatggcaa gcacgtaatg aagccttaca   16620
gttccgtaat gaggctgaga cttttcagaaa ccaagcggag ggcttaaga acgagtccag   16680 taccaacgct acgaacacaa agcagtggcg cgatgagacc aagggtttcc gagacgaagc   16740
```

```
caagcggttc aagaatacgg ctggtcaata cgctacatct gctgggaact ctgcttccgc    16800
tgcgcatcaa tctgaggtaa acgctgagaa ctctgccaca gcatccgcta actctgctca    16860
tttggcagaa cagcaagcag accgtgcgga acgtgaggca gacaagctgg aaaattacaa    16920
tggattggct ggtgcaattg ataaggtaga tggaaccaat gtgtactgga aaggaaatat    16980
tcacgctaac gggcgccttt acatgaccac aaacggtttt gactgtggcc agtatcaaca    17040
gttctttggt ggtgtcacta atcgttactc tgtcatggag tggggagatg agaacggatg    17100
gctgatgtat gttcaacgta gagagtggac aacagcgata ggcggtaaca tccagttagt    17160
agtaaacgga cagatcatca cccaaggtgg agccatgacc ggtcagctaa aattgcagaa    17220
tgggcatgtt cttcaattag agtccgcatc cgacaaggcg cactatattc tatctaaaga    17280
tggtaacagg aataactggt acattggtag agggtcagat aacaacaatg actgtacctt    17340
ccactcctat gtacatggta cgaccttaac actcaagcag gactatgcag tagttaacaa    17400
acacttccac gtaggtcagg ccgttgtggc cactgatggt aatattcaag gtactaagtg    17460
gggaggtaaa tggctggatg cttacctacg tgacagcttc gttgcgaagt ccaaggcgtg    17520
gactcaggtg tggtctggta gtgctggcgg tggggtaagt gtgactgttt cacaggatct    17580
ccgcttccgc aatatctgga ttaagtgtgc caacaactct tggaacttct tccgtactgg    17640
ccccgatgga atctacttca tagcctctga tggtggatgg ttacgattcc aaatacactc    17700
caacggtctc ggattcaaga atattgcaga cagtcgttca gtacctaatg caatcatggt    17760
ggagaacgag taattggtaa atcacaagga aagacgtgta gtccacggat ggactctcaa    17820
ggaggtacaa gtatgtatgg aaaaggataa gagccttatt acattcttag agatgttgga    17880
cactgcgatg gctcagcgta tgcttgcgga cctttcggac catgagcgtc gctctccgca    17940
actctataat gctattaaca aactgttaga ccgccacaag ttccagattg gtaagttgca    18000
gccggatgtt cacatcttag gtggccttgc tggtgctctt gaagagtaca agagaaagt    18060 cggtgataac ggtcttacgg atgatgatat ttacacatta cagtgatata ctcaaggcag    18120
atagtggtct ttatggatgt cattgtctat acgagatgct cctacgtgaa atctgaaagt    18180
taacgggagg cattgaaatc aagtaaggag gcaatgtgtc tactcaatcc aatcgtaatg    18240
cgctcgtagt ggcgcaactg aaaggagact tcgtggcgtt cctattcgtc ttatggaagg    18300
cgctaaacct accggtgccc actaagtgtc agattgacat ggctaaggtg ctggcgaatg    18360
gagacaacaa gaagttcatc ttacaggctt ccgtggtat cggtaagtcg ttcatcacat    18420
gtgcgttcgt tgtgtggtcc ttatggagag accctcagtt gaagatactt atcgtatcag    18480
cctctaagga gcgtgcagac gctaactcca tctttattaa gaacatcatt gacctgctgc    18540
cattcctatc tgagttaaag ccaagacccg gacagcgtga ctcggtaatc agctttgatg    18600
taggcccagc caatcctgac cactctccta gtgtgaaatc agtaggtatc actggtcagt    18660
taactggtag ccgtgctgac attatcattg cggatgacgt tgagattccg tctaacagcg    18720
caactatggg tgcccgtgag aagctatgga ctctggttca ggagttcgct gcgttactta    18780
aaccgctgcc ttcctctcgc gttatctacc ttggtacacc tcagacagag atgactctct    18840
ataaggaact tgaggataac cgtgggtaca caaccattat ctggcctgct ctgtacccaa    18900
ggacacgtga agagaacctc tattactcac agcgtcttgc tcctatgtta cgcgctgagt    18960
acgatgagaa ccctgaggca cttgctggga ctccaacaga cccagtgcgc tttgaccgtg    19020
atgacctgcg cgagcgtgag ttggaatacg gtaaggctgg cttttacgcta cagttcatgc    19080 ttaaccctaa ccttagtgat gccgagaagt acccgctgag gcttcgtgac gctatcgtag    19140
```

```
cggccttaga cttagagaag gccccaatgc attaccagtg gcttccgaac cgtcagaaca    19200
tcattgagga ccttcctaac gttggcctta agggtgatga cctgcatacg taccacgatt    19260
gttccaacaa ctcaggtcag taccaacaga agattctggt cattgaccct agtggtcgcg    19320
gtaaggacga aacaggttac gctgtgctgt acacactgaa cggttacatc taccttatgg    19380
aagctggagg tttccgtgat ggctactccg ataagaccct tgagttactc gctaagaagg    19440
caaagcaatg gggagtccag acggttgtct acgagagtaa cttcggtgac ggtatgttcg    19500
gtaaggtatt cagtcctatc cttcttaaac accacaactg tgcgatggaa gagattcgtg    19560
cccgtggtat gaaagagatg cgtatttgcg atacccttga gccagtcatg cagactcacc    19620
gccttgtaat tcgtgatgag gtcattaggg ccgactacca gtccgctcgt gacgtagacg    19680
gtaagcatga cgttaagtac tcgttgttct accagatgac ccgtatcact cgtgagaaag    19740
gcgctctggc tcatgatgac cgattggatg cccttgcgtt aggcattgag tatctccgtg    19800
agtccatgca gttggattcc gttaaagtag aaggcgaggt tttagcagat ttttttagaag    19860 agcatatgat gcgcccaacc gtagcagcaa cccacattat cgaaatgagc gttggtggtg    19920
tggacgttta tagtgaagat gacgaaggct atggcaccag ctttatcgaa tggtaaggac    19980
caacataaag ggaggagact catgttccgc ttattgttga acctactgcg gcatagagtc    20040
acctaccgat ttcttgtggt actttgtgct gcccttgggt acgcatctct tactggagac    20100
ctcagttcac tggagtctgt cgtttgctct atactcactt gtagcgatta gggtcttcct    20160
gaccgactga tggctcaccg agggattcag cggtatgatt gcatcacacc acttcatccc    20220
tatagagtca agtcctaagg tatacccata aagagcctct aatggtctat cctaaggtct    20280
atacctaaag ataggccatc ctatcagtgt cacctaaaga gggtcttaga                20330

<210> SEQ ID NO 9
<211> LENGTH: 3555
<212> TYPE: DNA
<213> ORGANISM: Artificial Sequence
<220> FEATURE:
<223> OTHER INFORMATION: Payload pJ23115-GFP T7 cos 2.0

<400> SEQUENCE: 9 ccttttaggga aatatgctaa gttttcaccg taacacgcca catcttgact atatatgtgt     60
agaaactgcc ggaaatcgtc gtggtattct gaccagagcg atgaaaacgt ttcagtttgc    120
tcatggaaaa cggtgtaaca agggtgaaca ctatcccata tcaccagctc accgtctttc    180
attgccatac gaaactccgg atgtgcattc atcaggcggg caagaatgtg aataaaggcc    240
ggataaaact tgtgcttatt tttctttacg gtttttaaaa aggccgtaat atccagctga    300 acggttttggt tataggtgca ctgagcaact gactggaatg cctcaaaatg ttctttacga    360
tgccattgac ttatatcaac tgtagtatat ccagtgattt ttttctccat tttagcttcc    420
ttagcttgcg aaatctcgat aactcaaaaa atagtagtga tcttatttca ttatggtgaa    480
agttgtctta cgtgcaacat tttcgcaaaa agttggcgct tgatttcagt gcaatttatc    540
tcttcaaatg tagcacttta tagctagctc agcccttggt acaatgctag cgttttcatt    600
aaagaggaga aggaagccca tgagtaaagg tgaggaatta tttactggtg ttgttccgat    660
cttagttgaa ctggacggcg atgttaacgg tcataaattc agtgttcgtg gtgaaggtga    720
aggtgatgca accaacggta agctgaccct gaaattcatc tgcactactg gaaaattacc    780
agtaccgtgg cctactctgg tgactaccct gacctatggt gttcagtgtt tttctcgtta    840
```

```
ccctgaccac atgaagcaac atgatttctt caaatctgca atgccggaag gttatgtaca    900
ggagcgcacc atttctttca aagacgatgg cacgtataaa acccgtgcag aggttaaatt    960
tgaaggtgac actctggtga atcgtattga actgaaaggc attgatttca aagaggacgg   1020
caatatttta ggccacaaac tggaatataa cttcaactcc cataacgttt acatcaccgc   1080
agacaaacaa aagaacggta tcaaagctaa cttcaaaatt cgccataacg ttgaagacgg   1140
tagcgtacag ctggcggatc attaccaaca gaacactccg attggagatg ctcctgtttt   1200
actgccggat aaccactacc tgtccaccca gtctaaactg tcgaaggatc cgaacgaaaa   1260
gcgcgaccac atggtgttat tagagttcgt taccgctagt ggtatcacgc acggtatgga   1320
tgaactctac aaataagtca gtttcacctg ttttacgtta aaacccgctt cggcgggttt   1380
ttacttttgg gtttagccga acgccatagt acatgtaggt cgagggtgaa gtacttgctg   1440
acttccttga ggaacacatg atgcgtccta cggttgctgc tacgcatatc attgagatgt   1500
ctgtgggagg agttgatgtg tactctgagg acgatgaggg ttacggtacg tctttcattg   1560
agtggtgatt tatgcattag gactgcatag ggatgcacta tagaccacgg atggtcagtt   1620
ctttaagtta ctgaaaagac acgataaatt aatacgactc actataggga gaggagggac   1680
gaaaggttac tatatagata ctgaatgaat acttatagag tgcataaagt atgcataatg   1740
gtgtacctag agtgacctct aagaatggtg attatattgt attagtatca ccttaactta   1800
aggcgggatc gtcaccctca gcagcgaaag acagctgtcg gtcagagcgt cattgcgaag   1860
ctgagtgtga tcgatgccat cagcgaaggg cccaaactcc gagcgattaa gcgtttgctg   1920
gctgtcacgc ctgcctgttg cttgcttgga cttgcgatgt acgtgctcag ctgtctttcg   1980
ctgctgaggg tgacgatccc gcgagggcct atggagttcc tatagggtcc tttaaaatat   2040
accataaaaa tctgagtgac tatctcacag tgtacgacc taaagttccc ccataggggg   2100
tacctaaagc ccagccaatc acctaaagtc aaccttcggt tgaccttgag ggttccctaa   2160
gggttgggga tgaccttggg gtttgtcttt gggtgttacc ttgagtgtct ctctgtgtcc   2220
ctatctgtta cagtctccta agtatcctc ctaaagtcac ctcctaacgt agaaatattt    2280
tatctgatta ataagatgat cttcttgaga tcgttttggt ctgcgcgtaa tctcttgctc   2340
tgaaaacgaa aaaaccgcct tgcagggcgg ttttccgaag gttctctgag ctaccaactc   2400
tttgaaccga gtaactggc ttggaggagc gcagtcgcca aaacttgtcc tttcagttta    2460
gccttatccg gcgcatgact tcaagactaa ctcctctaaa tcaattacca gtggctgctg   2520
ccagtggtgc ttttgcatgt cttccgggt tggactcaag acgatagtta ccggataagg    2580
cgcagcggtc ggactgaacg gggggttcgt gcatacagtc cagcttggag cgaactgcct   2640
acccggaact gagtgtcagg cgtggaatga gacaaactcg gccgtaacag aggaatgaca   2700
ccggcaaacc gaaaggcagg aacaggagag cgcacgaggg agccgccagg gggaaacgcc   2760
tggtatcttt atagtcctgt caggtttcgc caccactgat ttgagcgtca gatttcgtga   2820
tgcttgtcag gggggcggag cctatggaaa acggctttg ccgcgaccct ctcacttccc    2880
tgttaagtat cttcctggca tcttccagga atctccgcc ccgttcgtaa gccatttccg    2940
ctcgccacag tcgaacgacc gagcgtagcg agtcagtgag cgaggaagcg gaatatatcc   3000
tgtatcacat attctgctga cgcaccgatg cagccttttt tctcctgcca catgaagcac   3060
ttcacttaca ccctcatcag tgccaacata gtaagccagt atacactccg ctagcgcaga   3120
tgtccggcgg tgcttttgcc gttacgcact actttagtca gttccgcagt accgtcagta   3180
gctgaacagg agggacagtg ttgatatcgg gtagcaccag aagtctatag catgtgcata   3240
```

```
cctttggtcg aaaaaaaaag cccgcactgt caggtgcggg cttttttcag tgtttccttg   3300
ccggattacg ccccgccctg ccactcatcg cagtattgtt gtaattcatt aagcattctg   3360
ccgacatgga agccatcaca aacggcatga tgaacttgga tcgccagtgg cattaacacc   3420
ttgtcgcctt gcgtataata ttttcccata gtgaaaacgg gggcgaagaa gttgtccata   3480
tttgctacgt ttaaatcaaa actggtgaaa ctcacccagg gattggcact gacgaaaaac   3540
atattttcga taaac                                                    3555
```

<210> SEQ ID NO 10
<211> LENGTH: 6594
<212> TYPE: DNA
<213> ORGANISM: Artificial Sequence
<220> FEATURE:
<223> OTHER INFORMATION: p1884 plasmid

<400> SEQUENCE: 10

```
tcagatcctt ccgtatttag ccagtatgtt ctctagtgtg gttcgttgtt tttgcgtgag     60
ccatgagaac gaaccattga gatcatactt actttgcatg tcactcaaaa attttgcctc    120
aaaactggtg agctgaattt ttgcagttaa agcatcgtgt agtgttttc ttagtccgtt    180 acgtaggtag gaatctgatg taatggttgt tggtattttg tcaccattca tttttatctg    240
gttgttctca agttcggtta cgagatccat ttgtctatct agttcaactt ggaaaatcaa    300
cgtatcagtc gggcggcctc gcttatcaac caccaatttc atattgctgt aagtgtttaa    360
atctttactt attggtttca aacccattg gttaagcctt ttaaactcat ggtagttatt    420
ttcaagcatt aacatgaact taaattcatc aaggctaatc tctatatttg ccttgtgagt    480
tttcttttgt gttagttctt ttaataacca ctcataaatc ctcatagagt atttgttttc    540
aaaagactta acatgttcca gattatattt tatgaatttt tttaactgga aaagataagg    600
caatatctct tcactaaaaa ctaattctaa ttttttcgctt gagaacttgg catagtttgt    660
ccactggaaa atctcaaagc ctttaaccaa aggattcctg atttccacag ttctcgtcat    720
cagctctctg gttgctttag ctaatacacc ataagcattt tccctactga tgttcatcat    780
ctgagcgtat tggttataag tgaacgatac cgtccgttct ttccttgtag ggttttcaat    840
cgtggggttg agtagtgcca cacagcataa aattagcttg gtttcatgct ccgttaagtc    900
atagcgacta atcgctagtt catttgcttt gaaacaact aattcagaca tacatctcaa    960
ttggtctagg tgattttaat cactatacca attgagatgg gctagtcaat gataattact   1020 agtcctttc ctttgagttg tgggtatctg taaattctgc tagaccttg ctggaaaact    1080 tgtaaattct gctagaccct ctgtaaattc cgctagacct tgtgtgtttt ttttgttta    1140 tattcaagtg gttataattt atagaataaa gaaagaataa aaaaagataa aagaataga   1200 tcccagccct gtgtataact cactacttta gtcagttccg cagtattaca aaaggatgtc   1260
gcaaacgctg tttgctcctc tacaaaacag accttaaaac cctaaaggct taagtagcac   1320
cctcgcaagc tcggttgcgg ccgcaatcgg gcaaatcgct gaatattcct tttgtctccg   1380
accatcaggc acctgagtcg ctgtctttt cgtgacattc agttcgctgc gctcacggct   1440
ctggcagtga atgggggtaa atggcactac aggcgccttt tatggattca tgcaaggaaa   1500
ctacccataa tacaagaaaa gcccgtcacg ggcttctcag ggcgttttat ggcgggtctg   1560
ctatgtggtg ctatctgact ttttgctgtt cagcagttcc tgccctctga ttttccagtc   1620
tgaccacttc ggattatccc gtgacaggtc attcagactg gctaatgcac ccagtaaggc   1680
```

-continued

```
agcggtatca tcaacggggt ctgacgctca gtggaacgaa aactcacgtt aagggatttt    1740
ggtcatgaga ttatcaaaaa ggatcttcac ctagatcctt ttaaattaaa aatgaagttt    1800
taaatcaatc taaagtatat atgagtaaac ttggtctgac agttacgttt ccacaaccaa    1860
ttaaccaatt ctgatttaga aaaactcatc gagcatcaaa tgaaactgca atttattcat    1920
atcaggatta tcaataccat atttttgaaa aagccgtttc tgtaatgaag gagaaaactc    1980
accgaggcag ttccatagga tggcaagatc ctggtatcgg tctgcgattc cgactcgtcc    2040
aacatcaata caacctatta atttcccctc gtcaaaaata aggttatcaa gtgagaaatc    2100
accatgagtg acgactgaat ccggtgagaa tggcaaaagc ttatgcattt ctttccagac    2160
ttgttcaaca ggccagccat tacgctcgtc atcaaaatca ctcgcatcaa ccaaaccgtt    2220
attcattcgt gattgcgcct gagcgagacg aaatacgcga tcgctgttaa aggacaatt     2280 acaaacagga atcgaatgca accggcgcag gaacactgcc agcgcatcaa caatattttc    2340
acctgaatca ggatattctt ctaatacctg gaatgctgtt ttcccgggga tcgcagtggt    2400
gagtaaccat gcatcatcag gagtacggat aaaatgcttg atggtcggaa gaggcataaa    2460
ttccgtcagc cagtttagtc tgaccatctc atctgtaaca tcattggcaa cgctaccttt    2520
gccatgtttc agaaacaact ctggcgcatc gggcttccca tacaatcgat agattgtcgc    2580
acctgattgc ccgacattat cgcgagccca tttatcccca tataaatcag catccatgtt    2640
ggaatttaat cgcggcctcg agcaagacgt ttcccgttga atatggctca taacaccccct   2700 tgtattactg tttatgtaag cagacagttt tattgttcat gatgatatat ttttatcttg    2760
tgcaatgtaa catcagagat tttgagacac aacgtggctt tccctgcagg atttcggagg    2820
cctgcgttat ccctgattc tgtggataac cgtattaccg cctttgagtg agctgatacc    2880
gctcgccgca gccgaacgcc gactagtgga ttttacggct agctcagtcc taggtacaat    2940
gctagcgaat tcattaaaga ggagaaaggt acccatggca cgtaccccga ccgtagcag    3000 cattggtagc ctgcgtagtc cgcatacca taaagcaatt ctgaccagca ccattgaaat    3060
cctgaaagaa tgtggttata gcggtctgag cattgaaagc gttgcacgtc gtgccggtgc    3120
aagcaaaccg accatttatc gttggtggac caataaagca gcactgattg ccgaagtgta    3180
tgaaaatgaa agcgaacagg tgcgtaaatt tccggatctg ggtagcttta aagccgatct    3240
ggattttctg ctgcgtaatc tgtggaaagt ttggcgtgaa accatttgtg gtgaagcatt    3300
tcgttgtgtt attgcagaag cacagctgga ccctgcaacc ctgacccagc tgaaagatca    3360
gtttatggaa cgtcgtcgtg agatgccgaa aaaactggtt gaaaatgcca ttagcaatgg    3420
tgaactgccg aaagatacca atcgtgaact gctgctggat atgattttg gttttgttg     3480 gtatcgcctg ctgaccgaac agctgaccgt tgaacaggat attgaagaat ttaccttcct    3540
gctaattaat ggtgtttgtc cgggtacaca gcgttaacta gggcccatac ccccaattat    3600
tgaaggccgc taacgcggcc tttttttgtt tctggtctgc cgacgtacg gtgaatctga     3660 ttcgttacca attgacatga tacgaaacgt accgtatcgt taaggtatt actaactgga    3720 agaggcacta aatgaacacg attaacatcg ctaagaacga cttctctgac atcgaactgg    3780
ctgctatccc gttcaacact ctggctgacc attacggtga gcgtttagct cgcgaacagt    3840
tggcccttga gcatgagtct tacgagatgg gtgaagcacg cttccgcaag atgtttgagc    3900
gtcaacttaa agctggtgag gttgcggata acgctgccgc caagcctctc atcactaccc    3960
tactccctaa gatgattgca cgcatcaacg actggtttga ggaagtgaaa gctaagcgcg    4020
gcaagcgccc gacagccttc cagttcctgc aagaaatcaa gccggaagcc gtagcgtaca    4080
```

```
tcaccattaa gaccactctg gcttgcctaa ccagtgctga caatacaacc gttcaggctg    4140
tagcaagcgc aatcggtcgg gccattgagg acgaggctcg cttcggtcgt atccgtgacc    4200
ttgaagctaa gcacttcaag aaaaacgttg aggaacaact caacaagcgc gtagggcacg    4260
tctacaagaa agcatttatg caagttgtcg aggctgacat gctctctaag ggtctactcg    4320
gtggcgaggc gtggtcttcg tggcataagg aagactctat tcatgtagga gtacgctgca    4380
tcgagatgct cattgagtca accggaatgg ttagcttaca ccgccaaaat gctggcgtag    4440
taggtcaaga ctctgagact atcgaactcg cacctgaata cgctgaggct atcgcaaccc    4500
gtgcaggtgc gctggctggc atctctccga tgttccaacc ttgcgtagtt cctcctaagc    4560
cgtggactgg cattactggt ggtggctatt gggctaacgg tcgtcgtcct ctggcgctgg    4620
tgcgtactca cagtaagaaa gcactgatgc gctacgaaga cgtttacatg cctgaggtgt    4680
acaaagcgat taacattgcg caaaacaccg catggaaaat caacaagaaa gtcctagcgg    4740
tcgccaacgt aatcaccaag tggaagcatt gtccggtcga ggacatccct gcgattgagc    4800
gtgaagaact cccgatgaaa ccggaagaca tcgacatgaa tcctgaggct ctcaccgcgt    4860
ggaaacgtgc tgccgctgct gtgtaccgca aggacaaggc tcgcaagtct cgccgtatca    4920
gccttgagtt catgcttgag caagccaata agtttgctaa ccataaggcc atctggttcc    4980
cttacaacat ggactggcgc ggtcgtgttt acgctgtgtc aatgttcaac ccgcaaggta    5040
acgatatgac caaaggactg cttacgctgg cgaaaggtaa accaatcggt aaggaaggtt    5100
actactggct gaaaatccac ggtgcaaact gtgcgggtgt cgataaggtt ccgttccctg    5160
agcgcatcaa gttcattgag gaaaaccacg agaacatcat ggcttgcgct aagtctccac    5220
tggagaacac ttggtgggct gagcaagatt ctccgttctg cttccttgcg ttctgctttg    5280
agtacgctgg ggtacagcac cacggcctga gctataactg ctcccttccg ctggcgtttg    5340
acgggtcttg ctctggcatc cagcacttct ccgcgatgct ccgagatgag gtaggtggtc    5400
gcgcggttaa cttgcttcct agtgaaaccg ttcaggacat ctacgggatt gttgctaaga    5460
aagtcaacga gattctacaa gcagacgcaa tcaatgggac cgataacgaa gtagttaccg    5520
tgaccgatga gaacactggt gaaatctctg agaaagtcaa gctgggcact aaggcactgg    5580
ctggtcaatg gctggcttac ggtgttactc gcagtgtgac taagcgttca gtcatgacgc    5640
tggcttacgg gtccaaagag ttcggcttcc gtcaacaagt gctggaagat accattcagc    5700
cagctattga ttccggcaag ggtctgatgt tcactcagcc gaatcaggct gctggataca    5760
tggctaagct gatttgggaa tctgtgagcg tgacggtggt agctgcggtt gaagcaatga    5820
actggcttaa gtctgctgct aagctgctgg ctgctgaggt caaagataag aagactggag    5880
agattcttcg caagcgttgc gctgtgcatt gggtaactcc tgatggtttc cctgtgtggc    5940
aggaatacaa gaagcctatt cagacgcgct tgaacctgat gttcctcggt cagttccgct    6000
tacagcctac cattaacacc aacaaagata gcgagattga tgcacacaaa caggagtctg    6060
gtatcgctcc taactttgta cacagccaag acggtagcca ccttcgtaag actgtagtgt    6120
gggcacacga gaagtacgga atcgaatctt ttgcactgat tcacgactcc ttcggtacca    6180
ttccggctga cgctgcgaac ctgttcaaag cagtgcgcga actatggtt gacacatatg    6240 agtcttgtga tgtactggct gatttctacg accagttcgc tgaccagttg cacgagtctc    6300
aattggacaa aatgccagca cttccggcta aaggtaactt gaacctccgt gacatcttag    6360
agtcggactt cgcgttcgcg gcggctaacg acgagaacta cgctgcggca gtgtaataat    6420
```

-continued

| | |
|---|---|
| gacgcatcct cacgataata tccgggtagg acgaacaata aggccgcaaa tcgcggcctt | 6480 |
| ttttattgat aacaaaagga cagttttccc tttgatatgt aacggtgaac agttgttcta | 6540 |
| cttttgtttg ttagtcttga tgcttcactg atagatacaa gagccataag aacc | 6594 |

<210> SEQ ID NO 11
<211> LENGTH: 6594
<212> TYPE: DNA
<213> ORGANISM: Artificial Sequence
<220> FEATURE:
<223> OTHER INFORMATION: p1885 plasmid

<400> SEQUENCE: 11

| | |
|---|---|
| tcagatcctt ccgtatttag ccagtatgtt ctctagtgtg gttcgttgtt tttgcgtgag | 60 |
| ccatgagaac gaaccattga gatcatactt actttgcatg tcactcaaaa attttgcctc | 120 |
| aaaactggtg agctgaattt tgcagttaa agcatcgtgt agtgttttc ttagtccgtt | 180 |
| acgtaggtag gaatctgatg taatggttgt tggtattttg tcaccattca tttttatctg | 240 |
| gttgttctca agttcggtta cgagatccat ttgtctatct agttcaactt ggaaaatcaa | 300 |
| cgtatcagtc gggcggcctc gcttatcaac caccaatttc atattgctgt aagtgtttaa | 360 |
| atctttactt attggtttca aaacccattg gttaagcctt ttaaactcat ggtagttatt | 420 |
| ttcaagcatt aacatgaact taaattcatc aaggctaatc tctatatttg ccttgtgagt | 480 |
| tttcttttgt gttagttctt ttaataacca ctcataaatc ctcatagagt atttgttttc | 540 |
| aaaagactta acatgttcca gattatattt tatgaatttt tttaactgga aaagataagg | 600 |
| caatatctct tcactaaaaa ctaattctaa tttttcgctt gagaacttgg catagtttgt | 660 |
| ccactggaaa atctcaaagc ctttaaccaa aggattcctg atttccacag ttctcgtcat | 720 |
| cagctctctg gttgctttag ctaatacacc ataagcattt tccctactga tgttcatcat | 780 |
| ctgagcgtat tggttataag tgaacgatac cgtccgttct ttccttgtag ggttttcaat | 840 |
| cgtgggggtta agtagtgcca cacagcataa aattagcttg gtttcatgct ccgttaagtc | 900 |
| atagcgacta atcgctagtt catttgcttt gaaaacaact aattcagaca tacatctcaa | 960 |
| ttggtctagg tgattttaat cactatacca attgagatgg gctagtcaat gataattact | 1020 |
| agtccttttc ctttgagttg tgggtatctg taaattctgc tagacctttg ctggaaaact | 1080 |
| tgtaaattct gctagaccct ctgtaaattc cgctagaccct ttgtgtgttt tttttgttta | 1140 |
| tattcaagtg gttataattt atagaataaa gaaagaataa aaaagataa aagaataga | 1200 |
| tcccagccct gtgtataact cactactttta gtcagttccg cagtattaca aaaggatgtc | 1260 |
| gcaaacgctg tttgctcctc tacaaaacag accttaaaac cctaaaggct taagtagcac | 1320 |
| cctcgcaagc tcggttgcgg ccgcaatcgg gcaaatcgct gaatattcct tttgtctccg | 1380 |
| accatcaggc acctgagtcg ctgtctttttt cgtgacattc agttcgctgc gctcacggct | 1440 |
| ctggcagtga atgggggtaa atggcactac aggcgccttt tatggattca tgcaaggaaa | 1500 |
| ctacccataa tacaagaaaa gcccgtcacg ggcttctcag ggcgttttat ggcgggtctg | 1560 |
| ctatgtggtg ctatctgact ttttgctgtt cagcagttcc tgccctctga ttttccagtc | 1620 |
| tgaccacttc ggattatccc gtgacaggtc attcagactg gctaatgcac ccagtaaggc | 1680 |
| agcggtatca tcaacggggt ctgacgctca gtggaacgaa aactcacgtt aagggatttt | 1740 |
| ggtcatgaga ttatcaaaaa ggatcttcac ctagatcctt ttaaattaaa aatgaagttt | 1800 |
| taaatcaatc taaagtatat atgagtaaac ttggtctgac agttacgttt ccacaaccaa | 1860 |
| ttaaccaatt ctgatttaga aaaactcatc gagcatcaaa tgaaactgca atttattcat | 1920 |

```
atcaggatta tcaataccat attttttgaaa aagccgtttc tgtaatgaag gagaaaactc    1980
accgaggcag ttccatagga tggcaagatc ctggtatcgg tctgcgattc cgactcgtcc    2040
aacatcaata caacctatta atttcccctc gtcaaaaata aggttatcaa gtgagaaatc    2100
accatgagtg acgactgaat ccggtgagaa tggcaaaagc ttatgcattt ctttccagac    2160
ttgttcaaca ggccagccat tacgctcgtc atcaaaatca ctcgcatcaa ccaaaccgtt    2220
attcattcgt gattgcgcct gagcgagacg aaatacgcga tcgctgttaa aaggacaatt    2280
acaaacagga atcgaatgca accggcgcag gaacactgcc agcgcatcaa caatattttc    2340
acctgaatca ggatattctt ctaatacctg gaatgctgtt ttcccgggga tcgcagtggt    2400
gagtaaccat gcatcatcag gagtacggat aaaatgcttg atggtcggaa gaggcataaa    2460
ttccgtcagc cagtttagtc tgaccatctc atctgtaaca tcattggcaa cgctaccttt    2520
gccatgtttc agaaacaact ctggcgcatc gggcttccca tacaatcgat agattgtcgc    2580
acctgattgc ccgacattat cgcgagccca tttatacccca tataaatcag catccatgtt    2640
ggaatttaat cgcggcctcg agcaagacgt ttcccgttga atatggctca taacacccct    2700
tgtattactg tttatgtaag cagacagttt tattgttcat gatgatatat ttttatcttg    2760
tgcaatgtaa catcagagat tttgagacac aacgtggctt tccctgcagg atttcggagg    2820
cctgcgttat cccctgattc tgtggataac cgtattaccg cctttgagtg agctgatacc    2880
gctcgccgca gccgaacgcc gactagtgga ttttacggct agctcagtcc taggtacaat    2940
gctagcgaat tcattaaaga ggagaaaggt acccatggca cgtacccga gccgtagcag    3000 cattggtagc ctgcgtagtc cgcatacccca taaagcaatt ctgaccagca ccattgaaat    3060
cctgaaagaa tgtggttata gcggtctgag cattgaaagc gttgcacgtc gtgccggtgc    3120
aagcaaaccg accatttatc gttggtggac caataaagca gcactgattg ccgaagtgta    3180
tgaaaatgaa agcgaacagg tgcgtaaatt tccggatctg ggtagcttta aagccgatct    3240
ggattttctg ctgcgtaatc tgtggaaagt ttggcgtgaa accatttgtg gtgaagcatt    3300
tcgttgtgtt attgcagaag cacagctgga ccctgcaacc ctgacccagc tgaaagatca    3360
gtttatggaa cgtcgtcgtg agatgccgaa aaaactggtt gaaaatgcca ttagcaatgg    3420
tgaactgccg aaagatacca atcgtgaact gctgctggat atgattttg gttttgttg    3480 gtatcgcctg ctgaccgaac agctgaccgt tgaacaggat attgaagaat ttaccttcct    3540
gctaattaat ggtgttgtc cgggtacaca gcgttaacta gggcccatac ccccaattat    3600
tgaaggccgc taacgcggcc ttttttttgtt tctggtctgc ccgacgtacg gtgaatctga    3660
ttcgttacca attgacatga tacgaaacgt accgtatcgt taaggtattt actaactgga    3720
agaggcacta aatgaacacg attaacatcg ctaagaacga cttctctgac atcgaactgg    3780
ctgctatccc gttcaacact ctggctgacc attacggtga gcgtttagct cgcgaacagt    3840
tggcccttga gcatgagtct tacgagatgg gtgaagcacg cttccgcaag atgtttgagc    3900
gtcaacttaa agctggtgag gttgcggata acgctgccgc caagcctctc atcactaccc    3960
tactccctaa gatgattgca cgcatcaacg actggtttga ggaagtgaaa gctaagcgcg    4020
gcaagcgccc gacagccttc cagttcctgc aagaaatcaa gccggaagcc gtagcgtaca    4080
tcaccattaa gaccactctg gcttgcctaa ccagtgctga caatacaacc gttcaggctg    4140
tagcaagcgc aatcggtcgg gccattgagg acgaggctcg cttcggtcgt atccgtgacc    4200
ttgaagctaa gcacttcaag aaaaacgttg aggaacaact caacaagcgc gtagggcacg    4260
```

| | |
|---|---|
| tctacaagaa agcatttatg caagttgtcg aggctgacat gctctctaag ggtctactcg | 4320 |
| gtggcgaggc gtggtcttcg tggcataagg aagactctat tcatgtagga gtacgctgca | 4380 |
| tcgagatgct cattgagtca accggaatgg ttagcttaca ccgccaaaat gctggcgtag | 4440 |
| taggtcaaga ctctgagact atcgaactcg cacctgaata cgctgaggct atcgcaaccc | 4500 |
| gtgcaggtgc gctggctggc atctctccga tgttccaacc ttgcgtagtt cctcctaagc | 4560 |
| cgtggactgg cattactggt ggtggctatt gggctaacgg tcgtcgtcct ctggcgctgg | 4620 |
| tgcgtactca cagtaagaaa gcactgatgc gctacgaaga cgtttacatg cctgaggtgt | 4680 |
| acaaagcgat taacattgcg caaaacaccg catggaaaat caacaagaaa gtcctagcgg | 4740 |
| tcgccaacgt aatcaccaag tggaagcatt gtccggtcga ggacatccct gcgattgagc | 4800 |
| gtgaagaact cccgatgaaa ccggaagaca tcgacatgaa tcctgaggct ctcaccgcgt | 4860 |
| ggaaacgtgc tgccgctgct gtgtaccgca aggacaaggc tcgcaagtct cgccgtatca | 4920 |
| gccttgagtt catgcttgag caagccaata agtttgctaa ccataaggcc atctggttcc | 4980 |
| cttacaacat ggactggcgc ggtcgtgttt acgctgtgtc aatgttcaac ccgcaaggta | 5040 |
| acgatatgac caaaggactg cttacgctgg cgaaaggtaa accaatcggt aaggaaggtt | 5100 |
| actactggct gaaaatccac ggtgcaaact gtgcgggtgt cgataaggtt ccgttccctg | 5160 |
| agcgcatcaa gttcattgag gaaaaccacg agaacatcat ggcttgcgct aagtctccac | 5220 |
| tggagaacac ttggtgggct gagcaagatt ctccgttctg cttccttgcg ttctgctttg | 5280 |
| agtacgctgg ggtacagcac cacggcctga gctataactg ctcccttccg ctggcgtttg | 5340 |
| acgggtcttg ctctggcatc cagcacttct ccgcgatgct ccgagatgag gtaggtggtc | 5400 |
| gcgcggttaa cttgcttcct agtgaaaccg ttcaggacat ctacgggatt gttgctaaga | 5460 |
| aagtcaacga gattctacaa gcagacgcaa tcaatgggac cgataacgaa gtagttaccg | 5520 |
| tgaccgatga gaacactggt gaaatctctg agaaagtcaa gctgggcact aaggcactgg | 5580 |
| ctggtcaatg gctggcttac ggtgttactc gcagtgtgac taagcgttca gtcatgacgc | 5640 |
| tggcttacgg gtccaaagag ttcggcttcc gtcaacaagt gctggaagat accattcagc | 5700 |
| cagctattga ttccggcaag ggtctgatgt tcactcagcc gaatcaggct gctggataca | 5760 |
| tggctaagct gatttgggaa tctgtgagcg tgacggtggt agctgcggtt gaagcaatga | 5820 |
| actggcttaa gtctgctgct aagctgctgg ctgctgaggt caaagataag aagactggag | 5880 |
| agattcttcg caagcgttgc gctgtgcatt gggtaactcc tgatggtttc cctgtgtggc | 5940 |
| aggaatacaa gaagcctatt cagacgcgct gaacctgat gttcctcggt cagttccgct | 6000 |
| tacagcctac cattaacacc aacaaagata gcgagattga tgcacacaaa caggagtctg | 6060 |
| gtatcgctcc taactttgta cacagccaag acggtagcca ccttcgtaag actgtagtgt | 6120 |
| gggcacacga gaagtacgga atcgaatctt ttgcactgat tcacgactcc ttcggtacca | 6180 |
| ttccggctga cgctgcgaac ctgttcaaag cagtgcgcga aactatggtt gacacatatg | 6240 |
| agtcttgtga tgtactggct gatttctacg accagttcgc tgaccagttg cacgagtctc | 6300 |
| aattggacaa aatgccagca cttccggcta aaggtaactt gaacctccgt gacatcttag | 6360 |
| agtcggactt cgcgttcgcg gcagcgaacg acgaaaacta tgccctggta gcctaataat | 6420 |
| gacgcatcct cacgataata tccgggtagg acgaacaata aggccgcaaa tcgcggcctt | 6480 |
| ttttattgat aacaaaagga cagttttccc tttgatatgt aacggtgaac agttgttcta | 6540 |
| cttttgtttg ttagtcttga tgcttcactg atagatacaa gagccataag aacc | 6594 |

<210> SEQ ID NO 12
<211> LENGTH: 2682
<212> TYPE: DNA
<213> ORGANISM: Artificial Sequence
<220> FEATURE:
<223> OTHER INFORMATION: T7 RNA polymerase version AAV

<400> SEQUENCE: 12

| | | | | | |
|---|---|---|---|---|---|
| atgaacacga | ttaacatcgc | taagaacgac | ttctctgaca | tcgaactggc | tgctatcccg | 60 |
| ttcaacactc | tggctgacca | ttacggtgag | cgtttagctc | gcgaacagtt | ggcccttgag | 120 |
| catgagtctt | acgagatggg | tgaagcacgc | ttccgcaaga | tgtttgagcg | tcaacttaaa | 180 |
| gctggtgagg | ttgcggataa | cgctgccgcc | aagcctctca | tcactaccct | actccctaag | 240 |
| atgattgcac | gcatcaacga | ctggtttgag | gaagtgaaag | ctaagcgcgg | caagcgcccg | 300 |
| acagccttcc | agttcctgca | agaaatcaag | ccggaagccg | tagcgtacat | caccattaag | 360 |
| accactctgg | cttgcctaac | cagtgctgac | aatacaaccg | ttcaggctgt | agcaagcgca | 420 |
| atcggtcggg | ccattgagga | cgaggctcgc | ttcggtcgta | tccgtgacct | tgaagctaag | 480 |
| cacttcaaga | aaaacgttga | ggaacaactc | aacaagcgcg | tagggcacgt | ctacaagaaa | 540 |
| gcatttatgc | aagttgtcga | ggctgacatg | ctctctaagg | gtctactcgg | tggcgaggcg | 600 |
| tggtcttcgt | ggcataagga | agactctatt | catgtaggag | tacgctgcat | cgagatgctc | 660 |
| attgagtcaa | ccggaatggt | tagcttacac | cgccaaaatg | ctggcgtagt | aggtcaagac | 720 |
| tctgagacta | tcgaactcgc | acctgaatac | gctgaggcta | tcgcaacccg | tgcaggtgcg | 780 |
| ctggctggca | tctctccgat | gttccaacct | tgcgtagttc | ctcctaagcc | gtggactggc | 840 |
| attactggtg | gtggctattg | ggctaacggt | cgtcgtcctc | tggcgctggt | gcgtactcac | 900 |
| agtaagaaag | cactgatgcg | ctacgaagac | gtttacatgc | tgaggtgta | caaagcgatt | 960 |
| aacattgcgc | aaaacaccgc | atggaaaatc | aacaagaaag | tcctagcggt | cgccaacgta | 1020 |
| atcaccaagt | ggaagcattg | tccggtcgag | gacatccctg | cgattgagcg | tgaagaactc | 1080 |
| ccgatgaaac | cggaagacat | cgacatgaat | cctgaggctc | tcaccgcgtg | gaaacgtgct | 1140 |
| gccgctgctg | tgtaccgcaa | ggacaaggct | cgcaagtctc | gccgtatcag | ccttgagttc | 1200 |
| atgcttgagc | aagccaataa | gtttgctaac | cataaggcca | tctggttccc | ttacaacatg | 1260 |
| gactggcgcg | gtcgtgttta | cgctgtgtca | atgttcaacc | cgcaaggtaa | cgatatgacc | 1320 |
| aaaggactgc | ttacgctggc | gaaaggtaaa | ccaatcggta | aggaaggtta | ctactggctg | 1380 |
| aaaatccacg | gtgcaaactg | tgcgggtgtc | gataaggttc | cgttccctga | gcgcatcaag | 1440 |
| ttcattgagg | aaaaccacga | gaacatcatg | gcttgcgcta | agtctccact | ggagaacact | 1500 |
| tggtgggctg | agcaagattc | tccgttctgc | ttccttgcgt | tctgctttga | gtacgctggg | 1560 |
| gtacagcacc | acgcctgag | ctataactgc | tcccttccgc | tggcgtttga | cgggtcttgc | 1620 |
| tctggcatcc | agcacttctc | cgcgatgctc | cgagatgagg | taggtggtcg | cgcggttaac | 1680 |
| ttgcttccta | gtgaaaccgt | tcaggacatc | tacgggattg | ttgctaagaa | agtcaacgag | 1740 |
| attctacaag | cagacgcaat | caatgggacc | gataacgaag | tagttaccgt | gaccgatgag | 1800 |
| aacactggtg | aaatctctga | aaagtcaag | ctgggcacta | aggcactggc | tggtcaatgg | 1860 |
| ctggcttacg | gtgttactcg | cagtgtgact | aagcgttcag | tcatgacgct | ggcttacggg | 1920 |
| tccaaagagt | tcggcttccg | tcaacaagtg | ctggaagata | ccattcagcc | agctattgat | 1980 |
| tccggcaagg | gtctgatgtt | cactcagccg | aatcaggctg | ctggatacat | ggctaagctg | 2040 |
| atttgggaat | ctgtgagcgt | gacggtggta | gctgcggttg | aagcaatgaa | ctggcttaag | 2100 |

-continued

```
tctgctgcta agctgctggc tgctgaggtc aaagataaga agactggaga gattcttcgc    2160
aagcgttgcg ctgtgcattg ggtaactcct gatggtttcc ctgtgtggca ggaatacaag    2220
aagcctattc agacgcgctt gaacctgatg ttcctcggtc agttccgctt acagcctacc    2280
attaacacca caaagatag cgagattgat gcacacaaac aggagtctgg tatcgctcct     2340
aactttgtac acagccaaga cggtagccac cttcgtaaga ctgtagtgtg gcacacgag     2400 aagtacggaa tcgaatcttt tgcactgatt cacgactcct tcggtaccat tccggctgac    2460
gctgcgaacc tgttcaaagc agtgcgcgaa actatggttg acacatatga gtcttgtgat    2520
gtactggctg atttctacga ccagttcgct gaccagttgc acgagtctca attggacaaa    2580
atgccagcac ttccggctaa aggtaacttg aacctccgtg acatcttaga gtcggacttc    2640
gcgttcgcgg cggctaacga cgagaactac gctgcggcag tg                      2682
```

<210> SEQ ID NO 13
<211> LENGTH: 894
<212> TYPE: PRT
<213> ORGANISM: Artificial Sequence
<220> FEATURE:
<223> OTHER INFORMATION: T7 RNA polymerase version AAV

<400> SEQUENCE: 13

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
```

```
            260                 265                 270
Val Pro Pro Lys Pro Trp Thr Gly Ile Thr Gly Gly Tyr Trp Ala
        275                 280                 285

Asn Gly Arg Arg Pro Leu Ala Leu Val Arg Thr His Ser Lys Lys Ala
        290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
                340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
        370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
        450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
        530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685
```

```
Val Val Ala Ala Val Glu Ala Met Asn Trp Leu Lys Ser Ala Ala Lys
            690                 695                 700
Leu Leu Ala Ala Glu Val Lys Asp Lys Lys Thr Gly Glu Ile Leu Arg
705                 710                 715                 720
Lys Arg Cys Ala Val His Trp Val Thr Pro Asp Gly Phe Pro Val Trp
                725                 730                 735
Gln Glu Tyr Lys Lys Pro Ile Gln Thr Arg Leu Asn Leu Met Phe Leu
            740                 745                 750
Gly Gln Phe Arg Leu Gln Pro Thr Ile Asn Thr Asn Lys Asp Ser Glu
        755                 760                 765
Ile Asp Ala His Lys Gln Glu Ser Gly Ile Ala Pro Asn Phe Val His
770                 775                 780
Ser Gln Asp Gly Ser His Leu Arg Lys Thr Val Val Trp Ala His Glu
785                 790                 795                 800
Lys Tyr Gly Ile Glu Ser Phe Ala Leu Ile His Asp Ser Phe Gly Thr
                805                 810                 815
Ile Pro Ala Asp Ala Ala Asn Leu Phe Lys Ala Val Arg Glu Thr Met
            820                 825                 830
Val Asp Thr Tyr Glu Ser Cys Asp Val Leu Ala Asp Phe Tyr Asp Gln
        835                 840                 845
Phe Ala Asp Gln Leu His Glu Ser Gln Leu Asp Lys Met Pro Ala Leu
850                 855                 860
Pro Ala Lys Gly Asn Leu Asn Leu Arg Asp Ile Leu Glu Ser Asp Phe
865                 870                 875                 880
Ala Phe Ala Ala Ala Asn Asp Glu Asn Tyr Ala Ala Ala Val
                885                 890

<210> SEQ ID NO 14
<211> LENGTH: 2682
<212> TYPE: DNA
<213> ORGANISM: Artificial Sequence
<220> FEATURE:
<223> OTHER INFORMATION: T7 RNA polymerase version LVA

<400> SEQUENCE: 14
atgaacacga ttaacatcgc taagaacgac ttctctgaca tcgaactggc tgctatcccg      60
ttcaacactc tggctgacca ttacggtgag cgtttagctc gcgaacagtt ggcccttgag     120
catgagtctt acgagatggg tgaagcacgc ttccgcaaga tgtttgagcg tcaacttaaa     180
gctggtgagg ttgcggataa cgctgccgcc aagcctctca tcactaccct actccctaag     240
atgattgcac gcatcaacga ctggtttgag gaagtgaaag ctaagcgcgg caagcgcccg     300
acagccttcc agttcctgca agaaatcaag ccggaagccg tagcgtacat caccattaag     360
accactctgg cttgcctaac cagtgctgac aatacaaccg ttcaggctgt agcaagcgca     420
atcggtcggg ccattgagga cgaggctcgc ttcggtcgta tccgtgacct tgaagctaag     480
cacttcaaga aaacgttga ggaacaactc aacaagcgcg tagggcacgt ctacaagaaa     540
gcatttatgc aagttgtcga ggctgacatg ctctctaagg tctactcggt ggcgaggcg     600
tggtcttcgt ggcataagga agactctatt catgtaggag tacgctgcat cgagatgctc     660
attgagtcaa ccggaatggt tagcttacac cgccaaaatg ctggcgtagt aggtcaagac     720
tctgagacta tcgaactcgc acctgaatac gctgaggcta tcgcaacccg tgcaggtgcg     780
ctggctggca tctctccgat gttccaacct tgctagttc ctcctaagcc gtggactggc     840
attactggtg gtggctattg gctaacggt cgtcgtcctc tggcgctggt gcgtactcac     900
```

```
agtaagaaag cactgatgcg ctacgaagac gtttacatgc ctgaggtgta caaagcgatt   960
aacattgcgc aaaacaccgc atggaaaatc aacaagaaag tcctagcggt cgccaacgta  1020
atcaccaagt ggaagcattg tccggtcgag acatccctg cgattgagcg tgaagaactc  1080
ccgatgaaac cggaagacat cgacatgaat cctgaggctc tcaccgcgtg gaaacgtgct  1140
gccgctgctg tgtaccgcaa ggacaaggct cgcaagtctc gccgtatcag ccttgagttc  1200
atgcttgagc aagccaataa gtttgctaac cataaggcca tctggttccc ttacaacatg  1260
gactggcgcg gtcgtgttta cgctgtgtca atgttcaacc cgcaaggtaa cgatatgacc  1320
aaaggactgc ttacgctggc gaaaggtaaa ccaatcggta aggaaggtta ctactggctg  1380
aaaatccacg gtgcaaactg tgcgggtgtc gataaggttc cgttccctga gcgcatcaag  1440
ttcattgagg aaaaccacga gaacatcatg gcttgcgcta agtctccact ggagaacact  1500
tggtgggctg agcaagattc tccgttctgc ttccttgcgt tctgctttga gtacgctggg  1560
gtacagcacc acggcctgag ctataactgc tcccttccgc tggcgtttga cgggtcttgc  1620
tctggcatcc agcacttctc cgcgatgctc cgagatgagg taggtggtcg cgcggttaac  1680
ttgcttccta gtgaaaccgt tcaggacatc tacgggattg ttgctaagaa agtcaacgag  1740
attctacaag cagacgcaat caatgggacc gataacgaag tagttaccgt gaccgatgag  1800
aacactggtg aaatctctga gaaagtcaag ctgggcacta aggcactggc tggtcaatgg  1860
ctggcttacg gtgttactcg cagtgtgact aagcgttcag tcatgacgct ggcttacggg  1920
tccaaagagt tcggcttccg tcaacaagtg ctggaagata ccattcagcc agctattgat  1980
tccggcaagg gtctgatgtt cactcagccg aatcaggctg ctggatacat ggctaagctg  2040
atttgggaat ctgtgagcgt gacggtggta gctgcggttg aagcaatgaa ctggcttaag  2100
tctgctgcta agctgctggc tgctgaggtc aaagataaga agactggaga gattcttcgc  2160
aagcgttgcg ctgtgcattg ggtaactcct gatggtttcc ctgtgtggca ggaatacaag  2220
aagcctattc agacgcgctt gaacctgatg ttcctcggtc agttccgctt acagcctacc  2280
attaacacca caaagatag cgagattgat gcacacaaac aggagtctgg tatcgctcct  2340
aactttgtac acagccaaga cggtagccac cttcgtaaga ctgtagtgtg ggcacacgag  2400
aagtacggaa tcgaatcttt tgcactgatt cacgactcct tcggtaccat tccggctgac  2460
gctgcgaacc tgttcaaagc agtgcgcgaa actatggttg acacatatga gtcttgtgat  2520
gtactggctg atttctacga ccagttcgct gaccagttgc acgagtctca attggacaaa  2580
atgccagcac ttccggctaa aggtaacttg aacctccgtg acatcttaga gtcggacttc  2640
gcgttcgcgg cagcgaacga cgaaaactat gccctggtag cc                    2682
```

<210> SEQ ID NO 15
<211> LENGTH: 894
<212> TYPE: PRT
<213> ORGANISM: Artificial Sequence
<220> FEATURE:
<223> OTHER INFORMATION: T7 RNA polymerase version LVA

<400> SEQUENCE: 15

```
Met Asn Thr Ile Asn Ile Ala Lys Asn Asp Phe Ser Asp Ile Glu Leu
  1               5                  10                  15

Ala Ala Ile Pro Phe Asn Thr Leu Ala Asp His Tyr Gly Glu Arg Leu
             20                  25                  30

Ala Arg Glu Gln Leu Ala Leu Glu His Glu Ser Tyr Glu Met Gly Glu
         35                  40                  45
```

```
Ala Arg Phe Arg Lys Met Phe Glu Arg Gln Leu Lys Ala Gly Glu Val
 50                  55                  60

Ala Asp Asn Ala Ala Ala Lys Pro Leu Ile Thr Thr Leu Leu Pro Lys
 65                  70                  75                  80

Met Ile Ala Arg Ile Asn Asp Trp Phe Glu Glu Val Lys Ala Lys Arg
                 85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
                115                 120                 125

Ala Asp Asn Thr Thr Val Gln Ala Val Ala Ser Ala Ile Gly Arg Ala
130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
                180                 185                 190

Lys Gly Leu Leu Gly Gly Glu Ala Trp Ser Ser Trp His Lys Glu Asp
            195                 200                 205

Ser Ile His Val Gly Val Arg Cys Ile Glu Met Leu Ile Glu Ser Thr
            210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Tyr Trp Ala
            275                 280                 285

Asn Gly Arg Arg Pro Leu Ala Leu Val Arg Thr His Ser Lys Lys Ala
            290                 295                 300

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
                340                 345                 350

Pro Ala Ile Glu Arg Glu Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
            450                 455                 460
```

```
Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
        500                 505                 510

Ala Phe Cys Phe Glu Tyr Ala Gly Val Gln His His Gly Leu Ser Tyr
    515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
                595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
        690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp
            725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
            805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala Ala Ala Asn Asp Glu Asn Tyr Ala Leu Val Ala
```

-continued

```
                     885           890
```

<210> SEQ ID NO 16
<211> LENGTH: 20
<212> TYPE: DNA
<213> ORGANISM: Artificial Sequence
<220> FEATURE:
<223> OTHER INFORMATION: AD1334 primer

<400> SEQUENCE: 16
ggacctccca ccattccaag                                               20

<210> SEQ ID NO 17
<211> LENGTH: 20
<212> TYPE: DNA
<213> ORGANISM: Artificial Sequence
<220> FEATURE:
<223> OTHER INFORMATION: AD1335 primer

<400> SEQUENCE: 17
acggcgatgt tcaggttctt                                               20

<210> SEQ ID NO 18
<211> LENGTH: 20
<212> TYPE: DNA
<213> ORGANISM: Artificial Sequence
<220> FEATURE:
<223> OTHER INFORMATION: AD1336 primer

<400> SEQUENCE: 18
ggcgaaagaa gacctggtca                                               20

<210> SEQ ID NO 19
<211> LENGTH: 20
<212> TYPE: DNA
<213> ORGANISM: Artificial Sequence
<220> FEATURE:
<223> OTHER INFORMATION: AD1337 primer

<400> SEQUENCE: 19
tagccggcga aatggatgtt                                               20

<210> SEQ ID NO 20
<211> LENGTH: 20
<212> TYPE: DNA
<213> ORGANISM: Artificial Sequence
<220> FEATURE:
<223> OTHER INFORMATION: AD1322 primer

<400> SEQUENCE: 20
catcagaccg cattcgcttg                                               20

<210> SEQ ID NO 21
<211> LENGTH: 20
<212> TYPE: DNA
<213> ORGANISM: Artificial Sequence
<220> FEATURE:
<223> OTHER INFORMATION: AD1323 primer

<400> SEQUENCE: 21
ggacgaagat gtggaagcca                                               20

<210> SEQ ID NO 22
<211> LENGTH: 32767
<212> TYPE: DNA
<213> ORGANISM: BW4 phage

<400> SEQUENCE: 22

```
agcgatatct ccccgggttt ttccacaggg tgtccgccca gggcgtcgct gtcgagctca    60
cagcgcacgc tgaacgcccg ccagcactcg aggcgatccg aacagcctcg ctccgagtgc   120
gtcgggcctg tgtggatcgc tcatgagttt cgtaacaagc ccctagccac agcccgattc   180
agatagaata ggagcatgga agggcagtgc ggatggtgcg gtcgggcatt cgatcgtgcc   240
cggacgggtc gcccgcgacg cttctgctcg gcccgctgtc gggtcgccgc gtcccggtgt   300
gcgatcccgc tggccatgag gtcccgcact gcgtgggtcc gctgcgacgg caagcgcccc   360
atcaccctgg ctggcgctcc ggcctcatcc acggacccgg gcacatggtc tggctggtcg   420
caggtgcgac gcgccacggc cggcgatggc ttcgggacca tgctcggtga cgggctgggg   480
tgctgggatc tcgaccactt cgacgatcag ggcgcccggg ccttcatcga ccggatcgat   540
aagccgatca tcttcgccga gcggtcggtg tcggggcatg gcttccacat cttcgtccgg   600
actgacgagg cccccggacg ccgcaccgga aacatcgagt tctactcacg ccatcggttc   660
atcagggtca caggagacca gttcgtctga agaaggggt gcgccatggc tgcacaggtc   720
agggccgtgg accccgatga gcgcccaccc gcccgcaagc gggccaagac catcacccag   780
gccgcgaagt ccggcactga ggttgaactg ttggaggcac tgcaggctcg cgtggcccgc   840
gccgtgcagg accgtgacac tccgccgcgc gatctggcag cgctgacgaa gcggctgatg   900
gacatcaccc gggagctcga ggcggcccgg gtcaaggatc aggaggcggg atctgatggt   960
gccgtcaccg cagacgaaac atggcgaccg caagctctct gaggtcgcca agcacctgat  1020
ccttcctgaa gggatcgtct cgacgggctg gccggccgtg cgtgaccggt gtggcgagtg  1080
gggtgtggtc ttcgaccgtt ggcaggacgg catgggccgg gtgatcctgt cgaagcgcgg  1140
cagcggcctg ttcgccgctg gtgtgggcgg ggtcggcatg tcgatcccgc gccagaccgg  1200
caagaccttc accgtcggca tgatcatcct cgggctgtgc tcgctgagcg aggagctcac  1260
ggtgctgtgg acctcccacc attccaagac gaccaccaag actttcgagt cgctgcgggg  1320
catggcccag cgtaagaagg tcgccccgtt gatccgtcag gtccgaacag gaaacggtga  1380
ccagcagatc attttcagca acggttcgag gatctacttc ggtgcccggg aacagggctt  1440
cgggcgtggc ttcgacgacg tggacatcga gatctttgac gaggcgcaga tcctgtccga  1500
gcaggccctc tccgacatgg ttcccgcggc gaatgtgagc accaatccgc tgatcatctt  1560
catgggcacc ccgccgcgtc cctcggaccc gtcggaggcg ttcgcgaacc gccgcgccga  1620
agctctggcg ggcgacgccc cggacgccgc ctggatcgaa ttcggagcgg acgagcacgc  1680
cgacccgacc agccgcgccc aatggcgtaa ggcaaaccca tcctttcctc accgcacgtc  1740
ggagacctcc attctgcgga tgaagaagat gctcgggccc gagtccttca acgcgaggg   1800
cttgggcatc tgggatgaga cggcatcggt ccgcgcgatc ccagccgaag ggtggcgcgt  1860
cctgaccgta aaggaaccac ccgccgacgc gatccagtcc ttcggcatca gttcgccat   1920
cgacgggagt gcggtcgccc tggcagccgc cctgaaaccc aaggacgggc cgatctatgt  1980
cgaaggaatc gagcagcgct cggcatccga cggcatcgaa tggctcgccg actacctgac  2040
gcccctgtgg cgcaacacgg cccagatcgt catcgatggc aagtccggcg ccggtgccct  2100
ggttgatgcg ctgcgccgtg gtggcgtggc tgcgaaggtg atcctcaccc cgagcgtcgc  2160
cgacgtgatc accgcccaca gcctgactct ggaggccatc aagaccggtg gactgtcgca  2220
cctggctgac ccggagctgg atcggcaggt ccgcatcgcc acgaagcgaa agatcggggc  2280
```

```
cgccggggc ttcggctggc aggcccccga aggcgacacc gtcgccctcc tcgacgccat   2340
cacgcttgcc cactgggcgg ccctcaccac gaagcgacat cccggcagga aggcggtggc   2400
actggcatga gcctcctcgt caaccccdat gcgtcgccgt ccttcttctc gtccccgtcc   2460
gtggtcggac tcggagcaga cgagcaggag ctcctggacg agctggtggc cctgtgggca   2520
cgcaagaagc cccgcaacgt gctgcgcggc ctgtaccttg acggcaagca gcagatcaag   2580
aacctgaaca tcgccgtgcc cgacgagatc gccgacagtc tccagatcgt ggtcggctgg   2640
cccgagaagg ccgtcttcgg gctatcgaac ctgtgcatgt gggatggcgt cgtcactccc   2700
acaggcgacg agaatccctt cgggcttgac gatctcctgt cggccaaccg cttcgacgtc   2760
gagatcaatg aaacgatcac ctcggccatg gcgaactccg tggccttcct gaccgtatcg   2820 gcggcaacg tgtccatagg tgagccgccg gtggtgatca tgccgttctc cgccgaatgg   2880
gcctcagccc tgtgggaccg gcgcacccgc tcaatcaagg cgggactgac catcggcgac   2940
atcgactacc tgggccgccc caccagcctc tcgctcttca cccgcaccgc caccatcacc   3000
tgcgtggggt cccggctggg atggatgatc gaagatcgcg ccgagcacgg gctgaaccgc   3060
gtcccgatgg agccggtccc gttccgccca acccttgacc gcccttcgg gcgctcgcgg   3120 atctcgcgcc aggtgatgac catcgtggac cgcgccatgc gcgcggccct gcgcatggac   3180
atctcctcag agctgttcac cgcacccggc ctgctcctca acggaatcac cccggagcag   3240
tgggcagaga tccagaagtg gacatggaag ctcggcacgg tgcgcggcct gactcgcgac   3300
gaggatggcg agaccgcatc ggtcgagacg atcccccagc agtcgatgga accgttcatc   3360
gcgcagctgc gcgagctggc cgaggaattc gcctcagcca catccatgcc gctgtctgca   3420 ttggggtcg tccaagacaa ccctcctcg gctgacgcca tctacgcggc gaaagaagac   3480
ctggtcatcg aggccaccaa cgccaaccgg atcaccggct acgcgctatc ccgggtcttc   3540
caagacgcgg tgatgatgcg cgacggcctg accgagatgc ccgacgagct cggcggggtc   3600
gccgccaagt ggcgcaaccc ggcgatgccg tcgatcgtgt cccagtccga cgcgatggtc   3660
aagcagattt cggcgatccc cgggctggcc gctaccgacg tcgccttcga acagctcggc   3720
tattcggcgc ctgacatcgt gcggattcgt acccagatgc cgagccca ggctgcggac   3780 ggcctgactt cgttgctggc caaaccagcc acgtcgtcaa cgcctggcgc ggagccctct   3840
cagtccgcaa gtccgacgga gccagctgca agcactccgc tgccggacct cgaaggggcc   3900
cctggtgacc gatcgtgatg acctgaacca tttccacgag gccaatgacg cgatccagcg   3960
gcgcgcaatc aacgacctga caagtttttg ggcgcggctt gccaagtcag acccgaaagc   4020
cgttcgcgca gccatggact tattcgtccc ccagctcatc gcctcctacg gagagttggc   4080
cgccgaagcc gctgcccgtt ggtatgagga actacggccc gccgacaaga gaacttcca   4140 ggccgaactc gcggaccctg tgtccgacga catcatcgag gcagatgtgg ctgaggccct   4200
ggggaccagc ggcgcctggg acaccgaggc ggtgcgaggg agcctggccg atgcgatcag   4260
gcgtcagatc ttctacatgg cgcgggcgac tgtcgcacgc aacatcgctc acgacccgaa   4320
gcgtccaagg tttgcacgag ttcctcgggg cgcggtcacg tgcgcgttct gcaccatgct   4380
cgcctccagg gggtgggtgt actacaccgc gaagactgcc gggatcacac gaccctggca   4440
tcgcaagtgc gactgccaga tcgtgcctga gtggaaacgc ggcaacatcc atttcgccgg   4500
ctacgaccct gacaagatgt tcgagcagta tgccgaatcg gtcgatgcgg tggggtcgag   4560
cttcgacacg aaggcaatcc tcgccgacat gcgccgacgc catcccgaag cgctgaccga   4620
cggggtcgtc aacatgagtg aaggacaggg tccggtgacc agtgattaga cagtcggtga   4680
```

```
acggatgact acgccgtcgg cgctgcgccg ccgcctggaa tggctactgg agaaccgtga    4740
acggcttctc aggagccatg gcgagtcgga cttt gccgag atgctggatg cgcccgtca    4800
cgagcttgat gaggcccgcg agcaggcagg cctggccgcg cagtcaaacc caatctgtag    4860
caagccccgt tccaccttcg ggtgggcggg gctttgtcat gcccgcatcc gggcatccaa    4920
ttccgtccca ccgcgagggt ggggcgtcga cctggtggcg cgatgccgcc gaactaatcc    4980
ctggaagggg aaactgctat gcacaagaag ctcatgccgt gggtccgtct catcgaggcg    5040
gtcgagactc ctgctggagc cgcccccacg cccgcgatcg atccgaagga tccggcagcc    5100
aatcccacca ctgagccgaa gccggccgac gcgacgtcgg agaagcctct cggcgaggcg    5160
ggcaaggttg cgttggatcg cgagcgcgag gctcgccgca gcgccgacaa gcgcgccagt    5220
gagttggagg cccgtgtgca ccagctcgag gacgcgggca agaccgaggc ccagaagcag    5280
gccgacgaac tcaagcgcac ccagtccgag ctggagacgc tgaggggcga gaaggcacgg    5340
ctggaggtgg cgtccgcgac gggcgtcccg gtcgatctgc tcgctggccc cggcgacgat    5400
ctggatgcct acgcgcaggc cctgaacgcc tggcgcgaca agcagtccga aaagccagcc    5460
gcccctgcgg tggacacccc ttccccttcg ccgtccgggg tgaccggaca gcccgtgcag    5520
ccgaaccgga cggtcgatga actcatcgcg gccgccgaga agaacggcga tctggcaacc    5580
gcgaagcaac tcaaattgat gaagctcgac gcactgcgtc ggacgtcctg atcagaaagg    5640
caccactatg ccgggcatta ccggacaggg caccacctac aaccttccga actatgtggg    5700
ggagcttttt gcggcatctc ccgaagacac cccgctgctg tcggcgatcg ggggactgac    5760
cggcggcgag tcggtcggcg cccgccagtt cgaatggcag ggctacgacc tgcgcgacgc    5820
cgacggttcg cgccagcgcc tcagggagc caacgccccc gacggtgagg agcgcacccg    5880
ctactccgcc tccaatgtgg tcgagatcca ccaggagtcg gtggaggtgt cctacaccaa    5940
gcaggccgcg aaccgtgagc gggctaccaa cggtgccgcc acggtccagc tggcgggctc    6000
cgtgctgccg gccgatgagc tcacctggca gatcgaccag cagctcaagc aggtcgcccg    6060
cgatgtcgag aagtccttca tcgcgggcac ctaccagctg cccaccgaca cgccaagcc    6120
gcgccgcacg cgtggcctgc tggaggcgac caccacgaac gtggccgcct cgacccacac    6180
cgcaaaggaa ctcaccgtgg aggagatcct cgacctgttc cagaaggtgt gggagaacgg    6240
cggcatccag gaagccgaga cccgcaccgt cattgtcggt gccgccctga gcggaccct    6300
gacgcgcctg ttcatcaccg acgtcaagta ccaggaagaa tcccgcaacg ttggcggtgt    6360
gaacctgcag accttcgaaa ccgacttcgg caaggcgaac atcatgctcg accgcttcat    6420
gccgagcgac accctcgtgg tcgcgtcgct ggaggacctg aagccggcct tcctcgacat    6480
ccccggcaag ggccacttct tcgccgagcc gctcgcaag accggtgcag ccgacaaggt    6540
gcagatttac ggcgaggtcg ggctgcagta cgggaaccag cgcaagcacg aaagctcac    6600
tgtcgcaccc gcaaccccg ccaagtaatc acgatcggt tgaggttgc ctgatgaaag    6660
tcacctcgac catcccgaac ctgactgttc tcgacctgga catccagttc gttgacggtc    6720
aggccgatgt ggacccgcat ctcgccgaga ggctgcgtcg cctcgagcct ctcggcgtgc    6780
gggtccccac agccagccgc aagccgccca cgcggtcgcg gcgtaagcag ggggtcagcc    6840
atggtcgcac ctgatccgga actgccgttc gccaccgtct ccgatatgga gaccggtgg    6900
cgttctttgt ctaaggacga gcacacgcgg gccgaggccc ttctggacga tgcgagcggg    6960
ttgatcgttg atacctgccc gcgctgggaa caggcctcac cggccaccct gcggcgtgtg    7020
```

```
acgtgctctg tcgtgcgccg ggcgatggcc gcagacgatg aggacatcgg cgcaacctcg    7080
ctcatggaca cgacgggccc cttcaccact cagcgcgcct actcatcacc ggccggggat    7140
ctcttcttga ccaaggccga gaaggccgcg ctcggcgggg tcaccggcgc attcgagacg    7200
agccttctgg ggctgacatg aagcgctcat ggccgacacc cgtggaacgt ctccgcgagg    7260
gtccgcccga gattgaccgt gacggtgatc cgattgccgg ctccggagtg atcaccaagg    7320
atcctctccc tgatgccctg ttcgcgccgg cggctcgca gatcctcgtc gccccggcg     7380
tggcggcagt cgtggacgaa cccaccctct actggcgcgg atcagaagtg atcgatgtgg    7440
tggccaccga caaggtccgg atagccggcc gagtctggac ccctgaagga atcctgcgc    7500
gatggccgaa gggcgtcgtg ctcaagctca aggcccagga ggcaaagaat cgtggctaat    7560
ttccgtttcg aacccaatac gaaggcgttc accgagtggg cgcagcgcga ctgcgacgcg    7620
cacctgatcg ccggcatcac ggcctcgatg ggggccaagg cgggcgaggg tttctcgacg    7680
atggtctcca caatggcga ccgcaccccgc ggttatctcg cgacggcctc cacgaagggc    7740
cgtatgcggc aggcgcaggg gcatgtcatc gagcgggtca tcggatcgag cggcgtgtga    7800
aaccgcccga cctccacacg ctcgtcgccc accatctggc tgagctcctc gacgtgccgg    7860
tcgtctccac ccgccccgag ggagagacg cgccgtccaa gttcgttcgg atcatctcga    7920
ccggcggagc gggccgctat ggccgggtct tccagggcat ccagctgacg atcggctcct    7980
acgcgggatc ggcggcgacc gcccgtgatc tcgcgatgca ggtggacgag gccatgaatg    8040
ggctgccggt ctcgccgttg ccggtctcca aggtcaccgg caacaccccg tcggacgacc    8100
ccgatcccga cactcagcag gcccgccaca cggccaccta ccaactcacc accccttatct    8160
cttaggagtc attcatggct gtcaattccg tcaacgtgca cgtcttcggg tccgatgacg    8220
acgtgctcta cctgggcccg tcaggtctga atctgggcaa catttcgctg gaaaccgcga    8280
tcccgaagga gatgatcgac accggctggc tcactgatga cggtgtgacc ctcggcatga    8340
aggactctgt caaggccatc cagggccacc agggccacgc gaatgtgctt cagttcatgg    8400
actcgtcgga taccacccct gaggcgaccc tcatggagtc tcagctgcag accttcctgt    8460
ggaacctcga cgcggacgct gaggacatcg acggggtcac caagatcacc gcggccagct    8520
cccgcaaggt cctcaacctg tgcgcgatct gggacaccct cgacacccag cacagcggca    8580
tccattggcg ctacgtcttc ccctcgctca ccctgggcga gcgcgatgac atcccccttca    8640
aggtgggcga agccagcgct tacaagtatt cgctgggtgt gctggagaag ttcttcgtct    8700
tcaccaacgc ggcagcgatg aaggccggtg gagcatccgc caagacggtg accggtgtga    8760
agatcaccac caccgacggt gcgaccgtgg gcctcccgtc gtcgctgaag gtggggagaa    8820
aggtgtccct cgccgccgag atctcctaca gcgacgggac gaaggcgtc aagcagacca    8880
atgccgtggg cctcacctgg acgtcctcgg acaaggccaa ggccaccatc gatggcggcg    8940
tggtcaccgg agtctcggca ggcaaggccg acatcaccgc ctcgatcgac ggcaagactt    9000
ccgaagcgct gtcgctgacc atcaacaccg ccgcctgacc aaccctcaaa ccctccgccc    9060
cggtcgtcct ctcgcgccgg ggcggagcct tgccacaccc gcgagaggtc aacttttctg    9120
cgagaggaaa ccatcatggc cgaggccaag aagatcagcg ccgccgagaa ggcgcgccgc    9180
gagacccagt ccgcgaagga caccggcacg atcaccgaca ccaccgtgca gatcggcgat    9240
atcgagttga ccgtgcccgc cgccgtcttc gaagacgact gggaattcca ggaggcgatc    9300
ctgatggcca acgatcccga tgccaccgac gaggatcggg ccaggcaag catgacgctg    9360
ttccgtcgtc tggtcggaaa ccgccaccgc gaagtgcttg accagctgcg cgacgagtcg    9420
```

```
gggcgtgtgc cggtgtctaa ggtcaccgag accgtcaaga aggtcatgga cgcggtcaac  9480
ccaaactgat gagcctcttc cagctcctcg ccacacattg ggaggagctg gaggggact   9540 tccaagaggc ctaccgcgtc gacctgcggg acttgtggcg tggtcggctg agcccggcgc  9600
gctgctgggt gctgctgaca caactgccac ccgggtctcg gctctggcgg atgctcggcg  9660
gccccatggc gtggggcatg gtcgagcgcg ccgtccgtga agagggctgg cgactcgcct  9720
cccagaacgc tggtaaggaa ctgcctcggc cggagccgcc tgcgccggga tggcgcgaca  9780
agcaggacga cctgcgacgc cgcgaagagc gccgtcttgc ccgcttcatg caacgccacg  9840
cagaacgcaa caactgaaca gtgcaccgtc ccgggaggtt ccatggctc tagatctcgg   9900 taccgcctgg gtgcaggtgt ctccgtcctt caggggcttc gcctccacgg tgaacaaaga  9960
ggtcggttcg gcagtgggcg gggccttcaa gtctgcggcc aaggtcggca ccaccgcgat 10020
cgccacgatc ggtgcggccg tcggtgggct ggcgctcaag ggcggcatcg accgcgccct 10080
gtcgatcgag caggcgcagg ccaagctgaa gggcctgggc cacgacgcag ggtcgatcac 10140
cgagatcatg aacgacgccc tcgcctcggt gaagggcacc gccttcggtc tgggcgatgc 10200
cgcgacggtt gccgcgtcga tgtcggctgc cggcgtcaag tcgggcgagc agatgaccgg 10260
tgtgctgaag acggttgccg acaccgccca gatttcgggg cgctcgctca ccgatatcgg 10320
tgcgatcttc gggtcggtgg cggcccgcgg caagctgcag ggcgacgaca tgctgcagct 10380
catgagctcc ggcgtgccgg tgctccaatt cctttccgac cagctcggcg tcaccaccgc 10440
cgacgtgtcg gacatggtgt ccaaggggca gatcgacttc gccactttct ccgccgccat 10500
gcagaagggt cttggtggtg cggcactggc tggcggcgaa accttcaccg gtgccatggc 10560
caacgtccgc gccgccctgt cccggctggg tgaggctgcc gccaagcctg ccctggacgg 10620
gctgcgcaat gtcttcaacg cgctgatccc ggcgattgat gccgccacaa atgcgctcaa 10680
gcccatcgcc agcgccctgg cgaaccgaat ttcgcaagca gcagaggcgg cttccgcctc 10740
gatcgggcgc ctcaccggct ccctcacgag catcacgaat ctcaatacag ggatgctcgg 10800
cgcggccttc tcatcgatgc tgccgatcat cggagcactg tcggggcagc ttggctcctt 10860
gcttggcggg atcccggtcg tcgggcaggc cttcgcaggg atcactgggc cggtgggatt 10920
ggctgccggc gtgctggtcg agatcgtggc ggcttcatcg tcgctgcgtc aggccctggg 10980
cacgctggtc ggggtcgtcg ggtctcagtt gtccggtgtg atgacgggca tcgtcgcggt 11040
gtttgccggc ttcaggtccg tgcttggtgc cgtcggtgac gttctggccc cgttcgtgga 11100
ccgtgcggcg gacgccgcca atgtggtcct gcccttgctg ggggtgcgc tgtcggctgc  11160 cggtggcatc ctgcagtctt ttgcgggttt catcgagcgc aaccatgtgg cgctctccat 11220
tcttgcgggt gcgtggttg cggccgcgac gagttggaag atctataccg gcgcgcaaga  11280
tcttgcgcgg ctggcaacga cgaagctcgg gctcgcgaca acgtcctga agggcaagct  11340 gtcatcgatg ggggcggcgt tcaagacgaa tccgttcggt gtcatcctca tggcgatctc 11400
ggcgctggtg ggggcgttct cgattgccta ccagtcctct gagacgttcc gcaacggtgt 11460
gcagggattt ctcggctcgc tggcgccggt gttttcctcc ctgatgggga cgctgtcggg 11520
gctattccag caggtcgcgg gcgctgtcgg gccggtgctg tcgtcgatcg tctcgacgct 11580
ggcgtcggtg ttctcggcga tcggtcccgt cctgtcgcag ctggccggca ccatcggatc 11640
tgtcttctcg gcgatcggtc ccgtcctggc gtcggtcttc gggtcgatcg ggtcggttct 11700
ggcgagtgtc ttctccgggg tgatgagtgt cgtggcgccg atgctcaccg cgttgcagcc 11760
```

```
gctgttcacg cagctgtcgg cttcggcggg gcagatcggt gcggcgttcg gtcctgttgg    11820
tcaggcgctg tcgtcgtcct tccagcaggt cggtgccgcg ctggcgccgc tgctgccgat    11880
gcttggtcag cagttcgggg cgatcctgtc tcagctggct gcggccctgg ctccggtcat    11940
gggtcagttg ctggctgcgg ctgctcaggt gttgccgacg ttggcgcagg ccttcgggca    12000
ggtcgccggg gtgctgatcg ggtcgctggg tcaggctctg acccagatcg ctccgctgat    12060
aggccagctg gtgggggtgc tgatcgggtc gctgggtcag gctctgacgc agattgcccc    12120
gctggtgggc accctggtcg gggtggtcgc gcagctgttc gcccagctgg cccctttggt    12180
gggtcagctg ctggtgcagc ttgttccggt tgtcgcggga atccttgtgg cgatcgtgcc    12240
gatcgtcggg atgctgatta gtcagctcgt tccggtgatc gtcacgctgc tccaggtgat    12300
caccccgatt atcaccatgc taatcagcgc gctggtgccg gtgatccagg tcgtgaccca    12360
gctggtgctg gcgatcatcc aggcggtgat cccgttgatc tcggcgatcc tgccggcgat    12420
ctcggcactc atctcggcgc tgctgccggt gatcgtcatg atcatccagg tggtggcgca    12480
ggtgctgcag tggctggcgc cgctgatctc caccctgatc acggcactga ttccggtgat    12540
caccacgatc atccaggtgg tcatcacggt cgtgtcgaca atttggtcgg tggtcggggc    12600
ggtcattggc tggttccagt ccacggttgt gcccatcatc ggcaccgttg ttggtgcgat    12660
cgcgaacgct ttcggttggg tgcgcgaccg tatttccgat gcctggaact ggattaagga    12720
ccgcattgtc gccccggttg tcgagtggtt ccagtccacg gtggtgccga agttcgaggc    12780
ggtgcgcgac tccgtggtgc gggccttcga gacgctgaag gatggcgttg gtcgcgcctg    12840
ggatgcgttg aaggatctcg caaagaagcc ggtcgaattc gtcgtgaaca cggtggctgc    12900
cgggttggtg cgggcctaca actgggtggc gacgaagttc ggtgccgacg aggtcaagga    12960
gcctcatgtc gagttcgcca acggcggttt cgcgggacgt gaggccggct tcgcgtcgtc    13020
gccgatcctg tgggccgagg ccggcccgga agcctatatc ccgttggatc cggccaagcg    13080
gacacgctcg ctggggatct gggccaagac cgggcagatg ctcggcgctc tacccatggc    13140
tgacggcggg atcatcggga acatcattgg cgggatcggc aacgccgctg cggcgatcgg    13200
caatttcatc aagtcaccga tcgagtggct catgggccgg gtccgggacc tgatcgatga    13260
tgtgggcagc tcaccgttcg cccagatcgc cgcgaagatc cccggcaaga tcgccgacga    13320
tatcggcgcc tgggtcaagg aacacatggc ctccatattc ggcggcggcg gttccggatc    13380
ggaagcgttc gacggctggt ggaacgcggc tgtcgccatc aatcctgata tggcccccctt    13440 caagcagatc gccgccacgg tcgcccagaa cgaatccgga ttcaacccga acgtcatgaa    13500
caactgggat tcgaacgctg cggcgggcac gccgtcgggt gggctgatgc agttcatcca    13560
gcccaccttc gaggcctaca gtggccccgg attcgacaat tggatgggtg cggtcgatca    13620
gatcctcgcc tggtggaagt acgtgaatgc ccgctatggc gggccgttca atattcccgg    13680
aattgcctcg ctggcgggtg gcggcggata tgtcggctac gccggaggca ccctgaacgc    13740
ggctgccggc acggcatggg tgggggagaa cggccccgag ctggtcgatt tcggtggcgg    13800
cgagtcggtc tacaaccgct cccagattga cggtctggag gatcggatcg ctgaccggac    13860 gatttccccgg ctgcagcagc tgagggtggc gctgatcgtg gacggacatc agatgggtca    13920
ggtcatcgac ggccgcatct ccatggctgg cgctgctgca cacggatcga ggtggtgaca    13980
tggcgatcat tgcgacgcgc cgcgactggc ctgaggctcc gcaacgcttc cagtccgccg    14040
atgggcggct ggtggcggag ctggaccctg accggtgcgg agtgcgactg cgcggcaccg    14100
acctggaggc gtggagcgtc accctcaccc gtgatggcga ggtgatccac accggcgacc    14160
```

```
ccatggtcac accgggagga acaggaatcg cctacgacct gtctgcaccg ttggatgctg    14220
atgtcgtcta cgaggcgcac gcgggtgggg cggtgctcac gcaggtggcc gtccacaccg    14280
gcggcttgcc tttcgagtgg gggatggtga ccccgctggc cgaccccgac aagggcctga    14340
tgctacggac cgtcgccgac accccacgc tgggcaggtc ggcacgccag aagctgtctg    14400
cggtgccctc atcgaggctg caggcaggtg gctgggacgt ccccaccgac gcggcacagg    14460
gatggacgtg gctcgcggga ttccccgacg cctccaaagc gctcgccgag cgcgacgcga    14520
tcatggaggc cctatcgctg gggccggtct acttccggcc cgaaacctcg atcggcttcc    14580
cgcccatgtg ggcactgccc ggcgacgtgt cagcgaccaa gcaggcgac gcctggacgg    14640 tgtcgtgcac gctgacgccg atcaccgctc ccgcgaccgc cgacctgccc gcctgggcgc    14700
ccggcaacag ctatgcgcgt gtggcggcca cccgggggag cctcgccgag ctcgcccgca    14760
catccaagac attcctcgag ctagtggggt tctgatgatt gaagtatcca agcgatgggc    14820
ctcctcagta ggggccggtg cacgctggtc ggtgatggtc tcctggtcct ccgacggagg    14880
ccagacctgg catgacgtgg tgcccaccgc ctgctcggtg gacgagtcta ccggccagca    14940
ggtgcggtgg aagctgtcct gcaccctgcg caaggccgac gccagggcc tgaccgtctt    15000 cggttgcagg gcgcgcgtct tcgtgtcgat gcatcacacc gacagctggg aggagacgat    15060
ccagctcggc gaattccgca ttgacaccac ctctgacacc accctcgccg ggccgtccgg    15120
tgcgcaggtc gcggcagttc aggtgagcgg ttcgagctgg gagcagcagc tgatggactc    15180
gcggctggtt gagccgcgtg aggtgtcggg tgccgcgatc gatgtgctcg gcggcctgat    15240
ccgggaggtg ctccctgacg cagagatcgt cttcgacggc gggatcgatc cgggccgcaa    15300
cattccggcg acggtggtgg agcgtgaccg gtgggccttc attgacggct cgaattcgtc    15360
ggagacgtcg gtggcgcgga tgctcggcgc ccaggtctcg accgacgcac ggggcgtgtg    15420
gcatgtggcc ccgcctccgg tgctggacgg gacggcggcg tggacgatcg aggccggcaa    15480
gggcggtgcg ctcctgtcgg cggtggccag cgaggaccgc tccacgatcc gtaacgccgt    15540
catcgcgcgc ggcgagtcaa ccgataagag cgtgccggtg ttgggtccgg tgaccgtggc    15600
tgatcacaat gcgtggtcac caaccaacgt ggacactccg gtctccaggg gcggcttcgg    15660
cacagtcccg atcttctaca cttcgagcct tttcaccgac acgacgcagg tggaggcggc    15720
agcgaaggcg atgctgcagc cgcgcctggg cgtcaaacgc accctggacc tgacaacgct    15780
cttcgaccct gccaaacgcg ccggggatgt gggtgtggtg cagaccactg atggtccggt    15840
caccgtcgtg ctcgaatcag tgtcgtgcga cctggtggcg gcgtcgatga cctgccagac    15900
gcgcggcacg accggcaccg agctgatcac gaccgaaacc acgacaacca ctggggagaa    15960
gatctcatga gtgcaccaga cattgccctg caaggactga tcgggaaga caccgagcag    16020 gtggcgcttg cccaggtgct cggcgtgggc gtcgacgggc ggtcggtgcg tgtccagcgc    16080
ggcactctca cccacgaggt ccgccggctc gatagctaca agccttcagc gggagaccgg    16140
gcgctgctgt acggctatc tggcggcgaa tgggtgctga tcggcgccct cgcctgacct    16200
tgacgaccta acctctgaca acctgaaaag gagccctcca tggcaaccgt ctatggccct    16260
gacaaattca ccgtcccgac tggtccggac gcaccgacg tgccggcgac gatcatcacg    16320
ctgctggact cgatgcgtcc ctcgctgatc gggcatgcgt cttcgatcgc tgaccgcacc    16380
gcgaaatatg gcgggcatc cgcgtcgagc attcaggcgc cgaagggcac agtggtggtg    16440
tctgccgagc tgaacgcaat ttgggtgaaa acatcggaca cgctggatga gtgggcgacg    16500
```

```
atcattcagc actcggatga ggtggcgacc gtgtcggtgg tgtccaccca gtccgaccag    16560
gtgaccacgg tccagaagtt cacgattccc gagtcgggca tctatgcgct gtatgcatcg    16620
atgaatgacc agaacggctt ggatgtcgat gggtcgatcc gtgagataca tgttctggtg    16680
aacgggacct ggaagttcgg tgggatcttc ccggcgagca agttctggct ctggtcgggt    16740
tcgcggacga cctttctcaa taagggcgac acctatcaga tcgactttat gcaacgctca    16800
ggcggggaga ggtccctgaa ggtaacgctg tcttatcaaa ggattttgta atggcgacgt    16860
gggattacgg gtatgcgccg gctgatgtgg tgaccgatgc ggccggggat gtgctggccg    16920
gcatcgaact gcgggtgtgg gacgccgagg tggcagggaa agccgtcgcc gtccagcagg    16980
accgtggcga cggatggaaa cccgcgtcaa gagtcctcac cgacgacgtg ggccgctacc    17040
gatttcgtgc cgaagcgggc cccacggtgt gggtggagga cgtgtcaggg cggcgctggc    17100
ggatggatgc ctggcagacg ctcggcacga tgatcgactc cgcacagagc gccaccgccg    17160
cggccgagtc ggccaactca atcgcccacg aagccatgtc agtcgcccaa caagcccaga    17220
cgtcggcgaa ggccgccgcc gactccgccg ccgccgtgca gggggttgcc ccgtccgacg    17280
cgaatgtgtc gccgatcatc accggcgggg cgaagactgc tgaggcggtg cggaaggcgg    17340
cgctggctgc tttcccgacg accgggccga cgatcttcac gcacttcttg acgcgcgacg    17400
aggccctgca tgtggcgatc tccaccgacg gtgtgacggt ggaggacacc ggcctgcggt    17460
ggaagccgaa gaacgacacc accctggggg agtgcttcgt gcgcgaccca tcggtgtgtt    17520
tctggaaggg tgcctattgg gtcgccttca cccggcccac gaagggcggg ggtgacgctt    17580
tcgggacgac caagtcgttc ggactgatga agaccacgga ctggcggacc ttccaggagc    17640
tcccgccggt cgtgatgccg agtcaatttc agcagacgtg ggcgccgcag tggttcatcg    17700
gctccgacgg ggtgccgcat atctttgtgg ccctcggcac caccaccacg cccaacgcgt    17760
acttcaccca gtatgagctg cggccgctcg atgacgcgat gacgtcctgg tcggacccgg    17820
tggtcatgtc tggactgcca gcgaattgca tcgatgtcgc ggtgatcgag gacgccggta    17880
ccttccacgc cttccgtcc aaccagaaga cgtcaacggt cgagcagtgg acgtcaaccg    17940
ggctcaccgc cccctacacg aagctggcgg ccagcgactt ccccggtgcc ggtgtcgaag    18000
gaccccagcc agtgccgctg aagacgggcg gctggcggat ctacgtcgac aattacgcgg    18060
agaccgactc gatctatttc gccgagagca cggacttgct gcattggtcg gcgctcaggc    18120
cggtcaccct gccgatgcgt cacgtcggcg cggtcgcggt ggactccttc ggtgcgctac    18180
gcacccgcga gctgtggcag ccgaacatcc cgggcatgag ggggatgggg gcacccttct    18240
ggggcgtacc cttcgccgcg gggaacgtgc tgaaggaatt cgcgcagatc gtgtccatgc    18300
gcaccgacgg cggcggcgaa atcgatctgg caaaggcggc cacgctgggc ttcaccggca    18360
tcgattacat ctcggcgacg gctgtcgcga acgtcgagat tctgcagatc gagcccgaca    18420
ttcgcgctgt cgacagcatg atccacggcg tcgccctgcg aggaccgagt acgccgcaga    18480
tcgatacaga cgtgaaggtc gcctggcggg tgctcggctg ggcgatccg agcacgccat    18540 gagcagggac gctgacgtga ccaagcaggg atccttgcct cggcgggtct gggacatgct    18600
ggcagagccg aagtcggtga cggtcctcat gacgattgcc tacgcggcgc tcgtcgcgct    18660
cggcttctgg gcgatcgacg acgcctccac gatggggtc cgcgacatga tgggcggcct    18720
gctcatcgct ggtggcgtgt gcgggctgat cggatgcccg tggggccagt ggtggatcga    18780
gcgcgccggt ctggtggcga tcggtgccgc tttcgcggta cacctgtctt tcgtcgtggc    18840
gatctccccg cccgacggac cgtgggaagt ggcctcggcg ctgggctgc tgcttctcgt    18900
```

```
ggcgacacgc tggatcagga tcaggacgct gccagccgac ccgacgctgc ctcggcccgg   18960
gcctccagag gcgggggatg aatgaatgac ttccagacct ggatcacagt gctgggcggc   19020
gccggattcc ttggcgcgct cgtcacgctc atcaaggggc tggttgggtg gcgcaccggc   19080
aagtccggcc gcaaaatgag ggccgcccac gacgccatcg actcgctgaa tctggcgggc   19140
ttgtgggctg aagcctactg gcacgctcgc ggctattgcc gcagccacca tgaatggacc   19200
agcgattacg ccgacggcta tccacccccc cccgacgaca ccaacacccc tgactgagcc   19260
ccgccttgtg cggggctttc tcattcctca aagacttgga gacattcatg gactggacca   19320
atctgaacgc tgacgtgacg aagctgatgg gcgtgcactt cacccccgga cgtgaaggca   19380
ggacgatcga caagatcgtg atccaccaca acggcggcaa cctgagcatc gaccagatct   19440
ggaatgtgtg gcagacccgt gaagcctccg cgcattatca ggtggaggcg ggtggccgta   19500
tcggccagct cgtcaacgat ttggacaccg cgtggcatgc cggcgactgg gacgccaacc   19560
tgacctcgat cggcatcgag catgccgacg actcgaccga cccgtggcat gtgtctgatg   19620
ctgccgtcga tgccggcgcg cacctggtgg ctgcactgtg tcgcggctac aaccttggcc   19680
ggccggagtg gatgcgcaac gtcttcccgc actctcagtt cacgtccacg tcgtgcccgg   19740
cgtcgctggc ccgggaccag ctcggcgact acatggggcg cgcacaagcc tacttcgatg   19800
gcgcgccggt ggctgcggtc catcagtcgg tccctgcccc cgcccagcg cccagccgtc   19860 atgtggacct gcccgcgtgg aatctccccg agggcaactt ctacggcctc gtcagcggcg   19920
gaaacgactc ccacgcggc ttctatcccg ccgagcgtcc cgctgtgagg gccatccagc   19980
tgtggctcat ccgtcacggc tacgccggcg cggtgcctga cagttgggcg gacggcatct   20040
acgagcagcc gaccgccgac gccgtgaccg ctttccagca cgccgagcgc cccaacagca   20100
cggaccggtg gggcgaggtc tgggccgacg acctggccac catggccgcc aacaactgac   20160
aaggagctga tgccaagtga tctggactct cgcattctgg aagggcgcag gcgagcgcgc   20220
catcaaaacc gccgcgcaga ccgccgtcgg cctcatgggt acctcgacgc tcatcgaaca   20280
ggtgccgtgg actgtcgtcg cctccggcac cgccatggct gtggtgctgt cgctgatcac   20340
ctcgatcggc aacgccgact tcaccgccgg cgtccccact accgcaagg gctcgaggc   20400 gacgaccgtg ggcaagacgg acaccacgcc cgtcacgcca ccggcgcgcg tcgccgaaga   20460
ggtcccagcc ggcttcgtcc cggacacggc cccggatccc gtgccgaccg tctgacctga   20520
gggggtgacg gcgaccctgc gccggatagc cactcaagca acctgagcga cacaagaccg   20580
cccactctga ccttcgcggg tcggagtggg cggccttttt gcgtctcagg ggcgcagatg   20640
atgactcgtc gtctttaatt ctagcagtac gcgttcagcg tcgccagacc atgactttct   20700
cggctgcctg gagcggcgca ccttcgggc ctttgaggta gggggcgatg tagatgagct   20760
tgcgcagtcc atgcttgggg ccgtgcgcct ggtgggtcca gtgcccgcgg accatgaacc   20820
gcacggtgag cttgtgcccg gttccgtcgt cgcggtcggt gaccacggtg cgcacggac    20880 gcagatcgac cagggtgacg tgacggtcgg ggcgtggcgt gcggggcctg tgctcggtgc   20940
ccggggcctt gccggtgcgg gagtcgatcg tgccgcgctc ggcgacggtg ggggtgtcca   21000
tgagcacgct catcgccatc agcagcgacg cggacatgcg ggcctcgggg ctcagcgtgg   21060
catccagatc ggattcgggg cggatgagaa tcgacaggat ctcgacaagg ggaccgtcca   21120
cgtcagcgaa gccgggcgga tagtcgccca gccgccccag cagctggatc atggtgcccc   21180
caccgggagc gggaagccag gcgatggccc acacgggagg attcccctgc caggtgcggc   21240
```

```
cgccgggcag gtcgaaggtg cgcggcttgg gccccggcag gggtttggcg aagcaggcca    21300
gtccggtcgg ggtgatcagc tggctcgggc tccactcggg cacgtccagg gcagcatcca    21360
gagcgagcgc cgccatctcg ccactcaccc agaacagcga cgcattaccg agccgctcgg    21420
cactccaccc gaagccggac atcggcagtg ccttgtcgcc catggcttca gccaccgcat    21480
cagggtgggt ggcggccagt tgctccaggc gctcgtcgag gtggcgggag tcccgcacaa    21540
agcggcgacg cagcccgggc actccgcggg gtgtccacgt ccagctctcc ggggctgcca    21600
tgtcaggcga cgactcgaat gcccaggctc cgccacgcct cggcggtgtg gtcgagcccc    21660
agatcccacc actgggtcag cgcgtgttcc atggcgatcg tggcgcaggc cgacagctgc    21720
gaggccttgt cgcgagccga cagcaggtcg gcgctgtcgg tgccgtcggg cgtgaagtcc    21780
tgcagggcga tagtgatgtc tccgccggga agctgggaga ccgtgtcggc ggtcatgcct    21840
gcctgggtgg cgtcggcgat gatgcccagc tcgaccagcg tccagccggt gcgggccagg    21900
tcgatgcgct gggcctcgcg ccacaggtcc atctcggtgc gggtgcgtgc cgacaggctc    21960
gggggtgcgg ccacatcggc tccgcgtcgg gccatccatg cggccatgtc gtcggtgggc    22020
cgccaggtga ttgtgctggc catgaagatc ctcctcggag tggaaagtgg aaaggggagg    22080
ggccggagcc cctcccctga tggttgatgt ggtcagcgga tccaggtgaa gggctggtcg    22140
ccgatgatcg agcggaccgc gaggtcgtag ggggcctcgt cctcgctgga ctcgacatcg    22200
accgcgtcga gctcgacacc gtcgcgggtg atggtgatgg tgtcggtcgt ggtggcccga    22260
ccgtcgatca ccgtcggagt gttgatgctg gtgaactctg cggtgatgcc gaccagctcg    22320
tggtcggcga ccgcttccca gaaggcgtcc tcgtcggctt cgatggagaa gtgcacgctg    22380
gaggcgatcg tcgcaccctc ggaggtctcc tcgctgtgga gcgtgaccag ctcgtcggcg    22440
atggcgtcga ggtcatactc ggcgcgggcg tcggcgactg cacctccggc ctcgatggca    22500
tcgatgatag aggcgatggc ctcgccgcgg gtggagaagg tagtgtcggt agaatcggtc    22560
atgatcctgt ccctttcagg gtcttggcct catcggggtg cttcccggtg gggcctcttg    22620
ctttgtcctt gtgacaccca ctgtcgtcac agtgttggaa catgtcaagc cagtgggcca    22680
cctttcttta aagagatttc agcgggcgac cgcgccgcct cggacacctg ggcccagtag    22740
ccctggaggg cgcactgaat caattggttg tcaattggtt gtcaaacctg accgtcgac    22800 ggggagtgag gaggtggtac cggctgatct acgcctgaaa cagatggagc gggcgacggg    22860
aatcgaaccc gcgtgtctag cttgggaaac gggcatcgtg ctagtctggg gaccgccgaa    22920
atgacgattt caggcgtaaa ccggcctccg gtgtcttacc ctgatagctg ggtgatagca    22980
ccgaattggt tgtcagattg gttgtcagat cgccccagga ggatggtcgc attgtcacgc    23040
gcaagctacg gggacggcac ccagccgacc cggcgttccg acgggcgctg ggcagcatcg    23100
gcctatgacg gctggcaggc gaacgggaac cgccggcgcc gatgggtgta cggccgcacc    23160
caggccgaat gcaagcggaa gctgcgcgac ctgaagcggg agatctggtc agacacccag    23220
cagatgaatg tgaaccccag ggagaccgtc aagagctgga cggcatcatg gctggacgac    23280
taccgatcga ttgccagacc aacaaccttc gccaccgacg agtccatggt gcgcaactgg    23340
atcgtcccag ccatcggtgc ccggcgcctg tccgaactga cagcgcgcga cgcctcgaag    23400
ctgcaacggg tctgccgaga cggggactg tcggcgacaa cgtctcacta tgccgggctg    23460
ctcctgcggc gcatcctgaa ggctgcccgc gcaacggct accgcatccc cgactccgtc    23520
atgctggccc ggatcccggg catcggcgca tccaacaggt ccgccctgag cgccatccag    23580
gcggccaacc tgctctcgac ggcaaacgca cgcgacacct ggccggagcc gcccagcctt    23640
```

```
cccgacctgc cctacggggc catctcgaag ctcgcaccag cagaagcgca gaagcgtgaa   23700
caactcaaga tggagcggtt ggaatggact gccgcccaaa acacggaccc ctccaggtgg   23760
gctgccgcac tcatgcaggg acttcggtca ggagaggctc gaggcctcac gtgggatcgt   23820
gtcgatctcg ataaggggac gatcaccatt gatcgtcaac tccagcgcat caagcccgac   23880
gcggcgcttc caccgggata caaggtcacc cggctggaag gcagccactg cctcgtggca   23940
ccgaaatctc gatcagggat ccgccgcgtc ccgatcgtcc cctggatggg ccaggctctc   24000
acccgctggc gcgacataca gggcgacagc cccttcgggc tcgtgtggcc gctgcccacc   24060
ggggcgccgc ccacgcgggt ccatgacctg cgggcatggc gtggactcca gcgcgtcgcc   24120
ggggtccaca aggaggatgg aaacctctac gtcctccacg aagcacgaca ctccaccgtg   24180
tcgctgctgc ttgctgccgg ggtcccggaa tcagtggtca tcgcgatcgt cgggcatgca   24240
agcttcgcgg cgaccgagca ctacgcccac accgacctcg aagcagcacg cgccgccctc   24300
atgaaggtgc aggaccgcct cgggctggag ctcgagagct gagcatgcaa agagccgccc   24360
accggaccaa tcgcggtctg gtgggcggct cttttgcgcc ttagagcacg tccgtcacca   24420
cgcctggaag ttgctgacga cgggtgcctg gtcggtgccg gtcacgtcgc agtgaaccgt   24480
gtatttggcg gagccgacgt cggcgccgat gttgacgttc cacagatcgt cggtcttatt   24540
gagggcggcg accgaatcga cggttgagtg gaccttgatc ttaagcgatg ggtattgctt   24600
gcccaaggca tccctcgcat aggtgccaca gccagaggtt gcgccggtca tggtgagtcc   24660
agtggtcgtt gcctcgacgg gtgtgggcgt ggcggacgca gtgggcgtct tcgtggccgt   24720
cggcgtcttc gccgctttcg gagtcttgga ggctgatgat gacgatcctg atgtctgggg   24780
atcgcacgcg gtcagcgcgc cggcgaggca gagtgacgca agcagggcga tggggacgag   24840
cgccttgcgg cgcatggtgt gggtcattcg ggttccttgg ttggttggtt cacatgctgt   24900
ccacagcaac ctagccgcgg aacctgcccg cctgggggtg atgagggcaa gtggcaagaa   24960
ttacatcgat gggattctcg ccacccctg aagagcgtgg gtggcgaggt ctacattcgt   25020
acgcatgtac gaaacatgga agcctctcgg acacggctcg atctctggtg gatcggcccg   25080
cacaatggag tgcactgaag tagcggagtg ggcagagcgt cgtgcgcgtg ggtggggctc   25140
agcgctggta tcgcgcctgc gcggcgtcca tgaagacgcc gggttcaaag tcgagcacgc   25200
gagcaagctc aaagaggagt gcgacaggga gatcccgctt gccctgctcg atcctgatga   25260
tggtggattc gctgactcca gcgagtcgag cggtctcgac ctgggttaag cccttggcgg   25320
ctcgctcggc tcgaagctgg gcggcgatcg cggcgcgaat tgcatcacgc ttgctggcct   25380
ggttctggtc catgctgtca gcatagccgc cacattggac agttttccgg tccgattggg   25440
atgctcggca cttgcatctg gccatatggc atggcaagct gtccatatgg ccagttcaga   25500
catcaacctg gaggctgcgg acatgatctc cgccgccatc gagcgaagcg acaccagtcg   25560
ggctgaagtc gccacgctga cgggaatccc gttgaccact ctgcgtcgga agctcatggg   25620
ccgatcgccc gtcaacatcg aggacatctt cctgatcgcc ggcgcgctcg ggataccgcc   25680
tgtgagtatc acgcccgacg ttctcacgag tgaagccgcc gcctagcccc caaacagaag   25740
aagcccccgc ctgctgtcac agacgggagc caaccaaagg agtttccaat gagcattcta   25800
cccttcgact accacggtca ggaagtccgg ttcatcaccg atgagtccgg cgagcctcag   25860
gtcgtcgcgt cagatctcgc gaaggccctc aactatcgga acgcacccga catgatgcgt   25920
tccatcgacc tagaggaaag gggtacgcgt ccggtgcgta cccctggcgg tgagcaggag   25980
```

-continued

```
atgctcacgc tgaccgaggc cggcatgtac caagccatcc tgcaacgcca gacaggccgg   26040
atggtcgacg tcgcccaacg agccgctgtg aagcgattcc agcattgggt tacccacgag   26100
gtgattccct cgatccgcaa gcgcggcatg tatgccactc cggatgcagt cgaggcgatg   26160
ctggccgatc cggacgttat gatccggacg ctcaccgagc tgaaggccca gcgggccagg   26220
gtggcccagc tgcagcccaa ggccgactac gttgacgcct tcgtggccga cgaggatctg   26280
cggctcctgc gcaatgtggc caagtcgatc ggagtgcagg agggcgccat cgcgacgcc   26340 ttgctcgcac acgagtggat ctacgcggag gagtcctcgc gctggtcgaa ctctcagggc   26400
tgcaaggtca tcgagcaccg ctattccacg cgctctgaca aggcccgata cttcgcccg   26460 gtcccgaatc accaggcacc ccgatttaag ggcgaggtaa tgcacaccct gaaggtcact   26520
ccggcagggg ctgaggcgat ctccaagatg gcaaagcgct ggggcctcgt cgtccaggag   26580
gtggcggcat gacctcgact ctcaccggca acatcatcgc cctgctgatc gtggccggcg   26640
tgatcgtcct cgccgatgggg gtgcgccgtg aaggtcgatg acttcgacga tgtgcgcccc   26700
ctgacgcaga aggacgtcgc cgagctactc cacgcaagcg tcggttacgt gcgctcctgc   26760
cgcctggcga cgaagccgaa aggccgggtc ttcccgatgc ccggctggaa gaccgacgga   26820
aagcgctatc tgcttcccgc ttggcggttc gcgagtgggg tcgaaagctt gcccgatgcc   26880
tagcccgcgc cgcttcctaa tcctgatcgc cctgggtgcc gccgccgtcg gtttcgcgcc   26940
ctcctcaatt caatttctct tcatggccgc gcttgtgctc ggcctcacca tcacatgcct   27000
caaggagtcc aaccatgcct gacacacagc cccgtcgtgc gcgtcgtcgc acgctgtccg   27060
agatcctcgc ccccgcgccg gcgccccgca gagcggaggc aacggcatga ggccaccagc   27120
cgttgaaacc cctgatgtga aggcgccggc cacgcctgct ggttcccggc tcttcaaggc   27180
tgtccgtcct gacggcttcg acttccacag cgggactgtc cggtggctcc ctgctgatgg   27240
cgcaccgatc ccggagggcg ggtggcttgt cgagcatccg catcctggtg aggttggcag   27300
ctgggatgca gctttttatc tgtcggcgtc gtcggtggag acggactgca caggtttcca   27360
gtggcctgct ctcctcctgt ccgtggagcc cgtaggtgcc atgtggaccc ctcgccccga   27420
caaatttcct cgcaagcggg ccgcgcacgc gtggcgcgtc atagaagagc tccccgcatg   27480
gcggcttttc ggtccccagg ggcggacggt cctggacatc atcgagcaaa ccgctcatct   27540
gaccaaacgc cagatcgcgg ccctgaacag ggctctggac gccgcacggg acaccgtttg   27600
ggacgttgct tggaacgccg cgtggcacgc cgctcgggtc gctgctcggg tcgctgctcg   27660
gggcgctgct cggggcgctg ctcggtacgc cgccttggga cgctgctcggg gcgctgcttg   27720 gtacgccact tgggtcgctg ctcggggcgc tgctctcgga tggctcgtca aggacctgat   27780
ctccgtcgag gacttccgca ccctgacggg ccgtgggag caggtcatgg gtccgatcga   27840
ggtggcggca tgaaccgcac ctatttcaag gccgttaggg cggacggcac tgacttctac   27900
accggcaagg tccgctggct gcccgatgat ggcgcaccga tccctgccgg gggttgggtc   27960
gttgagcatc cgacgagcga acgcgtgggg gacgacgccc gcacctatct ctcggtttcg   28020
acggtggaaa ccgactgcgc cgggatgggc tggccgtgcc gtctcctgcg ggtcgtcccc   28080
gacggcagac aggtgagcat ccctgaaccc gtggggctgc ccagcacgag ggcctcgatc   28140
aggtggcgcg tcatcgaaga gctccccgca tggcaggcgc ttggaccccca ggggcgcgag   28200 attgaggcgc tgctcggaca ggttgagagt ctcacggagg accagaccct cgaaatgtct   28260
gccgctcggg gcttcgctcg gggcttcgct cgggacgtcg cgcggttcgc cgctctggtc   28320
gcctctcggg gcggtgctct gaacgctgcc cagggcggtg cttgggcac tgctctgaac   28380
```

```
gctgttcggg acgctgttct cggatggctc gtcaaagatt ttatctctga tgaggaattc   28440
cgcaccctcg tgggcccgtg ggagcaggtc atgggtcggg tgatcgcatg atgccgatca   28500
ccaagccgtg cgcggttaag gacatgccgg agggcgagta tcactcggat ccctgcgtcg   28560
agccgtccct gtcgtccacg atggcgaaaa ccattgtttc gggtgaggct ggcccggccc   28620
gtctgcgaga gatcatgtct cacgggcagg aacataaggc cgtcttcgat ttcggcagcg   28680
ccgcgcacga gaaggtgctg ggacgcgcg ccggtgtcga ggtgctggat ttccctgcct   28740
ggaccacgaa ggcttcgcgt gaggcgcgtc aggccgtgtg ggatgccggc ggaactcccg   28800
tgctggcgaa ggattccgcc caggtggatg cgatggctga ggcgatcctg tccaatcctg   28860
tggcaggtga gctgttcacg cgcggggctg gttctcctga attgtcgatg ttcaccattg   28920
acgaggagac gggacgctgg cagcggggac ggctcgactt cctggcggac cgcaagacca   28980
tcgtcgactt caagacatct ggacagtccg tcgagctgcc cgactggatc aagcacagct   29040
ggcagttcgg ctaccacatc caagccgccg cctatatgga ccaggcgatc tcgctggatc   29100
tggtcgatga ggacgccatc ttcctgcatg tcgtgcagga gacgaagccg cccttcttgc   29160
tcgcgatcta tcaggtttca gctgaccagc tggccgaggg caggcgtcag atgcgtcgtg   29220
ccctggacct gtgggaccgc tgcctgaccc tcgacgaatg gccgcgatc cctgcggtga   29280 tccaactatc caagctgccc gattgggtgc acaccactga tgacgaaaag gactcctgac   29340
atgaccgaaa ccacacctag caccgacatt gaaaccaccg cccccacccc gtcgggtcg   29400 atcgcggcgg tcggctccga gacggcaggc ctgacgcttc agcagaagct cgactatgcc   29460
tctgccctgg ccgactccga gctcctgccc gccgcctaca agggcaagcc cgcgaatgtg   29520
ttggtggcga tggagtacgg cggcgagctg ggcatcggca cgctcgtcgc ggtgaaccag   29580
atcacggtga tcaacggcgg cgtctccatg gaggcgaagc tcatgatgac gctcgcccgc   29640
cgagccgggc acatcgtgcg cctgtccggc gacgacaagc aggccacctg catcatcatc   29700
cgcgccgacg atcccgggca cgaatcggtc gtcacttggg acgaggccaa ggcgaagacc   29760
gccggactgt ggggcaaggg ccactggcag aagaacccgg gcttgatgtt gaagtaccgg   29820
gcggcctcgg agaacatccg gctcacctgc cctgaggtgc tggcggggat tgtctacaca   29880
cccgaagagc tcgatgagcg caccgagcgt gcaggccggt ccacgatgcg tgtccatcag   29940
gtcgtggccg agccggagaa gaccgctgcc tacttcatga aggccctcca cctgaacggc   30000
ggccagttca aggagtttgc ccagcgcgtg ctgggacatc cgttgaagag ctgggaatcg   30060
ctggccaagg cagacaagca gcgtgtcctg ggcgctctcg ccagctggga aacagcgggg   30120
gccgatccca ccactggcga ggtcctcgac gccgagccgg tcgagggcgg tgcggcatga   30180
gcaccttgcc tgcggatgct gccgagaggt ggcagcagtg ggatgccctg gcccgcacga   30240
tcctcgccct tcatctcggc ctgactgatc ttgagatggt cgagctggtg ggcgggctca   30300
tcggtgccgg ctggcatcag gatgggccgg tggagtcatg agctgcccg aggagcacca   30360 cgacgtgtgg gcgggtgtcg aggacgccat ccctgagtgg gtgagcgaca aggtggcctg   30420
ctcggtgcgg tcggatgccg attggaatgc cgacgaggac agccgcaagg ccgtggcggc   30480
ggtgaggatc tgcgagcggt gcgccttaac cgagcagtgc ctggattggg cgctggccca   30540
ccacgaggcc ggcatctggg gtgggctcac cgcctccgac cgcgagcgca tcgagcgtgg   30600
cgcgccggtg cggcgggtcc gcgagattcg tcggcgtcgc acggcggtta ggcaggtgca   30660
ggagtcatga gcgcaccact gaccaaggcc cagaaggtcg cggcggtcgt cgagcagctg   30720
```

-continued

```
ttgcgtggcg gcgccgacac cagcacgctc ctggaggcga cggggggccga ccggcccgga    30780
cgattgcggg acacccttcg ccgcgctggc cgtgacgacc tcgccgcccg gatcatcacc    30840
accgaccggg cagcccagcg cagacgggaa gtcatcgagg cggtcgagaa gctggtctgg    30900
gtggacaggg ccgacgagat cgccgccgaa ctcggctaca gctcgcgcta cggcctgcaa    30960
cagtccttgc gcggctgggg gcgtcgggac cttgccgatc agatcgtgct gacccgcgag    31020
acgcaccgcg acagggtcat cgctgacgtg aatggatcg ccggtacacg gggccccgag    31080
gatgtcgccc gggcgaccgg ataccgcaac gcggcggcgc tgcaggccgc cctgaccggg    31140
tggggccgca aggacctcgc cgaccggatc gtcggagcat cacgcaacga cacgggccgc    31200
ttccgcttca catggagggc cgcatgagcg ccaaccgctc ccgccgcgcc acgtacaacc    31260
acacggggat cttcgtccat ctgcgcgaag ccgccgagcc gtccgaacag ccacccctccg   31320
accagacatg cccagccctg catgtcatcg ccggactgac accctgggcc gaccaccagc    31380
cccgccacgc cctcggcgtc gacgggcgat gccggcactg ccacaccacc atcaaaggaa    31440
acccatgatc ttcaaagaca ccacgatcgg gccgctcgaa acacggttca cctggtcgat    31500
gaggtgcgac cgctgcggga cgccgctcga ctggctcgtc gccgcttcgt gcaagaccga    31560
gcgtagtgag gtaatcgccg tcaagttcct gagggagcgt gcccgcgatg gcgggggcct    31620
cagagagtgg ggggagctgg acctttgccc ttcatgcttc tcggtgatgg acgcatgatt    31680
accaccacac aactcggaga agcagaccgg tggggccgtg gcctccaagt ccgctcgatc    31740
ctgtgcaacg gctgcggcat agctctggcg accgacatcg gccttcgtgg agacgccacc    31800
gccctccaag tgcaatccga cctgcacgcc cgagcacgca ccgccggctg gacacacccc    31860
gcctggcgcg tcgacctctg cccgcaatgc accaccacaa ccaaaggagc atgaccatga    31920
aggccaccca gtacgccaaa tcgaccgacc ctgaagtcat cgccaccatc gaagagaacg    31980
agctgtcacg acgggcatgg atcgacgaca ccaaggcgtg gttcggcaag acgatccgga    32040
caggaatccc gggcgccaaa ttgttcctct tttccacccg gaccgctatc aggctgttgg    32100
ggatcgtgac gtcggacgag aagaagcctg ccgggtggaa gttctgctgg cgttcacgct    32160
ctcggttcga gccacgaaag aacaatccct tgcgcgccac atgggacgca cgccggtggc    32220
aagcagcgtc gatcccaggt ctgcccgtgg ttctcacgtc ctccgtgtcg ggagagttac    32280
agagctggtt gaggatgtat ccctgcccct tcatctctag tggtgccgca tggctggacc    32340
tggagcacat gcctgacct gacagtccgc acttcggacc gcagtggact gaagtccgtg     32400
catcgcagg aatggcagcc aaggaagcat tgaaggacgc gtcatgagca ctccgggatc     32460
actgcgcgcc gcgctcgacc agctggacga gatcggcatc gccgaccatg tgcagtcctt    32520
ggaatgggat cgggccggcg cccgcaccac agcctggctc gagacctgcg gcgacttcgc    32580
tgcggcctgc cagtggggcg atgccgcggg cgaatgggtc acgtgggaca tcaccgacgt    32640
ggccgaggcg gacgtcagcc cccggctgcg cgtcaagcac atgcacctgc gagccaggcc    32700
ctgtgctgat gcgcccgcga aggcggtggc ggcatgagca aggcccttga cccactggat    32760
caccttc                                                              32767
```

<210> SEQ ID NO 23
<211> LENGTH: 29768
<212> TYPE: DNA
<213> ORGANISM: PAC7 phage

<400> SEQUENCE: 23

```
tcgtacggct tagtgaaata cctccctttt gttgtttat cgttttgtcg actttttgtt     60
```

-continued

```
tggtggtgtg tgtggtgcag cctgagcttc ctgatagtcg tgattggtgt ggggagacgc    120
gtcggtggtg gtgtgtgtgg ggcgaggatc cgcgtgccgg gtttgtgtct gatgaggagt    180
ggttgtttct catggatgct gcggtgattc atgatgtggt gtggcgtgag ggtcgcgcgg    240
atttggtggc ttcgttgcgt gctcatgtga aggcttttat gggtatgttg ataggtatt    300
cggttgatgt ggcgtctggt ggccgtggtg ggggttctgc ggtagcgatg attgaccggt    360
ataggaagcg taggggggct tgagtaggtg tctggtgttg ttgggtctca ggttcctcgt    420
caccgggtgg ctgtggcgta ttcggtgtct gctggcgggg atgctgggga gcttggtagg    480
gcttatgggt tgacgcctga tccgtggcag cagcaggtgt tggatgattg gcttgctgtg    540
ggtggtaatg gcaggcttgc ttcgggtgtg tgtggggtgt tgttccgcg gcagaatggc    600
aagaatgcta ttttggagat tgtggagttg tttaaggcga ctattcaggg tcgccgtatt    660
ttgcatacgg ctcacgagtt gaagtcggct cgtaaggcgt ttatgcggtt gcggtcgttt    720
tttgagaatg agcggcagtt tcctgacttg tatcgtatgg tgaagtcgat tcgtgcgacg    780
aatggccagg aggctattgt gttgcatcat ccggattgtg ccacgtttga aagaagtgt    840
ggttgtccgg gttggggttc ggttgagttt gtggctcgta gccggggttc tgctcgcggg    900
tttacggttg atgatttggt gtgtgatgag gctcaggagt tgtcggatga gcagttggag    960
gctttgcttc ctaccgtgag cgctgccccg tctggtgatc ctcagcagat ttttttgggt   1020
acgccgccgg ggccgttggc tgacgggtct gtggtgttgc gtcttcgcgg gcaggctttg   1080
tcggtggta acggtttgc gtggacgag ttttcgattc ctgacgagtc tgatccggat     1140
gatgtgtcgc ggcagtggcg gaagttggcg ggtgacacta atccggcgtt ggggcgccgc   1200
ctgaatttcg ggacagtctc ggatgagcat gagtcgatgt ctgctgccgg gtttgctcgg   1260
gagcggcttg gctggtggga tcgtggccag tctgcttcgt ctgtgattcc ggcggataag   1320
tgggttcagt cggctgtggt tgaggcggct ctggttggcg ggaaggtttt tggtgtctcg   1380
ttttctcgct cggggggatcg tgtcgcgttg gctggtgctg gtaaaacgga ttctggtgtg   1440
catgttgagg ttattgatgg cctgtctggg acgattgttg atggtgtggg ccagctggct   1500
gattggttgg cgttgcgttg gggtgacact gaaaaggtta tggttgcagg gtctggtgcg   1560
gtgttgttgc agaaggcttt gacggatcgt ggtgttccgg gtcgtggcgt gattgtggct   1620
gatactgggg tgtatgtgga ggcgtgtcaa gccttcctgg agggtgtcag gtctgggagc   1680
gtgtctcatc ctcgtgccga ttcgaggcgt gacatgttgg atattgctgt gaggtcggct   1740
gtgcagaaga agaagggttc tgcgtggggt tggggttcct cgtttaagga tggttctgag   1800
gttcctttgg aggctgtgtc tttggcgtat cttggtgcga agatggcgaa agcgaagcgg   1860
cgtgaacggt ctggtaggaa gcgggtgtct gtggtatgaa ctcggatgag ttggctctga   1920
ttgagggcat gtacgatcgt attcaagggt tgtcttcgtg gcattgccgt attgagggct   1980
actatgaggg ctctaatcgg gtgcgtgatt tggggggttgc tattccttcg gagttgcagc   2040
gggtgcagac ggtggtgtca tggcctggga ttgcggtgga tgctttggag gagcgtctgg   2100
attggcttgg ctggactaat ggtgacggct acggtttgga tggtgtgtat gctgcgaatc   2160
ggcttgctac ggcgtcgtgt gatgttcacc ttgatgcact gatttttggg ttgtcgtttg   2220
tggcgatcat tccccaagag gatgggtcgg tgttggttcg tcctcagtcg ccgaagaatt   2280
gtactggccg gttttctgcc gatgggtctt gtttggatgc tggccttgtg gtgcagcaga   2340
cgtgtgatcc tgaggttgtt gaggcggagt tgttgcttcc tgatgtgatt gttcaggtgg   2400
```

-continued

```
agcggcgggg ttcgcgtgag tgggttgaga cgggccgtat cgagaatgtg ttgggtgcgg    2460
ttccgttggt gcctgttgtg aatcgtcgcc gtacttctag gattgatggc cgttcggaga    2520
ttacgaggtc tattagggct tacacggatg aggctgttcg cacactgttg gggcagtctg    2580
tgaatcgtga tttttatgcg tatcctcagc gttgggtgac tggcgtgagc gcggatgagt    2640
tttcgcagcc gggttgggtt ctgtcgatgg cttctgtgtg ggctgtggat aaggatgatg    2700
atggtgacac tccgaatgtg gggtcgtttc ctgtgaattc tcctacaccg tattctgatc    2760
agatgcgttt gttggcgcag ttgactgcgg gtgaggcggc tgttccggaa cgctatttcg    2820
ggtttatcac ttctaacccg ccttctgggg aggctttggc tgcggaggag tctcggcttg    2880
tgaagcgtgc tgaacgcagg cagacgtcgt ttggtcaggg ctggctgtcg gttggtttcc    2940
tggctgcccg ggcgttggat tcgagtgttg atgaggccgc gttttttggt gatgttggtt    3000
tgcgttggcg tgatgcgtcg acgccgactc gggcggctac ggctgatgct gtgacgaagc    3060
ttgtgggtgc tggtattttg cctgctgatt ctcggacggt gttggagatg ttgggtttgg    3120
atgatgtgca ggttgaggct gtgatgcgtc atcgtgccga gtcttcggat ccgttggcgg    3180
cactggctgg ggctatttcc cgtcaaacta acgaggtttg ataggcgatg gcttcgggtg    3240
ctgtgtcgag gcttgctgcg actgagtatc agcgtgaggc tgtcaggttt gctgggaagt    3300
atgcgggcta ttatgccgag ttgggtcgtt tgtggcgtgc cggcaggatg agtgacacgc    3360
agtatgtgcg tttgtgtgtg gagttggagc gtgccggcca tgacggttca gcagctatgg    3420
cgggcaaatt cgtttcagat tttcgccggt tgaatggtgt cgatcctggt ttgatcgtgt    3480
atgacgagtt tgatgctgcg gcggcttttgg ctaggtcgtt ttcgactatg aagattatga    3540
atagtgaccc ggatagggcg aatgatacga ttgatgcgat ggctgcgggt gttaatcggg    3600
ctgttatgaa tgctggtcgt gacacggttg agtggtcggc gggtgcgcag ggtaggtcgt    3660
ggcgtcgggt gactgatggt gatccgtgtg cttttttgtgc catgttggct acgaggtcgg    3720
attatacgac taaagagcgg gcgcttacta ctggtcatac gcggcgtcat aagcgtgccg    3780
gtaggcgtcc gtttggttcg aagtatcatg atcattgtgg ttgtacggtg gttgaggttg    3840
ttggtccttg ggaaccgaat agggctgatg ccgagtatca gaggacgtat gagaaggctc    3900
gtgagtgggt tgatgatcat gggttgcagc agtcgtctgg caatatttg aaggctatgc    3960 gtactgttgg tggcatgaga taatttgatg tggtttccgg ttgtgtgccg ccggttatcg    4020
gtgcacaggg ttgtctcccg cacgggggtc aacaatgttg tgttgttttc cgcaaggagt    4080 gtaggggttag gctatggccg atcagagtat tgaggaacag aatgttgaca atgatgttgt    4140
ggagtccgga aaggataacg gcattgttga tacagtaaaa gacgatggcg ggcaggaggt    4200
agccgacaat cagttgaaga atgaaggcga gggtaaatcg ccggggactg attggaaggc    4260
ggaggcccgt aagtgggagt ctcgtgctaa aagtaatttc gccgagttgg agaagcttcg    4320
tacatcgagt gacgattctg gatctactat tgatgagctt cgccgcaaga atgaggaact    4380
cgaagaccgg attaacgggt tgttcttga gggtgtgaag cgcgaggtgg ctgccgagtg    4440
tggcctgtcg ggtgatgcga tcgcttttct tcacggtagc gataaggagt cgcttgccga    4500
gtctgctaag gctttgaagg gtttgatcga ccatagtagt ggtggtggcg cgggtgtgcg    4560
ccgtcttgcg gggagtgccc ccgttgatga tgttaaacga cgtgagggtg tcgcgtttgt    4620
ggatgctctt gtcaataatt ctaggagatg atttatcatg gctgacgatt ttctttctgc    4680
agggaagctt gagcttcctg gttctatgat tggtgcggtt cgtgaccgtg ctatcgattc    4740
tggtgttctt gctaaactgt caccggagca gccgactatt ttcgggcctg ttaagggcgc    4800
```

```
cgttttagt ggtgttccgc gcgctaagat tgttggcgag ggcgatgtta agccttccgc    4860
tagcgttgat gtttctgcgt ttactgcgca gcctatcaag gttgtgactc agcagcgtgt    4920
ctcggacgag tttatgtggg ctgacgccga ttaccgtctg ggtgtgcttc aggatctgat    4980
ttccccggcc ctgggtgctt ctattggtcg cgccgttgat cttattgctt ccatggtat    5040
tgatcctgct acgggtaagc ctgctgcggc tgtcaaggtg tcgctggata agacgaataa    5100
gacggttgat gccaccgatt ccgctacggc tgatcttgtt aaggctgttg gtctgattgc    5160
tggtgctggt ttgcaggttc ctaacggtgt tgctttggat ccggcgttct cgtttgctct    5220
gtcaactgag gtgtatccga agggttcgcc gcttgccggt cagccaatgt atcctgccgc    5280
cgggttcgcc ggcctggata attggcgcgg cctaaatgtt ggttcttctt cgactgtttc    5340
tggtgccccg gagatgtcgc ctgcttctgg tgttaaggct attgttggtg atttctctcg    5400
tgtccattgg gggttccagc gtaacttccc gattgagctg atcgagtatg gtgacccgga    5460
tcagacgggg cgtgacttga agggccataa tgaggttatg gttcgtgccg aggctgtgct    5520
gtatgttgcg attgagtcgc ttgattcgtt tgctgtcgtg aaggagaagg ctgccccgaa    5580
gcctaatccg ccggccggta actgattcat ttgttgcgat aatgtttatg ctgtgtgcag    5640
ggggtggtgt tgatgggtat cattttgaag cctgaggata ttgagccttt cgccgatatt    5700
cctagagaga agcttgaggc gatgattgcc gatgtggagg ctgtggctgt cagtgtcgcc    5760
ccctgtatcg ctaaaccgga tttcaaatat agggatgccg ctaaggctat tctgcgtagg    5820
gctttgttgc gctggaatga tactggcgtg tcgggtcagg tgcagtatga gtctgcgggc    5880
ccgtttgctc agactacacg gtcgaatact cctacgaatt tgttgtggcc ttctgagatt    5940
gccgcgttga agaagttgtg tgagggtgat agtggggctg gtaaggcgtt cactattaca    6000
ccgaccatga ggagtagtgt gaatcattct gaggtgtgtt ccacggtgtg gggtgagggt    6060
tgctcgtgcg ggtcgaatat taacggctat gctggcccgt tgtgggagat atgatatgac    6120
cggttttcct tacggtgaaa cggttgtgat gcttcagccg actgttcgtg tcgatgatct    6180
tggtgacaag gtggaggatt ggtctaagcc tgtcgagact gtgtaccata acgtggccat    6240
ctatgcttcc gtttcgcagg aggatgaggc cgcggggcgt gactcggatt atgagcattg    6300
gacactgctg ttcaagcagc ctgtcaaggc tgctggttat cggtgtcgtt ggcgtattcg    6360
gggtgttgtg tgggaggctg acgggtctcc tatggtgtgg catcatccga tgtctggctg    6420
ggatgctggt acgcaggtta atgtgaagcg taagaagggc tgatgggttg tggcacgtga    6480
tgttgatgtg aagctgaact tgccgggtat tcgtgaggtg ttgaagtctt ctggggtgca    6540
gggcatgttg gctgagcgtg gtgagcgtgt caagcgtgcg gcctcggcga atgtgggcgg    6600
taacgcttac gatagggccc agtatcgtgc cgggttgtcg tctgaggtgc aggttcaccg    6660
tgttgaggct gtggcgcgta ttggcaccac ctataagggt ggtaaaagga ttgaggctaa    6720
gcatggcacg ttggcgaggt cgattgggc tgcgtcgtga tcgtttacgg tgatcctcga    6780
atatgggcta aacgtgtgtt ggcggatgat ggttggctgt ctgatgtacc gtgcacgggt    6840
actgtgccgg atacatttga gggtgatctg atttggttgg cgttggatgg tggcccggag    6900
ttgcatgttc gtgagcgtgt ttttttgcgt gtgaatgtgt tttcggatac gccggatcgt    6960
gctatgtctt tggctcgccg ggttgaggct gtgctggctg atggtgtgga tggtgatccg    7020
gtggtgtttt gcaggcgttc gactgggcct gatttgctgg tggatggtgc acgttttgat    7080
gtgtattcgc ttttttgagct gatatgtagg cctgcggagt ctgaataagc ttattgtttt    7140
```

```
tgttttaatg taattgtttg atatttaatg ggggttgtga tggctgctac acgtaaagcg    7200
tctaatgttc gttcagcggt tactggcgac gtttatattg gtgacgcgca cgcgggtgat    7260
tctattaagg gtgtggaggc ggttccttcc gggcttacag ctttggggta tctgtctgat    7320
gacgggttta agattaagcc tgagcgtaaa acggatgatt tgaaggcttg gcagaatgcg    7380
gatgttgttc gcactgtggc tacggagtcg tctatcgaga tttctttcca gctgattgag    7440
tcgaagaagg aggttatcga actgttttgg cagtcgaagg ttactgccgg atctgattcg    7500
ggttcgttcg atatttctcc tggtgccaca acaggtgttc acgccctgtt gatggatatt    7560
gttgatggcg atcaggttat tcgctactat ttccctgagg ttgagctcat tgatcgtgac    7620
gagattaagg gcaagaatgg cgaagtgtac gggtatggtg tgacgttgaa ggcgtatcct    7680
gcccagatta ataagactgg taatgcggtg tcggtcgggg gtggatgacg gctttaaaa    7740
gctgatactc ctccgactcc tccgccggcc ccggttcctc cgaagcctca gccggatccg    7800
aatccgccgt ccggtaactg atacacgatt ttagggggatt gttaatagat gagtgacact    7860
ggtttcacgt tgaagattgg tgatcgtagc tgggtgttgg cggatgcgga ggagacggct    7920
caggctgttc ctgcccgcgt tttccgtcgt gccgccagga ttgcccagtc ggggggagtct   7980
gcggatttcg cccaggttga ggtgatgttt tctatgttgg aggctgccgc cccagctgac    8040
gcggtggagg ccctggaggg gcttcctatg gttcgtgtgg cggaggtttt ccgtgagtgg    8100
atggaataca agcctgacgg taagggtgcc tcgctggggg aatagtttgg ctccacggcc    8160
tgattgatga ttatcgtggg gccatcgaat acgatttccg caccaagttt ggtgtttctg    8220
tttatagtgt tggtggcccg cagatgtgtt ggggtgaggc tgtccggctg gctggcgtgt    8280
tgtgtaccga tacgtctagc cagttggcgg cccaccttaa tggttggcag cgcccgtttg    8340
agtggtgcga gtgggctgtg ttggacatgt tggatcatta caggtctgct aatagtgagg    8400
ggcagccgga gcctgtggcg aggccgactg atgagcgtcg ggcaaggttt acgtctgggc    8460
aggtggacga tatttggcg cgtgttcgtg ccggtggcgg ggtgtctcgc gagattgata    8520
ttatggggtg aatagtgtat gtctggtgag attgcttccg catatgtgtc gttgtatacg    8580
aagatgcctg gccttaaaag tgatgttggt aaacagttgt cgggtgttat gcctgctgag    8640
gggcagcgtt cgggtagcct gtttgctaaa ggcatgaagt tggcgcttgg tggtgcggcg    8700
atgatgggtg ccatcaatgt tgctaagaag ggcctcaagt ctatctatga tgtgactatt    8760
ggtggcggta ttgctcgcgc tatggctatt gatgaggctc aggctaaact gactggtttg    8820
ggtcacacgt cttctgatac gtcttcgatt atgaattcgg ctattgaggc tgtgactggt    8880
acgtcgtatg cgttggggga tgcggcgtct acggcggcgg cgttgtctgc ttcgggtgtg    8940
aagtctggcg gtcagatgac ggatgtgttg aagactgtcg cggatgtgtc ttatatttcg    9000
ggtaagtcgt ttcaggatac gggcgctatt tttacgtctg tgatggctcg cggtaagttg    9060
cagggcgatg acatgttgca gcttacgatg gctggtgttc ctgtgctgtc tttgcttgcc    9120
aggcagacgg gtaaaacctc ggctgaggtt tcgcagatgt gtcgaaggg gcagattgat    9180
tttgccacgt ttgcggctgc gatgaagctt ggcatgggtg gtgctgcgca ggcgtctggt    9240
aagacgtttg agggcgctat gaagaatgtt aagggcgctt tgggctattt gggtgctacg    9300
gctatggcgc cgtttcttaa cggcctgcgg cagattttg ttgcgttgaa tccggttatt    9360
aagtctatca cggattctgt gaagccgatg tttgctgccg tcgatgctgg tatccagcgg    9420
atgatgccgt ctatttttggc gtggattaac cgtatgccgg ctatgatcac gagaatgaat    9480
gcacagatgc gcgccaaggt ggagcagttg aagggcattt ttgcgagaat gcatttgcct    9540
```

```
gttcctaaag tgaatttggg tgccatgttt gctggcggca ccgcagtgtt tggtattgtt    9600
gctgcgggtg tggggaagct tgttgcaggg tttgctccgt tggcggttgc gttgaagaat    9660
ctgttgccgt cgtttggtgc tttgaggggt gccgccgggg ggcttggtgg cgtgtttcgc    9720
gccctgggtg gccctgtcgg gattgtgatc ggcttgtttg cggcaatgtt tgccacgaac    9780
gcccagttcc gtgccgctgt tatgcagctg gtggctgtgg ttggtcaggc gttgggccag    9840
attatggcag ctgtgcagcc gctgtttggt ttggttgctg gcgtggttgc caggttggcg    9900
ccggtgttcg gccagattat cggtatggtt gctggtttgg ctgcccggct ggtgcctgtt    9960
attggtatgc ttattgcccg gctggttcct gttatcaccc agattattgg tatggtaacc   10020
caggttgctg ccatgttgtt gcctatgctg atgccggtta ttcaggctgt tgttgctgtg   10080
atacggcagg ttattggtgt cattatgcag ttgatacctg ttttgatgcc ggttgtgcag   10140
cagattttgg gtgctgtcat gtctgttttg ccgccgattg ttggtttgat acggtcgctg   10200
ataccggtga tcatgtcgat tatgcgtgtg gtggtgcagg ttgttggtgc tgtgctacag   10260
gtggtggccc gtattattcc ggttgttatg ccgatttatg tttcggtgat tggattcatt   10320
gccaagattt atgctgcggt tatcgttttt gaggctaagg ttattggcgc tattcttcgt   10380
actattacgt ggattgtgaa tcattcagtg tctggcgtga ggtctatggg cacggccatc   10440
cagaatggct ggaatcatat taaatcgttt acgtctgcgt ttattaacgg ttttaagtcg   10500
atcatttctg gcggcgtgaa cgcggttgtg gggtttttta cgcggcttgg tttgtcggtt   10560
gcttcccatg tgaggtccgg ttttaacgct gcgaggggtg ctgtttcttc cgccatgaat   10620
gctattcgga gtgttgtgtc ttcggtggcg tctgctgttg gcgggttttt cagttcgatg   10680
gcgtctcgtg ttcggaatgg tgctgtgcgc gggtttaatg gtgcccggag tgcggcttct   10740
tctgctatgc atgctatggg gtccgctgtg tctagtggtg tgcatggtgt gctgggtttt   10800
ttccggaatt tgcctgacaa tattcggcgt gcgcttggta atatgggtc cctgttggtg   10860 tcggctggcc gtgatgtggt gtccggttta ggtaatggta tcaagaatgc tttgagtggc   10920
ctgttggata cggtgcgtaa tatgggttct caggttgcta atgcggcgaa gtcggtgttg   10980
ggtattcatt ccccgtctcg ggtgtttcgt gacgaggttg gccggcaggt tgttgccggt   11040
ttggctgagg gtattactgg taatgctggt ttggcgttgg atgcgatgtc gggtgtggct   11100
gggaggctgc ctgatgcggt tgatgcccgg tttggtgtgc gatcgtctgt gggttcgttt   11160
accccgtatg gcaggtatca gcgcatgaat gataagagtg ttgtggtgaa tgtgaatggg   11220
cctacttatg gggatcctgc cgagtttgcg aagcggattg agcggcagca gcgtgacgct   11280
ttgaacgcgt tggcttacgt gtgattttgg gggtgtggtg catgtttatt cctgacccgt   11340
ctgatcgttc tggtttgact gtgacttggt ctatgttgcc gttgattggt aatgatccgg   11400
agcgtgtgct tcatttgacg gattatacgg ggtcgtctcc gataatgttg ttgaatgatt   11460
cgttgcgcgt tttgggtgtt cctgaggtgg agcattttc tcaaactcat gttggggtgc   11520
atggctcgga gtggcgcggg tttaatgtga agcctcgcga ggtgacgcta ccggtgttgg   11580
tgtcgggtgt tggcccggat ccggtggggcg gttttcgtga cggttttttg aaggcgtatg   11640
acgagttgtg gtctgctttt cctcctggcg aggtggggga gttgtctgtg aagactcctg   11700
ccggtcgtga gcgtgtgttg aagtgccggt tgattcggt ggatgacacg tttacggtgg   11760
atccggtgaa caggggttat gcgcgttatc tgttgcattt gacggcttat gacccgtttt   11820
ggtatgggga tgagcagaag tttcgtttca gtaacgctaa gttgcaggat tggttgggtg   11880
```

```
gcggccctgt cgacggtaag ggtaccgcgt ttccggtggt gttgacgcct ggtgttggtt    11940
cgggttggga taatctgtct aataagggtg atgtgcctgc gtggcctgtg attcgtgttg    12000
aggggccgtt gtcgtcgtgg tctgtgcaga ttgatggttt gcgtgtgtcc tcggattggc    12060
cggtggagga gtatgattgg atcactattg atacggatcc tcgtaagcag tctgcgttgt    12120
tggacgggtt tgaggatgtg atggatcgtt tgaaggagtg ggagtttgcg cctatcccgc    12180
ctggcggttc tcggagtgtg aatattgaga tggttggttt gggtgccatt gttgtgtcgg    12240
tgcagtacag gttttgagg gcttggtgaa tagttgatgg ctggttttgt tccgcatgta    12300
acattgttta caccggatta tcgccgtgtg gcgcctatca attttttga gtcgttgaag    12360 ttgtcgttga agtggaatgg tttgtccact ttggagttgg tggtgtctgg tgatcattct    12420
aggcttgacg ggttgactag gccgggtgcg cggcttgtgg ttgattatgg tggtggccag    12480
attttttctg ggcctgtgcg tcgggtgcat ggtgtgggtc cgtggcgttc ttcgcgtgtg    12540
actatcacgt gtgaggatga tattcgtctg ttgtggcgta tgttgatgtg gcctgtgaat    12600
tatcgtcctg gtatggttgg tatggagtgg cgtgcggatc gggattatgc ccattattcg    12660
ggtgcggcgg agtcggtggc taagcgggtg ttgggggata atgcttggcg ttttccgtct    12720
ggtttgttta tgaacgatga tgagagtcgt ggccgctata ttaaggattt tcaggtgcgg    12780
tttcacgtgt ttgccgataa gttgttgccg gtgttgtcgt gggctcggat gactgtcacg    12840
gtgaaccagt ttgagaatgc gaagtttgat cagcgtggtt tggtgtttga ttgtgtgcct    12900
gctgtgaccc ggaaacatgt gttgactgcc gagtcgggtt cgattgtgtc gtgggagtat    12960
gtgcgtgacg ccccgaaggc gacatctgtg gtggttggtg gccgtggcga gggtaaggat    13020
cggctgtttt gtgaggatgt tgattcggcg gccgaggatg attggtttga tcgtgtcgag    13080
gtgtttaagg atgcccgtaa cacggattcc gagaaggtgt ctctcttcga tgaggctgag    13140
cgggtgttgt ccgagtcggg ggctacgtcg gggtttaaga ttgagttggc tgagtcggat    13200
gtgttgcggt ttggtcccgg caatctgatg cctgggggatt tgatctatgt ggatgtgggt    13260
tctgggccta ttgcggagat tgtgcggcag attgatgtgg agtgtgtatc gcctggtgat    13320
ggttggacga aggtgactcc ggttgcgggg gattatgagg ataatccgtc ggccctgttg    13380
gctcgccgtg tggctggttt ggctgcgggt gtgcgggatt tgcaaaagtt ttagtaagtg    13440 attgggttt gttgtgggta ttgtgtgtaa agggtttgat ggtgtgttga ccgagtatga    13500
ttgggctcaa atgtctggtc tgatgggtaa tatgccgtct gtgaaggggc ctgacgattt    13560
tcgtgtcggc acgacgattc agggttctac ggtgttgtgt gagatcctgc cggggcaggc    13620
ttgggctcac ggggtgatgt gcacgtcgaa tagtgttgag acggtgacgg gtcagcttcc    13680
gggcccgggt gagactcgat acgactatgt ggtgttgtct cgggattggc aggagaatac    13740
ggccaagttg gagattgttc ccggtgggcg tgcggagcgt gccagggatg tgttgagggc    13800
tgagcctggc gtgttttcatc agcagctact ggcgactttg gtgttgtcgt ctaacgggtt    13860
gcagcagcag ttggataggc gtgctgtggc ggctagggtt cgtttgggg agtctgctgc    13920 gtgtgatcct acccctgtgg agggtgaccg tgtgatggtt ccttcggggg ctgtgtgggc    13980
taaccatgcc ggcgagtgga tgttgttgtc tcccaggatt gagacgggtt cgaagtcgat    14040
catgtttggt ggttctgctg tgtatgctta cacgatcccg tttgagcgcc agttcagtag    14100
tccgcctgtt gtggtggcgt ctatggctac ggcggctggg ggcacggcac agattgatgt    14160
gaaagcctac aatgtgactg cccaaaattt tagtttggcg tttattacga atgatggttc    14220
gaagccgaat ggtgtgcctg cggtggcgaa ttggattgct gtccggcgtgt gactgcacgg    14280
```

```
gtgttgtggc ggatggtgtg atgttggggg gctgtggtgt cgtggtttac tcctgcactg   14340
gtggcctcta tttgtaccgc gttggccacg gttttgggtt ctgttcaggc tgtcacatcc   14400
cggtctagga agcgtttacg caggctgtcg gctcaggtgg atgcgatgga agagtatacg   14460
tggggtgtgc ggcgcgaggt gcgaaggttt aacgccgggc ttcctgatga tgtggagccg   14520
atgcatcttc ctgatttgcc cgagttttg aaagatactg ttgatggtgg aggtgagtag   14580
ggttgaggga gttggaggag gagaagcggc agcgccgcaa ttttgagaag gcttcactgg   14640
tgttgttgtt tttgtcgctt gtgttgttgg cggtggttgc tgcgggtgct ttgcgtttcg   14700
gggctgtatc ctctgagcgg gattcggagc aggcgagggc ccagtcgaat ggtacggctg   14760
ccagggtttt ggctgcccgt gtgaagcagg cgtgtgcttc gggtggggtg gagtctgtgc   14820
gtcttcaccg ttctggtttg tgtgtggatg ctgtgcgtgt tgagcagcgt gttcaggtg    14880 tgccgggtcc tgccggtgag cgcggcccgc aaggcccttc aggtcctgcc ggccgggatg   14940
gtgttaatgg ttcggctggg ctggttggcc ctgttggtcc gcaaggttct ccgggtttga   15000
atggtgtgaa aggtcctgac ggcttgcctg gcgctaacgg ttcggatggc cgtgatggtg   15060
ttccaggtcg tgcaggtgct gacggtgtga acggcgttga cggcgctgat ggtcgggatg   15120
gttctgccgg tgagcgcggc ccgcaaggcc cttcaggtcc tgccggcccg caaggtgcac   15180
agggtgaacg gggtgagcgt ggtcccgccg gtgcgaatgg atcggatggc catgatggta   15240
aggatgggcg ctcggtggtg tctgtgtact gttccggggg ccgcctggtt gtgaaatata   15300
gtgacggtgt ggcttccacg atatcgggtt cggcggcctg ccagggtgtg aaaccgtcgc   15360
ctctagtgac tatatcatcc cacaaataga aaggagtggc tgtgatggtg gtgtttggtg   15420
gtggtgtgtt gtgagatata ttcctgcggc gcatcattct gccggctcga atagtccggt   15480
gaatagggtt gtgattcatg cgacgtgccc ggatgtgggg tttccgtccg cctcgcgtaa   15540
aggacgggct gtgtccacgg caaactattt cgcttcccca tcgtctggtg gttcggcgca   15600
ttatgtgtgt gatattgggg agacggtgca atgcttgtcg gagtctacga ttgggtggca   15660
tgccccgccg aatccgcata gtttgggtat agagatttgc gcggatgggg gttcgcacgc   15720
ctcgttccgg gtgccggggc atgcttacac tcgtgagcag tggctggatc ctcgcgtgtg   15780
gcctgcggtt gagcgtgccg ccatcctgtg tagacgtttg tgtgacaagc atggtgttcc   15840
gaaaaggaaa ctgtctgtgg ccgatttgaa ggccggtaaa cggggtgttt gcgggcatgt   15900
ggatgttacg gatgcgtggc atcagtcgga tcatgacgat ccggggccgt ggtttccgtg   15960
ggacaaattt atggctgtgg ttaatggcca cggcggcggt tcaagtagtg aggagttgag   16020
tatggctgat gtacaagcgt tacataatca gattaaacag ttgtcggcac aggtggccca   16080
gtcggtgaat aagctgcatc acgatgttgg tgtggttcag gttcagaatg gtgatttggg   16140
taaacgtgtt gatgccttgt cgtgggtgaa gaatcctgtg acgggaagc tgtggcgcac    16200 taaggatgct ttgtggagtg tctggtatta cgtgttggag tgtcgtagcc gtcttgacag   16260
gctcgagtct gctgtcaacg atttgaaaaa gtgatggtgg tttgttgtgg gtaaacagtt   16320
ttggttaggt ttgctggagc gtgccctgaa aacttttgtt caaacgtttg ttgccgtgtt   16380
gggggttact gcgggtgtca cctatactgc ggagtcgttt cgtggtttgc cgtgggaatc   16440
cgcgctgatc acggcaacgg ttgctgctgt cctgtcggtt gctacctcgt ttggtagccc   16500
gtcgtttgtg gccggcaagc ccggcaagca gccccaggtg gatgcgggtt tggttccacc   16560
ggatgatggg ggcttggttg agccgcatat ggtggatgtg tcggatcctg gcatgatcga   16620
```

```
gccgacggat gatgcggatc ttgccggcta tgagcctcgg cgtgcagccg agtcggaggt    16680
tggcacggta gagtctactg ttgcataatt gaatatagat gtgtgcccca gcggtgctgc    16740
cacgattgtg tggtggcggc tgctggggca ctattttgt atatgcggtg tggctatgat    16800
tcgttgctgt cgatggtgtc ttcgagcatc tgatacaggt ggaggcaggt agagatagtt    16860
tcgctggcct gatcgagaac gttccggccg ataacgtttt tgtggttgtc gcggtggcgg    16920
atgatagccc acatgatctc gtcggctgcc gcctgtaata gtttggcctg gtatgcgatt    16980
ccggcgagcc agtctagtgc ttcctggctt gtataggggc tctggtcctc gctgttgccg    17040
cgggtgttgc tgttgtttgt ggggtgtcct gcactgtcgc atagccacag gatttcgctg    17100
cactcgtcta gcgtgtcttg gtcgatagcg agatcgtcga ggctgacatt gttgacggta    17160
aggttcacgt tgtcgaggga gatgggtaca ccgtactggt tttcgacact gtcaacaatg    17220
ttttccagct gttgcatgtt ggtgggctgt tgttggacga tacggtgtat cgctgtgttg    17280
agggtggtgt aggtgatgtt gtgtgtgttg tccatggttt ttatgccatt ccttcgttat    17340
cgtctggcat gtagtatgtg ctgtttgcgt actcggttaa cgtcatcagt gtttggtctg    17400
cccactgttt cacggtttgc cgggtgactc cgagtcgttg ggcggctgtg gcgtaggttt    17460
gatcataccc gtatacttcc cggaatgctg ccaacctagc taggtgtttc tctctgtttgg    17520 atggttcaca ggtgagggtg tagtcgtcga tggctagctg tagatcgatc atggagacga    17580
tgttgttgcc gtggtgttgt ggcgcggttg gtggggtgg cattcctggc tccacggagg    17640
gtttccaggg gccgccgttc cagatccatt gggcagcttg gatgatgtcg gcggtggtgt    17700
aggttcggtt cactggtcac ccctgaaca ggtcgttggt gttgttggtg tcgaatcgtc    17760
cgacgcagtg gcagtagtcg tacatgagtt taataatgtg ttggtggtct cccaaatagg    17820
tgtttccgct gatgctgtat gtggctgtgc cgtctttcgc gatggtgtat ttggcggtga    17880
tggtttcggg gttttcggtg tcggtgatga ttgctgtggt ggtggcgcct actgtttgga    17940
gtatggtggt ttgggttccg tcgtcgatgg tggttttaac catggtgtgt gttttcccctt    18000 ttgttagttg cttgtttggt tgtcggctag atgaataata tcgggtaaag gtttcggctg    18060
gtctaggtgt tgtatggttt tgttggctag ccgtttggct accctgtaac acattttggt    18120
gtagtgtttg ttgtctaggt tgtggtattg ttcccgcacc gcaatatata gcagggagtc    18180
ttggtacagg tcgtctgcac tgattgcggg gtagtgtgcg gctgttttgg tgcatgcccg    18240
gttgagtgtg cgaagatgat ggtctgtggc ccacacccac gatgcggtgg tggccaggtc    18300
ggcttttgtt ggtcgtctgc tcatggcact atttcatctc gctatctgat agttgtttgg    18360
tgttttgttg tggatagtgt agcacactag tcctgggtgg ccggtggtgc ctgtgcggtg    18420
acggaaccat gtggattcgc cttccatgga tgggcattgg atgaaggtgc gttgtccttg    18480
ctcggagatt tctaggtggt gccggtgccc ggccatgaga atattagata cggtgccgtt    18540
gtggaattct tggccgcgcc accaatcata gtgtttaccg gtcgccatt ggtgcccgtg    18600 ggcgtgcagt atccgtgtgc ctgccacatc aacggtggtg gtcatttcgt ctcggctggg    18660
gaagtggaag tgtaggttgg ggtattggtt attgagctgg taggcttctg cgatggcccg    18720
gcagcagtcc acgtcgaatg agtcatcgta ggtggtgact cctttaccga agcgcacggc    18780
ttcaccatgg ttgccgggga tggatgtgat ggtcacattt ttgcagtggt cgaattggtg    18840
gatgagttgc atcatggcca tgcgggtgag cctgatttgt tcggtgaggg gtgtttgtgt    18900
tcgccaggcg ttgttgcctc cttgtgacac gtatccttcg atcatgtcgc cgaggaaggc    18960
gatgtggact cgttcgggtt tgcctgcttg ttgccagcag tgttttgcga ctatgaggga    19020
```

```
gtgtaggtag ttgtcggcga agtgtgctgt ttctccgccg gggatgcctt tgccgatttg   19080
gaagtctcct gccccgatga cgaaggctgc ggtgctgtag tcggtgtggg tgtcttgttc   19140
gggttttggg ggtgtccatt cggctagttt atcgacgagt tcgtctaccg ggtaggggtt   19200
tgttgcgggt tggtggtcga tgatttttg tatggatcgg cctgtttctc cgttggggag   19260
tgtccattcg gagatgcgtg tgcggcgcac ggtgccgttg gctagattgt cgtcgatggt   19320
gtcgatggcg ttgtcgtggt tggctagctg tgtgagtagc cggtcaatat tgtctatcac   19380
tgggtatcct cctcttgcgg ggtggtgctg gcttgtttgc ggcgatagtc tttaataacg   19440
gtggcggaga tggggtatcc tgcctgggtg agctgttttg ctagccatga ggcgggata   19500
gacctgtcgg cgagcacgtc ggcggctttg ttgccgtagc gttgaataag ggtttcagtt   19560
ttggttgcca tgatgtccta tcggttgtgt ggtgggctgc catcctgtgc ggcagtcgcc   19620
gtcgtgtcct ggtttgcgtg tgcaccacga tacggttccg tctgtgtggt tgagtgtttt   19680
accgcacatg acgtttcgga gatgctccgg cagctggtca tcctggttgc tggtttgtgt   19740
gtcgaagagt gttttctggt tggtgaaatg ttctgacacg gtgccgttat gcacgggtag   19800
tatccatgtt ttccattgtt gttgtagcct ggtgttccag tggaattgtt tggcggcgtt   19860
ttcggcctgt tttaaggttt tgtggtagcc gactagtatg cgttgatgct gctggtctgg   19920
agggtttggg cctcgccagt attgtgccgc cacggcgtag cggttgctgt ctgtgaaggc   19980
gtcccagcag tattcgataa tgtgttgcaa catactgtct ggcaggctgt cagggttgat   20040
gttgatgttt tgggtgataa tgtcacggat ggcttgccgg tttttggtgg tgggtttgaa   20100
cgagatgctc acgatagtac cggctggtcg tcttgcatga actggttgaa ggtgttgttc   20160
ccggcgtgtt gggcttgtgt tatttgttgg tcggtccagt ctgggtgttg ctgtttcaga   20220
tagtgccagt ggcacgcatt gtaggtttcg tcttgtagcc gtgtgagatg gttttcggtg   20280
atgatttgtt tccacatggc ccatgacacg tcgagccggt cgaggatttc gagggctggg   20340
atgttgaatt ggttcaggaa gaggatttcg tgggtgtagt agttttctc gtaggcgtcc   20400
catccgcttc ggtgcctgtt gggctggttt ttggggtagg cttcccggca tactttgtgt   20460
aaacgcttgg ccatgtcgtc gggtagttta atgtcggggt tggcgcggat catggatcgc   20520
atcccatcat aggtggtgcc ccaggtgtgc atgatgtagg tggggtcttc tccgtcggcc   20580
cattttctg cacagatggc gaggcggata cgcctcctgg cagcttggct ggtgttgcgc   20640
cggttgggga ttgggcacgt gtcgagggga tccatgatgt tttagtgtac ctttctggtt   20700
tcgtgttgtt gacaggtttt actgtagcac agtgtctagt gcgtgtgtca accctgtttt   20760
tccggcttga aggtaggtgt ctgtgacatc ccctagggtg aggggcacgt gcacagcttg   20820
ggggagtgcc gcctggaggg tttgggccat ctggtcgcct gcggggtctg ggtctgacca   20880
gatgtagatg tggtcgtagc cttcaaaaaa tttggtccaa aaaatttgcc acgaggttgc   20940
gccgggtagg gcgacggccg accatccgca ttgttcgagg atcatggagt cgaattcgcc   21000
ttcgcaaatg tgcatttcgg ctgccgggtt ggccatggcg gccatgttgt agatggagcc   21060
tgtgtctcct gccggggtta ggtatttggg gtggttgtgg gttttgcagt cgtgcgggag   21120
tgagcagcgg aaacgcattt ttcttatttc ggctgggccg ccccaaacgg ggtacatgta   21180
tgggatggtg atgcactggt tgtagttttc gtggcctggg atgggtcat tgtcgatgta   21240
tccaaggtgg tggtagcggg ctgtttcttc gctgatgcct cttgctgaga gcaggtcgag   21300
tatgttttcg aggtgggttt cgtagcgggc tgaggctttc tggattcggc ggcgttccgc   21360
```

```
aatgttgtat gggcgtatgc tgtcgtacat ttgggttttc ttcttctaat cgttgttgta   21420
gcttggcgag tccgcctccg acaccgcatg tgtggcagta ccagacgccc ttgtcgaggt   21480
tgatgctcat ggagggctgg tggtcgtcgt ggaacgggca gagtatgtgt tgctcgttcc   21540
tggacggatt gtaccgtatc tgataatggt cgaggaggcg gcaggtgtca gaggtgtggg   21600
aggagctcgt tgagggttga taccacatag gcttcactcc atggcttgtt gcgctgtttc   21660
atcactacga gtccgatggt ggaattgttt tgtttgtttc ggtgtgtttc gtagttgcgt   21720
gcctcccggc tggcttgttt cacgaattgg gctaggtgtg gttgcccggc tttcgcctcg   21780
ataatgtagg ttttatggcc ggttgtgagg atgaggtcgc cttcgtcttc gcggccgttg   21840
aggtggaggc gttcgatatt gtgtccggtg tcgcgtagct ggtggaggag tcttgtttcc   21900
cattcggctc cggcccgccg gttgcgtgcc tgctgtgtgg ccatagtttt ttagagtcct   21960
ttgtgtgttg tggtcatgtt ccagggctgt ttttcggcga gtggcccgaa gaatgtgtat   22020
tcggggtatg ctctgagtcg ttcgtatcgg gtgccgtcgg ggctggattt gcctgtgcgc   22080
tgtttgagta cggcgatgcg tgcctctgcc ggtatcgata gcccgttgcc gttatcctcg   22140
ccaccataca atgagactcc gaggatgagt tgtggttttt cggagaggcc gttttttgatt   22200 tctcgccgtg ctggcgggtg ttcgatgtcg gttccggttt tgtcggttgc gtggtgtgtg   22260
acaataatgg tggagccagt atccctgccc aatgctgtga tccattgcat ggcttcttgc   22320
tgtgcctggt agtcggattc gcagtcttga atgtccatca ggttgtcgat aacaatgagt   22380
ggtgggaagg tgttccacat ttccatgtag gcttgtaact ccatggtgat gtctgtccat   22440
gtgatgggtg actggaatga gaatgtgatg tgttggccgt ggtggatgct gtctcgatag   22500
tattctggcc cgtagtcgtc gatgttttgt tgtatttgtt gggtggtgtg ttgtgtgttg   22560
agggagatga ttcgtgtgga ggcctcccag ggtgtcatgt cccctgatat gtagagggcg   22620
ggctggttga gcatcgctgt gatgaacatg gctagccctg attttttggct gccggaccgc   22680 cccgcgatca tcaccaagtc gcccttatgg atgtgcaaat cttggttatc atatagtggt   22740
gcgagttgtg gtatgcgggg tagttcggct gcggtttggg aggctctctc gaaggatcgt   22800
tgtagagaga gcatcgggac cttaatctat ctgtctgttg gttgtgtggc tggtcagatg   22860
gagtcgatat cgatatcagc atcagcagag gctgaagtgt catctagctg accattatcg   22920
cgcttgtcta cgtattcggc aaccttatcg tagatggcgt cgtccaatgt tttgagcacg   22980
accgcgttga aaccgttttt ggtgcgcacg gtggctagtt tgaaggcctg ctcctcgcca   23040
aggtatgcct ctagttcgcg gatcatggag tgtgggcggt cgttattgcc gcgggctttc   23100
tcaataatag cgttggggat ggtttctggg gtgccgttgt tgagatcgtc tagggtgtgg   23160
aagatggtga catcagcgta gatgcggtct gcgacctgtc caccgtagcc ttcagtgttg   23220
tgctggacgt cgtgcacttt gaaggcgatg gccgtggcgt cctggtttcg ggaggggttg   23280
aagaaggtgc tgttgctgtt gttgcggtag tttgcgagtc ccataactat tgtttccttt   23340
tactgttgtg tctgttttgg ttggcttata ttggtttatc gggtgaggct gtttcgctta   23400
gtgcggaaag cgtcggaaac atcactgtta ctggtgatga tcttcttgta ctgttttaga   23460
aggtctgcta gctgtgcctt gcttgttgca ttgttgattt tgttgatgac gatggtgttt   23520
tctttggatg cgattttgtt gacgtagtct ttggctgcct ggttgtatcg gtcttggagg   23580
atgattgatg cgctcgctac gagtgttgct agatcccagt cttttggacac gtcatcgttt   23640 ttgagtccgc ctagcaggtc gatgatggcc tgttttgtct gctctgctgt gtctcctcgg   23700
atgaccgccc atggtgcagc atagtctcca ccatatttga gtgtgatcgt gagtcgatca   23760
```

```
ttgtcgatct tgtctttatc tgtcatttgg tgtcctttc tttattgtct gtttctggtg   23820
gctgtacggt ggattctacc gggtatctgt acgagttttt gccgttgacg gcccagcagg   23880
cgtctcgtac ggggcatcct ttacagagtg ttgtgacgtg ggggacgaag atgccttcgc   23940
tgattccttt cattgcttga ctgtacatgg atgatacatg ccggtaggtg ttgttgtcaa   24000
ggtcgtagag ttcggtggat gtgccttgtg tcggggactt gtcgtcgttg cggctggtgg   24060
ctggcgtcca aaacatgcct ttcgtgacat ggatgtcgtg ttggttgagc atgtaccggt   24120
atgtgtgcag ctgcatactg tcggcgggta ggcgtccggt tttgaggtcg aggatgaagg   24180
tttcgccggt gtcggtgtcg gtgaaaacac ggtcgatgta gccgactatt tttgtgtcat   24240
cgtcgaggat ggtttctacc gggtattcga tgcctggttt accgtccagg attgcggtga   24300
tgtattctgg gtggttgcgc ctccatgttt tccagcggtc cacaaaggtg gggccgtaaa   24360
ccatccacca gtcgtagtct ttcttgtgtg gtccgcctga ctcgcacatg ttttttgcata   24420
ttctgccgga gggtttgatt tctgtgcctt cggattcggc gagggctacc tgggtgtcga   24480
aaatgttttt gaaggatgag agtttgtctg gcagtgcagg gtattcggcg ggattgtaca   24540
ggtgtaggtc gtattgttcg gtgatgtggt gtatggcgct tccggcgatg gtggcgtacc   24600
aggtgtggtg ttgggcgtga tagccgtggg ataggcgcca tttttctccg cattcggccc   24660
actgggtgag tgaactgtag gagatgtgtc ctgggtggct gatggtttc gggtattgtg   24720
ctagaggcat tacttgtcgc ttgtgttcca tgtgttgcgg gtgtcttggc cggcgtggtg   24780
ttgctggtag gcgaggagtg cgaggcagtg ccaggctgcg tgtgctagat ggggtagccc   24840
ggattcgtgg tcgaggttgt tgccttgctg ccatgatagt agatgcctgt agagggcgtc   24900
gacactgtgg ctccacgggt atcctccggt ccagttgttg tcgccatatt tggtggcacc   24960
gtatccggct acttcgccta gggcgtgaag ggatgctggg tcgatgaggg agagcctgca   25020
gagtttcaat tcttttcggg caccgctgtt ggggtcggtg tacatgcggg tgggctcatc   25080
catggggtgt gtgctcctta agggtgggtt actggttgtt gttgtgggct agggcggcgg   25140
cgagaataat gatggcgagg gtttcggcta tcagtatggg tgttgtgatc atttggtgtc   25200
tcggggattg ttggtgagtg ttgaggcacc caggagggtg gcgagggcgc atgcggcaat   25260
aatggcgagg gctgccttgt gtggggtgcc ggttgcgtac atccatgtga tgatggcacc   25320
ttggatccag gctaggctgg tgaagaaggt ttcgtagctg tgcagctcaa tgttgttgtt   25380
gggtgtgttc atgcttgctc ctgaagaatg gtgttgatgg ttttataaat gttgtacagg   25440
tcggtttcga tagataacag ttggttgatt tggtggtcga gatcaatgtc tgggttgagt   25500
gtgttgatgc gggaggcaat atcggtggct gtgcgtagtg tgccgccggt gtggtgaata   25560
atgtgtgccg tgtcggcgag tccggtggtg acggcgtagt gggataggag aggcatagcg   25620
gggatgctcc ttggcgggtt actgttgcgg gttgatgttg aggtcggtga cgtgcggtga   25680
gttttctgtt ccggtgacga ggcagtggac ggtgacgggg agtttggatg ctcccggctg   25740
gcggacggtg gcgccgtaga cgatgctgaa tgtgtcttta ccgatggttt tgtggagttg   25800
gaggtcgatg tcgggggttgc cgttccagtt gacaccttgc gctgcggcct gttgttcggc   25860
tttgtggttg caggtgtgtg ctgccgtgat catggtgagt ccggtggcgg tttcttcacc   25920
ccttgcttgg gcttgcttgt gggctttggc ctgctcggct tgtagggatc gggtggcggc   25980
tgcctgccgt gccgctttct cggctttgcg ctgttgggta gtcttggggg tccatgtggt   26040
gttggctgtg gttgcctgtg gggctggctg tgaggtgagt ggcgggttgt cgtctggtgc   26100
```

```
tggcatgaat gaggcggcgg caatgatggc ggctgtgatg cctgcgatgg tgtagccgtt    26160
tttcttgttc atgttttgtg tcccctttcc ggggtgttgt tcgttgctga catggttaat    26220
actttcagcg gctgggccca ctgtcaaggc tgcgctcagt ttgtgtgagc gtttggtgtg    26280
tggctagggg ttttgtcatg taagcgtgac atgtcactac cttgcgtcca gtatccatgg    26340
cggttgcgag ccatcccttt ggcgagcatc tcgtccacag tgaggcacct gcggcgattg    26400
gggccttcct tgaccccgtg atcgcctatg cggtgcatgt ccccggcata agtgccatta    26460
aatgtttcgt ggcagactgt gcagtgttct ggtcggtatc cgatgattgt gctatcgcac    26520
ttgtggcatg tccattgcat gattggtcct tctttcgtgt tttaagcttg tgctctgagg    26580
attagagcga ctttcagccc ttgggggtag gattatatag gtcaggtatt tctaggcgat    26640
tctaggctca ttgtgtgtgg ttggggtttt atcgggcgca tagggttagc aggtggccca    26700
cattggtgcg gctcacattc cagtagagtt gcgtggcttc cttactggtg agcggcttcc    26760
actcgtcatg gctgaacacg gtgccatcgg atgcgatgaa cgtgttgggg cgtagcttgt    26820
gaagctcggc ttccacatgc tgccggtagg cttcggcgag gctctcaaaa tccatgtggt    26880
cgcaggagag gttttcgagg cgtgtcaggt cgaaaggctc cgggcagtcg tagctggctg    26940
gagtgtagag ctgggtgaag tggtcggcga tcttctgcat ggcgggttcc tttctggtgt    27000
gtggatggtt tttatcgtgt ggatgcgaca aggatggcgt ctacgtcgat catgtcgatc    27060
atgtcgttga gttcctcggc ctcattctcg gagaggtggc gccagtcggg tggcccgtat    27120
acggcgccgt cgagggtgac agtccacagg ggccggatga gtcgtatggc ttcttcgact    27180
ttggcgtggt acatgcggcg caccatatcc agatcgatgt cgtctgaatg gtttccggtg    27240
aggctgtgga ggctgagcgg gtcgatttct gtctgcctgt agaggctggt gaatgatggt    27300
gtgatgagtg tgccatccat gagtgtgctc ctttctaggg gttgttgtgg tttctagagt    27360
gtgtgggctg tgaccccaca gtcaaggcta cgctcatttg gattgagcgt ttcatatggg    27420
tgtggcatga aatctacacc ctcatactgt gtgagatgta tcacatcccc ctggcttggt    27480
gtgcacccct caagactact ctgccgacct ggcgtggagg gtgtagccca gaaatgccgt    27540
ttaaagcttc aggggtacgc ctaggagcgc cttacagggt gggggctagg tatttatacc    27600
cccagcatat tctgatcgat tctagacgac tcccagagcc cgatacacga tcaaccatct    27660
cgacatagac catcagcccc tatcctggtt agctaagcct caactatgtg gacagtgtgg    27720
gacactgtgg gggaagaagg acacggtaca agaaagaggg gggagcatca gccttaaagc    27780
cttaagatct tagcgcttag caccgatggt cttagcagtt agcaccgagc ccttgagggg    27840
gctcggcatc agcctcatcg ggctcagctc atcaggcaca gccctgaaaa gggtacacgc    27900
catcagggaa ggcttgagag tacgaggagc cctagcgacg agtactcgaa agcctgaggg    27960
aacaccctca gtactgatga gcctagcgta ttcggaaagg acgcaagagt aaagtgtgac    28020
agctatccgg gagtgaaacc cgttccgact aggggtttca gccttaacca ccctcaaagg    28080
ttacaagact ctaagaaaat ttaagaaact tcttaggaag aaagttgtgt tcatatcccc    28140
ctaaaaacac ccaaaatagt cctcaaaccc gcctatagag ccaaacagtc aagtttgact    28200
cgtctagacg gcgtatgata ggctggacag gtagccagct ggacgcaagg ccagaaagtg    28260
ctgacgcact tcccgacctc gcttaccatc agtctaccaa acactttaaa gcttcaaggc    28320
ttagcgctaa gcccttaaga tcttaacgct tagcaccgag ccccccctcaa gggctcgaca    28380 tcagtcttaa agtcttaaac actttaagta actttaaagc ttcaaggctt agcccttaag    28440
gatctaagtt actataaaag ctttaaacac ttaaagtaac tataaagctt taagagctta    28500
```

```
acatttaagg atataaataa acattaaagc tttaaagtct taaagtaaat ataaacctt   28560 aacacttaag ttaagtataa aaccttaaag gcttagcact taaggatata aacttaacat   28620
cagtgtttaa gacttaaaga gttaaagtaa ctattaagac ttaaaggctt ataagcttta   28680
atactttaag tagctataag actttaaaaa cctgaagtac ttaaagttaa ccatcagtct   28740
taaactttaa tattataagt attaaagctt ataagttata aaagttttta gaagagttaa   28800
agggttaact tctttacttc tcttctctct ttggtttctt ctctcttctc ttcttttctt   28860
catcagggga gaagaggaac ctttaaccgt caacgctgat ggacttttca ccgtgtgact   28920
cgtgtgcttc tggtcgcaag ctcccatcgc acactcccca cactcttca cccgtgcccc    28980 tttacggctt agcgtgttcg tcggaaggcg tacgcgtgt cacgcttaaa cccttaacac    29040
caggtaagac ttaaagtgca tattataagt agaagacttt aaaacctata aggtgttccc   29100
gcttagcccg tgttccttta acgctaggcg ctcagcgcta agatgtgaaa cgtgaacacc   29160 catccaccc cattttctt ccgtgtcctt ctccttttga caccgctggg gggcgatgtg   29220
atatttctca catgccaggg ggtagtggag aaaacaacca ccccggaacg tttaagacac   29280
cccctcaaac gaacaaaaca gggcctagaa tcgatcagca gggcaccggt agggtattcc   29340
tacccccaga cgattcaagg ccattacagg agcaatgaga ggctcacagg ggccatggga   29400
gattgggggg cgtgatggca cacaccaacc gcacagccag ccaagcccac cggcgctggc   29460
gggcaaggct catcacccaa gcccgacaac aaggccaaac cgaatgccca ctctgcggag   29520
tcaccatcac ctggaacacc cacgacctgc caaccagccc cgaagccgac cacatcacac   29580
ccgtcagccg gggaggactc aacaccctcg acaacgggca aatcatctgc agaacatgca   29640
acagaagcaa aggcaacaga acacaaccaa acatcaaatt ccaacaacaa accacaaaaa   29700
cattgattcc atggtgaaaa acccgccaac ccccaccggg cacacccct gcacacccgt    29760 gcaagacc                                                            29768
```

<210> SEQ ID NO 24
<211> LENGTH: 11979
<212> TYPE: DNA
<213> ORGANISM: Artificial Sequence
<220> FEATURE:
<223> OTHER INFORMATION: pANS514 plasmid

<400> SEQUENCE: 24

```
catggttgcg ccatgcagca caggccaagc gtgaggccca agcacgagga ctcgcccgct     60
gcccactgtg cggcgtctgg atggactacg aggtcggcaa gcgacccaac tcggccgaag    120
cagaccacat cagaccgcat tcgcttggtg gttcagacga catcgacaac attcgcgtca    180
tttgtcgtcg ttgcaatcaa tcgcgcgaa acggcctgaa gcgaccaggg cgccaacgtc    240
agcgtccaat caagcgcatc gagctggccc aaccggcccg cagtggggca tttcctgccc    300
cgccggcatg aatggaaggg cagtgcggat ggtgcggtcg ggcattcgat cgtgcccgga    360
cgggtcgccc gcgacgcttc tgctcggccc gctgtcgggt cgccgcgtcc cggtgtgcga    420
tcccgctggc catgaggtcc cgcactgcgt gggtccgctg cgacggcaag cgccccatca    480
ccctggctgg cgctccggcc tcatccacgg acccgggcac atggtctggc tggtcgcagg    540
tgcgacgcgc cacggccggc gatggcttcg ggaccatgct cggtgacggg ctggggtgct    600
gggatctcga ccacttcgac gatcaggcg cccgggcctt catcgaccgg atcgataagc    660
cgatcatctt cgccgagcgg tcggtgtcgg ggcatggctt ccacatcttc gtccggactg    720
```

```
acgaggcccc cggacgccgc accggaaaca tcgagttcta ctcacgccat cggttcatca   780
gggtcacagg agaccagttc gtctgaaggt cgtgccgggt ttgtgtctga tgaggagtgg   840
ttgtttctca tggatgctgc ggtgattcat gatgtggtgt ggcgtgaggg tcgcgcggat   900
ttggtggctt cgttgcgtgc tcatgtgaag gcttttatgg gtatgttgga taggtattcg   960
gttgatgtgg cgtctggtgg ccgtggtggg ggttctgcgg tagcgatgat tgaccggtat  1020
aggaagcgta gggggcttg agtaggtgtc tggtgttgtt gggtctcagg ttcctcgtca  1080
ccgggtggct gtggcgtatt cggtgtctgc tggcggggat gctggggagc ttggtagggc  1140
ttatggggttg acgcctgatc cgtggcagca gcaggtgttg gatgattggc ttgctgtggg  1200
tggtaatggc aggcttgctt cgggtgtgtg tggggtgttt gttccgcggc agaatggcaa  1260
gaatgctatt ttggagattg tggagttgtt taaggcgact attcagggtc gccgtatttt  1320
gcatacggct cacgagttga agtcggctcg taaggcgttt atgcggttgc ggtcgttttt  1380
tgagaatgag cggcagtttc ctgacttgta tcgtatggtg aagtcgattc gtgcgacgaa  1440
tggccaggag gctattgtgt tgcatcatcc ggattgtgcc acgtttgaga agaagtgtgg  1500
ttgtccgggt tggggttcgg ttgagtttgt ggctcgtagc cggggttctg ctcgcgggtt  1560
tacgttgat gatttggtgt gtgatgaggc tcaggagttg tcggatgagc agttggaggc  1620
tttgcttcct accgtgagcg ctgccccgtc tggtgatcct cagcagattt ttttgggtac  1680
gccgccgggg ccgttggctg acgggtctgt ggtgttgcgt cttcgcgggc aggctttgtc  1740
gggtggtaaa cggtttgcgt ggacggagtt ttcgattcct gacgagtctg atccggatga  1800
tgtgtcgcgg cagtggcgga agttggcggg tgacactaat ccggcgttgg ggcgccgcct  1860
gaatttcggg acagtctcgg atgagcatga gtcgatgtct gctgccgggt ttgctcggga  1920
gcggcttggc tggtgggatc gtggccagtc tgcttcgtct gtgattccgg cggataagtg  1980
ggttcagtcg gctgtggttg aggcggctct ggttggcggg aaggttttg gtgtctcgtt  2040
ttctcgctcg ggggatcgtg tcgcgttggc tggtgctggt aaaacggatt ctggtgtgca  2100
tgttgaggtt attgatggcc tgtctgggac gattgttgat ggtgtgggcc agctggctga  2160
ttggttggcg ttgcgttggg gtgacactga aaaggttatg gttgcagggt ctggtgcggt  2220
gttgttgcag aaggctttga cggatcgtgg tgttccgggt cgtggcgtga ttgtggctga  2280
tactggggtg tatgtggagg cgtgtcaagc cttcctggag ggtgtcaggt ctgggagcgt  2340
gtctcatcct cgtgccgatt cgaggcgtga catgttggat attgctgtga ggtcggctgt  2400
gcagaagaag aagggttctg cgtgggggttg gggttcctcg tttaaggatg gttctgaggt  2460
tcctttggag gctgtgtctt tggcgtatct tggtgcgaag atggcgaaag cgaagcggcg  2520
tgaacggtct ggtaggaagc gggtgtctgt ggtatgaact cggatgagtt ggctctgatt  2580
gagggcatgt acgatcgtat tcaagggttg tcttcgtggc attgccgtat tgagggctac  2640
tatgagggct ctaatcgggt gcgtgatttg ggggttgcta ttccttcgga gttgcagcgg  2700
gtgcagacgg tggtgtcatg gcctgggatt gcggtggatg cttttggagga gcgtctggat  2760
tggcttggct ggactaatgg tgacggctac ggtttggatg gtgtgtatgc tgcgaatcgg  2820
cttgctacgg cgtcgtgtga tgttcacctt gatgcactga ttttttgggtt gtcgtttgtg  2880
gcgatcattc cccaagagga tgggtcggtg ttggttcgtc ctcagtcgcc gaagaattgt  2940
actggccggt tttctgccga tgggtcttgt ttggatgctg gccttgtggt gcagcagacg  3000
tgtgatcctg aggttgttga ggcggagttg ttgcttcctg atgtgattgt tcaggtggag  3060
cggcggggtt cgcgtgagtg ggttgagacg ggccgtatcg agaatgtgtt gggtgcggtt  3120
```

```
ccgttggtgc ctgttgtgaa tcgtcgccgt acttctagga ttgatggccg ttcggagatt    3180
acgaggtcta ttagggctta cacgatgag gctgttcgca cactgttggg gcagtctgtg    3240
aatcgtgatt tttatgcgta tcctcagcgt tgggtgactg gcgtgagcgc ggatgagttt    3300
tcgcagccgg gttgggttct gtcgatggct tctgtgtggg ctgtggataa ggatgatgat    3360
ggtgacactc cgaatgtggg gtcgtttcct gtgaattctc ctacaccgta ttctgatcag    3420
atgcgtttgt tggcgcagtt gactgcgggt gaggcggctg ttccggaacg ctatttcggg    3480
tttatcactt ctaacccgcc ttctggggag gctttggctg cggaggagtc tcggcttgtg    3540
aagcgtgctg aacgcaggca gacgtcgttt ggtcagggct ggctgtcggt tggtttcctg    3600
gctgcccggg cgttggattc gagtgttgat gaggccgcgt tttttggtga tgttggtttg    3660
cgttggcgta atgcgtcgac gccgactcgg gcggctacgg ctgatgctgt gacgaagctt    3720
gtgggtgctg gtattttgcc tgctgattct cggacggtgt tggagatgtt gggtttggat    3780
gatgtgcagg ttgaggctgt gatgcgtcat cgtgccgagt cttcggatcc gttggcggca    3840
ctggctgggg ctatttcccg tcaaactaac gaggtttgat aggcgatggc ttcgggtgct    3900
gtgtcgaggc ttgctgcgac tgagtatcag cgtgaggctg tcaggtttgc tgggaagtat    3960
gcgggctatt atgccgagtt gggtcgtttg tggcgtgccg gcaggatgag tgacacgcag    4020
tatgtgcgtt tgtgtgtgga gttggagcgt gccggccatg acggttcagc agctatggcg    4080
ggcaaattcg tttcagattt tcgccggttg aatggtgtcg atcctggttt gatcgtgtat    4140
gacgagtttg atgctgcggc ggcttttggct aggtcgtttt cgactatgaa gattatgaat    4200
agtgacccgg ataggggcgaa tgatacgatt gatgcgatgg ctgcgggtgt taatcgggct    4260
gttatgaatg ctggtcgtga cacggttgag tggtcggcgg gtgcgcaggg taggtcgtgg    4320
cgtcgggtga ctgatggtga tccgtgtgct ttttgtgcca tgttggctac gaggtcggat    4380
tatacgacta aagagcgggc gcttactact ggtcatacgc ggcgtcataa gcgtgccggt    4440
aggcgtccgt ttggttcgaa gtatcatgat cattgtggtt gtacggtggt tgaggttgtt    4500
ggtccttggg aaccgaatag ggctgatgcc gagtatcaga ggacgtatga gaaggctcgt    4560
gagtgggttg atgatcatgg gttgcagcag tcgtctggca atattttgaa ggctatgcgt    4620
actgttggtg gcatgagata atttgatgtg gtttccggtt gtgtgccgcc ggttatcggt    4680
gcacagggtt gtctcccgca cggggtcaa caatgttgtg ttgttttccg caaggagtgt    4740
agggttaggc tatggccgat cagagtattg aggaacagaa tgttgacaat gatgttgtgg    4800
agtccggaaa ggataacggc attgttgata cagtaaaaga cgatggcggg caggaggtag    4860
ccgacaatca gttgaagaat gaaggcgagg gtaaatcgcc ggggactgat tggaaggcgg    4920
aggcccgtaa gtgggagtct cgtgctaaaa gtaatttcgc cgagttggag aagcttcgta    4980
catcgagtga cgattctgga tctactattg atgagcttcg ccgcaagaat gaggaactcg    5040
aagaccggat taacgggttt gttcttgagg gtgtgaagcg cgaggtggct gccgagtgtg    5100
gcctgtcggg tgatgcgatc gcttttcttc acggtagcga taaggagtcg cttgccgagt    5160
ctgctaaggc tttgaagggt ttgatcgacc atagtagtgg tggtggcgcg ggtgtgcgcc    5220
gtcttgcggg gagtgccccc gttgatgatg ttaaacgacg tgagggtgtc gcgtttgtgg    5280
atgctcttgt caataattct aggagatgat ttatcatggc tgacgatttt ctttctgcag    5340
ggaagcttga gcttcctggt tctatgattg gtgcggttcg tgaccgtgct atcgattctg    5400
gtgttcttgc taaactgtca ccggagcagc cgactatttt cgggcctgtt aagggcgccg    5460
```

```
tttttagtgg tgttccgcgc gctaagattg ttggcgaggg cgatgttaag ccttccgcta    5520
gcgttgatgt ttctgcgttt actgcgcagc ctatcaaggt tgtgactcag cagcgtgtct    5580
cggacgagtt tatgtgggct gacgccgatt accgtctggg tgtgcttcag gatctgattt    5640
ccccggccct gggtgcttct attggtcgcg ccgttgatct tattgctttc catggtattg    5700
atcctgctac gggtaagcct gctgcggctg tcaaggtgtc gctggataag acgaataaga    5760
cggttgatgc caccgattcc gctacggctg atcttgttaa ggctgttggt ctgattgctg    5820
gtgctggttt gcaggttcct aacggtgttg ctttggatcc ggcgttctcg tttgctctgt    5880
caactgaggt gtatccgaag ggttcgccgc ttgccggtca gccaatgtat cctgccgccg    5940
ggttcgccgg cctggataat tggcgcggcc taaatgttgg ttcttcttcg actgtttctg    6000
gtgccccgga gatgtcgcct gcttctggtg ttaaggctat tgttggtgat ttctctcgtg    6060
tccattgggg gttccagcgt aacttcccga ttgagctgat cgagtatggt gacccggatc    6120
agacggggcg tgacttgaag ggccataatg aggttatggt tcgtgccgag gctgtgctgt    6180
atgttgcgat tgagtcgctt gattcgtttg ctgtcgtgaa ggagaaggct gccccgaagc    6240
ctaatccgcc ggccggtaac tgattcattt gttgcgataa tgtttatgct gtgtgcaggg    6300
ggtggtgttg atgggtatca ttttgaagcc tgaggatatt gagcctttcg ccgatattcc    6360
tagagagaag cttgaggcga tgattgccga tgtggaggct gtggctgtca gtgtcgcccc    6420
ctgtatcgct aaaccggatt tcaaatatag ggatgccgct aaggctattc tgcgtagggc    6480
tttgttgcgc tggaatgata ctggcgtgtc gggtcaggtg cagtatgagt ctgcgggccc    6540
gtttgctcag actacacggt cgaatactcc tacgaatttg ttgtggcctt ctgagattgc    6600
cgcgttgaag aagttgtgtg agggtgatag tggggctggt aaggcgttca ctattacacc    6660
gaccatgagg agtagtgtga atcattctga ggtgtgttcc acggtgtggg gtgagggttg    6720
ctcgtgcggg tcgaatatta acggctatgc tggcccgttg tgggagatat gatatgaccg    6780
gttttcctta cggtgaaacg gttgtgatgc ttcagccgac tgttcgtgtc gatgatcttg    6840
gtgacaaggt ggaggattgg tctaagcctg tcgagactgt gtaccataac gtggccatct    6900
atgcttccgt ttcgcaggag gatgaggccg cggggcgtga ctcggattat gagcattgga    6960
cactgctgtt caagcagcct gtcaaggctg ctggttatcg gtgtcgttgg cgtattcggg    7020
gtgttgtgtg ggaggctgac gggtctccta tggtgtggca tcatccgatg tctggctggg    7080
atgctggtac gcaggttaat gtgaagcgta agaagggctg atgggttgtg gcacgtgatg    7140
ttgatgtgaa gctgaacttg ccgggtattc gtgaggtgtt gaagtcttct gggggtgcagg    7200 gcatgttggc tgagcgtggt gagcgtgtca gcgtgcggc ctcggcgaat gtgggcggta    7260
acgcttacga tagggcccag tatcgtgccg ggttgtcgtc tgaggtgcag gttcaccgtg    7320
ttgaggctgt ggcgcgtatt ggcaccacct ataagggtgg taaaaggatt gaggctaagc    7380
atggcacgtt ggcgaggtcg attggggctg cgtcgtgatc gtttacggtg atcctcgaat    7440
atgggctaaa cgtgtgttgg cggatgatgg ttggctgtct gatgtaccgt gcacgggtac    7500
tgtgccggat acatttgagg gtgatctgat ttggttggcg ttggatggtg gcccggagtt    7560
gcatgttcgt gagcgtgttt ttttgcgtgt gaatgtgttt tcggatacgc cggatcgtgc    7620
tatgtctttg gctcgccggg ttgaggctgt gctggctgat ggtgtggatg gtgatccggt    7680
ggtgttttgc aggcgttcga ctgggcctga tttgctggtg gatggtgcac gttttgatgt    7740
gtattcgctt tttgagctga tatgtaggcc tgcggagtct gaataagctt attgttttg    7800 ttttaatgta attgtttgat atttaatggg ggttgtgatg gctgctacac gtaaagcgtc    7860
```

```
taatgttcgt tcagcggtta ctggcgacgt ttatattggt gacgcgcacg cgggtgattc    7920
tattaagggt gtggaggcgg ttccttccgg gcttacagct ttggggtatc tgtctgatga    7980
cgggtttaag attaagcctg agcgtaaaac ggatgatttg aaggcttggc agaatgcgga    8040
tgttgttcgc actgtggcta cggagtcgtc tatcgagatt tctttccagc tgattgagtc    8100
gaagaaggag gttatcgaac tgttttggca gtcgaaggtt actgccggat ctgattcggg    8160
ttcgttcgat atttctcctg gtgccacaac aggtgttcac gccctgttga tggatattgt    8220
tgatggcgat caggttattc gctactattt ccctgaggtt gagctcattg atcgtgacga    8280
gattaagggc aagaatggcg aagtgtacgg gtatggtgtg acgttgaagg cgtatcctgc    8340
ccagattaat aagactggta atgcggtgtc gggtcggggg tggatgacgg ctttaaaagc    8400
tgatactcct ccgactcctc cgccggcccc ggttcctccg aagcctcagc cggatccgaa    8460
tccgccgtcc ggtaactgat acacgatttt aggggattgt taatagatga gtgacactgg    8520
tttcacgttg aagattggtg atcgtagctg ggtgttggcg gatgcggagg agacggctca    8580
ggctgttcct gcccgcgttt tccgtcgtgc cgccaggatt gcccagtcgg gggagtctgc    8640
ggatttcgcc caggttgagg tgatgttttc tatgttggag gctgccgccc agctgacgc    8700
ggtggaggcc ctggaggggc ttcctatggt tcgtgtggcg gaggttttcc gtgagtggat    8760
ggaatacaag cctgacggta agggtgcctc gctgggggaa tagtttggct ccacggcctg    8820
attgatgatt atcgtggggc catcgaatac gatttccgca ccaagtttgg tgtttctgtt    8880
tatagtgttg gtgcccgca gatgtgttgg ggtgaggctg tccggctggc tggcgtgttg    8940
tgtaccgata cgtctagcca gttggcggcc caccttaatg gttggcagcg cccgtttgag    9000
tggtgcgagt gggctgtgtt ggacatgttg gatcattaca ggtctgctaa tagtgagggg    9060
cagccggagc ctgtggcgag gccgactgat gagcgtcggg caaggtttac gtctgggcag    9120
gtggacgata ttttgcgcg tgttcgtgcc ggtggcgggg tgtctcgcga gattgatatt    9180
atggggtgaa tagtgtatgt ctggtgagat tgcttccgca tatgtgtcgt tgtatacgaa    9240
gatgcctggc cttaaaagtg atgttggtaa acagttgtcg ggtgttatgc ctgctgaggg    9300
gcagcgttcg ggtagcctgt ttgctaaagg catgaagttg gcgcttggtg gtgcggcgat    9360
gatgggtgcc atcaatgttg ctaagaaggg cctcaagtct atctatgatg tgactattgg    9420
tggcggtatt gctcgcgcta tggctattga tgaggctcag gctaaactga ctggtttggg    9480
tcacacgtct tctgatacgt cttcgattat gaattcggct attgaggctg tgactggtac    9540
gtcgtatgcg ttgggggatg cggcgtctac ggcggcgggc ttgtctgctt cgggtgtgaa    9600
gtctggcggt cagatgacgg atgtgttgaa gactgtcgcg gatgtgtctt atatttcggg    9660
taagtcgttt caggatacgg gcgctatttt tacgtctgtg atggctcgcg gtaagttgca    9720
gggcgatgac atgttgcagc ttacgatggc tggtgttcct gtgctgtctt tgcttgccag    9780
gcagacgggt aaaaccctcg gctgaggtttc gcagatggtg tcgaagggc agattgattt    9840
tgccacgttt gcggctgcga tgaagcttgg catgggtggt gctgcgcagg cgtctggtaa    9900
gacgttgag ggcgctatga agaatgttaa gggcgctttg gctatttgg gtgctacggc    9960
tatgcgccg tttcttaacg gcctgcggca gattttgtt gcgttgaatc cggttattaa    10020
gtctatcacg gattctgtga agccgatgtt tgctgccgtc gatgctggta tccagcggat    10080
gatgccgtca atttttggcg tggattaaccg tatgccggct atgatcacga gaatgaatgc    10140
acagatgcgc gccaaggtgg agcagttgaa gggcatttttt gcgagaatgc atttgcctgt    10200
```

```
tcctaaagtg aatttgggtg ccatgtttgc tggcggcacc gcagtgtttg gtattgttgc   10260
tgcgggtgtg gggaagcttg ttgcagggtt tgctccgttg gcggttgcgt tgaagaatct   10320
gttgccgtcg tttggtgctt tgaggggtgc cgccgggggg cttggtggcg tgtttcgcgc   10380
cctgggtggc cctgtcggga ttgtgatcgg cttgtttgcg gcaatgtttg ccacgaacgc   10440
ccagttccgt gccgctgtta tgcagctggt ggctgtggtt ggtcaggcgt tgggccagat   10500
tatggcagct gtgcagccgc tgtttggttt ggttgctggc gtggttgcca ggttggcgcc   10560
ggtgttcggc cagattatcg gtatggttgc tggtttggct gcccggctgg tgcctgttat   10620
tggtatgctt attgcccggc tggttcctgt tatcacccag attattggta tggtaaccca   10680
ggttgctgcc atgttgttgc ctatgctgat gccggttatt caggctgttg ttgctgtgat   10740
acggcaggtt attggtgtca ttatgcagtt gatacctgtt ttgatgccgg ttgtgcagca   10800
gattttgggt gctgtcatgt ctgttttgcc gccgattgtt ggtttgatac ggtcgctgat   10860
accggtgatc atgtcgatta tgcgtgtggt ggtgcaggtt gttggtgctg tgctacaggt   10920
ggtggcccgt attattccgg ttgttatgcc gatttatgtt tcggtgattg gattcattgc   10980
caagatttat gctgcggtta tcgttttttga ggctaaggtt attggcgcta ttcttcgtac   11040
tattacgtgg attgtgaatc attcagtgtc tggcgtgagg tctatgggca cggccatcca   11100
gaatggctgg aatcatatta aatcgtttac gtctgcgttt attaacggtt ttaagtcgat   11160
catttctggc ggcgtgaacg cggttgtggg gttttttacg cggcttggtt tgtcggttgc   11220
ttcccatgtg aggtccggtt ttaacgctgc gagggggtgct gtttcttccg ccatgaatgc   11280
tattcggagt gttgtgtctt cggtggcgtc tgctgttggc gggttttttca gttcgatggc   11340 gtctcgtgtt cggaatggtg ctgtgcgcgg gtttaatggt gcccggagtg cggcttcttc   11400
tgctatgcat gctatggggt ccgctgtgtc tagtggtgtg catggtgtgc tgggttttttt   11460 ccggaatttg cctgacaata ttcggcgtgc gcttggtaat atggggtccc tgttggtgtc   11520
ggctggccgt gatgtggtgt ccggtttagg taatggtatc aagaatgctt tgagtggcct   11580
gttggatacg gtgcgtaata tgggttctca ggttgctaat gcggcgaagt cggtgttggg   11640
tattcattcc ccgtctcggg tgtttcgtga cgaggttggc cggcaggttg ttgccggttt   11700
ggctgagggt attactggta atgctggttt ggcgttggat gcgatgtcgg gtgtggctgg   11760
gaggctgcct gatgcggttg atgcccggtt tggtgtgcga tcgtctgtgg gttcgtttac   11820
cccgtatggc aggtatcagc gcatgaatga taagagtgtt gtggtgaatg tgaatgggcc   11880
tacttatggg gatcctgccg agtttgcgaa gcggattgag cggcagcagc gtgacgctttt   11940 gaacgcgttg gcttacgtgt gattttgggg gtgtggtgc                          11979
```

```
<210> SEQ ID NO 25
<211> LENGTH: 83
<212> TYPE: DNA
<213> ORGANISM: Artificial Sequence
<220> FEATURE:
<223> OTHER INFORMATION: PAC7 cos of pAN594

<400> SEQUENCE: 25
acaaaaggga ggtatttcac taagccgtac gaggtcttgc acgggtgtgc aggggggtgtg   60 cccggtgggg gttggcgggt ttt                                             83

<210> SEQ ID NO 26
<211> LENGTH: 4670
<212> TYPE: DNA
<213> ORGANISM: Artificial Sequence
```

<220> FEATURE:
<223> OTHER INFORMATION: operon of gp15-gp19+gp45

<400> SEQUENCE: 26

```
cgacgcggcg gtctgccgac ccggcaacga ccaactcccc gacgggcgct gacaccggcc      60
cggcagcgtg catgcgtgca tttccaccct caagaaccat tgactggcga cgcgcaggtg     120
ggagaattga actgaacgct tgaacgcgt tggcttacgt gtgattttgg gggtgtggtg      180
catgtttatt cctgacccgt ctgatcgttc tggtttgact gtgacttggt ctatgttgcc     240
gttgattggt aatgatccgg agcgtgtgct tcatttgacg gattatacgg ggtcgtctcc     300
gataatgttg ttgaatgatt cgttgcgcgg tttgggtgtt cctgaggtgg agcattttc      360
tcaaactcat gttggggtgc atggctcgga gtggcgcggg tttaatgtga agcctcgcga     420
ggtgacgcta ccggtgttgg tgtcgggtgt tggcccggat ccgtgggcg gttttcgtga     480
cggtttttg aaggcgtatg acgagttgtg gtctgctttt cctcctggcg aggtggggga     540
gttgtctgtg aagactcctg ccggtcgtga gcgtgtgttg aagtgccggt ttgattcggt     600
ggatgacacg tttacggtgg atccggtgaa caggggttat gcgcgttatc tgttgcattt     660
gacggcttat gacccgtttt ggtatgggga tgagcagaag tttcgtttca gtaacgctaa     720
gttgcaggat tggttgggtg gcggccctgt cgacggtaag ggtaccgcgt ttccggtggt     780
gttgacgcct ggtgttggtt cgggttggga taatctgtct aataagggtg atgtgcctgc     840
gtggcctgtg attcgtgttg aggggccgtt gtcgtcgtgg tctgtgcaga ttgatggttt     900
gcgtgtgtcc tcggattggc cggtggagga gtatgattgg atcactattg atacggatcc     960
tcgtaagcag tctgcgttgt tggacgggtt tgaggatgtg atggatcgtt tgaaggagtg    1020
ggagtttgcg cctatcccgc ctggcggttc tcggagtgtg aatattgaga tggttggttt    1080
gggtgccatt gttgtgtcgg tgcagtacag gttttttgagg gcttggtgaa tagttgatgg    1140
ctggtttttgt tccgcatgta acattgttta caccggatta tcgccgtgtg gcgcctatca    1200
attttttttga gtcgttgaag ttgtcgttga agtggaatgg tttgtccact ttggagttgg    1260
tggtgtctgg tgatcattct aggcttgacg ggttgactag gccgggtgcg cggcttgtgg    1320
ttgattatgg tggtggccag attttttttctg gccctgtgcg tcgggtgcat ggtgtgggtc    1380
cgtggcgttc ttcgcgtgtg actatcacgt gtgaggatga tattcgtctg ttgtggcgta    1440
tgttgatgtg gcctgtgaat tatcgtcctg gtatggttgg tatggagtgg cgtgcggatc    1500
gggattatgc ccattattcg ggtgcggcgg agtcggtggc taagcgggtg ttgggggata    1560
atgcttggcg ttttccgtct ggtttgttta tgaacgatga tgagagtcgt ggccgctata    1620
ttaaggattt tcaggtgcgg tttcacgtgt ttgccgataa gttgttgccg gtgttgtcgt    1680
gggctcggat gactgtcacg gtgaaccagt tgagaatgc gaagtttgat cagcgtggtt    1740
tggtgtttga ttgtgtgcct gctgtgaccc ggaaacatgt gttgactgcc gagtcgggtt    1800
cgattgtgtc gtgggagtat gtgcgtgacg ccccgaaggc gacatctgtg gtggttggtg    1860
gccgtggcga gggtaaggat cggctgtttt gtgaggatgt tgattcggcg gccgaggatg    1920
attggtttga tcgtgtcgag gtgtttaagg atgcccgtaa cacggattcc gagaaggtgt    1980
ctctcttcga tgaggctgag cgggtgttgt ccgagtcggg ggctacgtcg gggtttaaga    2040
ttgagttggc tgagtcggat gtgttgcggt ttggtcccgg caatctgatg cctggggatt    2100
tgatctatgt ggatgtgggt tctgggccta ttgcggagat tgtgcggcag attgatgtgg    2160
agtgtgtatc gcctggtgat ggttggacga aggtgactcc ggttgcgggg gattatgagg    2220
```

```
ataatccgtc ggccctgttg gctcgccgtg tggctggttt ggctgcgggt gtgcgggatt    2280
tgcaaaagtt ttagtaagtg attggggttt gttgtgggta ttgtgtgtaa agggtttgat    2340
ggtgtgttga ccgagtatga ttgggctcaa atgtctggtc tgatgggtaa tatgccgtct    2400
gtgaaggggc ctgacgattt tcgtgtcggc acgacgattc agggttctac ggtgttgtgt    2460
gagatcctgc cggggcaggc ttgggctcac ggggtgatgt gcacgtcgaa tagtgttgag    2520
acggtgacgg tcagcttcc gggcccgggt gagactcgat acgactatgt ggtgttgtct    2580
cgggattggc aggagaatac ggccaagttg agattgttc ccggtgggcg tgcggagcgt    2640
gccagggatg tgttgagggc tgagcctggc gtgtttcatc agcagctact ggcgactttg    2700
gtgttgtcgt ctaacggggtt gcagcagcag ttggataggc gtgctgtggc ggctagggtt    2760
gcgtttgggg agtctgctgc gtgtgatcct acccctgtgg agggtgaccg tgtgatggtt    2820
ccttcggggg ctgtgtgggc taaccatgcc ggcgagtgga tgttgttgtc tcccaggatt    2880
gagacgggtt cgaagtcgat catgtttggt ggttctgctg tgtatgctta cacgatcccg    2940
tttgagcgcc agttcagtag tccgcctgtt gtggtggcgt ctatggctac ggcggctggg    3000
ggcacggcac agattgatgt gaaagcctac aatgtgactg cccaaaattt tagtttggcg    3060
tttattacga atgatggttc gaagccgaat ggtgtgcctg cggtggcgaa ttggattgct    3120
gtcggcgtgt gactgcacgg gtgttgtggc ggatggtgtg atgttggggg gctgtggtgt    3180
cgtggtttac tcctgcactg gtggcctcta tttgtaccgc gttggccacg gttttgggtt    3240
ctgttcaggc tgtcacatcc cggtctagga agcgtttacg caggctgtcg gctcaggtgg    3300
atgcgatgga agagtatacg tggggtgtgc ggcgcgaggt gcgaaggttt aacgccgggc    3360
ttcctgatga tgtggagccg atgcatcttc ctgatttgcc cgagtttttg aaagatactg    3420
ttgatggtgg aggtgagtag ggttgaggga gttggaggag gagaagcggc agcgccgcaa    3480
ttttgagaag gcttcactgg tgttgttgtt tttgtcgctt gtgttgttgg cggtggttgc    3540
tgcgggtgct ttgcgtttcg ggctgtatc ctctgagcgg gattcggagc aggcgagggc    3600
ccagtcgaat ggtacggctg ccaggggttt ggctgcccgt gtgaagcagg cgtgtgcttc    3660
gggtgggggtg gagtctgtgc gtcttcaccg ttctggtttg tgtgtggatg ctgtgcgtgt    3720
tgagcagcgt gttcagggtg tgccgggtcc tgccggtgag cgcggcccgc aaggcccttc    3780
aggtcctgcc ggccgggatg tgttaatgg ttcggctggg ctggttgcc ctgttggtcc    3840
gcaaggttct ccgggtttga atggtgtgaa aggtcctgac ggcttgcctg gcgctaacgg    3900
ttcggatggc cgtgatggtg ttccaggtcg tgcaggtgct gacggtgtga acggcgttga    3960
cggcgctgat ggtcgggatg gttctgccgg tgagcgcggc ccgcaaggcc cttcaggtcc    4020
tgccggcccg caaggtgcac agggtgaacg gggtgagcgt ggtcccgccg gtgcgaatgg    4080
atcggatggc catgatggta aggatgggcg ctcggtggtg tctgtgtact gttccggggg    4140
ccgcctggtt gtgaaatata gtgacggtgt ggcttccacg atatcggtt cggcggcctg    4200
ccagggtgtg aaaccgtcgc ctctagtgac tatatcatcc cacaaataga ggctcacagg    4260
ggccatggga gattgggggg cgtgatggca cacaccaacc gcacagccag ccaagcccac    4320
cggcgctggc gggcaaggct catcacccaa gcccgacaac aaggccaaac cgaatgccca    4380
ctctgcggag tcaccatcac ctggaacacc cacgacctgc caaccagccc cgaagccgac    4440
cacatcacac ccgtcagccg gggaggactc aacaccctcg acaacgggca aatcatctgc    4500
agaacatgca acagaagcaa aggcaacaga acacaaccaa acatcaaatt ccaacaacaa    4560
accacaaaaa cattgattcc atggtgagga tatccacgag ctgcgttcgg ctaaacccaa    4620
```

| | |
|---|---|
| aagtaaaaac ccgccgaagc gggttttaac gtaaaacagg tgaaactgac | 4670 |

<210> SEQ ID NO 27
<211> LENGTH: 1910
<212> TYPE: DNA
<213> ORGANISM: Artificial Sequence
<220> FEATURE:
<223> OTHER INFORMATION: pAN241 vector

<400> SEQUENCE: 27

| | |
|---|---|
| caagtggccc atcgaagagg acggcaccac catctcgccg gcaagctca aggacgtgtc | 60 |
| caggctgacg ctcacggtgc tgctgcaccc ctcgtgcgcc atcatcgtgg atccccaaga | 120 |
| ttgtccggac ggcggttgag cgcggcctga taggcgccgc agctcctgct cccgggccgc | 180 |
| cccggtcggc ggtttactcc tttcctgccg gccggggcac tcaagacaac cgggggccct | 240 |
| cgcgaaattg agggggcccg cctgattgca agggggtgcc catgaagcaa cccgggcccc | 300 |
| accaaagaat gcgggctacc ttcaaggccg acagggctg gcgagtggca tgcccacggt | 360 |
| gcgcctggca tgccaccagc acccaccttg catggctcat ggatcaggcc agcacacaca | 420 |
| cctgtgcacc cctgctgttg tcgcccacgc caccgacgt ggagctggca ccggcaggcg | 480 |
| acgggctgtc cgtcctgtgg cccgaggtgg acggtgacgt gcagttcacc tgcatccaca | 540 |
| ccagcaccgc cacgtgcagg caggacgcac catgagcacc agtcgcaccg gcacggccac | 600 |
| atggttgcgc catgcagcac aggccaagcg tgaggcccaa gcacgaggac tcgcccgctg | 660 |
| cccactgtgc ggcgtctgga tggactacga ggtcggcaag cgacccaact cggccgaagc | 720 |
| agaccacatc agaccgcatt cgcttggtgg ttcagacgac atcgacaaca ttcgcgtcat | 780 |
| ttgtcgtcgt tgcaatcaat cgcgcggaaa cggcctgaag cgaccagggc gccaacgtca | 840 |
| gcgtccaatc aagcgcatcg agctggccca accggcccgc agtggggcat ttcctgcccc | 900 |
| gccggcatga atggaagggc agtgcggatg gtgcggtcgg gcattcgatc gtgcccggac | 960 |
| gggtcgcccg cgacgcttct gctcggcccg ctgtcgggtc gccgcgtccc ggtgtgcgat | 1020 |
| cccgctggcc atgaggtccc gcactgcgtg gtccgctgc acggcaagc gccccatcac | 1080 |
| cctggctggc gctccggcct catccacgga cccgggcaca tggtctggct ggtcgcaggt | 1140 |
| gcgacgcgcc acggccggcg atggcttcgg gaccatgctc ggtgacgggc tggggtgctg | 1200 |
| ggatctcgac cacttcgacg atcagggcgc ccgggccttc atcgaccgga tcgataagcc | 1260 |
| gatcatcttc gccgagcggt cggtgtcggg gcatggcttc cacatcttcg tccggactga | 1320 |
| cgaggccccc ggacgccgca ccggaaacat cgagttctac tcacgccatc ggttcatcag | 1380 |
| ggtcacagga gaccagttcg tctgaagaag ggggtgcgcc atggctgcac aggtcagggc | 1440 |
| cgtggacccc gatgagcgcc cacccgcccg caagcgggcc aagaccatca cccaggccgc | 1500 |
| gaagtccggc actgaggttg aactgttgga ggcactgcag gctcgcgtgg cccgcgccgt | 1560 |
| gcaggaccgt gacactccgc cgcgcgatct ggcagcgctg acgaagcggc tgatggacat | 1620 |
| cacccgggag ctcgaggcgg cccgggtcaa ggatcaggag gcgggatctg atggtgccgt | 1680 |
| caccgcagac gaaacatggc gaccgcaagc tctctgaggt cgccaagcac ctgatccttc | 1740 |
| ctgaagggat cgtctcgacg ggctggccgg ccgtgcgtga ccgtgtggc gagtggggtg | 1800 |
| tggtcttcga ccgttggcag gacggcatgg gccgggtgat cctgtcgaag cgcggcagcg | 1860 |
| gcctgttcgc cgctggtgtg ggcggggtcg gcatgtcgat cccgcgccag | 1910 |